US012084704B2

(12) United States Patent
Chayot et al.

(10) Patent No.: US 12,084,704 B2
(45) Date of Patent: Sep. 10, 2024

(54) METHODS FOR PRODUCING ISOBUTENE FROM 3-METHYLCROTONIC ACID

(71) Applicant: Global Bioenergies, Evry (FR)

(72) Inventors: Romain Chayot, Paris (FR); Mathieu Allard, Saint-Vrain (FR); Maria Anissimova, Nozay (FR)

(73) Assignee: Global Bioenergies, Evry (FR)

( * ) Notice: Subject to any disclaimer, the term of this patent is extended or adjusted under 35 U.S.C. 154(b) by 1256 days.

(21) Appl. No.: 16/612,065

(22) PCT Filed: Apr. 19, 2018

(86) PCT No.: PCT/EP2018/060051
§ 371 (c)(1),
(2) Date: Nov. 8, 2019

(87) PCT Pub. No.: WO2018/206262
PCT Pub. Date: Nov. 15, 2018

(65) Prior Publication Data

US 2021/0277425 A1 Sep. 9, 2021

(30) Foreign Application Priority Data

May 10, 2017 (EP) .................................... 17170429

(51) Int. Cl.
*C12P 5/02* (2006.01)

(52) U.S. Cl.
CPC ............. *C12P 5/026* (2013.01); *C12Y 205/01* (2013.01); *C12Y 207/0105* (2013.01); *C12Y 207/04026* (2015.07); *C12Y 207/06002* (2013.01); *C12Y 207/06003* (2013.01); *C12Y 401/01* (2013.01); *C12Y 503/03002* (2013.01)

(58) Field of Classification Search
None
See application file for complete search history.

(56) References Cited

FOREIGN PATENT DOCUMENTS

| WO | WO-2013186215 A1 * | 12/2013 | .............. C10G 3/42 |
|---|---|---|---|
| WO | 2017085167 A2 | 5/2017 | |

OTHER PUBLICATIONS

White ("UbiX is a flavin prenyltransferase required for bacterial ubiquinone biosynthesis" Nature, vol. 522, 2015, 502-519) (Year: 2015).*

Zheng ("Metabolic engineering of *Escerichia coli* for high-specificity production of isoprenol and prenol as next generation of biofuels", Biotechnology for Biofuels, 2013, 6:57) (Year: 2013).*

Arunrattanamook ("Kinetic Characterization of Prenyl-Flavin Synthase form *Saccharomyces cerevisae*", Biochemistry, 2018, 57, 696-700, Published Dec. 12, 2017) (Year: 2017).*

Kegg ("Enzyme: 5.3.3.2", available at https://www.genome.jp/dbget-bin/www_bget?enzyme+5.3.3.2, accessed on Jul. 31, 2023). (Year: 2023).*

Kang (Isopentenyl diphosphate (IPP)-bypass mevalonate pathways for isopentenol production, Metabolic engineering, 34 (2016), 25-35), (Year: 2016).*

Kegg2 ("Enzyme: 3.6.1.67", available at https://www.genome.jp/dbget-bin/www_bget?ec:3.6.1.67, accessed on Jul. 31, 2023) (Year: 2023).*

Cheyot et al., "Session 6: Metabolic Engineering of Industrial Microorganisms—Bio-Based Isobutene", Metabolic Engineering 11 Conference, Retrieved from the Internet: URL:http://toc.proceedings.com/32408webtoc.pdf, p. 1, 4, (2016).

Ferguson et al., "Mechanism of the Novel Prenylated Flavin-Containing Enzyme Ferulic Acid Decarboxylase Probed by Isotope Effects and Linear Free-Energy Relationships", Biochemistry, vol. 55, pp. 2857-2863, (2016).

(Continued)

*Primary Examiner* — Robert J Yamasaki
*Assistant Examiner* — Charles Zoltan Constantine
(74) *Attorney, Agent, or Firm* — Michele M. Wales; Inhouse Patent Counsel

(57) ABSTRACT

Described are methods for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) into a flavin-derived cofactor, wherein said method further comprises providing said DMAP enzymatically by: (i) the enzymatic conversion of dimethylallyl pyrophosphate (DMAPP) into said DMAP; or (ii) a single enzymatic step in which prenol is directly enzymatically converted into said DMAP; or (iii) two enzymatic steps comprising: first enzymatically converting DMAPP into prenol; and then enzymatically converting the thus obtained prenol into said DMAP; or (iv) the enzymatic conversion of isopentenyl monophosphate (IMP) into said DMAP, or by a combination of any one of (i) to (iv). Moreover, described are methods for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl pyrophosphate (DMAPP), wherein said method further comprises providing said DMAPP enzymatically by: (v) the enzymatic conversion of isopentenyl pyrophosphate (IPP) into said DMAPP; or (vi) the enzymatic conversion of dimethylallyl phosphate (DMAP) into said DMAPP; or (vii) the enzymatic conversion of prenol into said DMAPP; (viii) or by a combination of any one of (v) to (vii). Moreover, described are methods for providing said flavin cofactor enzymatically by the enzymatic conversion of riboflavin into flavin mononucleotide (FMN).

20 Claims, 20 Drawing Sheets

Figure 1:
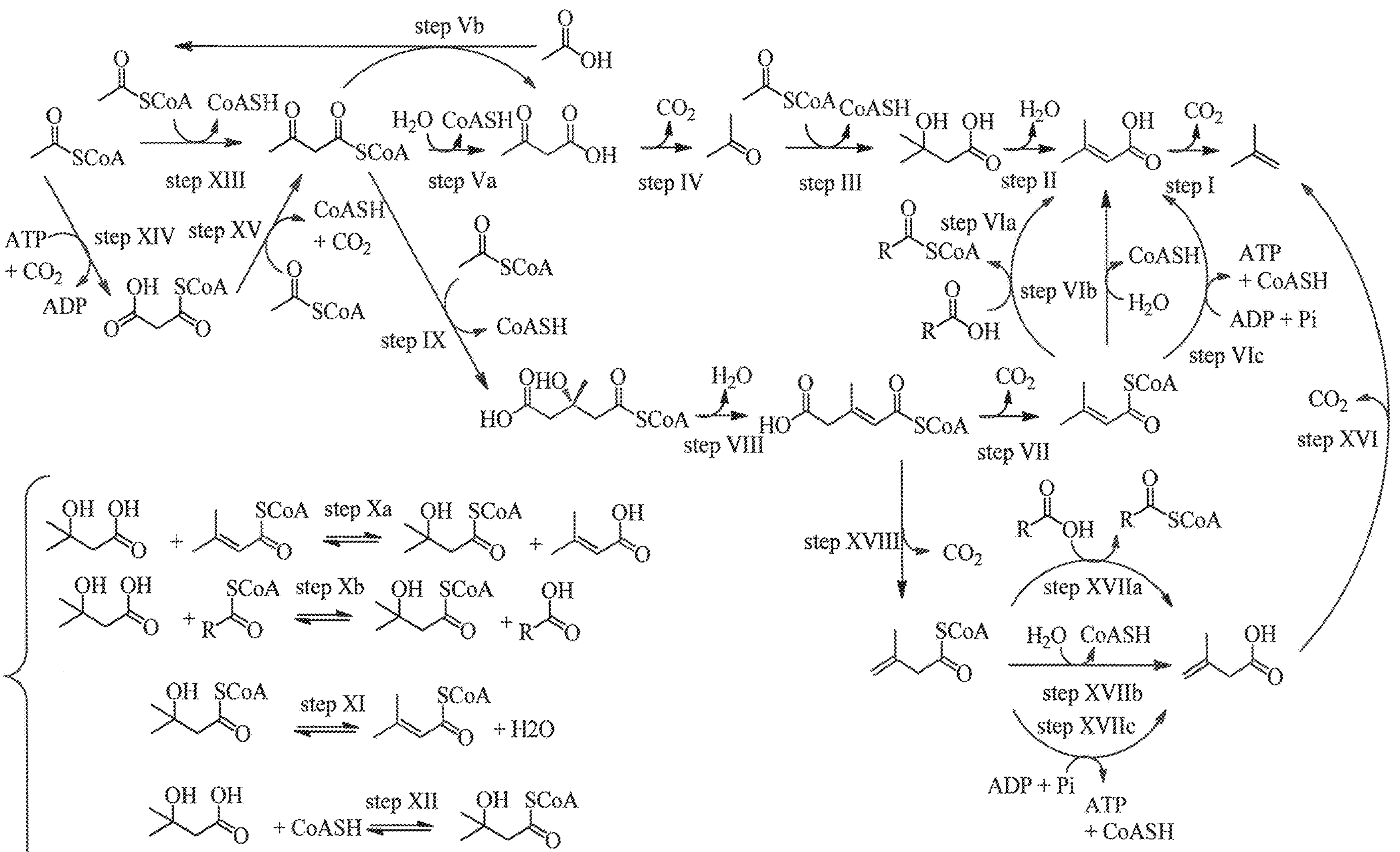

Specification includes a Sequence Listing.

(56) References Cited

OTHER PUBLICATIONS

Henry et al., "Orthologs of the Archaeal Isopentenyl Phosphate Kinase Regulate Terpenoid Production in Plants", PNAS, vol. 112, No. 32, pp. 10050-10055, (2015).

International Search Report and Written Opinion dated Jun. 19, 2018 and received in PCT/EP2018/060051.

Marliere et al., "Bioproduction fermentaire de l'isobutene", L'Actualite Chimique, vol. 415, pp. 44-49, (2017).

Wang et al., "Biosynthesis and Activity of Prenylated FMN Cofactors", Cell Chemical Biology, vol. 25, pp. 560-570, (2018).

Zheng, Y. et al., "Metabolic Engineering of *Escherichia Coli* for High-Specificity Production of Isoprenol and Prenol as Next Generation of Biofuels", Biotechnology for Biofuels, vol. 6, No. 57, http://www.biotechnologyforbiofuels.com/content/6/1/57, pp. 1-13, (2013).

Chen et al., "Characterization of Thermophilic Archaeal Isopentenyl Phosphate Kinases", Biochemistry, vol. 49, No. 1, pp. 207-217 (2010).

EPO Office Action dated Dec. 16, 2020 received in corresponding EP Application 16/612,065.

International Preliminary Report of Patentability dated Nov. 28, 2019 and received in PCT/EP2018/060051.

* cited by examiner

METHODS FOR PRODUCING ISOBUTENE FROM 3-METHYLCROTONIC ACID

CROSS-REFERENCE TO RELATED APPLICATIONS

This application is a § 371 National Stage Application of PCT/EP2018/060051 filed on Apr. 19, 2018, which claims priority to EP 17170429.9 filed on May 10, 2017, which are both hereby incorporated by reference in their entirety.

The present invention relates to methods for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) into a flavin-derived cofactor, wherein said method further comprises providing said DMAP enzymatically by: (i) the enzymatic conversion of dimethylallyl pyrophosphate (DMAPP) into said DMAP; or (ii) a single enzymatic step in which prenol is directly enzymatically converted into said DMAP; or (iii) two enzymatic steps comprising: first enzymatically converting DMAPP into prenol; and then enzymatically converting the thus obtained prenol into said DMAP; or (iv) the enzymatic conversion of isopentenyl monophosphate (IMP) into said DMAP, or by a combination of any one of (i) to (iv). Moreover, the present invention relates to methods for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl pyrophosphate (DMAPP), wherein said method further comprises providing said DMAPP enzymatically by: (v) the enzymatic conversion of isopentenyl pyrophosphate (IPP) into said DMAPP; or (vi) the enzymatic conversion of dimethylallyl phosphate (DMAP) into said DMAPP; or (vii) the enzymatic conversion of prenol into said DMAPP; or (viii) by a combination of any one of (v) to (vii). Moreover, the present invention relates to methods for providing said flavin cofactor enzymatically by the enzymatic conversion of riboflavin into flavin mononucleotide (FMN).

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Butylene exists in four forms, one of which, isobutene (also referred to as isobutylene), enters into the composition of methyl-tert-butyl-ether (MTBE), an anti-knock additive for automobile fuel. Isobutene can also be used to produce isooctene, which in turn can be reduced to isooctane (2,2,4-trimethylpentane); the very high octane rating of isooctane makes it the best fuel for so-called "gasoline" engines. Alkenes such as isobutene are currently produced by catalytic cracking of petroleum products (or by a derivative of the Fischer-Tropsch process in the case of hexene, from coal or gas). The production costs are therefore tightly linked to the price of oil. Moreover, catalytic cracking is sometimes associated with considerable technical difficulties which increase process complexity and production costs.

The production by a biological pathway of alkenes such as isobutene is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al. (Process Biochemistry 41 (2006), 1001) and Wackett (Current Opinions in Chemical Biology 21 (2008), 187). The conversion of isovalerate to isobutene by the yeast *Rhodotorula minuta* has been described (Fujii et al. (Appl. Environ. Microbiol. 54 (1988), 583)), but the efficiency of this reaction, less than 1 millionth per minute, or about 1 for 1000 per day, is far from permitting an industrial application. The reaction mechanism was elucidated by Fukuda et al. (BBRC 201 (1994), 516) and involves a cytochrome P450 enzyme which decarboxylates isovalerate by reduction of an oxoferryl group $Fe^{V}$=O. Large-scale biosynthesis of isobutene by this pathway seems highly unfavourable, since it would require the synthesis and degradation of one molecule of leucine to form one molecule of isobutene. Also, the enzyme catalyzing the reaction uses heme as cofactor, poorly lending itself to recombinant expression in bacteria and to improvement of enzyme parameters. For all these reasons, it appears very unlikely that this pathway can serve as a basis for industrial exploitation. Other microorganisms have been described as being marginally capable of naturally producing isobutene from isovalerate; the yields obtained are even lower than those obtained with *Rhodotorula minuta* (Fukuda et al. (Agric. Biol. Chem. 48 (1984), 1679)).

Gogerty et al. (Appl. Environm. Microbiol. 76 (2010), 8004-8010) and van Leeuwen et al. (Appl. Microbiol. Biotechnol. 93 (2012), 1377-1387) describe the production of isobutene from acetoacetyl-CoA by enzymatic conversions wherein the last step of the proposed pathway is the conversion of 3-hydroxy-3-methylbutyric acid (also referred to as 3-hydroxyisovalerate (HIV)) by making use of a mevalonate diphosphate decarboxylase. This reaction for the production of isobutene from 3-hydroxy-3-methylbutyric acid is also described in WO2010/001078. In Gogerty et al. (loc. cit.) and in van Leeuwen et al. (loc. cit.) the production of 3-hydroxy-3-methylbutyric acid is proposed to be achieved by the conversion of 3-methylcrotonyl-CoA via 3-hydroxy-3-methylbutyryl-CoA. In order to further improve the efficiency and variability of methods for producing isobutene from renewable resources, alternative routes for the provision of isobutene and its precursors have been developed by providing methods for the production of isobutene comprising the enzymatic conversion of 3-methylcrotonic acid (also termed 3-methyl-2-butenoic acid, 3,3-dimethylacrylic acid or senecioic acid) into isobutene.

The enzymatic conversion of 3-methylcrotonic acid into isobutene is a decarboxylation reaction. A decarboxylation is a chemical reaction that removes a carboxyl group and releases carbon dioxide ($CO_2$).

The decarboxylation of 3-methylcrotonic acid has already been suggested in US-A1-2009/0092975 while there is no experimental evidence for this conversion. In US-A1-2009/0092975, a nucleic acid sequence called PAD1 derived from *Saccharomyces cerevisiae* is described and is disclosed to encode a decarboxylation enzyme. This enzyme is suggested to be useful as a selectable marker in a recombinant organism while it is described that a "weak acid" may be used as the selecting agent. 3-methylcrotonic acid is mentioned, among many others, as a potential "weak acid".

However, it was only later found that the above PAD1, in reality, does not provide for the decarboxylase activity.

In fact, the bacterial ubiD and ubiX or the homologous eukaryotic fdc1 and pad1 genes have been implicated in the non-oxidative reversible decarboxylation. The combined action of phenylacrylic acid decarboxylase (PAD) and ferulic acid decarboxylase (FDC) is considered to be essential for the decarboxylation of phenylacrylic acid in *Saccharomyces cerevisiae* (J. Biosci. Bioeng. 109, (2010), 564-569; AMB Express, 5:12 (2015) 1-5; ACS Chem. Biol. 10 (2015), 1137-1144).

Recently, the above enzyme family described as phenylacrylic acid decarboxylase (PAD) was characterized as an FMN prenyl-transferase and no longer as a decarboxylase. It has been shown that Fdc1 (but not PAD) is solely responsible for the reversible decarboxylase activity and that it requires a new type of cofactor, namely a prenylated flavin synthesized by the associated UbiX (or Pad1) protein. Thus, the real enzymatic activity of this PAD enzyme has been identified as the transformation of a flavin mononucleotide (FMN) cofactor with a prenyl moiety (from di-methyl-allyl-phosphate or pyrophosphate called DMAP or DMAPP).

Accordingly, in contrast to the prior art's belief, the real decarboxylase is the ferulic acid decarboxylase (FDC) in association with the modified FMN (prenylated-FMN). This mechanism of the ferulic acid decarboxylase (FDC) in association with the modified FMN (prenylated-FMN) (the latter provided by the PAD enzyme) was recently described and involves a surprising enzymatic mechanism, i.e., an α,β-unsaturated acid decarboxylation via a 1,3-dipolar cyclo-addition. Moreover, the structure of this FDC decarboxylase has recently been elucidated (Nature 522 (2015), 497-501; Nature, 522 (2015), 502-505; Appl. Environ. Microbiol. 81 (2015), 4216-4223).

The use of the above family of enzymes has previously been described for the conversion of α-β unsaturated carboxylic acid into terminal alkenes in US-A1-2009/0092975 as mentioned above while WO2012/018624 is directed to microorganisms and methods for the biosynthesis of aromatics, 2,4-pentadienoate and 1,3-butadiene and WO2013/028519 is directed to microorganisms and methods for producing 2,4-pentadienoate, butadiene, propylene, 1,3-butanediol and related alcohols.

Moreover, WO2013/186215 describes a method for preparing a mono-unsaturated alkene comprising contacting an aliphatic mono-unsaturated carboxylic acid with an Fdc1 polypeptide and a Pad1 polypeptide. However, in WO2013/186215, both, the Fdc1 polypeptide and the Pad1 polypeptide are classified as enzymes having a decarboxylase activity.

In contrast, in light of this background, methods have been developed wherein the above enzymes are artificially implemented in a pathway which ultimately leads to the production of isobutene. Thus, methods for the production of isobutene have been developed comprising the enzymatic conversion of 3-methylcrotonic acid into isobutene (step I as shown in FIG. 1), wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) into a flavin-derived cofactor while it has only been speculated that said FMN prenyl transferase also catalyzes the prenylation of a flavin cofactor (FMN or FAD) into a flavin-derived cofactor when utilizing dimethylallyl pyrophosphate (DMAPP).

Moreover, methods have been developed, wherein such a method further comprises (a) providing the 3-methylcrotonic acid by the enzymatic conversion of 3-methylcrotonyl-CoA into 3-methylcrotonic acid (steps VIa, VIb or VIc as shown in FIG. 1), or (b) providing the 3-methylcrotonic acid by the enzymatic conversion of 3-hydroxyisovalerate (HIV) into 3-methylcrotonic acid (step II as shown in FIG. 1).

The above method which has been developed for the production of isobutene from 3-methylcrotonyl-CoA via 3-methylcrotonic acid or from 3-hydroxyisovalerate (HIV) via 3-methylcrotonic acid may be embedded in a pathway for the production of isobutene starting from acetyl-CoA which is a central component and an important key molecule in metabolism used in many biochemical reactions. The corresponding reactions are schematically shown in FIG. 1.

As outlined in more detail further below, the present invention has also found that 3-methylcrotonic acid is enzymatically converted into isobutene by making use of an FMN-dependent decarboxylase associated with an FMN prenyl transferase when dimethylallyl pyrophosphate (DMAPP) instead of DMAP is used.

In the above described methods, the enzymatic conversion of 3-methylcrotonic acid into isobutene which is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) and/or dimethylallyl pyrophosphate (DMAPP) into a flavin-derived cofactor is a key step of the above overall metabolic pathway. In this key step, the availability of dimethylallyl phosphate (DMAP) and/or dimethylallyl pyrophosphate (DMAPP) as well as the availability of the flavin cofactor FMN are limiting factors. Therefore, there is a need for improved methods by increasing the pool/amount of dimethylallyl phosphate (DMAP) and/or dimethylallyl pyrophosphate (DMAPP) in order to ensure the efficient biosynthesis of the prenylated flavin cofactor (FMN or FAD). In addition, in order to ensure the efficient biosynthesis of the prenylated flavin cofactor (FMN or FAD) there is, therefore, also a need for the provision of an increased pool of the flavin cofactor FMN.

The present invention meets this demand by providing a method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) into a flavin-derived cofactor, wherein said method further comprises providing said DMAP enzymatically by:

(i) the enzymatic conversion of dimethylallyl pyrophosphate (DMAPP) into said DMAP; or (ii) a single enzymatic step in which prenol is directly enzymatically converted into said DMAP; or (iii) two enzymatic steps comprising: first enzymatically converting DMAPP into prenol; and then enzymatically converting the thus obtained prenol into said DMAP; or (iv) the enzymatic conversion of isopentenyl monophosphate (IMP) into said DMAP, or by a combination of any one of (i) to (iv).

Moreover, the present invention has found that the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) into a flavin-derived cofactor, also when utilizing dimethylallyl pyrophosphate (DMAPP).

Therefore, the present invention also meets the above demand by providing a method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl pyrophosphate (DMAPP), wherein said method further comprises providing said DMAPP enzymatically by:

(v) the enzymatic conversion of isopentenyl pyrophosphate (IPP) into said DMAPP; or (vi) the enzymatic conversion of dimethylallyl phosphate (DMAP) into said DMAPP; or (vii) the enzymatic conversion of prenol into said DMAPP; or (viii) by a combination of any one of (v) to (vii).

Moreover, the present invention provides a method for providing said flavin cofactor enzymatically by the enzymatic conversion of riboflavin into flavin mononucleotide (FMN).

The method according to the present invention is in particular useful for large scale production of isobutene in vitro or in vivo, in particular for a commercial production. Thus, the present invention relates to a method for large scale production, in particular the commercial production of isobutene wherein said method comprises the steps as described above.

The Enzymatic Conversion of 3-Methylcrotonic Acid into Isobutene

Figure 2A:
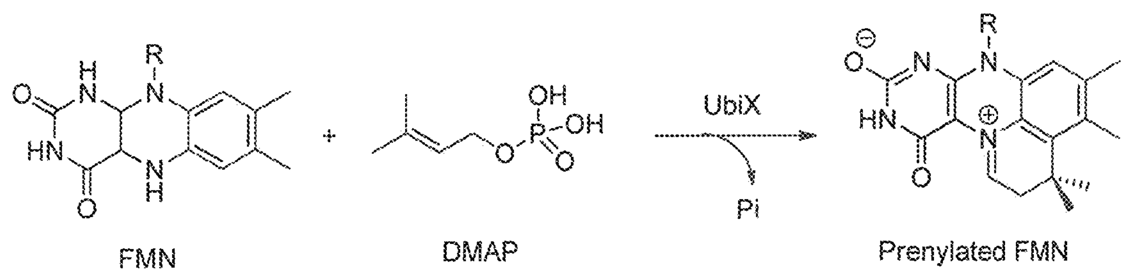
Figure 2B:
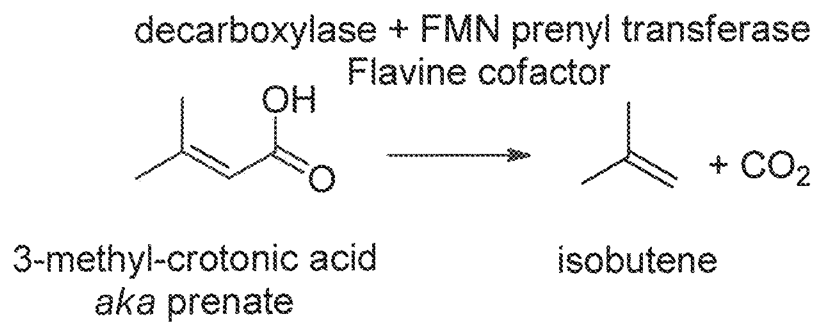

The enzymatic conversion of 3-methylcrotonic acid into isobutene (step I as shown in FIG. 1) is schematically shown in FIG. 2B.

According to the present invention, the enzymatic conversion of 3-methylcrotonic acid (also termed 3-methyl-2-butenoic acid or 3,3-dimethyl-acrylic acid) into isobutene (also termed isobutylene or 2-methyl-propene) can be achieved by a decarboxylation by making use of an FMN-dependent decarboxylase associated with an FMN prenyl transferase. "Decarboxylation" is generally a chemical reaction that removes a carboxyl group and releases carbon dioxide ($CO_2$).

The enzymatic conversion of 3-methylcrotonic acid into isobutene utilizing an FMN-dependent decarboxylase associated with an FMN prenyl transferase relies on a reaction of two consecutive steps catalyzed by the two enzymes, i.e., the FMN-dependent decarboxylase (catalyzing the actual decarboxylation of 3-methylcrotonic acid into isobutene) with an associated FMN prenyl transferase which provides the modified flavin cofactor.

The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism.

Thus, in the conversion of 3-methylcrotonic acid into isobutene, in a first step, a flavin cofactor (FMN or FAD) is modified into a (modified) flavin-derived cofactor. This modification is catalyzed by said FMN prenyl transferase. FMN prenyl transferase prenylates the flavin ring of the flavin cofactor (FMN or FAD) into a (modified) prenylated flavin cofactor. This reaction is schematically illustrated in FIG. 2A.

In a second step, the actual conversion of 3-methylcrotonic acid into isobutene is catalyzed by said FMN-dependent decarboxylase via a 1,3-dipolar cycloaddition based mechanism wherein said FMN-dependent decarboxylase uses the prenylated flavin cofactor (FMN or FAD) provided by the associated FMN prenyl transferase. This reaction is schematically illustrated in FIG. 2B.

In a preferred embodiment, said FMN prenyl transferase which modifies the flavin cofactor (FMN or FAD) into a (modified) flavin-derived cofactor is a phenylacrylic acid decarboxylase (PAD)-type protein, or the closely related prokaryotic enzyme UbiX, an enzyme which is involved in ubiquinone biosynthesis in prokaryotes.

In *Escherichia coli*, the protein UbiX (also termed 3-octaprenyl-4-hydroxybenzoate carboxy-lyase) has been shown to be involved in the third step of ubiquinone biosynthesis. It catalyses the reaction 3-octaprenyl-4-hydroxybenzoate ⇆ 2-octaprenylphenol+$CO_2$.

Moreover, the knockout of the homologous protein in yeast (Pad1) has been shown to confer sensitivity to phenylacrylic acid, showing that this enzyme functions as a phenylacrylic acid decarboxylase. *E. coli* strains also contain, in addition to UbiX, a second paralogue named Pad1. Its amino acid sequence shows 52% identity to UbiX and slightly higher sequence identity to *Saccharomyces cerevisiae* phenylacrylic acid decarboxylase Pad1. Despite its higher sequence similarity with yeast Pad1, *E. coli* Pad1 does not seem to have phenylacrylic acid decarboxylase activity. Its function is unknown, Pad1 may remove the carboxylate group from derivatives of benzoic acid but not from substituted phenolic acids.

Thus, in a preferred embodiment, the modification of a flavin cofactor (FMN or FAD) into the corresponding (modified) flavin-derived cofactor is catalyzed by the FMN-containing protein phenylacrylic acid decarboxylase (PAD). The enzymes involved in the modification of the flavin cofactor (FMN or FAD) into the corresponding modified flavin-derived cofactor were initially annotated as decarboxylases (EC 4.1.1.-). Some phenylacrylic acid decarboxylases (PAD) are now annotated as flavin prenyl transferases as EC 2.5.1.-.

Moreover, enzymes capable of catalyzing the enzymatic reaction described herein for flavin prenyl transferases have recently also been annotated as flavin prenyl transferases as EC 2.5.1.129.

In a more preferred embodiment, the conversion of 3-methylcrotonic acid into isobutene makes use of a phenylacrylic acid decarboxylase (PAD)-type protein as the FMN prenyl transferase which modifies a flavin cofactor (FMN or FAD) into the corresponding (modified) flavin-derived cofactor wherein said phenylacrylic acid decarboxylase (PAD)-type protein is derived from *Candida albicans* (Uniprot accession number Q5A8L8), *Aspergillus niger* (Uniprot accession number A3F715), *Saccharomyces cerevisiae* (Uniprot accession number P33751) or *Cryptococcus gattii* (Uniprot accession number E6R9Z0).

In a preferred embodiment, the phenylacrylic acid decarboxylase (PAD)-type protein employed in the method of the present invention is a phenylacrylic acid decarboxylase (PAD)-type protein derived from *Candida albicans* (Uniprot accession number Q5A8L8; SEQ ID NO:1), *Aspergillus niger* (Uniprot accession number A3F715; SEQ ID NO:2), *Saccharomyces cerevisiae* (Uniprot accession number P33751; SEQ ID NO:3), *Cryptococcus gattii* (Uniprot accession number E6R9Z0; SEQ ID NO:4) or *Hypocrea atroviridis* (also termed *Trichoderma atroviride*; Uniprot accession number G9NTN1) having the amino acid sequence as shown in SEQ ID NO:1, SEQ ID NO:2, SEQ ID NO:3, SEQ ID NO:4 and SEQ ID NO:71, respectively.

In a preferred embodiment of the present invention the phenylacrylic acid decarboxylase (PAD)-type protein is an enzyme comprising an amino acid sequence selected from the group consisting of SEQ ID NOs: 1 to 4 and 71 or a sequence which is at least n % identical to any of SEQ ID NOs: 1 to 4 and 71 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor.

As regards the determination of sequence identity, the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in any one of SEQ ID NOs:1 to 4 and 71 can be identified by the skilled person by methods known in the art. For example, such amino acid residues can be identified by aligning the sequence in question with the sequence shown in any one of SEQ ID NOs:1 to 4 and 71 and by identifying the positions which correspond to the above indicated positions of any one of SEQ ID NOs:1 to 4 and 71. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

In another preferred embodiment, the modification of a flavin cofactor (FMN or FAD) into the corresponding (modified) flavin-derived cofactor is catalyzed by the FMN-containing protein 3-octaprenyl-4-hydroxybenzoate carboxy-lyase also termed UbiX (initially annotated EC 4.1.1.-). As mentioned above, the enzymes involved in the modification of the flavin cofactor (FMN or FAD) into the corresponding modified flavin-derived cofactor were initially annotated as decarboxylases. Some phenylacrylic acid decarboxylases (PAD) are now annotated as flavin prenyl transferases as EC 2.5.1.-.

As mentioned above, enzymes capable of catalyzing the enzymatic reaction described herein for flavin prenyl transferases have recently also been annotated as flavin prenyl transferases as EC 2.5.1.129.

In a more preferred embodiment, the conversion of 3-methylcrotonic acid into isobutene makes use of a 3-octaprenyl-4-hydroxybenzoate carboxy-lyase (also termed UbiX) as the FMN prenyl transferase which modifies the flavin cofactor (FMN or FAD) into the corresponding (modified) flavin-derived cofactor wherein said 3-octaprenyl-4-hydroxybenzoate carboxy-lyase (also termed UbiX) is derived from *Escherichia coli* (Uniprot accession number P0AG03), *Bacillus subtilis* (Uniprot accession, number A0A086WXG4), *Pseudomonas aeruginosa* (Uniprot accession number A0A072ZCW8) or *Enterobacter* sp. DC4 (Uniprot accession number W7P6B1).

In an even more preferred embodiment, the 3-octaprenyl-4-hydroxybenzoate carboxy-lyase (also termed UbiX) employed in the method of the present invention is a 3-octaprenyl-4-hydroxybenzoate carboxy-lyase (also termed UbiX) derived from *Escherichia coli* (Uniprot accession number P0AG03; SEQ ID NO:5), *Bacillus subtilis* (Uniprot accession, number A0A086WXG4; SEQ ID NO:6), *Pseudomonas aeruginosa* (Uniprot accession number A0A072ZCW8; SEQ ID NO:7) or *Enterobacter* sp. DC4 (Uniprot accession number W7P6B1; SEQ ID NO:8) having the amino acid sequence as shown in SEQ ID NO:5, SEQ ID NO:6, SEQ ID NO:7 and SEQ ID NO:8, respectively.

In a preferred embodiment of the present invention the 3-octaprenyl-4-hydroxybenzoate carboxy-lyase is an enzyme comprising an amino acid sequence selected from the group consisting of SEQ ID NOs: 5 to 8 or a sequence which is at least n % identical to any of SEQ ID NOs: 5 to 8 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of the sequence identity, the same applies as has been set forth above.

In another preferred embodiment, the modification of a flavin cofactor (FMN or FAD) into the corresponding (modified) flavin-derived cofactor is catalyzed by an Ubx-like flavin prenyl transferase derived from *E. coli* encoded by kpdB and ecdB, respectively (UniProt accession number A0A023LDW3 and UniProt accession number P69772, respectively; SEQ ID NO: 66), and an Ubx-like flavin prenyl transferase derived from *Klebsiella pneumoniae* encoded by kpdB (UniProt accession number Q462H4; SEQ ID NO:70).

In a preferred embodiment of the present invention the Ubx-like flavin prenyl transferase is an enzyme comprising an amino acid sequence of selected from the group consisting of SEQ ID NO: 66 and SEQ ID NO: 70 or a sequence which is at least n % identical to SEQ ID NO: 66 or SEQ ID NO: 70 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of the sequence identity, the same applies as has been set forth above.

In another preferred embodiment, the modification of a flavin cofactor (FMN or FAD) into the corresponding (modified) flavin-derived cofactor is catalyzed by a flavin prenyl transferase.

As mentioned above, the actual decarboxylation, i.e., the conversion of 3-methylcrotonic acid into isobutene is catalyzed by an FMN-dependent decarboxylase via a 1,3-dipolar cycloaddition based mechanism wherein said FMN-dependent decarboxylase uses the prenylated flavin cofactor (FMN or FAD) provided by any of the above described associated FMN prenyl transferases.

In a preferred embodiment, said FMN-dependent decarboxylase catalyzing the decarboxylation of 3-methylcrotonic acid into isobutene is catalyzed by a ferulic acid decarboxylase (FDC). Ferulic acid decarboxylases (FDC) belong to the enzyme class EC 4.1.1.-.

In an even more preferred embodiment, the conversion of 3-methylcrotonic acid into isobutene makes use of a ferulic acid decarboxylases (FDC) which is derived from *Saccharomyces cerevisiae* (Uniprot accession number Q03034), *Enterobacter* sp. (Uniprot accession number V3P7U0), *Bacillus pumilus* (Uniprot accession number Q45361), *Aspergillus niger* (Uniprot accession number A2R0P7) or *Candida* dubliniensis (Uniprot accession number B9WJ66).

In a preferred embodiment, the ferulic acid decarboxylases (FDC) employed in the method of the present invention is a ferulic acid decarboxylases (FDC) derived from *Saccharomyces cerevisiae* (Uniprot accession number Q03034; SEQ ID NO:9), *Enterobacter* sp. (Uniprot accession number V3P7U0; SEQ ID NO:10), *Bacillus pumilus* (Uniprot accession number Q45361; SEQ ID NO:11), *Aspergillus niger* (Uniprot accession number A2R0P7; SEQ ID NO:12) or *Candida* dubliniensis (Uniprot accession number B9WJ66; SEQ ID NO:13) having the amino acid sequence as shown in SEQ ID NO:9, SEQ ID NO:10, SEQ ID NO:11, SEQ ID NO:12 and SEQ ID NO:13, respectively.

In another more preferred embodiment, the conversion of 3-methylcrotonic acid into isobutene makes use of a protocatechuate decarboxylase (EC 4.1.1.63).

Thus, in one preferred embodiment, the conversion of 3-methylcrotonic acid into isobutene is catalyzed by a protocatechuate (PCA) decarboxylase (EC 4.1.1.63). PCA decarboxylases (also termed AroY) are known to catalyze the following reaction, i.e., the enzymatic conversion of protocatechuate (PCA) into catechol (Johnson et al., Metabolic Engineering Communications 3 (2016), 111):

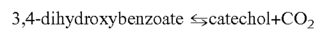

This enzyme occurs in a variety of organisms and has, e.g., been described in *Enterobacter aerogenes, Enterobacter cloacae, Rhodopseudomonas* sp. and *Sedimentibacter hydroxybenzoicus*.

In a preferred embodiment of the present invention, the PCA decarboxylase employed in the method of the present invention is a PCA decarboxylase which is derived from *Klebsiella pneumoniae* (Uniprot accession number B9AM6), *Leptolyngbya* sp. (Uniprot accession number A0A0S3U6D8), or Phascolarctobacterium sp. (Uniprot accession number R611V6).

In a preferred embodiment, the PCA decarboxylase employed in the method of the present invention is an enzyme derived from *Klebsiella pneumonia* (SEQ ID NO:14), *Leptolyngbya* sp. (SEQ ID NO:15), or Phascolarctobacterium sp. (SEQ ID NO:16).

In a preferred embodiment of the present invention the PCA decarboxylase is an enzyme comprising an amino acid sequence selected from the group consisting of SEQ ID NOs: 14 to 16 or a sequence which is at least n % identical to any of SEQ ID NOs: 14 to 16 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

In a preferred embodiment of the present invention the ferulic acid decarboxylase (FDC) is an enzyme comprising an amino acid sequence selected from the group consisting of SEQ ID NOs: 9 to 13 or a sequence which is at least n % identical to any of SEQ ID NOs: 9 to 13 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

In another preferred embodiment, said FMN-dependent decarboxylase catalyzing the decarboxylation of 3-methylcrotonic acid into isobutene is an enzyme which is closely related to the above ferulic acid decarboxylase (FDC), namely a 3-polyprenyl-4-hydroxybenzoate decarboxylase (also termed UbiD). 3-polyprenyl-4-hydroxybenzoate decarboxylase belongs to the UbiD decarboxylase family classified as EC 4.1.1.-.

In a more preferred embodiment, the conversion of 3-methylcrotonic acid into isobutene makes use of a 3-polyprenyl-4-hydroxybenzoate decarboxylase (UbiD) which is derived from *Hypocrea atroviridis* (UniProt Accession number G9NLP8), *Sphaerulina musiva* (UniProt Accession number M3DF95), *Penecillinum requeforti* (UniProt Accession number W6QKP7), *Fusarium oxysporum* f. sp. *lycopersici* (UniProt Accession number W9LTH3), *Saccharomyces kudriavzevii* (UniProt Accession number J8TRN5), *Saccaromyces cerevisiae, Aspergillus parasiticus, Candida albicans, Grosmannia clavigera, Escherichia coli* (Uniprot accession number POAAB4), *Bacillus megaterium* (Uniprot accession number D5DTL4), *Methanothermobacter* sp. CaT2 (Uniprot accession number T2GKK5), *Mycobacte-*

*rium* chelonae 1518 (Uniprot accession number X8EX86) or *Enterobacter cloacae* (Uniprot accession number V3DX94).

In an even more preferred embodiment, the 3-polyprenyl-4-hydroxybenzoate decarboxylase (UbiD) employed in the method of the present invention is a 3-polyprenyl-4-hydroxybenzoate decarboxylase (UbiD) derived from *Escherichia coli* (Uniprot accession number POAAB4; SEQ ID NO:17), *Bacillus megaterium* (Uniprot accession number D5DTL4; SEQ ID NO:18), *Methanothermobacter* sp. CaT2 (Uniprot accession number T2GKK5; SEQ ID NO:19) *Mycobacterium* chelonae 1518 (Uniprot accession number X8EX86; SEQ ID NO:20), *Hypocrea atroviridis* (SEQ ID NO:21), *Sphaerulina musiva* (SEQ ID NO:22), *Penecillinum requeforti* (SEQ ID NO:23), *Fusarium oxysporum* f. sp. *lycopersici* (SEQ ID NO:24), *Saccharomyces kudriavzevii* (SEQ ID NO:25), *Saccaromyces cerevisiae* (SEQ ID NO:26), *Aspergillus parasiticus* (SEQ ID NO:27), *Candida albicans* (SEQ ID NO:28), *Grosmannia clavigera* (SEQ ID NO:29) or *Enterobacter cloacae* (SEQ ID NO:30) having the amino acid sequence as shown in SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30, respectively.

In a preferred embodiment of the present invention the 3-polyprenyl-4-hydroxybenzoate decarboxylase (UbiD) is an enzyme comprising an amino acid sequence selected from the group consisting of SEQ ID NOs: 17 to 30 or a sequence which is at least n % identical to any of SEQ ID NOs: 17 to 30 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

The Provision of DMAP

Figure 3:
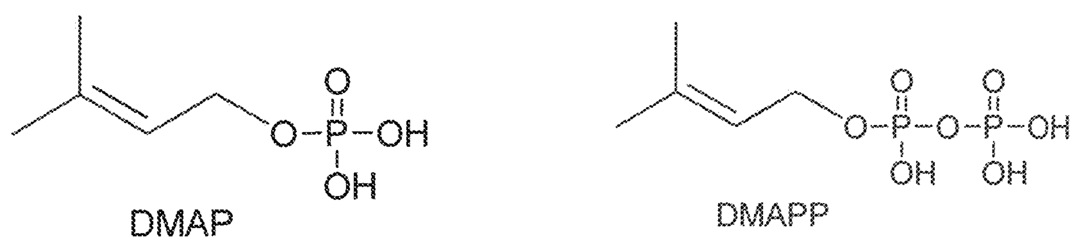

As mentioned above, in the method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) or dimethylallyl pyrophosphate (DMAPP) into a flavin-derived cofactor, the availability of DMAP is one limiting factor. The chemical structure of dimethylallyl phosphate (DMAP) (also termed 3-methylbut-2-en-1-yl phosphate, 3,3-dimethylallyl phosphate and prenyl phosphate) is shown in FIG. 3. DMAPP contains one additional phosphate as compared to DMAP and its chemical structure is also shown in FIG. 3.

As mentioned above, the mechanism of the ferulic acid decarboxylase (FDC) in association with the modified FMN (prenylated-FMN) (the latter provided by the PAD enzyme) was recently described (Nature 522 (2015), 497-501; Nature, 522 (2015), 502-505). However, the metabolic route for the provision of DMAP (required for the prenylation of the flavin cofactor by the FMN prenyl transferase) remained unclear while the metabolic routes leading to the formation of dimethylallyl pyrophosphate (DMAPP) via the mevalonate (MEVA) and 1-deoxy-D-xylulose-5-phosphate (DXP) pathways are known in the art. In fact, it has only previously been described by Wang et al. (Cell Chem Biol. 25 (2018) 1-11) that *E. coli* produces DMAP by phosphorylation of prenol and dephosphorylation of DMAPP.

As the exogenous supplementation of DMAP and/or DMAPP in a culture medium is not feasible since DMAP and/or DMAPP is assumed to not enter the cell, the present invention provides methods for endogenously generating DMAP and/or DMAPP and, preferably, to increase the pool of DMAP and/or DMAPP.

Figure 4:
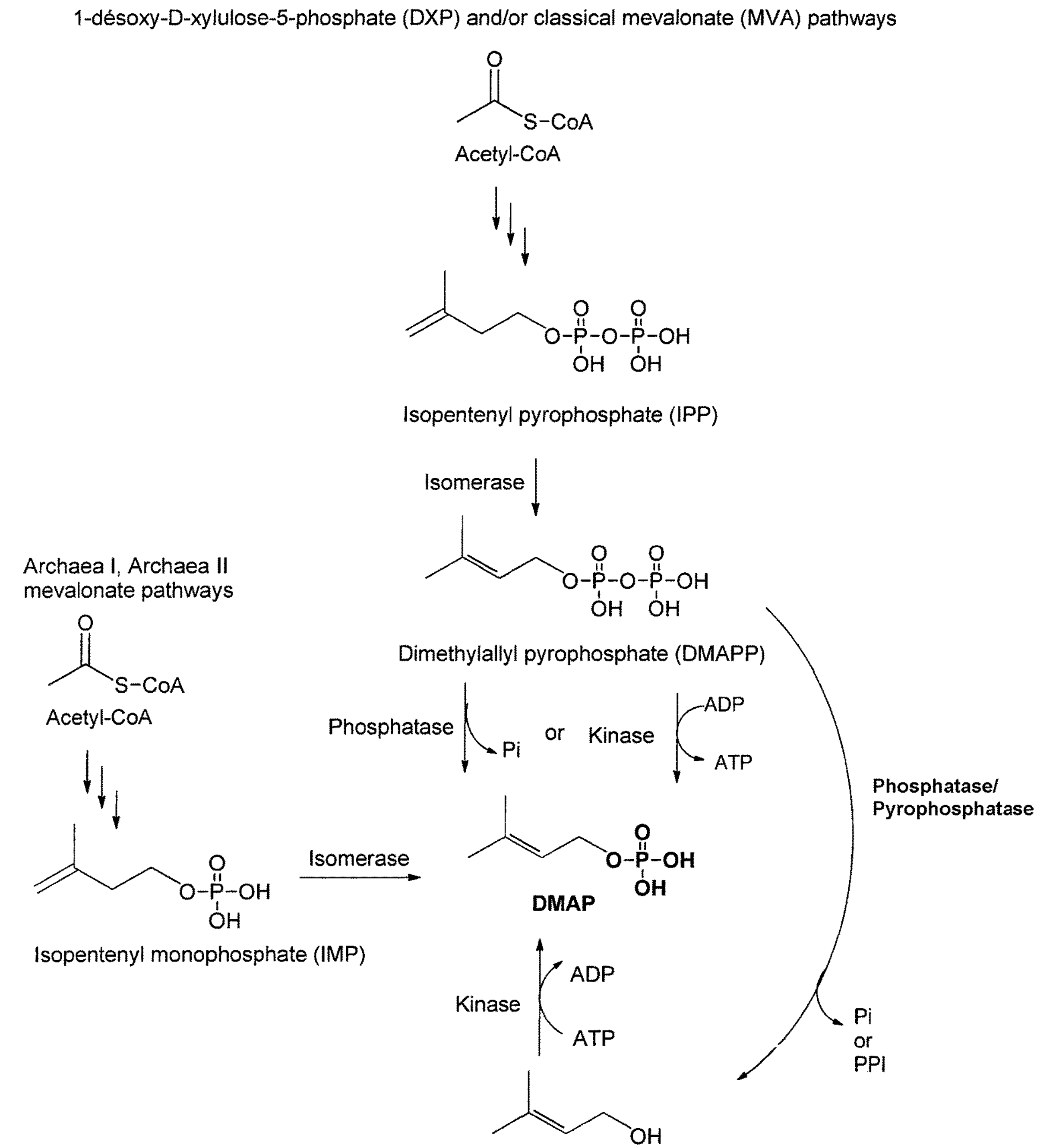

While the provision of DMAPP is described further below, according to the present invention, DMAP can be provided via different routes (in the following referred to as route (i), (ii), (iii) and (iv), respectively) which are schematically shown in FIG. 4.

Accordingly, the above described method for the production of isobutene comprising the enzymatic conversion of 3-methylcrotonic acid into isobutene further comprises providing said DMAP enzymatically by:

(i) the enzymatic conversion of dimethylallyl pyrophosphate (DMAPP) into said DMAP; or
(ii) a single enzymatic step in which prenol is directly enzymatically converted into said DMAP; or
(iii) two enzymatic steps comprising: first enzymatically converting DMAPP into prenol; and then enzymatically converting the thus obtained prenol into said DMAP; or
(iv) the enzymatic conversion of isopentenyl monophosphate (IMP) into said DMAP, or by a combination of any one of (i) to (iv).

Preferably, in the method for the production of isobutene comprising the enzymatic conversion of 3-methylcrotonic acid into isobutene, the enzymatic provision of said DMAP is enhanced/increased over naturally occurring (enzymatic) reactions/conversions leading to the production of DMAP, preferably by overexpressing corresponding enzymes capable of catalyzing any of the above reactions (i) to (iv). Means and methods for increasing/enhancing the expression of an enzyme are described in more detail further below.

These different routes (i), (ii), (iii) and (iv) for the provision of DMAP are illustrated in FIG. 4 while each of the above conversions is described in more detail in the following:

Route (i): The Provision of DMAP by the Enzymatic Conversion of Dimethylallyl Pyrophosphate (DMAPP) into Said DMAP According to the present invention, DMAP can be provided enzymatically by the enzymatic conversion of dimethylallyl pyrophosphate (DMAPP) into said DMAP.

In a preferred embodiment, the enzymatic conversion of DMAPP into said DMAP is achieved by making use of a phosphatase. Phosphatases are known in the art and are generally known as enzymes capable of removing a phosphate group ($PO_4^{3-}$) from its substrate by hydrolysing phosphoric acid monoesters into a phosphate ion and a molecule with a free hydroxyl group in a reaction called dephosphorylation. The term "dephosphorylation" refers to the removal of a phosphate group from an organic compound by hydrolysis.

Figure 5:
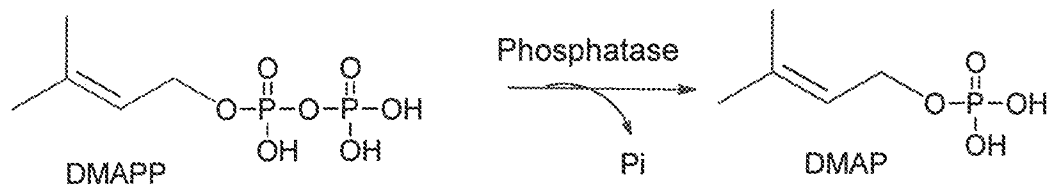

Enzymes catalyzing the conversion (i.e., the dephosphorylation) of dimethylallyl pyrophosphate (DMAPP) into DMAP are enzymes which catalyze the reaction as shown in FIG. 5.

In case the above conversion is performed in a cell, said DMAPP is preferably metabolically provided by naturally occurring or artificially introduced metabolic routes leading to the formation of dimethylallyl pyrophosphate (DMAPP), e.g., via the mevalonate (MEVA) and/or 1-deoxy-D-xylulose-5-phosphate (DXP) pathways which are known in the art.

In case the above conversion is performed in vitro, said DMAPP is preferably added to the reaction.

Preferably, in the method for the production of isobutene comprising the enzymatic conversion of 3-methylcrotonic acid into isobutene of the present invention wherein the method further comprises the enzymatic conversion of DMAPP into said DMAP by making use of a phosphatase, the expression of said phosphatase is increased/enhanced. Preferably, said phosphatase is overexpressed. Means and methods for increasing/enhancing/overexpressing the expression of an enzyme are described in more detail further below.

In a preferred embodiment, the phosphatase is:

an enzyme acting on phosphorous containing anhydrides (EC 3.6.1.-); or a phosphoric-monoester hydrolase (EC 3.1.3.-).

Thus, in one preferred embodiment, the enzymatic conversion of DMAPP into DMAP is achieved by the use of an enzyme belonging to the family of enzymes acting on phosphorous containing anhydrides (EC 3.6.1.-).

Preferred examples of such enzymes which are classified as EC 3.6.1.- (i.e., enzymes acting on phosphorous containing anhydrides) are:

ADP-ribose pyrophosphatase (EC 3.6.1.13),
8-oxo-dGTP diphosphatase (EC 3.6.1.55),
bis(5'-nucleosyl)-tetraphosphatase (EC 3.6.1.41),
UDP-sugar diphosphatase (EC 3.6.1.45),
exopolyphosphatase (EC 3.6.1.11),
guanosine-5'-triphosphate/3'-diphosphate pyrophosphatase (EC 3.6.1.40),
NADH pyrophosphatase (EC 3.6.1.22),
nucleotide diphosphatase (EC 3.6.1.9), and
acylphosphatase (EC 3.6.1.7).

Thus, in one preferred embodiment, the enzymatic conversion of DMAPP into DMAP is achieved by the use of an ADP-ribose pyrophosphatase (EC 3.6.1.13).

ADP-ribose pyrophosphatases (EC 3.6.1.13) are enzymes which catalyze the following reaction:

ADP-D-ribose+$H_2O$ ⇆AMP+D-ribose 5-phosphate

This enzyme is known from a variety of organisms, including eukaryotic and prokaryotic organisms such as plants, animals, fungi and bacteria. The enzyme has, e.g., been described in *Arabidopsis* sp., *Arabidopsis thaliana, Artemia* sp, *Autographa californica* multiple nucleopolyhedrovirus, *Bacillus subtilis* (Uniprot accession number P54570), *Danio rerio* (Uniprot accession number Q7T291), *Deinococcus* radiourans (Uniprot accession number Q9RSC1), *E. coli, Francisella tularensis* (Uniprot accession number Q5NHR1), *Haemophilus influencae* (Uniprot accession number P44684), *Homo sapiens, Methanocaldococcus jannaschii, Mus musculus, Oryctolagus cuniculus, Rattus norvegicus, Rhodobacter spaeroides, Saccharomyces cerevisiae, Synechococcus* sp. (SwissProt accession number Q83ZD0), *Synechocystis* sp., *Thermus thermophilus* and *Thermus thermophilus* DSM 579 (Uniprot accession number Q5SHB0).

In a preferred embodiment, the ADP-ribose pyrophosphatase (EC 3.6.1.13) is the *E. coli*-derived enzyme encoded by nudF (SEQ ID NO:39).

Thus, in a preferred embodiment of the present invention, the ADP-ribose pyrophosphatase is an enzyme comprising the amino acid sequence of SEQ ID NO:39 or a sequence which is at least n % identical to SEQ ID NO: 39 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of an 8-oxo-dGTP diphosphatase (EC 3.6.1.55). 8-oxo-dGTP diphosphatases (EC 3.6.1.55) are enzymes which catalyze the following reaction:

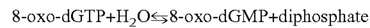
8-oxo-dGTP+$H_2O$⇆8-oxo-dGMP+diphosphate

This enzyme is known from a variety of organisms, including eukaryotic and prokaryotic organisms such as plants, animals, fungi and bacteria. The enzyme has, e.g., been described in *Bartonella henselae* (Uniprot accession number Q6G5F4), Ciona intestinalis, *E. coli, Homo sapiens* (SwissProt accession number P36639) and *Hordeum vulgare* subsp. *vulgare* (Uniprot accession number F2DYN1).

In a preferred embodiment, the 8-oxo-dGTP diphosphatases (EC 3.6.1.55) is the *E. coli*-derived enzyme encoded by mutT (SEQ ID NO:40).

Thus, in a preferred embodiment of the present invention, the 8-oxo-dGTP diphosphatase is an enzyme comprising the amino acid sequence of SEQ ID NO:40 or a sequence which is at least n % identical to SEQ ID NO: 40 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a bis(5'-nucleosyl)-tetraphosphatase (EC 3.6.1.41).

bis(5'-nucleosyl)-tetraphosphatases (EC 3.6.1.41) are enzymes which catalyze the following reaction:

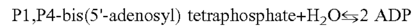
P1,P4-bis(5'-adenosyl) tetraphosphate+$H_2O$⇆2 ADP

This enzyme is known from a variety of organisms, including eukaryotic and prokaryotic organisms such as fungi and bacteria. The enzyme has, e.g., been described in Acidaminococcus *fermentans, E. coli, Myxococcus xanthus* (Uniprot accession number Q1CWE7 and Q1 DC62), *Physarum polycephalum, Pyrodictium occultum, Salmonella enterica* and *Shigella flexneri.*

In a preferred embodiment, the bis(5'-nucleosyl)-tetraphosphatase (EC 3.6.1.41) is the *E. coli*-derived enzyme encoded by apaH (SEQ ID NO:41).

Thus, in a preferred embodiment of the present invention, the bis(5'-nucleosyl)-tetraphosphatase is an enzyme comprising the amino acid sequence of SEQ ID NO:41 or a sequence which is at least n % identical to SEQ ID NO: 41 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a UDP-sugar diphosphatase (EC 3.6.1.45).

UDP-sugar diphosphatases (EC 3.6.1.45) are enzymes which catalyze the following reaction:

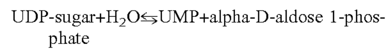
UDP-sugar+$H_2O$⇆UMP+alpha-D-aldose 1-phosphate

This enzyme is known from a variety of organisms, including eukaryotic and prokaryotic organisms such as animals, fungi and bacteria. The enzyme has, e.g., been described in *Corynebacterium glutamicum, Enterobacter aerogenes* (Uniprot accession number Q9RQT7), *E. coli* (Uniprot accession number P07024), *Homo sapiens* (Uniprot accession number O95848), *Mus musculus* (Uniprot accession number Q9D142), *Peptoclostridium difficile, Saccharomyces cerevisiae, Salmonella enterica, Salmonella* sp., *Sus scrofa* and *Yersinia intermedia* (Uniprot accession number A4URQ8).

In a preferred embodiment, the UDP-sugar diphosphatases (EC 3.6.1.45) is the *E. coli*-derived enzyme encoded by ushA (SEQ ID NO:42).

Thus, in a preferred embodiment of the present invention, the UDP-sugar diphosphatase is an enzyme comprising the amino acid sequence of SEQ ID NO:42 or a sequence which is at least n % identical to SEQ ID NO: 42 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of an exopolyphosphatase (EC 3.6.1.11).

Exopolyphosphatase (EC 3.6.1.11) are enzymes which catalyze the following reaction:

(polyphosphate)n+$H_2O$⇆(polyphosphate)n-1+phosphate

This enzyme is known from a variety of organisms, including eukaryotic and prokaryotic organisms such as animals, plants, fungi and bacteria. The enzyme has, e.g., been described in *Campylobacter jejuni* (Uniprot accession number A0A0H3PAT6 and A0A0H3PES2), *Chlorobaculum tepidum* (Uniprot accession number Q8KBS0 and Q8KG69), *Corynebacterium glutamicum* (Uniprot accession number Q8NRR8 and Q8NT99), *Cyberlindnera jadinii, Escherichia coli, Euglena gracilis, Funneliformis mosseae, Homo sapiens, Leishmania major, Lemna gibba, Lemna minor, Lemna trisulca, Magnusiomyces magnusii, Microlunatus phosphovorus, Mycobacterium tuberculosis* (Uniprot accession number P9WHV4 and P9WHV5), *Neisseria meningitidis, Pseudomonas aeruginosa* (SwissProt accession number Q95605), *Pseudomonas* sp., *Rhipicephalus microplus, Riccia fluitans, Saccharomyces cerevisiae, Solanum tuberosum, Streptomyces aureofaciens, Sulfolobus metallicus, Sulfolobus solfataricus, Tethya aurantium* (SwissProt accession number Q97YV9), *Trypanosoma brucei* (Uniprot accession number Q7Z032), *Trypanosoma cruzi* (SwissProt accession number Q6Y656) and *Wolffia arrhiza.*

In a preferred embodiment, the exopolyphosphatase (EC 3.6.1.11) is the *E. coli*-derived enzyme encoded by ppX (SEQ ID NO:43) or by gpp.

Thus, in a preferred embodiment of the present invention, the exopolyphosphatase is an enzyme comprising the amino acid sequence of SEQ ID NO:43 or a sequence which is at least n % identical to SEQ ID NO: 43 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a guanosine-5'-triphosphate/3'-diphosphate pyrophosphatase (EC 3.6.1.40).

Guanosine-5'-triphosphate/3'-diphosphate pyrophosphatases (EC 3.6.1.40) are enzymes which catalyze the following reaction:

guanosine 5'-triphosphate 3'-diphosphate+$H_2O$⇆guanosine 3',5'-bis(diphosphate)+phosphate This enzyme is known from a variety of organisms, including prokaryotic organisms such as bacteria. The enzyme has, e.g., been described in *Aquifex* aeolicus, *Campylobacter jejuni* (Uniprot accession number A0A0H3PAT6 and A0A0H3PES2), and *E. coli.*

In a preferred embodiment, the guanosine-5'-triphosphate/3'-diphosphate pyrophosphatase (EC 3.6.1.40) is the *E. coli*-derived enzyme encoded by gppA (SEQ ID NO:44).

Thus, in a preferred embodiment of the present invention, the guanosine-5'-triphosphate/3'-diphosphate pyrophosphatase is an enzyme comprising the amino acid sequence of SEQ ID NO:44 or a sequence which is at least n % identical to SEQ ID NO: 44 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of an NADH pyrophosphatase (EC 3.6.1.22).

NADH pyrophosphatases (EC 3.6.1.22) are enzymes which catalyze the following reaction:

NAD++$H_2O$⇆AMP+NMN

This enzyme is known from a variety of organisms, including eukaryotic and prokaryotic organisms such as animals, plants, fungi and bacteria. The enzyme has, e.g., been described in *Aedes aegypti, Arabidopsis* sp., *Caenorhabditis elegans, E. coli* (Uniprot accession number P07024), *Haemophilus influencae, Homo sapiens, Mycobacterium bovis* (Uniprot accession number C1AGW8), *Mycobacterium tuberculosis* (Uniprot accession number P9WIX5), *Nicotiana tabacum, Proteus vulgaris, Rattus norvegicus, Saccharomyces cerevisiae, Salmonella enterica* and *Solanum tuberosum.*

In a preferred embodiment, the NADH pyrophosphatase (EC 3.6.1.22) is the *E. coli*-derived enzyme encoded by nudC (SEQ ID NO: 45).

Thus, in a preferred embodiment of the present invention, the NADH pyrophosphatase is an enzyme comprising the amino acid sequence of SEQ ID NO: 45 or a sequence which is at least n % identical to SEQ ID NO: 45 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a nucleotide diphosphatase (EC 3.6.1.9).

Nucleotide diphosphatases (EC 3.6.1.9) are enzymes which catalyze the following reaction:

a dinucleotide+$H_2O$⇆2 mononucleotides

This enzyme is known from a variety of organisms, including eukaryotic and prokaryotic organisms such as animals, plants fungi and bacteria. The enzyme has, e.g., been described in *Amycolatopsis mediterranei, Bos taurus, Bothrops jararaca, Brassica oleracea, Clostridium perfringens, Columba livia, Crotalus adamanteus, Crotalus durissus, Dictyostelium discoideum, Escherichia coli, Glycine max, Haemophilus influenzae, Haemophilus parasuis, Homo sapiens, Hordeum vulgare, Lens culinaris, Mus musculus, Opuntia ficus-indica, Oryza sativa, Ovis aries aries, Proteus vulgaris, Rattus norvegicus, Saccharomyces cerevisiae, Solanum tuberosum, Sus scrofa, Triticum aestivum* (UniProt accession number D9YT79), *Vigna radiata* var. *radiata, Xanthomonas citri*, and *Xanthomonas citri* 306.

In a preferred embodiment, the nucleotide diphosphatase (EC 3.6.1.9) is the *E. coli*-derived enzyme encoded by yhdE (SEQ ID NO: 46).

Thus, in a preferred embodiment of the present invention, the nucleotide diphosphatase is an enzyme comprising the amino acid sequence of SEQ ID NO:46 or a sequence which is at least n % identical to SEQ ID NO: 46 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of an acylphosphatase (EC 3.6.1.7).

Acylphosphatases (EC 3.6.1.7) are enzymes which catalyze the following reaction:

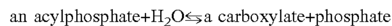
an acylphosphate+$H_2O \leftrightarrows$ a carboxylate+phosphate

This enzyme is known from a variety of organisms, including eukaryotic and prokaryotic organisms such as animals, plants, fungi and bacteria. The enzyme has, e.g., been described in *Anas platyrhynchos, Bacillus subtilis, Bos taurus, Cavia porcellus, Chondrichthyes, Drosophila mauritiana, Drosophila melanogaster, Drosophila simulans, Equus caballus, Escherichia coli, Gallus gallus, Homo sapiens, Meleagris gallopavo, Oryctolagus cuniculus, Pyrococcus horikoshii* (Uniprot accession number P84142), *Rattus norvegicus, Saccharomyces cerevisiae, Sulfolobus solfataricus* (Uniprot accession number Q97ZL0), *Sus scrofa, Thermus thermophilus* (Uniprot accession number Q5SKS6), *Vibrio cholerae* (Uniprot accession number A5F8G9) and *Vigna unguiculata.*

In a preferred embodiment, the acylphosphatase (EC 3.6.1.7) is the *E. coli*-derived enzyme encoded by yccX (SEQ ID NO: 67).

Thus, in a preferred embodiment of the present invention the acylphosphatase (EC 3.6.1.7) is an enzyme comprising the amino acid sequence of SEQ ID NO: 67 or a sequence which is at least n % identical to SEQ ID NO: 67 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of DMAPP into DMAP. As regards the determination of the sequence identity, the same applies as has been set forth above.

As mentioned above, in other preferred embodiments, the enzymatic conversion of DMAPP into DMAP is achieved by the use of an enzyme belonging to the family of phosphoric-monoester hydrolases (EC 3.1.3.-).

Preferred examples of such enzymes which are classified as EC 3.1.3.- (i.e., phosphoric-monoester hydrolases) are:

3'(2'), 5'-bisphosphate nucleotidase (EC 3.1.3.7);

5-amino-6-(5-phospho-D-ribitylamino) uracil phosphatase (belonging to the family of phosphoric-monoester hydrolases (EC 3.1.3.-); and fructose-1 6-bisphosphatase (EC 3.1.3.11).

Thus, in one preferred embodiment, the enzymatic conversion of DMAPP into DMAP is achieved by the use of a 3'(2'), 5'-bisphosphate nucleotidase (EC 3.1.3.7).

3'(2'), 5'-bisphosphate nucleotidases (EC 3.1.3.7) are enzymes which catalyze the following reaction:

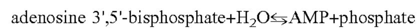
adenosine 3',5'-bisphosphate+$H_2O \leftrightarrows$AMP+phosphate

This enzyme is known from a variety of organisms, including eukaryotic and prokaryotic organisms such as animals, plants, fungi and bacteria. The enzyme has, e.g., been described in *Arabidopsis thaliana, Arthrospira platensis* (Uniprot accession number Q3LS17), *Chlorella pyrenoidosa, Chromobacterium violaceum* (Uniprot accession number Q7NXD4), *Debaryomyces hansenii, Drosophila melanogaster* (SwissProt accession number Q9VHS0), *Escherichia coli, Gossypium hirsutum* (Uniprot accession number Q8VWZ6), *Homo sapiens, Mus musculus, Mycobacterium tuberculosis* (Uniprot accession number P9WKJ1), *Oryctolagus cuniculus, Oryza sativa* (Uniprot accession number P0C5A3), *Rattus norvegicus, Saccharomyces cerevisiae, Schizosaccharomyces pombe, Solanum lycopersicum* and *Zea mays* (SwissProt accession number Q94FY6 and Q94G04).

In a preferred embodiment, the 3'(2'), 5'-bisphosphate nucleotidase (EC 3.1.3.7) is the *E. coli*-derived enzyme encoded by cysQ (SEQ ID NO: 47).

Thus, in a preferred embodiment of the present invention, the 3'(2'), 5'-bisphosphate nucleotidase is an enzyme comprising the amino acid sequence of SEQ ID NO:47 or a sequence which is at least n % identical to SEQ ID NO: 47 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a 5-amino-6-(5-phospho-D-ribitylamino) uracil phosphatase ( ). 5-amino-6-(5-phospho-D-ribitylamino) uracil phosphatases are enzymes which belong to the family of phosphoric-monoester hydrolases (EC 3.1.3.-) and catalyze the following reaction:

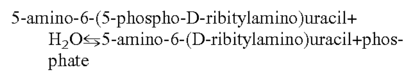
5-amino-6-(5-phospho-D-ribitylamino)uracil+$H_2O \leftrightarrows$5-amino-6-(D-ribitylamino)uracil+phosphate This enzyme is known from a variety of organisms, including eukaryotic and prokaryotic organisms such as plants and bacteria. The enzyme has, e.g., been described in *E. coli* or *Bacillus subtilis.*

In a preferred embodiment, the 5-amino-6-(5-phospho-D-ribitylamino) uracil phosphatase is encoded by yigB, ybjI, ywtE, yitU or ycsE.

In another preferred embodiment, the 5-amino-6-(5-phospho-D-ribitylamino) uracil phosphatase is the *Bacillus subtilis*-derived enzyme encoded by yitU (Uniprot P70947), ywtE (UniProt P96741) or by ycsE (Uniprot P42962).

In a preferred embodiment, the 5-amino-6-(5-phospho-D-ribitylamino) uracil phosphatase is the *E. coli*-derived enzyme encoded by yigB (Uniprot P0ADP0; SEQ ID NO: 48) or ybjI (Uniprot P75809; SEQ ID NO: 49).

Thus, in a preferred embodiment of the present invention, the 3'(2'), 5'-bisphosphate nucleotidase is an enzyme comprising the amino acid sequence of SEQ ID NO:48 or SEQ ID NO: 49 or a sequence which is at least n % identical to SEQ ID NO: 48 or SEQ ID NO: 49 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

In another preferred embodiment, the enzymatic conversion of DMAPP into DMAP is achieved by the use of a fructose-1,6-bisphosphatase (EC 3.1.3.11).

Fructose-1,6-bisphosphatases (EC 3.1.3.11) are enzymes which catalyze the following reaction:

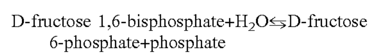

D-fructose 1,6-bisphosphate+$H_2O$⇆D-fructose 6-phosphate+phosphate

This reaction is a key step of gluconeogenesis and in the Calvin cycle which are both anabolic pathways found in most organisms. Thus, fructose-1,6-bisphosphatase is an ubiquituous enzyme which occurs in basically all organisms, including eukaryotic and prokaryotic organisms such as animals, plants, fungi and bacteria. The enzyme has, e.g., been described in *Anabaena* sp., *Arabidopsis thaliana, Archaeoglobus fulgidus, Bacillus licheniformis, Bacillus methanolicus, Bacillus subtilis, Beta vulgaris, Bombus terrestris, Bos taurus, Bothriocephalus scorpii, Brassica napus, Canis lupus familiaris, Cenarchaeum symbiosum, Citrus* x *paradisi, Clonorchis sinensis* (Uniprot accession number G7YVB4), *Coreus marginatus, Corynebacterium glutamicum, Cyberlindnera jadinii, Cyprinus carpio, Dactylis glomerata, Escherichia coli, Festuca rupicola, Filipendula vulgaris, Galdieria sulphuraria* (SwissProt accession number Q95AJ2), *Gallus gallus, Glycine max, Hominoidea, Homo sapiens, Ignicoccus hospitalis, Ilyocoris cimicoides, Kluyveromyces marxianus, Lactobacillus delbrueckii* subsp. *lactis, Leishmania major, Leptolyngbya boryana, Lygus pratensis, Malus domestica, Meleagris gallopavo, Methanococcus maripaludis, Mus musculus, Mycobacterium tuberculosis, Mytilus galloprovincialis, Neisseria meningitidis, Notostira elongata, Ogataea angusta, Oryctolagus cuniculus, Oryza coarctata, Oryza sativa, Ovis aries, Pelophylax esculentus, Peltigera rufescens, Phagocata sibirica, Phocidae, Pisum sativum, Polysphondylium pallidum, Ptyas dhumnades, Pyrobaculum neutrophilum* (Uniprot accession number B1YAL1), *Pyrococcus furiosus* (SwissProt accession number Q8TZH9), *Rattus norvegicus, Rhodococcus opacus, Rhodopseudomonas palustris, Ricinus communis, Saccharomyces cerevisiae, Salmonella enterica, Salvia nemorosa, Schizosaccharomyces pombe, Solanum lycopersicum, Solanum tuberosum, Sparus aurata* (Uniprot accession number Q8AYI5), *Spinacia oleracea, Struthio camelus, Sulfolobus tokodaii, Sulfolobus tokodaii* 7, *Sus scrofa, Sus scrofa domesticus, Synechococcus elongatus* PCC 7942 (Uniprot accession number Q59943), *Synechococcus* sp., *Synechocystis* sp., *Thermococcus kodakarensis, Thermococcus onnurineus, Thermotoga maritima, Thermus thermophilus* (Uniprot accession number Q5SJM8), *Triticum aestivum, Yarrowia lipolytica* (Uniprot accession number Q7Z8Q0) and *Zea mays*.

In a preferred embodiment, the fructose-1,6-bisphosphatase (EC 3.1.3.11) is the *E. coli*-derived enzyme encoded by fbp (SEQ ID NO: 50).

Thus, in a preferred embodiment of the present invention, the fructose-1,6-bisphosphatase is an enzyme comprising the amino acid sequence of SEQ ID NO: 50 or a sequence which is at least n % identical to SEQ ID NO: 50 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP. As regards the determination of the sequence identity, the same applies as has been set forth above.

According to the present invention, DMAP can also be provided enzymatically by the enzymatic conversion of dimethylallyl pyrophosphate (DMAPP) into said DMAP by the concomitant formation of ATP. Thus, the dephosphorylation of DMAPP into DMAPP can also be achieved by kinases capable of forming ATP from ADP having the promiscuous activity to catalyze the formation of DMAP from DMAPP.

Figure 6:
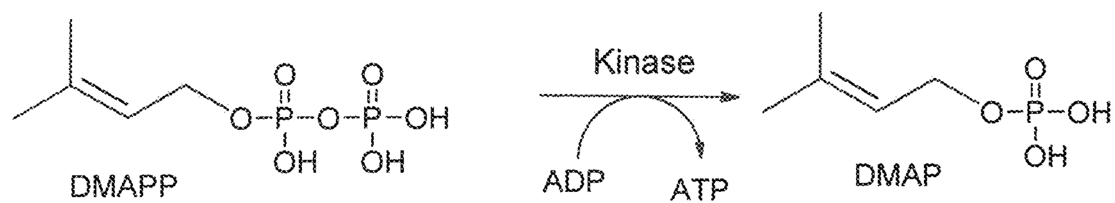

Kinases catalyzing the conversion (i.e., the dephosphorylation) of dimethylallyl pyrophosphate (DMAPP) into DMAP by concomitantly forming ATP from ADP are enzymes which catalyze the reaction as shown in FIG. 6.

In case the above conversion is performed in a cell, said DMAPP is preferably metabolically provided by naturally occurring or artificially introduced metabolic routes leading to the formation of dimethylallyl pyrophosphate (DMAPP), e.g., via the mevalonate (MEVA) and/or 1-deoxy-D-xylulose-5-phosphate (DXP) pathways which are known in the art.

In case the above conversion is performed in vitro, said DMAPP is preferably added to the reaction.

Preferably, in the method for the production of isobutene comprising the enzymatic conversion of 3-methylcrotonic acid into isobutene of the present invention wherein the method further comprises the enzymatic conversion of DMAPP into said DMAP by making use of a kinase, the expression of said kinase is increased/enhanced. Preferably, said kinase is overexpressed. Means and methods for increasing/enhancing/overexpressing the expression of an enzyme are described in more detail further below.

In a preferred embodiment, the kinase is an isopentenyl phosphate kinase (EC 2.7.4.26).

Isopentenyl phosphate kinases (EC 2.7.4.26) are enzymes which catalyze the following reaction:

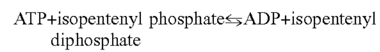

ATP+isopentenyl phosphate⇆ADP+isopentenyl diphosphate

This enzyme is known from a variety of organisms, including eukaryotic and prokaryotic organisms such as plants and bacteria. The enzyme has, e.g., been described in *Haloferax volcanii* (Uniprot accession number D4GWT7), *Mentha* x *piperita* (SwissProt accession number P56848), *Methanocaldococcus jannaschii* (SwissProt accession number Q60352), *Methanothermobacter thermautotrophicum* (Uniprot accession number Q26153), and *Thermoplasma acidophilum* (Uniprot accession number Q9HLX1).

In a preferred embodiment, the isopentenyl phosphate kinase (EC 2.7.4.26) is the enzyme derived from *Haloferax volcanii* (Uniprot accession number D4GWT7; SEQ ID NO:51), *Methanocaldococcus jannaschii* (SwissProt accession number Q60352; SEQ ID NO:53), *Methanothermobacter thermautotrophicum* (Uniprot accession number O26153; SEQ ID NO:52) or *Thermoplasma acidophilum* (Uniprot accession number Q9HLX1; SEQ ID NO:54).

As demonstrated in the appended examples, the isopentenyl phosphate kinase (EC 2.7.4.26) derived from *Methanocaldococcus jannaschii* (strain ATCC 43067; SwissProt Q60352) is capable of catalyzing the above conversion.

Thus, in a preferred embodiment, the enzymatic conversion of DMAPP into DMAP is achieved by the isopentenyl phosphate kinase (EC 2.7.4.26) of *Methanocaldococcus jannaschii* (strain ATCC 43067; SwissProt Q60352). In other preferred embodiments, the enzymatic conversion of DMAPP into DMAP is achieved by the isopentenyl phosphate kinase (EC 2.7.4.26) of *Thermoplasma acidophilum* (strain ATCC 25905; Uniprot accession number Q9HLX1) or of *Methanothermobacter thermautotrophicus* (strain ATCC 29096; Uniprot accession number O26153). The isopentenyl phosphate kinases derived from these organisms are described by Chen M and Poulter CD (Biochemistry 49 (2010), 207-210).

Thus, in a preferred embodiment of the present invention, the isopentenyl phosphate kinase (EC 2.7.4.26) is an enzyme comprising an amino acid sequence selected from the group consisting of SEQ ID NO:51 to SEQ ID NO:54 or a sequence which is at least n % identical to any one of SEQ ID NO: 51 to SEQ ID NO:54 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into DMAP by the concomitant formation of ATP. As regards the determination of the sequence identity, the same applies as has been set forth above.

The Provision of DMAPP (Corresponding to the Isomerisation Step Preceding the Dephosphorylation Step of Route 1)

The DMAPP which is converted into DMAP according to the method of the present invention may itself be provided by an enzymatic reaction.

According to the present invention, DMAPP can be provided enzymatically by the enzymatic conversion of isopentenyl pyrophosphate (IPP) into said dimethylallyl pyrophosphate (DMAPP).

In a preferred embodiment, the enzymatic conversion of isopentenyl pyrophosphate (IPP) into said dimethylallyl pyrophosphate (DMAPP) is achieved by making use of an isomerase. Isomerases are known in the art and are generally known as enzymes which convert a molecule from one isomer to another, meaning that the end product has the same molecular formula but a different physical structure.

Enzymes catalyzing the isomerisation, i.e., the enzymatic conversion of isopentenyl pyrophosphate (IPP) into said dimethylallyl pyrophosphate (DMAPP) are enzymes which catalyze the reaction as shown in the upper part of FIG. 4.

In case the above conversion is performed in a cell, said isopentenyl pyrophosphate is preferably metabolically provided by naturally occurring or artificially introduced metabolic routes leading to the formation of isopentenyl pyrophosphate, e.g., via the mevalonate (MEVA) and/or 1-deoxy-D-xylulose-5-phosphate (DXP) pathways which are known in the art.

In case the above conversion is performed in vitro, said isopentenyl pyrophosphate is preferably added to the reaction.

Preferably, in the method for the production of isobutene comprising the enzymatic conversion of 3-methylcrotonic acid into isobutene of the present invention wherein the method further comprises the enzymatic conversion of DMAPP into said DMAP wherein said DMAPP is itself provided enzymatically by the enzymatic conversion of isopentenyl pyrophosphate (IPP) into said dimethylallyl pyrophosphate (DMAPP) by making use of an isomerase, the expression of said isomerase is increased/enhanced. Preferably, said isomerase is overexpressed. Means and methods for increasing/enhancing/overexpressing the expression of an enzyme are described in more detail further below.

In a preferred embodiment, the isomerase is an isopentenyl-diphosphate DELTA isomerase (EC 5.3.3.2)

Thus, in one preferred embodiment, the enzymatic conversion of isopentenyl pyrophosphate (IPP) into said dimethylallyl pyrophosphate (DMAPP) is achieved by the use of an isopentenyl-diphosphate DELTA isomerase (EC 5.3.3.2).

Isopentenyl-diphosphate DELTA isomerases (EC 5.3.3.2) are enzymes which catalyze the following reaction:

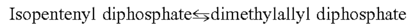
Isopentenyl diphosphate⇆dimethylallyl diphosphate

The occurrence of this enzyme has been described for a large number of organisms, e.g. for *E. coli, Staphylococcus aureus, Sulfolobus shibatae, Bacillus subtilis, Thermococcus kodakarensis, Solanum lycopersicum, Arabidopsis thaliana, Bombyx mori, Camptotheca acuminata, Capsicum annuum, Catharanthus roseus, Cinchona robusta, Citrus* sp., *Claviceps purpurea, Curcubita* sp., *Gallus gallus* and *Homo sapiens*, to name just some. In a preferred embodiment, the enzyme originating from *E. coli* or an enzyme derived therefrom and which still shows the activity as the enzyme from *E. coli* is employed in the methods according to the present invention.

Route (ii): The Provision of DMAP by a Single Enzymatic Step in which Prenol is Directly Enzymatically Converted into Said DMAP According to the present invention, DMAP can be provided enzymatically by the enzymatic conversion of prenol into said DMAP.

Prenol (also termed or 3-methyl-2-buten-1-ol or 3,3-dimethylallyl alcohol) is an alcohol and occurs naturally in citrus fruits, cranberry, bilberry, currants, grapes, raspberry, blackberry, tomato, white bread, hop oil, coffee, arctic bramble, cloudberry and passion fruit.

In case the above conversion of prenol into DMAP is performed in a cell (i.e., in vivo), said prenol is preferably metabolically provided by naturally occurring or artificially introduced metabolic routes leading to the formation of prenol.

Alternatively or in addition to the above, said prenol may preferably be supplemented/added to the culture medium.

In case the above conversion is performed in vitro, said prenol is preferably added to the in vitro reaction.

There are organisms known in the art which are capable of naturally producing prenol or by artificially introduced metabolic routes. Corresponding organisms may preferentially be used in the methods of the present invention for the conversion of prenol into DMAP.

WO2013/053824 describes a possible artificial route for the production of prenol. WO2009006429A1 and WO2013173437 describe the provision of prenol by the dephosphorylation of DMAPP.

A new oxido-reductase called 321-MB dehydrogenase derived from *Pseudomonas putida* was recently identified as being capable of catalyzing the reversible oxidation of 3-methylbuten-1-ol or prenol into 3-methylbutenal or prenal (Appl. Envir. Microbiol. 65(6) (1999), 2622).

Ginger et al. (J. Biol. Chem. 276(15) (2001), 11674) describe the involvement of leucine catabolism in sterol biosynthesis in the trypanosomatid *Leishmania mexicana*. A metabolic pathway composed of, in a first part, the degradation of leucine into 3-methylcrotonyl-CoA is described. In a second part, 3-methylcrotonyl-CoA is converted into hydroxyl-methylglutaryl-CoA (HMG-CoA) via 3-methylglutaconyl-CoA. The descried pathway corresponds to the reverse metabolic pathway described in WO2013/053824 mentioned above. In addition, the authors suggest a possible hypothetical pathway involving the enzymatic reduction of 3-methylcrotonyl-CoA into 3-methylbuten-1-ol (i.e., prenol).

The possibility of the enzymatic reduction of 3-methylcrotonyl-CoA into 3-methylbuten-1-ol (i.e., prenol) is also proposed by Mahmud at al. (ChemBioChem. 6 (2005), 322). They describe the biosynthetic shunt pathway of mevalonate towards branched carboxylic acids in Myxobacteria, such as *Myxococcus xanthus*. This pathway involves the conversion of hydroxyl-methylglutaryl-CoA (HMG-CoA) into 3-methylcrotonyl-CoA via 3-methylglutaconyl-CoA.

In a preferred embodiment, the enzymatic conversion of prenol into said DMAP is achieved by making use of a kinase. Kinases are known in the art and are generally known as enzymes capable of catalyzing the transfer of phosphate groups from high-energy, phosphate-donating molecules to specific substrates. This process is known as phosphorylation, where the substrate gains a phosphate group and the high-energy ATP molecule donates a phosphate group. This reaction is a transesterification and produces a phosphorylated substrate and ADP.

Figure 7:
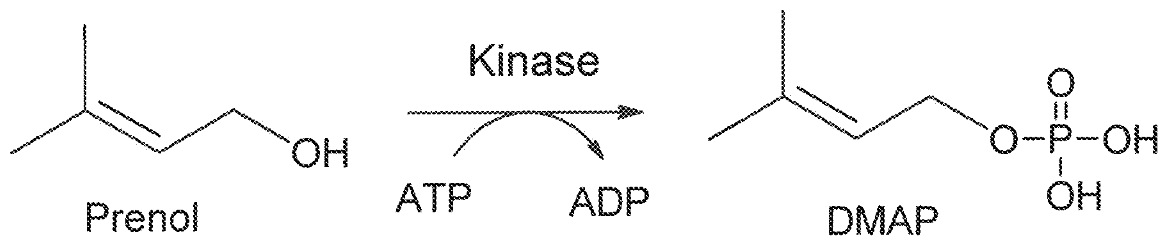

Enzymes catalyzing the enzymatic conversion (i.e., the phosphorylation) of prenol into said DMAP are enzymes which catalyze the reaction as shown in FIG. 7.

Preferably, in the method for the production of isobutene comprising the enzymatic conversion of 3-methylcrotonic acid into isobutene of the present invention wherein the method further comprises the enzymatic conversion of prenol into said DMAP by making use of a kinase, the expression of said kinase is increased/enhanced. Preferably, said kinase is overexpressed. Means and methods for increasing/enhancing/overexpressing the expression of an enzyme are described in more detail further below.

In a preferred embodiment, the kinase is a phosphotransferase with an alcohol group as acceptor (EC 2.7.1.-).

Preferably, ATP is the donor of the phospho group.

A preferred example of enzymes which are classified as EC 2.7.1.- (i.e., phosphotransferases with an alcohol group as acceptor) is hydroxyethylthiazole kinase (EC 2.7.1.50).

Hydroxyethylthiazole kinases (EC 2.7.1.50) are enzymes which catalyze the following reaction:

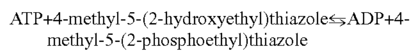
ATP+4-methyl-5-(2-hydroxyethyl)thiazole⇆ADP+4-methyl-5-(2-phosphoethyl)thiazole The occurrence of this enzyme has been described for several organisms, e.g. for *E. coli, Bacillus subtilis, Rhizobium leguminosarum, Pyrococcus horikoshii* OT3, *Saccharomyces cerevisiae.*

In principle, any known hydroxyethylthiazole kinase can be employed in the method according to the invention. In one aspect of the present invention, a hydroxyethylthiazole kinase of bacterial origin is used, such as a hydroxyethylthiazole kinase from a bacterium belonging to the genus *Escherichia, Bacillus* or *Rhizobium*, preferably of *E. coli, B. subtilis* or of *R. leguminosarum*. Amino acid and nucleotide sequences for these enzymes are available. Examples are provided in SEQ ID NOs: 31 to 33.

In a preferred embodiment of the present invention the hydroxyethylthiazole kinase is an enzyme comprising an amino acid sequence selected from the group consisting of SEQ ID NOs: 31 to 33 or a sequence which is at least n % identical to any of SEQ ID NOs: 31 to 33 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting prenol into DMAP. As regards the determination of the sequence identity, the same applies as has been set forth above.

Route (iii): The Provision of DMAP by Two Enzymatic Steps Comprising: First Enzymatically Converting DMAPP into Prenol; and then Enzymatically Converting the Thus Obtained Prenol into Said DMAP According to the present invention, DMAP can be provided enzymatically by two enzymatic steps comprising:

first enzymatically converting DMAPP into prenol; and then enzymatically converting the thus produced prenol into said DMAP.

In a preferred embodiment, the enzymatic conversion of DMAPP into said prenol is achieved by making use of a phosphatase or pyrophosphatase. In another preferred embodiment, the enzymatic conversion of the thus produced prenol into said DMAP is achieved by making use of a kinase.

As regards the enzymatic conversion of prenol into DMAP and the preferred embodiments for the enzymes capable of converting prenol into DMAP, preferably the kinases (particularly preferred the phosphotransferase with an alcohol group as acceptor (EC 2.7.1.-), preferably the hydroxyethylthiazole kinase (EC 2.7.1.50)), the same applies as has been set forth above in connection with the enzymatic conversion of route (ii) according to the invention.

Regarding the conversion of DMAPP into prenol, this conversion is preferably achieved by making use of a phosphatase or pyrophosphatase. Pyrophosphatases are known in the art and are generally known as acid anhydride hydrolases that act upon diphosphate bonds. Pyrophosphatases have, e.g., been described in WO2009/006429, WO2013173437 and in Biotechnology for biofuels 6 (2013), 1-13. As already defined above, phosphatases are known in the art and are generally known as enzymes capable of removing a phosphate group ($PO_4^{3-}$) from its substrate by hydrolysing phosphoric acid monoesters into a phosphate ion and a molecule with a free hydroxyl group in a reaction called dephosphorylation.

Figure 8:
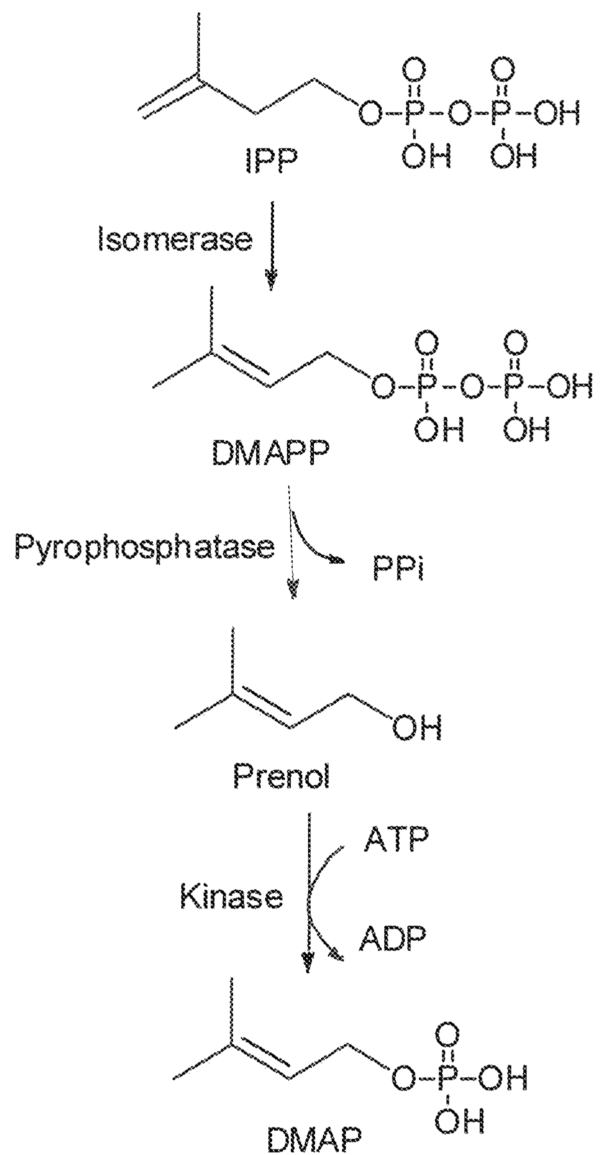

Enzymes catalyzing the conversion of dimethylallyl pyrophosphate (DMAPP) into prenol (by dephosphorylating DMAPP twice) are enzymes which catalyze the reaction as shown in the middle of FIG. 8.

In case the above conversion is performed in a cell, said DMAPP is preferably metabolically provided by naturally occurring or artificially introduced metabolic routes leading to the formation of dimethylallyl pyrophosphate (DMAPP), e.g., via the mevalonate (MEVA) and/or 1-deoxy-D-xylulose-5-phosphate (DXP) pathways which are known in the art.

In case the above conversion is performed in vitro, said DMAPP is preferably added to the reaction.

Preferably, in the method for the production of isobutene comprising the enzymatic conversion of 3-methylcrotonic acid into isobutene of the present invention wherein the method further comprises the enzymatic conversion of DMAPP into said prenol by making use of a phosphatase or pyrophosphatase, the expression of said phosphatase or pyrophosphatase is increased/enhanced. Preferably, said phosphatase or pyrophosphatase is overexpressed. Means and methods for increasing/enhancing/overexpressing the expression of an enzyme are described in more detail further below.

The pathway for the enzymatic provision of DMAP by two enzymatic steps comprising first enzymatically converting DMAPP into prenol and then enzymatically converting the thus produced prenol into said DMAP wherein said DMAPP may be provided by the enzymatic conversion of isopentenyl pyrophosphate (IPP; a product of the mevalonate (MEVA) and 1-deoxy-D-xylulose-5-phosphate (DXP) pathways) is shown in FIG. 8.

Preferably, in the methods of the present invention, the production of the DMAPP can be increased by overexpressing one or more of the genes encoding enzymes of the mevalonate (MEVA) and/or the 1-deoxy-D-xylulose-5-phosphate (DXP) pathway.

In a preferred embodiment, the phosphatase or pyrophosphatase for converting DMAPP into prenol is:

an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26)

Thus, in one preferred embodiment, the enzymatic conversion of DMAPP into prenol is achieved by the use of an alkaline phosphatase (EC 3.1.3.1).

Alkaline phosphatases (EC 3.1.3.1) are enzymes which catalyze the following reaction:

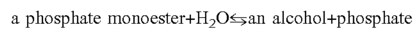
a phosphate monoester+$H_2O \leftrightharpoons$an alcohol+phosphate

This enzyme is known from a variety of organisms, including eukaryotic and prokaryotic organisms such as plants, animals, fungi and bacteria. The enzyme has, e.g., been described in *Aeropyrum pernix, Alexandrium catenella, Anabaena* sp., Antarctic bacterium TAB5 (UniProt accession number Q9KWY4), *Aspergillus caespitosus, Aspergillus oryzae, Aspergillus terricola, Bacillus licheniformis, Bacillus subtilis* (UniProt accession number P19406), *Bos taurus, Burkholderia cenocepacia* (UniProt accession number B4EKR2), *Callithrix jacchus, Camelus bactrianus, Campylobacter jejuni* (UniProt accession number A3ZF85), *Candida tropicalis, Canis lupus familiaris, Cavia porcellus, Chlorocebus sabaeus, Cobetia marina, Cricetulus griseus, Syrian hamster, Cyberlindnera jadinii, Cyrtograpsus angulatus, Daphnia magna, Debaryomyces hansenii, Dictyostelium* sp., *Drosophila melanogaster, Drosophila virilis, Echinococcus multilocularis, Eledone cirrhosa, Enterococcus faecalis, Equus caballus, Escherichia coli, Felis catus, Gadus morhua, Gallus gallus, Geobacillus caldoxylosilyticus* (UniProt accession number C1 K6P2), *Geobacillus stearothermophilus, Geobacillus thermodenitrificans* (UniProt accession number A8WEG4), *Glomus etunicatum, Haliotis diversicolor, Haloarcula marismortui, Halobacterium salinarum, Halomonas* sp., *Helicoverpa armigera, Heliothis virescens, Homo sapiens, Klebsiella pneumoniae, Lepus townsendii, Lysobacter enzymogenes, Macaca mulatta, Meretrix lusoria, Meriones unguiculatus, Mesocricetus auratus, Micrococcus sodonensis, Mus musculus, Neohelice granulata, Neurospora crassa, Nilaparvata lugens, Onchocerca ochengi, Ophicephalus punctatus Bloch, Oreochromis mossambicus, Oryctolagus cuniculus, Oryctolagus* sp., *Ovis aries, Oxybasis rubra, Pandalus borealis, Papio cynocephalus, Paramecium tetraurelia, Parawixia bistriata, Pasteurella multocida* (UniProt accession number A1C3J6), *Penaeus monodon, Penicillium chrysogenum, Phaeodactylum tricornutum, Phoca groenlandica, Physarum polycephalum, Pinctada fucata, Porphyromonas gingivalis, Prevotella intermedia, Prorocentrum donghaiense, Pseudomonas aeruginosa, Pyrococcus abyssi, Pyrococcus furiosus, Rattus norvegicus, Rhizopus microsporus, Roseobacter denitrificans, Saccharomyces cerevisiae, Saccharomyces pombe, Schistosoma mansoni* (UniProt accession number A8TKU6), *Scrobicularia plana, Scytalidium thermophilum, Serratia marcescens, Shewanella* sp., *Skeletonema costatum, Sphingomonas* sp. BSAR-1, *Sus scrofa, Synechococcus elongatus* PCC 7942, *Terfezia claveryi, Thermotoga maritima, Thermotoga neapolitana, Thermus* sp. (Swissprot accession number O86025), *Thermus thermophilus* (Swissprot accession number Q153J0), *Thermus yunnanensis, Ulva pertusa, Vibrio* sp. (UniProt accession number Q93P54) and *Walterinnesia aegyptia*.

In a preferred embodiment, the alkaline phosphatase (EC 3.1.3.1) is the *E. coli*-derived enzyme encoded by phoA (SEQ ID NO: 55).

Thus, in a preferred embodiment of the present invention, the alkaline phosphatase is an enzyme comprising the amino acid sequence of SEQ ID NO: 55 or a sequence which is at least n % identical to SEQ ID NO: 55 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a sugar phosphatase (EC 3.1.3.23).

Sugar phosphatases (EC 3.1.3.23) are enzymes which catalyze the following reaction:

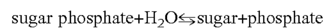
sugar phosphate+$H_2O \leftrightharpoons$sugar+phosphate

This enzyme is known from a variety of organisms, including eukaryotic and prokaryotic organisms such as plants, fungi and bacteria. The enzyme has, e.g., been described in *Arabidopsis thaliana, Bacillus subtilis* (Swissprot accession number Q9ZVJV), *Enterobacter aerogenes, Enterococcus faecalis, Escherichia acidilactici, Escherichia coli, Lactococcus lactis, Neisseria meningitidis, Plasmodium falciparum* (UniProt accession number Q81J74), *Saccharomyces cerevisiae, Streptococcus* equinus and *Streptococcus pyogenes*.

In a preferred embodiment, the sugar phosphatase (EC 3.1.3.23) is the *E. coli*-derived enzyme encoded by ybiV (SEQ ID NO: 56) or yidA (SEQ ID NO: 57).

Thus, in a preferred embodiment of the present invention, the sugar phosphatase is an enzyme comprising the amino acid sequence of SEQ ID NO: 56 or SEQ ID NO: 57 or a sequence which is at least n % identical to SEQ ID NO: 56 or SEQ ID NO: 57 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a phosphatidylglycerophosphatase (EC 3.1.3.27).

Phosphatidylglycerophosphatases (EC 3.1.3.27) are enzymes which catalyze the following reaction:

phosphatidylglycerophosphate+$H_2O$⇆phosphatidylglycerol+phosphate

This enzyme is known from a variety of organisms, including eukaryotic and prokaryotic organisms such as animals, fungi and bacteria. The enzyme has, e.g., been described in *Anabaena* sp., *Bacillus licheniformis, Enterobacter aerogenes, Escherichia coli, Listeria monocytogenes, Mesocricetus auratus, Syrian hamster, Micrococcus cerificans, Rattus* sp., *Rhodopirellula baltica, Saccharomyces cerevisiae, Salmonella enterica* subsp. *enterica* serovar *Typhimurium, Serratia marcescens, Streptococcus sanguinis* and *Vigna radiata.*

In a preferred embodiment, the phosphatidylglycerophosphatase (EC 3.1.3.27) is the *E. coli*-derived enzyme encoded by pgpA (SEQ ID NO: 58), pgpC (SEQ ID NO: 59) or pgpB (SEQ ID NO: 60).

Thus, in a preferred embodiment of the present invention, the phosphatidylglycerophosphatase (EC 3.1.3.27) is an enzyme comprising an amino acid sequence selected from the group consisting of any one of SEQ ID NO: 58 to SEQ ID NO: 60 or a sequence which is at least n % identical to SEQ ID NO: 58 to SEQ ID NO: 60 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a diacylglycerol pyrophosphate phosphatase (EC 3.1.3.81).

Diacylglycerol pyrophosphate phosphatases (EC 3.1.3.81) are enzymes which catalyze the following reaction:

1,2-diacyl-sn-glycerol 3-diphosphate+$H_2O$⇆1,2-diacyl-sn-glycerol 3-phosphate+phosphate This enzyme is known from a variety of organisms, including eukaryotic and prokaryotic organisms such as animals, fungi and bacteria. The enzyme has, e.g., been described in Catharanthus *roseus, Escherichia coli, Homo sapiens, Mus musculus* (Swissprot accession number Q61469) and *Saccharomyces cerevisiae.*

In a preferred embodiment, the pyrophosphate phosphatase (EC 3.1.3.81) is the *E. coli*-derived enzyme encoded by pgpB (SEQ ID NO: 60) already described above.

It is of note that pgpB has not only been classified under EC 3.1.3.81 but also under EC 3.1.3.27 as phosphatidylglycerophosphatase B enzymes (EC 3.1.3.27). Phosphatidylglycerophosphatase B enzymes (EC 3.1.3.27) are also termed diacylglycerol pyrophosphate phosphatases (EC 3.1.3.81), DGPP phosphatases, phosphatidate phosphatases (EC 3.1.3.4), undecaprenyl pyrophosphate phosphatases (EC 3.6.1.27) and undecaprenyl-diphosphatases.

Thus, in a preferred embodiment of the present invention, the pyrophosphate phosphatase is an enzyme comprising the amino acid sequence of SEQ ID NO: 60 or a sequence which is at least n % identical to SEQ ID NO: 60 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a phosphatidate phosphatase (EC 3.1.3.4).

Phosphatidate phosphatases (EC 3.1.3.4) are enzymes which catalyze the following reaction:

a 1,2-diacylglycerol 3-phosphate+$H_2O$⇆a 1,2-diacyl-sn-glycerol+phosphate

This enzyme is known from a variety of organisms, including eukaryotic and prokaryotic organisms such as plants, animals, fungi and bacteria. The enzyme has, e.g., been described in *Acholeplasma laidlawii, Arabidopsis thaliana, Arachis hypogaea, Bos taurus, Caenorhabditis elegans, Canis lupus familiaris, Cavia porcellus, Cricetulus griseus, Drosophila melanogaster, Escherichia coli, Geobacillus toebii* (UniProt accession number A5HKK6), *Homo sapiens, Mesocricetus auratus, Momordica charantia, Mus musculus, Rattus norvegicus, Rhodococcus jostii* (UniProt accession number Q0SKM5), *Saccharomyces cerevisiae, Spinacia oleracea, Streptomyces coelicolor, Sus scrofa, Vicia faba, Vigna radiata* and *Vigna unguiculata*. In a preferred embodiment, the phosphatidate phosphatase (EC 3.1.3.4) is the *S. cerevisiae*-derived enzyme encoded by pah1 (SEQ ID NO: 68).

Thus, in a preferred embodiment of the present invention, the phosphatidate phosphatase (EC 3.1.3.4) is an enzyme comprising the amino acid sequence of SEQ ID NO: 68 or a sequence which is at least n % identical to SEQ ID NO: 68 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a phosphoserine phosphatase (EC 3.1.3.3).

Phosphoserine phosphatases (EC 3.1.3.3) are enzymes which catalyze the following reaction:

O-phospho-L(or D)-serine+$H_2O$⇆L(or D)-serine+phosphate

This enzyme is known from a variety of organisms, including eukaryotic and prokaryotic organisms such as plants, animals, fungi and bacteria. The enzyme has, e.g., been described in *Arabidopsis thaliana, Bos taurus, Desulfovibrio desulfuricans, Escherichia coli, Gallus gallus, Homo sapiens, Hydrogenobacter thermophilus* (UniProt accession number D3DFG8), *Methanocaldococcus jannaschii* (Swissprot accession number Q58989), *Methylophilus methylotrophus, Mus musculus* (UniProt accession number Q99LS3), *Mycobacterium tuberculosis* (UniProt accession number 053289), *Pisum sativum, Porphyromonas gingivalis, Pseudomonas aeruginosa, Rattus norvegicus, Rhodobacter capsulatus, Saccharomyces cerevisiae* (Swissprot accession number P42941), *Streptomyces azureus* and *Thermococcus onnurineus* (UniProt accession number B6YX36).

In a preferred embodiment, the phosphoserine phosphatase (EC 3.1.3.3) is the *E. coli*-derived enzyme encoded by serB (SEQ ID NO: 61).

Thus, in a preferred embodiment of the present invention, the phosphoserine phosphatase is an enzyme comprising the amino acid sequence of SEQ ID NO: 61 or a sequence which is at least n % identical to SEQ ID NO: 61 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a phosphoglycolate phosphatase (EC 3.1.3.18).

Phosphoglycolate phosphatases (EC 3.1.3.18) are enzymes which catalyze the following reaction:

2-Phosphoglycolate+$H_2O$⇆glycolate+phosphate

This enzyme is known from a variety of organisms, including eukaryotic and prokaryotic organisms such as plants, animals, fungi and bacteria. The enzyme has, e.g., been described in *Agrobacterium tumefaciens*, in the alpha proteobacterium endosymbiont of *Amoeba proteus* (Swissprot accession number B3VBH3), in *Amaranthus caudatus, Anabaena variabilis, Aquifex* aeolicus (UniProt accession number O67359), *Arabidopsis thaliana, Chlamydomonas reinhardtii, Chlorella vulgaris, Cupriavidus necator, Enterobacter aerogenes* (UniProt accession number Q9Eyy5), *Escherichia coli, Glycine max, Haemophilus influenzae, Homo sapiens, Hordeum vulgare, Megathyrsus maximus, Nicotiana tabacum, Panicum miliaceum, Panicum milioides, Phaseolus vulgaris, Pisum sativum, Rattus norvegicus, Saccharomyces cerevisiae* (Swissprot accession number P19881), *Salmonella enterica, Shigella flexneri, Sorghum bicolor, Spinacia oleracea, Synechococcus elongatus* PCC 7942, *Synechocystis* sp. (Swissprot accession number Q8XC69), *Thermoplasma acidophilum* (UniProt accession number Q9HLQ2), *Triticum aestivum* and *Zea mays*.

In a preferred embodiment, the phosphoglycolate phosphatase (EC 3.1.3.18) is the *E. coli*-derived enzyme encoded by gph (SEQ ID NO: 62).

Thus, in a preferred embodiment of the present invention, the phosphoglycolate phosphatase is an enzyme comprising the amino acid sequence of SEQ ID NO: 62 or a sequence which is at least n % identical to SEQ ID NO: 62 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a pyrimidine 5'-nucleotidase (EC 3.1.3.5).

Pyrimidine 5'-nucleotidases (EC 3.1.3.5) are enzymes which catalyze the following reaction:

a 5'-ribonucleotide+$H_2O$⇆a ribonucleoside+phosphate

This enzyme is known from a variety of organisms, including eukaryotic and prokaryotic organisms such as plants, animals, fungi and bacteria. The enzyme has, e.g., been described in *Aliivibrio fischeri, Arachis hypogaea, Bacillus* sp., *Bos taurus*, Bothrops sp., Cajanus cajan, *Candida parapsilosis, Cavia porcellus, Columba* sp., *Corynebacterium glutamicum, Crocodylus siamensis, Crotalus* sp., *Daboia russelii, Danio rerio, Dictyostelium* sp., *Dosidicus gigas, Escherichia coli, Gadus macrocephalus, Gallus gallus, Giardia intestinalis, Gloydius brevicaudus* (UniProt accession number B6EWW8), *Haemophilus influenzae, Helicobacter pylori* (Swissprot accession number Q6UC93), *Hemachatus haemachatus, Homo sapiens, Kocuria varians, Lachesis muta muta, Legionella pneumophila* (UniProt accession number Q5ZZB6), *Leishmania chagasi, Loxosceles gaucho, Lutzomyia longipalpis, Micrurus frontalis, Mus musculus, Mycoplasma* sp., *Naja naja, Neurospora crassa, Oncorhynchus* sp., *Ovis aries, Photobacterium* sp., *Proteus vulgaris, Pseudomonas aeruginosa* (Swissprot accession number Q91767), *Rattus norvegicus, Rhipicephalus microplus, Saccharomyces cerevisiae, Salinivibrio costicola, Salmonella enterica, Salvator rufescens, Sebastes inermis, Shigella sonnei, Solanum tuberosum, Sturnus vulgaris, Sus scrofa, Torpedo marmorata, Trachurus japonicus, Triakis scyllium, Trichinella spiralis* (Swissprot accession number Q8MQS9), *Trichomonas* sp., *Tritrichomonas suis, Ureaplasma urealyticum, Varanus gouldii, Vibrio* sp., *Xylella fastidiosa* (UniProt accession number Q9PBQ1) and *Zea mays*.

In a preferred embodiment, the pyrimidine 5'-nucleotidase (EC 3.1.3.5) is the *E. coli*-derived enzyme encoded by yjjG (SEQ ID NO: 63).

Thus, in a preferred embodiment of the present invention, the pyrimidine 5'-nucleotidase is an enzyme comprising the amino acid sequence of SEQ ID NO: 63 or a sequence which is at least n % identical to SEQ ID NO: 63 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a pyridoxal phosphate phosphatase (EC 3.1.3.74).

Pyridoxal phosphate phosphatases (EC 3.1.3.74) are enzymes which catalyze the following reaction:

pyridoxal 5'-phosphate+$H_2O$⇆pyridoxal+phosphate

This enzyme is known from a variety of organisms, including eukaryotic and prokaryotic organisms such as animals, fungi and bacteria. The enzyme has, e.g., been described in *Bos taurus, Brachylagus idahoensis, Canis lupus familiaris, Escherichia coli, Felis catus, Gallus gallus, Homo sapiens, Meriones unguiculatus, Mus musculus, Paenibacillus thiaminolyticus, Rattus norvegicus, Sinorhizobium meliloti* and *Sus scrofa*.

In a preferred embodiment, the pyridoxal phosphate phosphatase (EC 3.1.3.74) is the *E. coli*-derived enzyme encoded by yigL (SEQ ID NO: 64).

Thus, in a preferred embodiment of the present invention, the pyridoxal phosphate phosphatase is an enzyme comprising the amino acid sequence of SEQ ID NO: 64 or a sequence which is at least n % identical to SEQ ID NO: 64 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a fructose-1, 6-bisphosphatase (EC 3.1.3.11).

Fructose-1, 6-bisphosphatases (EC 3.1.3.11) are enzymes which catalyze the following reaction:

D-fructose 1,6-bisphosphate+$H_2O$⇆D-fructose 6-phosphate+phosphate

As regards the preferred embodiments of said fructose-1, 6-bisphosphatase (EC 3.1.3.11) for the enzymatic conversion of DMAPP into prenol, the same applies, mutatis mutandis, as has been set forth above with respect to the fructose-1, 6-bisphosphatases (EC 3.1.3.11) in the enzymatic conversion of DMAPP into DMAP according to route (i) of the present invention.

In another preferred embodiment, the enzymatic conversion of DMAPP into prenol is achieved by the use of an UDP-sugar diphosphatase (EC 3.6.1.45).

UDP-sugar diphosphatases (EC 3.6.1.45) are enzymes which catalyze the following reaction:

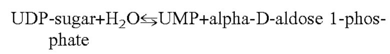

UDP-sugar+$H_2O \leftrightharpoons$UMP+alpha-D-aldose 1-phosphate

This enzyme is known from a variety of organisms, including eukaryotic and prokaryotic organisms such as animals, fungi and bacteria. The enzyme has, e.g., been described in *Corynebacterium glutamicum, Enterobacter aerogenes* (UniProt accession number Q9RQT7), *Escherichia coli* (UniProt accession number P07024), *Homo sapiens* (UniProt accession number O95848), *Mus musculus* (UniProt accession number Q9D142), *Peptoclostridium difficile, Saccharomyces cerevisiae, Salmonella* sp., *Sus scrofa* and *Yersinia intermedia* (UniProt accession number A4URQ8).

In a preferred embodiment, the UDP-sugar diphosphatase (EC 3.6.1.45) is the *E. coli*-derived enzyme encoded by ushA (SEQ ID NO: 65).

Thus, in a preferred embodiment of the present invention, the UDP-sugar diphosphatase is an enzyme comprising the amino acid sequence of SEQ ID NO: 65 or a sequence which is at least n % identical to SEQ ID NO: 65 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of an undecaprenyl pyrophosphate phosphatase (EC 3.6.1.27).

Undecaprenyl pyrophosphate phosphatase (EC 3.6.1.27) are enzymes which catalyze the following reaction:

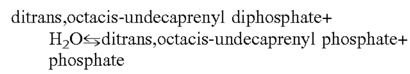

ditrans,octacis-undecaprenyl diphosphate+$H_2O \leftrightharpoons$ditrans,octacis-undecaprenyl phosphate+phosphate This enzyme is known from a variety of organisms, including eukaryotic and prokaryotic organisms such as plants, animals, fungi and bacteria. The enzyme has, e.g., been described in *Bacillus subtilis, Cupriavidus metallidurans, Enterococcus faecalis, Escherichia coli* and *Micrococcus luteus.*

In a preferred embodiment, the undecaprenyl pyrophosphate phosphatase (EC 3.6.1.27) is the *E. coli*-derived enzyme encoded by pgpB (SEQ ID NO: 60) already described above.

It is of note that pgpB has not only been classified under EC 3.1.3.81 but also under EC 3.1.3.27 as phosphatidylglycerophosphatase B enzymes (EC 3.1.3.27). Phosphatidylglycerophosphatase B enzymes (EC 3.1.3.27) are also termed diacylglycerol pyrophosphate phosphatases (EC 3.1.3.81), DGPP phosphatases, phosphatidate phosphatases (EC 3.1.3.4), undecaprenyl pyrophosphate phosphatases (EC 3.6.1.27) and undecaprenyl-diphosphatases.

Thus, in a preferred embodiment of the present invention, the undecaprenyl pyrophosphate phosphatase is an enzyme comprising the amino acid sequence of SEQ ID NO: 60 or a sequence which is at least n % identical to SEQ ID NO: 60 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting DMAPP into prenol. As regards the determination of the sequence identity, the same applies as has been set forth above.

In another preferred embodiment, the enzymatic conversion of DMAPP into prenol is achieved by the use of a prenyl-diphosphatase (EC 3.1.7.1).

Prenyl-diphosphatases (EC 3.1.7.1) are enzymes which catalyze the following reaction:

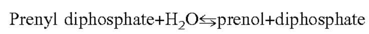

Prenyl diphosphate+$H_2O \leftrightharpoons$prenol+diphosphate

This enzyme is known from a variety of organisms, including eukaryotic and prokaryotic organisms such as plants and animals. The enzyme has, e.g., been described in *Citrus sinensis, Datura stramonium, Oryza sativa* and *Rattus norvegicus.*

In another preferred embodiment, the enzymatic conversion of DMAPP into prenol is achieved by the use of an isopentenyl phosphate kinase (EC 2.7.4.26).

As regards the preferred embodiments for isopentenyl phosphate kinase (EC 2.7.4.26) for the enzymatic conversion of DMAPP into prenol, the same applies as has been set forth above in connection with the enzymatic conversion of DMAPP into DMAP according to the invention.

Route (iv): The Provision of DMAP by the Enzymatic Conversion of Isopentenyl Monophosphate (IMP) into Said DMAP According to the present invention, DMAP can be provided enzymatically by the enzymatic conversion of isopentenyl monophosphate (IMP) into said DMAP.

In a preferred embodiment, the enzymatic conversion of isopentenyl monophosphate (IMP) into said DMAP is achieved by making use of an isomerase.

Preferably, in the method for the production of isobutene comprising the enzymatic conversion of 3-methylcrotonic acid into isobutene of the present invention wherein the method further comprises the enzymatic conversion of IMP into said DMAP by making use of a isomerase, the expression of said isomerase is increased/enhanced. Preferably, said isomerase is overexpressed. Means and methods for increasing/enhancing/overexpressing the expression of an enzyme are described in more detail further below.

As regards the preferred embodiments for enzymes catalyzing the enzymatic conversion of isopentenyl monophosphate (IMP) into said DMAP and the isomerases, the same applies as has been set forth above in connection with the conversion of IPP into DMAPP according to the invention.

In a preferred embodiment, the isomerase is an isopentenyl-diphosphate DELTA isomerase (EC 5.3.3.2).

In case the above conversion is performed in a cell, said isopentenyl monophosphate (IMP) may be metabolically provided by naturally occurring or artificially introduced metabolic routes leading to the formation of IMP from mevalonate-5-phosphate. Vinokur et al. (Biochemistry 53 (2014), 4161-4168) describes the existence of an alternative mevalonate pathway in Archaea wherein IMP is produced from mevalonate-5-phosphate.

Alternatively, in organisms which do not naturally have the metabolic routes leading to the formation of IMP from mevalonate-5-phosphate, the genes encoding the enzymes for the production of IMP can artificially be introduced (and preferably overexpressed) in a host cell.

Figure 44:
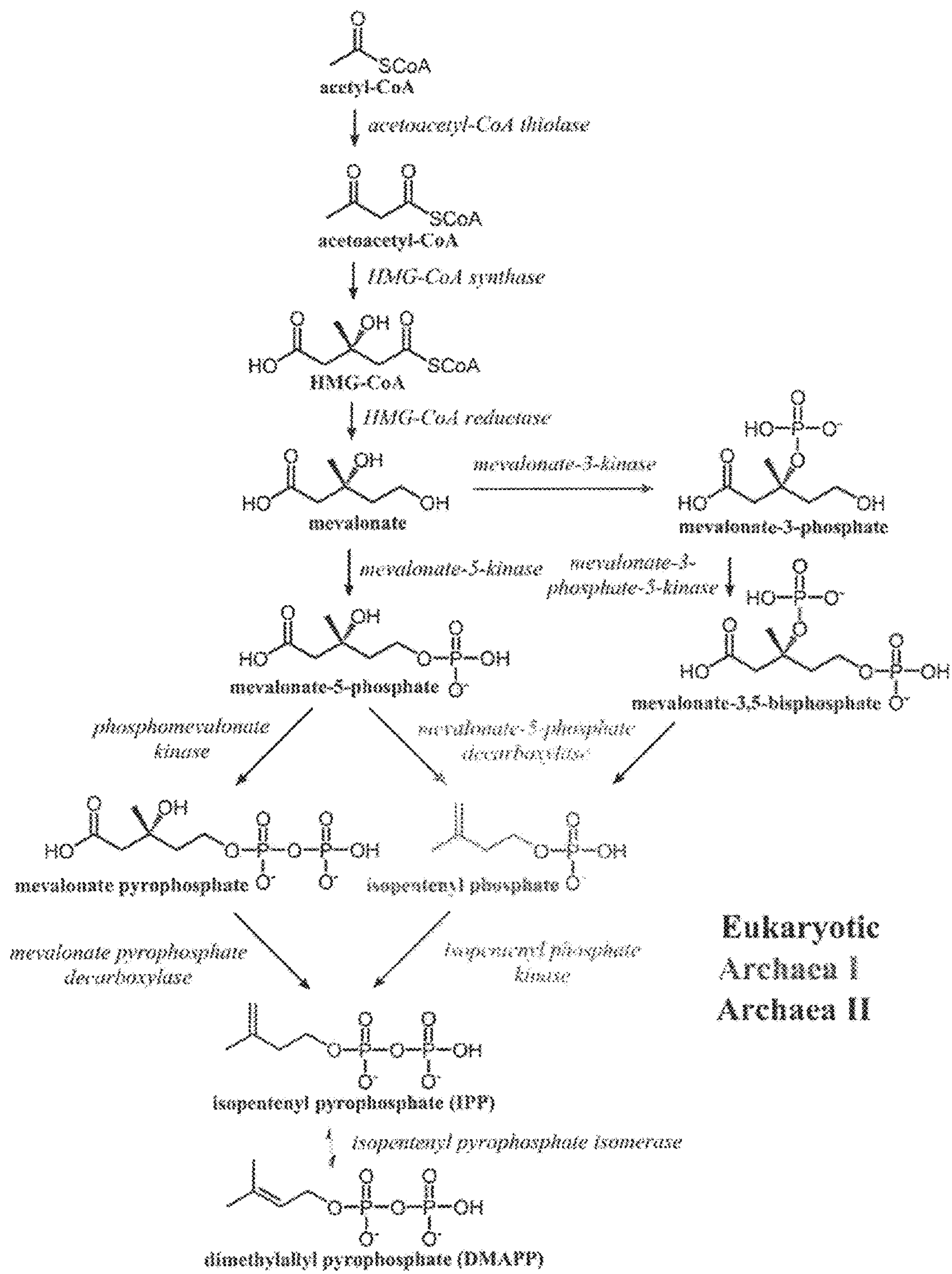

Genes encoding the enzymes for the production of IMP are known in the art and can be derived from the different reactions known for the mevalonate pathway shown in FIG. 44. These enzymes are termed acetoacetyl-CoA thiolase, HMG-CoA synthase, HMG-CoA reductase, mevalonate-5-kinase, mevalonate-3-kinase, mevalonate-3-phosphate-5-kinase, and mevalonate-5-phosphate-decarboxylase.

IMP (termed isopentenyl phosphate in FIG. 44) is known to be produced either by a pathway known as "Archaea I" or "Archaea II".

In the pathway known as "Archaea I" mevalonate is converted into mevalonate-5-phosphate by a mevalonate-5-kinase and the thus produced mevalonate-5-phosphate is converted into IMP by a mevalonate-5-phosphate decarboxylase.

In the pathway known as "Archaea II" mevalonate is converted into mevalonate-3-phosphate by a mevalonate-3-kinase wherein said mevalonate-3-phosphate is then further converted into mevalonate-3,5-bisphosphate by a mevalonate-3-phosphate-5-kinase wherein said mevalonate-3,5-bisphosphate is then further converted into said IMP by a mevalonate-5-phosphate-decarboxylase.

Thus, in one embodiment, in (micro-)organisms which naturally have the metabolic routes leading to the formation of mevalonate, the genes encoding the enzymes for the production of IMP from mevalonate can artificially be introduced (and preferably overexpressed) in a host cell. These genes are preferably the genes encoding mevalonate-3-kinase, mevalonate-3-phosphate-5-kinase, and mevalonate-5-phosphate-decarboxylase (in accordance with the above known pathway known as "Archaea II"). Alternatively (or additionally), these genes are preferably the genes encoding mevalonate-5-kinase and mevalonate-5-phosphate decarboxylase (in accordance with the above known pathway known as "Archaea I").

In this embodiment, the microorganism is preferably yeast, more preferably *S. cerevisiae* which is known to have the metabolic routes leading to the formation of mevalonate.

In another embodiment, in (micro-)organisms which do not naturally have the metabolic routes leading to the formation of mevalonate, mevalonate can be produced from the central metabolite acetyl-CoA by artificially introducing (and preferably overexpressing) in a host cell the genes encoding the enzymes for the production of mevalonate from acetyl-CoA. These genes are preferably the genes encoding acetoacetyl-CoA thiolase (converting acetyl-CoA into acetoacetyl-CoA), HMG-CoA synthase (converting acetoacetyl-CoA into HMG-CoA) and HMG-CoA reductase (converting HMG-CoA into mevalonate). In this host cell, the genes encoding the enzymes for the production of IMP from mevalonate can additionally artificially be introduced (and preferably overexpressed). These genes are preferably the genes encoding mevalonate-3-kinase, mevalonate-3-phosphate-5-kinase, and mevalonate-5-phosphate-decarboxylase (in accordance with the above known pathway known as "Archaea II"). Alternatively (or additionally), these genes are preferably the genes encoding mevalonate-5-kinase and mevalonate-5-phosphate decarboxylase (in accordance with the above known pathway known as "Archaea I"). In this embodiment, the microorganism is preferably *E. coli*, which is known to lack the metabolic routes leading to the formation of mevalonate.

In case the above conversion is performed in vitro, said IMP is preferably added to the reaction.

Increasing the Pool of DMAP by Reducing the Activity of Endogenous Phosphatases, Thereby Reducing the Leakage of DMAP When implementing the method of the present invention for providing DMAP enzymatically according to any one of steps (i) to (iv) in vivo, DMAP may be hydrolyzed into prenol by the activity of endogenous phosphatases, thereby reducing the pool of DMAP.

In order to reduce/prevent this leakage of DMAP, in a preferred embodiment of the present invention, the above methods for the provision of DMAP may further comprise a method wherein the activity/activities of enzymes capable of dephosphorylating DMAP into prenol is/are reduced, or lost/inactivated.

The term "dephosphorylation" refers to the removal of a phosphate group from an organic compound by hydrolysis as it, e.g., occurs in the conversion of DMAP into prenol.

Enzymes capable of dephosphorylating DMAP into prenol are preferably phosphatases.

Preferably, this reduction (or complete loss) of the activity of enzymes capable of dephosphorylating DMAP into prenol, preferably of phosphatases, is achieved by a genetic modification which leads to said inactivation or reduction. This can be achieved e.g., by random mutagenesis or site-directed mutagenesis of the promoter and/or the enzyme and subsequent selection of promoters and/or enzymes having the desired properties or by complementary nucleotide sequences or RNAi effect.

In the context of the present invention, a "reduced activity" means that the expression and/or the activity of an enzyme capable of dephosphorylating DMAP into prenol, preferably of a phosphatase, is at least 10%, preferably at least 20%, more preferably at least 30% or 50%, even more preferably at least 70% or 80% and particularly preferred at least 90% or 100% lower than the expression in the corresponding non-modified cell and than the activity of the non-modified enzyme respectively. Methods for measuring the level of expression of a given protein in a cell are well known to the person skilled in the art. In short, these methods may, e.g., employ methods of measuring the expression on the RNA-level (by, e.g., RT-PCR technologies) or on the protein level (by, e.g., Western blot methods).

Assays for measuring the reduced enzyme activity of dephosporylation are known in the art.

A genetic modification of the cell which leads to said inactivation or reduction of the dephosphorylation activity/activities is preferably achieved by inactivation of the gene(s) encoding said enzymes (preferably phosphatases) capable of dephosphorylating DMAP into prenol.

The inactivation of the gene(s) encoding an enzyme (preferably a phosphatase) capable of dephosphorylating DMAP into prenol in the context of the present invention means that the gene(s) coding for (an) enzyme(s) (preferably (a) phosphatase(s)) capable of dephosphorylating DMAP into prenol which is (are) present in the cell is (are) inactivated so that they are no longer expressed and/or do not lead to the synthesis of a functional enzyme having dephosphorylation activity. Inactivation can be achieved by many different ways known in the art. The inactivation can, e.g., be achieved by the disruption of the gene(s) encoding the corresponding enzyme or by clean deletion of said gene(s) through the introduction of a selection marker. Alternatively, the promoter of the gene(s) encoding the corresponding enzyme can be mutated in a way that the gene(s) is/are no longer transcribed into mRNA. Other ways to inactivate the gene(s) encoding the corresponding enzyme known in the art are: to express a polynucleotide encoding RNA having a nucleotide sequence complementary to the transcript of the gene encoding the enzyme having dephosphorylation activity so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through a co-suppression effect. These polynucleotides can be incorporated into a vector, which can be introduced into the cell by transformation to achieve the inactivation of the gene(s) encoding enzyme having dephosphorylation activity.

The term "inactivation" in the context of the present invention preferably means complete inactivation, i.e. that the cell does not show an enzyme having dephosporylation activity.

Preferably, "inactivation" means that the gene(s) encoding the enzyme having dephosporylation activity which are present in the cell are genetically modified so as to prevent the expression of the enzyme. This can be achieved, e.g., by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

The Provision of DMAPP

As mentioned above, the metabolic routes leading to the formation of dimethylallyl pyrophosphate (DMAPP) via the mevalonate (MEVA) and 1-deoxy-D-xylulose-5-phosphate (DXP) pathways are known in the art.

However, in the method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) into a flavin-derived cofactor (utilizing dimethylallyl phosphate (DMAP) or dimethylallyl pyrophosphate (DMAPP)), also the availability of DMAPP is another limiting factor.

The chemical structure of dimethylallyl pyrophosphate (DMAPP) is shown in FIG. 3.

As mentioned above, the mechanism of the ferulic acid decarboxylase (FDC) in association with the modified FMN (prenylated-FMN) (the latter provided by the PAD enzyme) was recently described (Nature 522 (2015), 497-501; Nature, 522 (2015), 502-505). Moreover, the metabolic routes leading to the formation of dimethylallyl pyrophosphate (DMAPP) via the mevalonate (MEVA) and 1-deoxy-D-xylulose-5-phosphate (DXP) pathways are known in the art. However, it remained unclear whether said FMN prenyl transferase (catalyzing the prenylation of a flavin cofactor (FMN or FAD) into a flavin-derived cofactor), in the context of the production of isobutene from 3-methylcrotonic acid, is also capable of utilizing dimethylallyl pyrophosphate (DMAPP). Indeed, it has only previously been described by Arunrattanamook and Marsh (Biochemistry 57(5) (2018), 696-700) that a prenyl transferase from *S. cerevisiae* uses DMAPP as a co-substrate.

Only the present invention has shown that it is possible to use a FMN prenyl transferase (catalyzing the prenylation of a flavin cofactor (FMN or FAD) into a flavin-derived cofactor), by utilizing dimethylallyl pyrophosphate (DMAPP), in a method for the production of isobutene in accordance with the present invention.

The exogenous supplementation of DMAPP in a culture medium is not feasible since DMAPP is assumed to not enter the cell. Moreover, although the metabolic routes leading to the formation of dimethylallyl pyrophosphate (DMAPP) via the mevalonate (MEVA) and 1-deoxy-D-xylulose-5-phosphate (DXP) pathways are known in the art, there is a need to increase the intracellular pool of DMAPP as the availability of DMAPP is limiting for the production of isobutene from 3-methylcrotonic acid in accordance with the present invention. Therefore, the present invention also provides methods for endogenously generating DMAPP and, preferably, to increase the pool of DMAPP.

Figure 45:
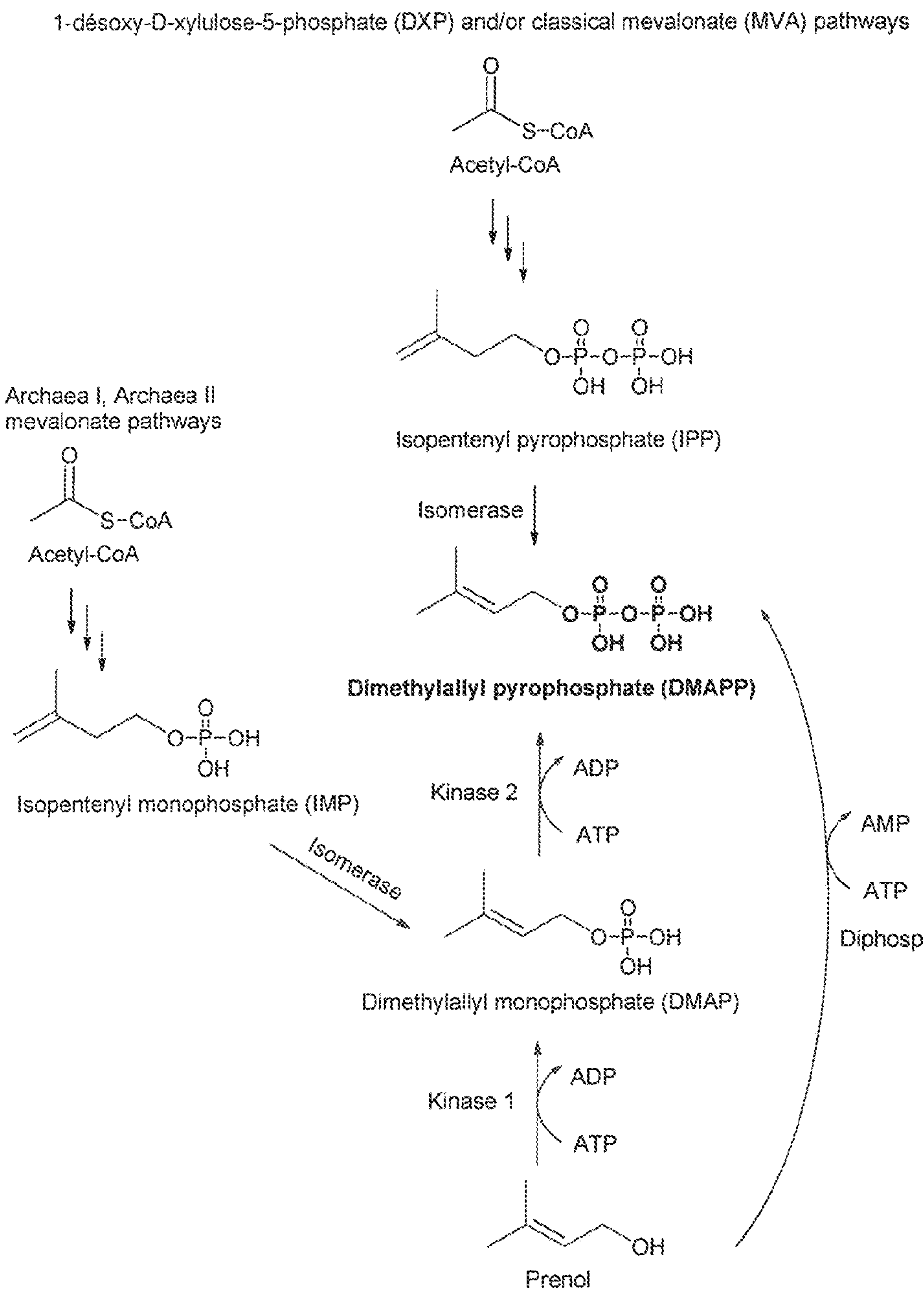

According to the present invention, DMAPP can be provided via different routes (in the following referred to as route (v), (vi) and (vii), respectively) which are schematically shown in FIG. 45 (and designated in said Figure with the names "Isomerase", "Kinase 2" and "Diphosphokinase", respectively).

Accordingly, the above described method for the production of isobutene comprising the enzymatic conversion of 3-methylcrotonic acid into isobutene further comprises providing said DMAPP enzymatically by:

(v) the enzymatic conversion of isopentenyl pyrophosphate (IPP) into said DMAPP; or (vi) the enzymatic conversion of dimethylallyl phosphate (DMAP) into said DMAPP; or (vii) the enzymatic conversion of prenol into said DMAPP; or by a combination of any one of (v) to (vii).

Preferably, in the method for the production of isobutene comprising the enzymatic conversion of 3-methylcrotonic acid into isobutene, the enzymatic provision of said DMAPP is enhanced/increased over naturally occurring (enzymatic) reactions/conversions leading to the production of DMAPP, preferably by overexpressing corresponding enzymes capable of catalyzing any of the above reactions (v) to (vii). Means and methods for increasing/enhancing the expression of an enzyme are described in more detail further below.

These different routes (v), (vi) and (vii) for the provision of DMAPP are illustrated in FIG. 45 while each of the above conversions is described in more detail in the following:

Route (v): The Provision of DMAPP by the Enzymatic Conversion of Isopentenyl Pyrophosphate (IPP) into Said DMAPP According to the present invention, DMAPP can be provided enzymatically by the enzymatic conversion of isopentenyl pyrophosphate (IPP) into said DMAPP.

In a preferred embodiment, the enzymatic conversion of isopentenyl pyrophosphate (IPP) into said DMAPP is achieved by making use of an isomerase, preferably an isopentenyl-diphosphate DELTA isomerase (EC 5.3.3.2).

As regards said isomerase and said isopentenyl-diphosphate DELTA isomerase (EC 5.3.3.2) for the enzymatic conversion of isopentenyl pyrophosphate (IPP) into DMAPP, the same applies, mutatis mutandis, as has already been set forth above.

In case the above conversion is performed in a cell, said isopentenyl pyrophosphate is preferably metabolically provided by naturally occurring or artificially introduced metabolic routes leading to the formation of isopentenyl pyrophosphate, e.g., via the mevalonate (MEVA) and/or 1-deoxy-D-xylulose-5-phosphate (DXP) pathways which are known in the art.

In case the above conversion is performed in vitro, said isopentenyl pyrophosphate is preferably added to the reaction.

Preferably, in the method for the production of isobutene comprising the enzymatic conversion of 3-methylcrotonic acid into isobutene of the present invention wherein the method further comprises the enzymatic conversion of IPP into said DMAPP by making use of an isomerase, preferably an isopentenyl-diphosphate DELTA isomerase (EC 5.3.3.2), the expression of said isomerase, preferably said isopentenyl-diphosphate DELTA isomerase (EC 5.3.3.2) is increased/enhanced. Preferably, said isomerase, more preferably said isopentenyl-diphosphate DELTA isomerase (EC 5.3.3.2), is overexpressed. Means and methods for increasing/enhancing/overexpressing the expression of an enzyme are described in more detail further below.

Route (vi): The Provision of DMAPP by the Enzymatic Conversion of Dimethylallyl Phosphate (DMAP) into Said DMAPP According to the present invention, DMAPP can be provided enzymatically by the enzymatic conversion dimethylallyl phosphate (DMAP) into said DMAPP.

In a preferred embodiment, the enzymatic conversion of DMAP into DMAPP is achieved by making use of a kinase. Kinases are known in the art and are generally known as enzymes capable of catalyzing the transfer of phosphate groups from high-energy, phosphate-donating molecules to specific substrates. This process is known as phosphorylation, where the substrate gains a phosphate group and the high-energy ATP molecule donates a phosphate group. This reaction is a transesterification and produces a phosphorylated substrate and ADP.

Figure 46:
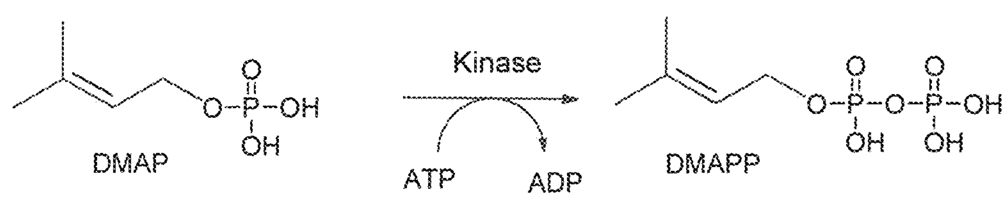

Enzymes catalyzing the enzymatic conversion (i.e., the phosphorylation) of DMAP into said DMAPP are enzymes which catalyze the reaction as shown in FIG. 46.

In case the above conversion is performed in a cell, said DMAP is preferably metabolically provided as described herein-above and below.

In case the above conversion is performed in vitro, said DMAP is preferably added to the reaction.

Preferably, in the method for the production of isobutene comprising the enzymatic conversion of 3-methylcrotonic acid into isobutene of the present invention wherein the method further comprises the enzymatic conversion of DMAP into said DMAPP by making use of a kinase, the expression of said kinase is increased/enhanced. Preferably, said kinase is overexpressed. Means and methods for increasing/enhancing/overexpressing the expression of an enzyme are described in more detail further below.

In a preferred embodiment, the kinase is an isopentenyl monophosphate kinase (EC 2.7.4.26).

Isopentenyl phosphate kinases (EC 2.7.4.26) are enzymes which catalyze the following reaction:

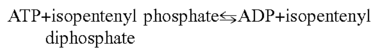
ATP+isopentenyl phosphate⇆ADP+isopentenyl diphosphate

This enzyme is known in the art and has, e.g., been described by Chen and Poulter (Biochemistry 49 (2010), 207-210). This enzyme has, e.g., been described in *Haloferax volcanii* (UniProt accession number D4GWT7), *Mentha* x *piperita* (SwissProt accession number P56848), *Methanocaldococcus jannaschii* (SwissProt accession number O60352), *Methanothermobacter thermautotrophicus* (UniProt O26153), and *Thermoplasma acidophilum* (UniProt accession number Q9HLX1).

The Provision of DMAP

The DMAP which is converted into DMAPP according to the method of the present invention may itself be provided by an enzymatic conversion as described herein above and below.

Preferably, according to the present invention, DMAP can be provided enzymatically by the enzymatic conversion of prenol into DMAP or by the enzymatic conversion of isopentenyl monophosphate (IMP) into DMAP.

In case the above conversion of prenol into DMAP is performed in a cell (i.e., in vivo), said prenol is preferably metabolically provided by naturally occurring or artificially introduced metabolic routes leading to the formation of prenol.

Alternatively or in addition to the above, said prenol may preferably be supplemented/added to the culture medium.

In case the above conversion is performed in vitro, said prenol is preferably added to the in vitro reaction.

As described above, there are organisms known in the art which are capable of naturally producing prenol or by artificially introduced metabolic routes. Thus, as described above, corresponding organisms may preferentially be used in the methods of the present invention for the conversion of prenol into DMAP.

As described above, in case the above conversion is performed in a cell, said isopentenyl monophosphate (IMP) may be metabolically provided by naturally occurring or artificially introduced metabolic routes leading to the formation of IMP from mevalonate-5-phosphate. Vinokur et al. (Biochemistry 53 (2014), 4161-4168) describes the existence of an alternative mevalonate pathway in Archaea wherein IMP is produced from mevalonate-5-phosphate.

Alternatively, in organisms which do not naturally have the metabolic routes leading to the formation of IMP from mevalonate-5-phosphate, the genes encoding the enzymes for the production of IMP can artificially be introduced (and preferably overexpressed) in a host cell as described above.

In a preferred embodiment, the enzymatic conversion of prenol into said DMAP is achieved by making use of a kinase, more preferably a phosphotransferase with an alcohol group as acceptor (EC 2.7.1.-) and even more preferably a hydroxyethylthiazole kinase (EC 2.7.1.50).

In another preferred embodiment, the enzymatic conversion of isopentenyl monophosphate (IMP) into DMAP is achieved by making use of an isomerase, preferably an isopentenyl-diphosphate DELTA isomerase (EC 5.3.3.2).

Preferably, in the method for the production of isobutene comprising the enzymatic conversion of 3-methylcrotonic acid into isobutene of the present invention wherein the method further comprises the enzymatic conversion of prenol into DMAP or the enzymatic conversion of isopentenyl monophosphate (IMP) into DMAP by making use of a kinase and isomerase, respectively, the expression of said kinase and isomerase, respectively, is increased/enhanced. Preferably, said kinase and isomerase, respectively, is overexpressed. Means and methods for increasing/enhancing/overexpressing the expression of an enzyme are described in more detail further below.

As regards said kinase, said phosphotransferase with an alcohol group as acceptor (EC 2.7.1.-), said hydroxyethylthiazole kinase (EC 2.7.1.50), said isomerase and said isopentenyl-diphosphate DELTA isomerase (EC 5.3.3.2), the same applies, mutatis mutandis, as has been set forth above.

Route (vii): The Provision of DMAPP by the Enzymatic Conversion of Prenol into Said DMAPP According to the present invention, DMAPP can be provided enzymatically by the direct enzymatic conversion of prenol into said DMAPP. The direct enzymatic conversion of prenol into said DMAPP in one step can, e.g., be achieved by the use of an enzyme which is able to catalyze the transfer of a diphosphate group, such as a diphosphotransferase, for example enzymes which are classified as EC 2.7.6.-(diphosphotransferases). Examples are 2-amino-4-hydroxy-6-hydroxymethyldihydropteridine diphosphokinase (EC 2.7.6.3) and thiamine diphosphokinase (EC 2.7.6.2). Preferably, ATP is the donor of the diphosphate group in such a reaction.

Previously, the use of a diphosphokinase EC 2.7.6.- has been described in WO 2013/040383 for the phosphorylation of dimethylallyl alcohol (i.e., prenol) to then produce isoprene.

In case the above conversion of prenol into DMAPP is performed in a cell (i.e., in vivo), said prenol is preferably metabolically provided by naturally occurring or artificially introduced metabolic routes leading to the formation of prenol.

Alternatively or in addition to the above, said prenol may preferably be supplemented/added to the culture medium.

In case the above conversion is performed in vitro, said prenol is preferably added to the in vitro reaction.

As described above, there are organisms known in the art which are capable of naturally producing prenol or by artificially introduced metabolic routes. Thus, as described above, corresponding organisms may preferentially be used in the methods of the present invention for the conversion of prenol into DMAPP.

In a preferred embodiment, the enzymatic conversion of prenol into DMAPP is achieved by making use of a diphosphotransferase (EC 2.7.6.-), preferably a thiamine diphosphokinase (EC 2.7.6.2) or a 2-amino-4-hydroxy-6-hydroxymethyldihydropteridine diphosphokinase (EC 2.7.6.3).

Thus, in one embodiment, the direct enzymatic conversion of prenol into DMAPP can be achieved by the use of a 2-amino-4-hydroxy-6-hydroxymethyldihydropteridine diphosphokinase (EC 2.7.6.3). This enzyme is an enzyme which catalyzes the following reaction:

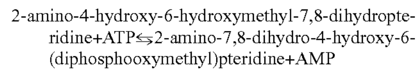
2-amino-4-hydroxy-6-hydroxymethyl-7,8-dihydropteridine+ATP⇆2-amino-7,8-dihydro-4-hydroxy-6-(diphosphooxymethyl)pteridine+AMP The occurrence of this enzyme has been described for several organisms, e.g. for *E. coli, Plasmodium falciparum, Plasmodium chabaudi, Streptococcus pneumoniae, Toxoplasma gondii, Yersinia pestis, Pneumocystis carinii, Haemophilus influenzae, S. cerevisiae, Arabidopsis thaliana* and *Pisum sativum.*

In principle, any known 2-amino-4-hydroxy-6-hydroxymethyldihydropteridine diphosphokinase can be employed in the method according to the invention.

In another embodiment the direct enzymatic conversion of prenol into DMAPP can be achieved by the use of a thiamine diphosphokinase (EC 2.7.6.2). This enzyme is an enzyme which catalyzes the following reaction:

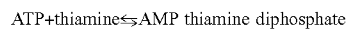
ATP+thiamine⇆AMP thiamine diphosphate

The occurrence of this enzyme has been described for several organisms, e.g. for *Salmonella enterica, Plasmodium falciparum, Saccharomyces cerevisiae, Schizosaccharomyces pombe, Candida albicans, Arabidopsis thaliana, Caenorhabditis elegans, Rattus norvegicus, Mus musculus* and *Homo sapiens*. In principle, any known thiamine diphosphokinase can be employed in the method according to the invention.

Preferably, in the method for the production of isobutene comprising the enzymatic conversion of 3-methylcrotonic acid into isobutene of the present invention wherein the method further comprises the enzymatic conversion of prenol into said DMAPP by making use of a diphosphotransferase (EC 2.7.6.-) (preferably a thiamine diphosphokinase (EC 2.7.6.2) or a 2-amino-4-hydroxy-6-hydroxymethyldihydropteridine diphosphokinase (EC 2.7.6.3)), the expression of said diphosphotransferase (EC 2.7.6.-) (preferably of said thiamine diphosphokinase (EC 2.7.6.2) or of said 2-amino-4-hydroxy-6-hydroxymethyldihydropteridine diphosphokinase (EC 2.7.6.3)) is increased/enhanced. Preferably, said enzyme is overexpressed. Means and methods for increasing/enhancing/overexpressing the expression of an enzyme are described in more detail further below.

The Provision of the Flavin Cofactor

As mentioned above, in the method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) and/or dimethylallyl pyrophosphate (DMAPP) into a flavin-derived cofactor, the availability of DMAP and/or DMAPP is one limiting factor. Another limiting factor may be the availability of the flavin cofactor FMN.

Figure 9:
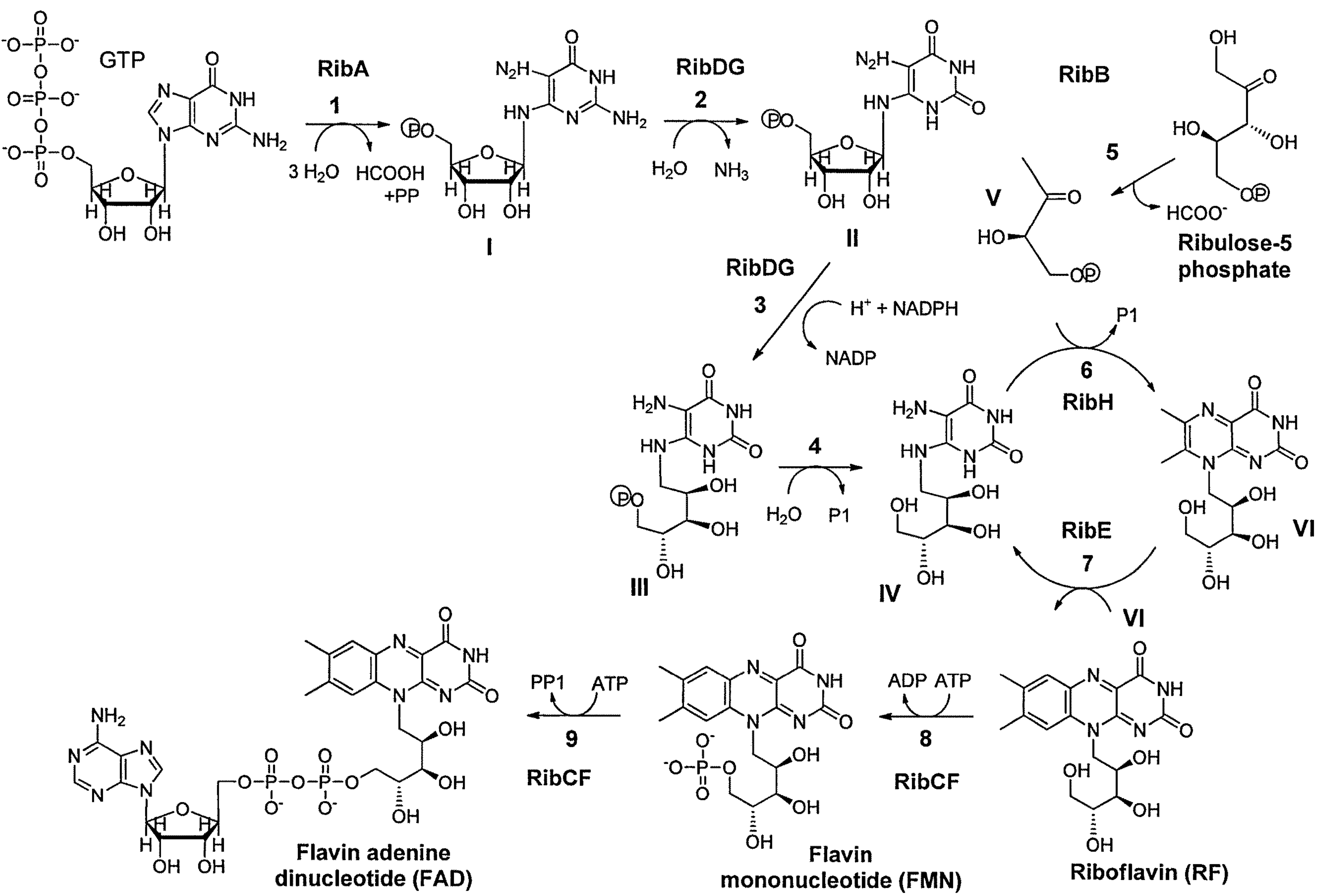

Flavin mononucleotide (FMN), also termed riboflavin-5'-phosphate, is a biomolecule produced from riboflavin (vitamin B2). FMN is known to be a co-factor for several enzymatic reactions. The pathway for its biosynthesis is known and has, e.g., been described in *E. coli*. The pathway for its biosynthesis starting from GTP is illustrated in FIG. 9.

As FMN is a co-factor for several enzymatic reactions, it is known to occur in many organisms. Because the availability of FMN in the method for the production of isobutene comprising the enzymatic conversion of 3-methylcrotonic acid into isobutene according to the present invention may be a limiting factor, the present invention provides, in accordance with the above described methods, a method increasing the intracellular pool of FMN, thereby increasing the availability of FMN. Accordingly, a method for providing said flavin cofactor enzymatically by the enzymatic conversion of riboflavin into flavin mononucleotide (FMN) is provided.

Accordingly, the present invention also relates to a method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) and/or dimethylallyl pyrophosphate (DMAPP) into a flavin-derived cofactor as described herein above, wherein said method further comprises providing said flavin cofactor enzymatically by the enzymatic conversion of riboflavin into flavin mononucleotide (FMN), thereby increasing the pool of FMN.

In case the above conversion is performed in a cell (i.e., in vivo), said riboflavin (i.e., the precursor of FMN) may be provided by naturally occurring metabolic routes leading to the formation of riboflavin by the pathway for its biosynthesis known to occur in many organisms or by artificially introduced metabolic routes. Alternatively, or in addition to the above, riboflavin may also be added to the culture medium which enters the (host) cell and is then enzymatically converted into FMN according to the above and below described methods.

In case the above conversion is performed in vitro, said riboflavin is preferably added to the reaction.

Preferably, in the method for the production of isobutene comprising the enzymatic conversion of 3-methylcrotonic acid into isobutene of the present invention wherein the method further comprises the provision of the flavin cofactor by the enzymatic conversion of riboflavin into flavin mononucleotide (FMN), the enzymatic conversion of riboflavin into FMN is achieved by making use of:

a kinase, preferably:

an archaeal riboflavin kinase (EC 2.7.1.161), flavokinases derived from *S. cerevisiae* or from *Rattus norvegicus,* a flavokinase derived from Megasphaera elsdenii, phosphotransferases with an alcohol group as acceptor (EC 2.7.1), preferably erythritol kinases (2.7.1.27) or glycerol kinases (2.7.1.30), phosphotransferases with a phosphate group as acceptor (EC 2.7.4), preferably isopentenyl phosphate kinases (EC 2.7.4.26); or a bifunctional riboflavin kinase/FMN adenylyltransferase (ribF); or a variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived.

In a preferred embodiment, in the enzymatic conversion of riboflavin into FMN, the expression of said kinase, preferably said archaeal riboflavin kinase (EC 2.7.1.161), said flavokinase derived from *S. cerevisiae* or from *Rattus norvegicus*, said flavokinase derived from Megasphaera elsdenii, said phosphotransferase with an alcohol group as acceptor (EC 2.7.1), said erythritol kinase (2.7.1.27), said glycerol kinase (2.7.1.30), said phosphotransferase with a phosphate group as acceptor (EC 2.7.4), said isopentenyl phosphate kinase (EC 2.7.4.26), said bifunctional riboflavin kinase/FMN adenylyltransferase (ribF) or said variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived is increased/enhanced.

Preferably, said enzyme(s) is/are overexpressed. Means and methods for increasing/enhancing/overexpressing the expression of an enzyme are described in more detail further below.

Thus, in a preferred embodiment, the enzymatic conversion of riboflavin into FMN is achieved by making use of a kinase, preferably an archaeal riboflavin kinase (EC 2.7.1.161), a flavokinase derived from *S. cerevisiae* or from *Rattus norvegicus*, or a flavokinase derived from Megasphaera elsdenii, a phosphotransferase with an alcohol group as acceptor (EC 2.7.1), preferably an erythritol kinase (2.7.1.27) or a glycerol kinase (2.7.1.30) or a phosphotransferase with a phosphate group as acceptor (EC 2.7.4), preferably an isopentenyl phosphate kinases (EC 2.7.4.26).

Thus, in a preferred embodiment, the enzymatic conversion of riboflavin into FMN is achieved by making use of an archaeal riboflavin kinase (EC 2.7.1.161). Archaeal riboflavin kinases (EC 2.7.1.161) are enzymes which catalyze the following reaction:

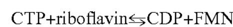
CTP+riboflavin⇆CDP+FMN

This enzyme is, e.g., known from *Methanocaldococcus jannaschii* and *Trichophyton rubrum.*

In a more preferred embodiment, the enzymatic conversion of riboflavin into FMN is achieved by making use of the archaeal riboflavin kinase derived from *Methanocaldococcus jannaschii* (UniProt accession number Q60365; SEQ ID NO: 69). This enzyme is described by Mashhadi et al. (Journal of Bacteriology 190 (7) (2008), 2615) to be monofunctional (only converting riboflavin into FMN).

Thus, in a preferred embodiment of the present invention, the archaeal riboflavin kinase (EC 2.7.1.161) is an enzyme comprising the amino acid sequence of SEQ ID NO: 69 or a sequence which is at least n % identical to SEQ ID NO: 69 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting riboflavin into FMN. As regards the determination of the sequence identity, the same applies as has been set forth above.

In another preferred embodiment, the enzymatic conversion of riboflavin into FMN is achieved by making use of an eukaryotic flavokinase enzyme derived from *Saccharomyces cerevisiae* or from *Rattus norvegicus*. Santos et al. (JBC 275 (2000), 28618) and Kasi et al. (J. Biochem. 107 (1990), 298) describe eukaryotic flavokinase enzymes derived from *Saccharomyces cerevisiae* and *Rattus norvegicus*, respectively, which may be used, in a preferred embodiment, for the enzymatic conversion of riboflavin into FMN.

In another preferred embodiment, the enzymatic conversion of riboflavin into FMN is achieved by making use of a phosphotransferase with an alcohol group as acceptor (EC 2.7.1.-).

In a preferred embodiment, the enzymatic conversion of riboflavin into FMN is achieved by making use of an erythritol kinase (2.7.1.27) or a glycerol kinase (2.7.1.30).

Erythritol kinases (2.7.1.27) are enzymes which catalyze the following reaction:

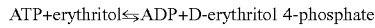
ATP+erythritol⇆ADP+D-erythritol 4-phosphate

This enzyme has been described, e.g., in *Brucella abortus* and *Propionibacterium acidipropionici.*

Glycerol kinases (2.7.1.30) are enzymes which catalyze the following reaction:

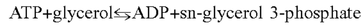
ATP+glycerol⇆ADP+sn-glycerol 3-phosphate

This enzyme is known from a variety of organisms, including eukaryotic and prokaryotic organisms such as plants, animals, fungi and bacteria. The enzyme has, e.g., been described in *Avena sativa, Bacillus subtilis, Bombus* sp., *Bombyx mori, Bos taurus, Candida mycoderma, Candida tropicalis, Cavia porcellus, Cellulomonas* sp., *Clostridium novyi, Columba* sp., *Cucumis sativus, Culex quinquefasciatus, Cyberlindnera jadinii, Debaryomyces hansenii, Drosophila melanogaster, Elizabethkingia meningoseptica, Enterobacter aerogenes, Enterococcus casseliflavus, Enterococcus faecalis, Epidermophyton floccosum, Escherichia coli, Felis catus, Gallus gallus, Geobacillus stearothermophilus, Geotrichum candidum, Gluconobacter oxydans, Haemophilus influenzae, Halobacterium salinarum, Haloferax volcanii, Homo sapiens, Mesocricetus auratus, Microsporum gypseum, Mus musculus, Mycobacterium butyricum, Mycobacterium smegmatis, Mycobacterium* sp., *Mycobacterium tuberculosis, Neurospora crassa, Nocardia asteroides, Oryctolagus cuniculus, Osmerus mordax, Pediococcus pentosaceus, Phaseolus vulgaris, Pisum sativum, Plasmodium falciparum* (UniProt accession number Q8ID14), *Pseudomonas aeruginosa, Rattus norvegicus, Saccharomyces cerevisiae, Shigella sonnei, Staphylococcus aureus, Sus scrofa, Thermococcus kodakarensis, Thermus aquaticus, Thermus thermophilus, Trypanosoma brucei* (UniProt accession number D3KVM3 and Q9NJP9), *Trypanosoma congolense* (UniProt accession number Q75T26), *Trypanosoma vivax* (UniProt accession number B01530), *Vicia faba, Vigna radiata* var. *radiata, Wickerhamomyces anomalus* and *Zea mays.*

In another preferred embodiment, the enzymatic conversion of riboflavin into FMN is achieved by making use of a phosphotransferase with a phosphate group as acceptor (EC 2.7.4-).

In a preferred embodiment, the enzymatic conversion of riboflavin into FMN is achieved by making use of isopentenyl phosphate kinase (EC 2.7.4.26).

Isopentenyl phosphate kinases (EC 2.7.4.26) are enzymes which catalyze the following reaction:

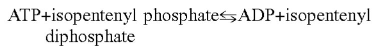

This enzyme has, e.g., been described in *Haloferax volcanii* (UniProt accession number D4GWT7), *Mentha* x *piperita* (SwissProt accession number P56848), *Methanocaldococcus jannaschii* (SwissProt accession number Q60352), *Methanothermobacter* thermautotrophicus (UniProt O26153), and *Thermoplasma acidophilum* (UniProt accession number Q9HLX1).

In another preferred embodiment, the enzymatic conversion of riboflavin into FMN is achieved by making use of a bifunctional riboflavin kinase/FMN adenylyltransferase (ribF).

Generally, riboflavin is converted into catalytically active cofactors (FAD and FMN) by the actions of riboflavin kinase EC 2.7.1.26, which converts it into FMN, and FAD synthetase EC 2.7.7.2, which adenylates FMN to FAD. Eukaryotes usually have two separate enzymes, while most prokaryotes have a single bifunctional protein that can carry out both catalyses.

ribF is a bifunctional enzyme having a riboflavin kinase activity and an FMN adenylyltransferase activity.

Generally, enzymes having a riboflavin kinase activity are enzymes which are classified as riboflavin kinases (EC 2.7.1.26) while enzymes having an FMN adenylyltransferase activity are enzymes which are classified as FMN adenylyltransferases (EC 2.7.7.2).

Riboflavin kinases (EC 2.7.1.26) are enzymes which catalyze the following reaction:

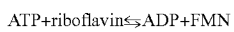

This enzyme is known from a variety of organisms, including eukaryotic and prokaryotic organisms such as plants, animals, fungi and bacteria. The enzyme has, e.g., been described in *Arabidopsis thaliana, Bacillus subtilis, Bos taurus, Corynebacterium ammoniagenes, Homo sapiens*, Megasphaera elsdenii, *Mus musculus, Neurospora crassa, Nicotiana tabacum, Rattus norvegicus, Saccharomyces cerevisiae, Schizosaccharomyces pombe* (UniProt accession number O74866), *Streptomyces davawensis* (Swissprot accession number A3FM23) and *Vigna radiata.*

FMN adenylyltransferases (EC 2.7.7.2) are enzymes which catalyze the following reaction:

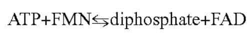

This enzyme is known from a variety of organisms, including eukaryotic and prokaryotic organisms such as plants, animals, fungi and bacteria. The enzyme has, e.g., been described in *Arabidopsis thaliana, Bacillus subtilis* (UniProt accession number P54575), *Bos taurus, Candida glabrata* (UniProt accession number Q6FNA9), *Corynebacterium ammoniagenes, Homo sapiens, Methanocaldococcus jannaschii* (UniProt accession number Q58579), *Nicotiana tabacum, Rattus norvegicus, Saccharomyces cerevisiae, Streptomyces davawensis* and *Thermotoga maritima.*

In a preferred embodiment, the bifunctional enzyme having a riboflavin kinase activity and an FMN adenylyltransferase activity is the enzyme encoded by the *E. coli*'s ribF gene (SEQ ID NO: 34). This enzyme catalyzes the following reactions:

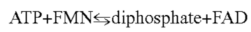

ATP+FMN⇆diphosphate+FAD

In a preferred embodiment of the present invention the bifunctional enzyme having a riboflavin kinase activity and an FMN adenylyltransferase activity is an enzyme comprising an amino acid sequence of SEQ ID NO: 34 or a sequence which is at least n % identical to SEQ ID NO: 34 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting riboflavin into FMN. As regards the determination of the sequence identity, the same applies as has been set forth above.

In another preferred embodiment, the enzymatic conversion of riboflavin into FMN is achieved by making use of a variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived.

Preferably, such a variant is a variant wherein the activity in converting riboflavin into FMN over the corresponding bifunctional riboflavin kinase/FMN adenylyltransferase from which it is derived is improved while the FMN adenylyltransferase activity is not increased. In another preferred embodiment, the latter activity may be reduced over the corresponding activity of a bifunctional riboflavin kinase/FMN adenylyltransferase from which it is derived.

Serrano et al. (Int. J. Mol. Sci. 13 (2012), 14492-14517) recently identified two positions in the *Corynebacterium ammoniagenes* bifunctional riboflavin kinase/FMN adenylyltransferase, i.e., H28 and H31, which, when mutated, lead to an improved activity in converting riboflavin into FMN over the corresponding bifunctional riboflavin kinase/FMN adenylyltransferase from which it is derived while the FMN adenylyltransferase activity of converting FMN into FAD was not affected or even reduced.

Based on this knowledge, it is possible for the skilled person to provide variants of a bifunctional riboflavin kinase/FMN adenylyltransferase (ribF) from bifunctional riboflavin kinase/FMN adenylyltransferase (ribF) enzymes from other organisms which show an improved activity in converting riboflavin into FMN (while, preferably, the FMN adenylyltransferase activity of converting FMN into FAD is not affected or even reduced).

The enzymatic activity of a bifunctional riboflavin kinase/FMN adenylyltransferase (ribF) to convert riboflavin into FMN and to convert FMN into FAD may be determined by methods known to the person skilled in the art.

In a preferred embodiment, the variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived is a variant having an amino acid sequence as shown in SEQ ID NO: 34 or an amino acid sequence having at least 30% sequence identity to SEQ ID NO: 34, in which one or more amino acid residues at a position selected from the group consisting of positions 29 and 32 in the amino acid sequence shown in SEQ ID NO: 34 or at a position corresponding to any of these positions, are substituted with another amino acid residue or deleted or wherein an insertion has been effected at one or more of these positions.

As regards the determination of the sequence identity, the same applies as has been set forth above.

Such variants can be produced by starting out from any known bifunctional riboflavin kinase/FMN adenylyltransferase (ribF) enzyme, e.g. any known naturally occurring bifunctional riboflavin kinase/FMN adenylyltransferase (ribF) enzyme, and by effecting the amino acid substitution(s) at the position(s) indicated above according to routine measures, such as site directed mutagenesis.

In a more preferred embodiment, the variant is a variant wherein (1) an amino acid residue at position 29 in the amino acid sequence shown in SEQ ID NO: 34 or at a position corresponding to this position, is deleted or substituted with alanine; and/or (2) an amino acid residue at position 32 in the amino acid sequence shown in SEQ ID NO: 34 or at a position corresponding to this position, is deleted or substituted with serine or alanine.

The Pathways for the Provision of 3-Methylcrotonic Acid which is then Further Converted into Isobutene As mentioned above, the method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with an FMN prenyl transferase according to the invention as defined above may be embedded in a pathway for the production of isobutene starting from acetyl-CoA via 3-methylcrotonyl-CoA and 3-methylcrotonic acid or via 3-hydroxyisovalerate (HIV) and 3-methylcrotonic acid. The corresponding reactions are schematically shown in FIG. 1 and will be described in more detail in the following.

The Enzymatic Conversion of 3-Hydroxyisovalerate (HIV) into 3-Methylcrotonic Acid: Step II as Shown in FIG. 1

The 3-methylcrotonic acid which is converted according to the method of the present invention into isobutene may itself be provided by an enzymatic reaction.

According to the present invention, the 3-methylcrotonic acid can be provided via different routes which are schematically shown in FIG. 1.

Figure 10:
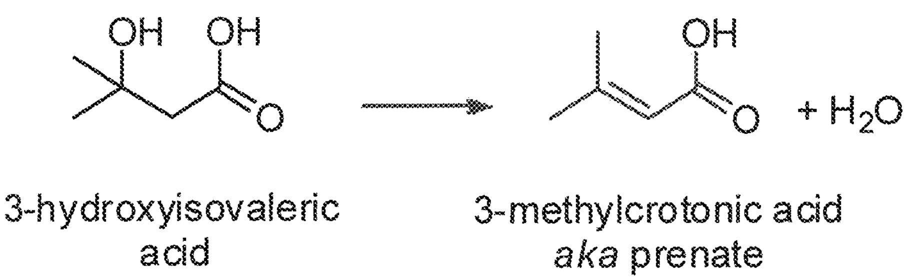

Thus, according to one option, the 3-methylcrotonic acid may itself be provided by the enzymatic conversion of 3-hydroxyisovalerate (HIV) into 3-methylcrotonic acid. The enzymatic conversion of 3-hydroxyisovalerate (HIV) into 3-methylcrotonic acid (step II as shown in FIG. 1) is schematically illustrated in FIG. 10.

According to the present invention, the enzymatic conversion of 3-hydroxyisovalerate (HIV) into said 3-methylcrotonic acid preferably makes use of an enzyme catalyzing the dehydration of a β-hydroxy acid (i.e., e.g., 3-hydroxyisovalerate (HIV)) into an α,β-unsaturated acid (i.e., e.g., 3-methylcrotonic acid). The term "dehydration" generally refers to a reaction involving the removal of $H_2O$. Enzymes catalyzing 3-hydroxyisovalerate (HIV) dehydration are enzymes which catalyze the reaction as shown in FIG. 10. Preferably, such an enzyme belongs to the family of hydrolyases (EC 4.2.-.-).

Preferred examples of such enzymes which are classified as EC 4.2.-.- (i.e., hydro-lyases) are:

aconitase (EC 4.2.1.3);

fumarase (EC 4.2.1.2); and enoyl-CoA hydratase/dehydratease (EC 4.2.1.17).

The Enzymatic Condensation of Acetone and Acetyl-CoA into 3-Hydroxyisovalerate (HIV): Step III as Shown in FIG. 1

Figure 11:
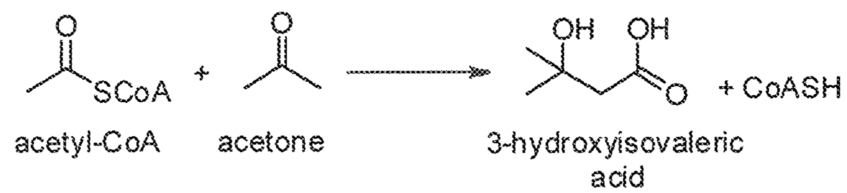

The 3-hydroxyisovalerate (HIV) which is converted according to the method of the present invention into 3-methylcrotonic acid may itself be provided by an enzymatic reaction, namely the enzymatic condensation of acetone and acetyl-CoA into said 3-hydroxyisovalerate (HIV). The condensation of acetone and acetyl-CoA into said 3-hydroxyisovalerate (HIV) (step III as shown in FIG. 1) is schematically illustrated in FIG. 11.

Thus, the present invention also relates to a method for producing isobutene from acetone in which acetone is first condensed with acetyl-CoA into 3-hydroxyisovalerate (HIV) which is then converted into 3-methylcrotonic acid. Further, 3-methylcrotonic acid is then converted into isobutene as described herein above.

According to the present invention, the condensation of acetone and acetyl-CoA into 3-hydroxyisovalerate (HIV) preferably makes use of an enzyme which is capable of catalyzing the formation of a covalent bond between the carbon atom of the oxo (i.e., the C═O) group of acetone and acetyl-CoA, in particular the methyl group of acetyl-CoA. According to this reaction scheme, the oxo group of acetone reacts as an electrophile and the methyl group of acetyl-CoA reacts as a nucleophile. The general reaction of the conversion of acetone and acetyl-CoA is shown in FIG. 11. Enyzmes which are capable of enzymatically condensing acetone and acetyl-CoA into 3-hydroxyisovalerate (HIV) are known in the art and have, e.g., been described in WO 2011/032934.

Preferably, the enzyme employed in the enzymatic condensation of acetone and acetyl-CoA into 3-hydroxyisovalerate (HIV) is an enzyme with the activity of a HMG CoA synthase (EC 2.3.3.10) and/or a PksG protein and/or an enzyme with the activity of a C—C bond cleavage/condensation lyase (preferably enzymes classified as isopropylmalate synthase (EC 2.3.3.13), as homocitrate synthase (EC 2.3.3.14) or as 4-hydroxy-2-ketovalerate aldolase (EC 4.1.3.39)), such as a HMG CoA lyase (EC 4.1.3.4).

The Enzymatic Conversion of Acetoacetate into Acetone: Step IV as Shown in FIG. 1

Figure 12:
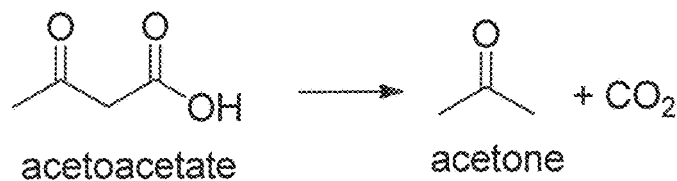

The acetone which is converted according to the method of the present invention into 3-hydroxyisovalerate (HIV) may itself be provided by an enzymatic reaction, namely the enzymatic conversion of acetoacetate into acetone. The conversion of acetoacetate into acetone (step IV as shown in FIG. 1) is schematically illustrated in FIG. 12. This reaction is a decarboxylation reaction and is a natural occurring reaction in organisms capable of producing acetone, i.e., organisms of the genus Clostridia.

Thus, the present invention also relates to a method for producing isobutene from acetoacetate in which acetoacetate is first converted into acetone which is then condensed with acetyl-CoA into 3-hydroxyisovalerate (HIV) which is then converted into 3-methylcrotonic acid as described herein above. Further, said 3-methylcrotonic acid is then converted into isobutene as described herein above.

According to the present invention, the conversion of acetoacetate into said acetone preferably makes use of an acetoacetate decarboxylase (EC 4.1.1.4).

The Enzymatic Conversion of Acetoacetyl-CoA into Acetoacetate: Step Va and Step Vb as Shown in FIG. 1

Figure 13:
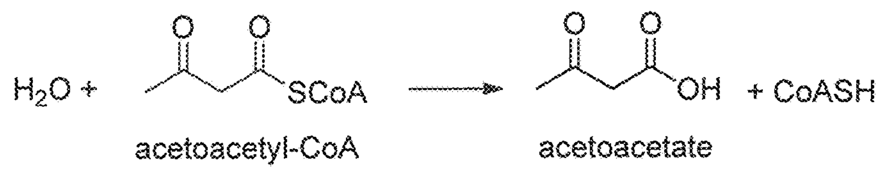
Figure 14:
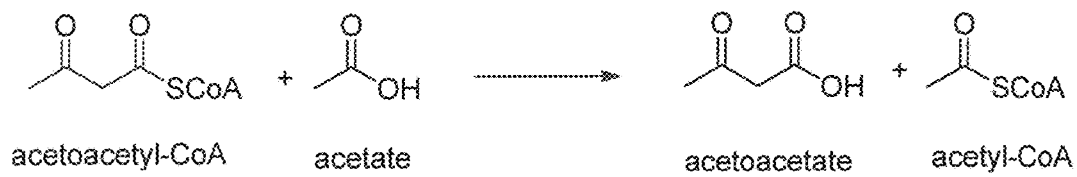

The acetoacetate which is converted according to the method of the present invention into acetone may itself be provided by an enzymatic reaction, namely the enzymatic conversion of acetoacetyl-CoA into acetoacetate. The conversion of acetoacetyl-CoA into acetoacetate can be achieved by two different routes. One possibility is the conversion of acetoacetyl-CoA into acetoacetate by hydrolysing the CoA thioester of acetoacetyl-CoA into acetoacetate. This reaction (step Va as shown in FIG. 1) is schematically illustrated in FIG. 13. In another, more preferred, aspect the CoA group of acetoacetyl-CoA is transferred on acetate, resulting in the formation of acetoacetate and acetyl-CoA. This reaction (step Vb as shown in FIG. 1) is schematically illustrated in FIG. 14.

Thus, the present invention also relates to a method for producing isobutene from acetoacetyl-CoA in which acetoacetyl-CoA is first converted into acetoacetate which is then converted into acetone which is then condensed with acetyl-CoA into 3-hydroxyisovalerate (HIV) which is then converted into 3-methylcrotonic acid as described herein above. Further, said 3-methylcrotonic acid is then converted into isobutene as described herein above.

As mentioned, in one aspect, the CoA thioester of acetoacetyl-CoA is hydrolyzed to result in acetoacetate. According to this aspect of the present invention, the enzymatic conversion of acetoacetyl-CoA into acetoacetate is achieved by preferably making use of an acetoacetyl-CoA hydrolase (EC 3.1.2.11) which naturally catalyzes this reaction.

As mentioned, in another, more preferred, possibility, the CoA group of acetoacetyl-CoA is transferred on acetate, resulting in the formation of acetoacetate and acetyl-CoA. According to this possibility of the present invention, the enzymatic conversion of acetoacetyl-CoA into acetoacetate is achieved by preferably making use of an enzyme which is capable of transferring the CoA group of acetoacetyl-CoA on acetate.

Preferably, such an enzyme capable of transferring the CoA group of acetoacetyl-CoA on acetate belongs to the family of CoA transferases (EC 2.8.3.-).

Thus, the present invention relates to a method for the enzymatic conversion of acetoacetyl-CoA into acetoacetate by making use of an enzyme capable of transferring the CoA group of acetoacetyl-CoA on acetate, preferably a CoA transferase (EC 2.8.3.-). A preferred example of an enzyme catalysing the conversion of acetoacetyl-CoA into acetoacetate which can be employed in the method of the present invention is an enzyme classified as an acetate CoA transferase (EC 2.8.3.8).

The Enzymatic Conversion of 3-Methylcrotonyl-CoA into 3-Methyicrotonic Acid: Step VI as Shown in FIG. 1

The 3-methyicrotonic acid can be provided by another possible route which is described in the following.

Figure 15:
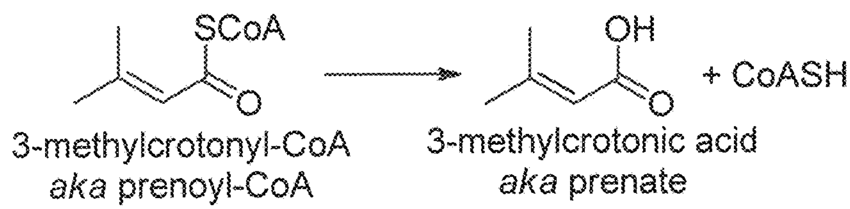

Thus, in another embodiment, the 3-methylcrotonic acid which is converted into isobutene may itself be provided by another enzymatic reaction, namely the enzymatic conversion of 3-methylcrotonyl-CoA into 3-methylcrotonic acid. The conversion of 3-methylcrotonyl-CoA into 3-methylcrotonic acid (step VI as shown in FIG. 1) is schematically illustrated in FIG. 15.

The conversion of 3-methylcrotonyl-CoA into 3-methylcrotonic acid can, e.g., be achieved in different ways, e.g., by three alternative enzymatic routes described in the following and as shown in FIG. 1 (step VIa, step VIb or step VIc as shown in FIG. 1).

Thus, the enzymatic conversion of 3-methylcrotonyl-CoA into 3-methylcrotonic acid may be achieved by (a) a single enzymatic reaction in which 3-methylcrotonyl-CoA is directly converted into 3-methylcrotonic acid, preferably by making use of a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step VIa as shown in FIG. 1);

(b) a single enzymatic reaction in which 3-methylcrotonyl-CoA is directly converted into 3-methylcrotonic acid, preferably by making use of a thioester hydrolase (EC 3.1.2.-), preferably an acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step VIb as shown in FIG. 1); or (c) two enzymatic steps comprising
  - (i) first enzymatically converting 3-methylcrotonyl-CoA into 3-methylcrotonyl phosphate; and
  - (ii) then enzymatically converting the thus obtained 3-methylcrotonyl phosphate into said 3-methylcrotonic acid (step VIc as shown in FIG. 1).

Figure 16:
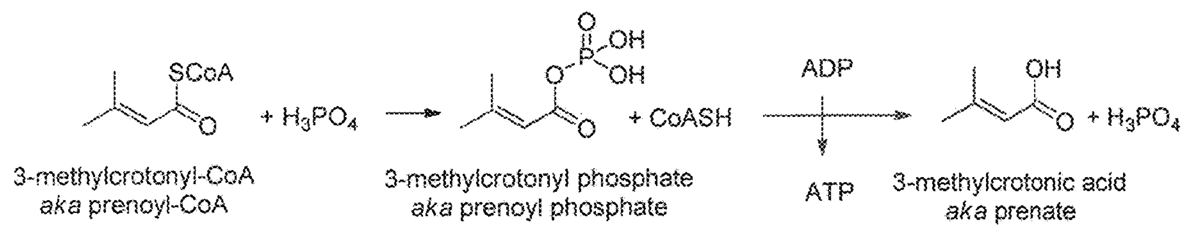

As regards (c), i.e., the enzymatic conversion of 3-methylcrotonyl-CoA into 3-methylcrotonic acid which is achieved by two enzymatic steps comprising (i) first enzymatically converting 3-methylcrotonyl-CoA into 3-methylcrotonyl phosphate; and (ii) then enzymatically converting the thus obtained 3-methylcrotonyl phosphate into said 3-methylcrotonic acid, the corresponding reaction is schematically shown in FIG. 16.

The conversion of 3-methylcrotonyl-CoA into 3-methylcrotonyl phosphate can, e.g., be achieved by the use of a phosphate butyryltransferase (EC 2.3.1.19) or a phosphate acetyltransferase (EC 2.3.1.8).

The conversion of 3-methylcrotonyl phosphate into 3-methylcrotonic acid can, e.g., be achieved by making use of an enzyme which is classified as EC 2.7.2.-, i.e., a phosphotransferase. Such enzymes use a carboxy group as acceptor. Thus, the conversion of 3-methylcrotonyl phosphate into 3-methylcrotonic acid can, e.g., be achieved by making use of an enzyme with a carboxy group as acceptor (EC 2.7.2.-). In a preferred embodiment, the conversion of 3-methylcrotonyl phosphate into 3-methylcrotonic acid is achieved by the use of a propionate kinase (EC 2.7.2.15), an acetate kinase (EC 2.7.2.1), a butyrate kinase (EC 2.7.2.7) or a branched-chain-fatty-acid kinase (EC 2.7.2.14).

As mentioned above, the conversion of 3-methylcrotonyl-CoA into 3-methylcrotonic acid can also be achieved by two alternative conversions wherein 3-methylcrotonyl-CoA is directly converted into 3-methylcrotonic acid.

Figure 17:
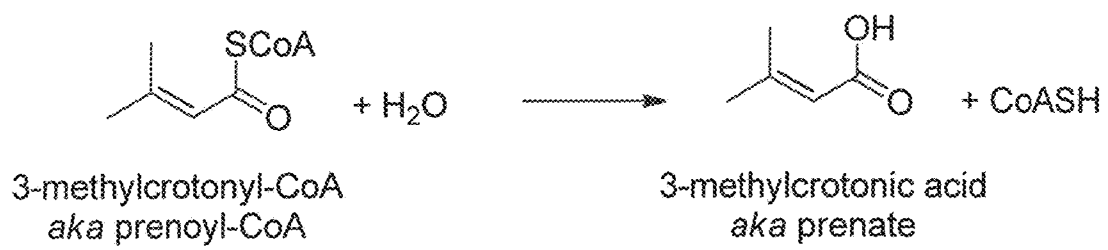

Preferably, in one embodiment, 3-methylcrotonyl-CoA is directly converted into 3-methylcrotonic acid by hydrolyzing the thioester bond of 3-methylcrotonyl-CoA into 3-methylcrotonic acid by making use of an enzyme which belongs to the family of thioester hydrolases (in the following referred to as thioesterases (EC 3.1.2.-)). This reaction is schematically shown in FIG. 17.

Examples for preferred thioester hydrolases (EC 3.1.2.-) are an acetyl-CoA hydrolase (EC 3.1.2.1), an ADP-dependent short-chain-acyl-CoA hydrolase (EC 3.1.2.18) and an acyl-CoA hydrolase (EC 3.1.2.20) (step VIb as shown in FIG. 1).

Figure 18:
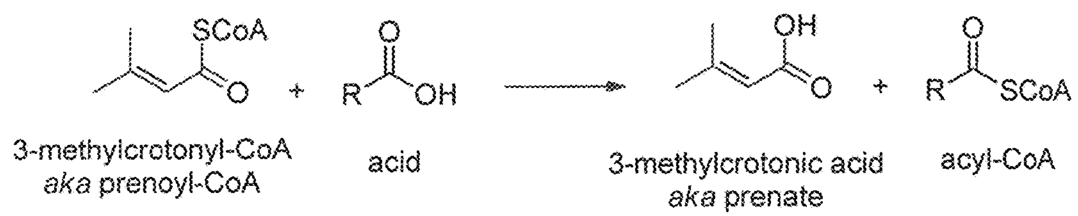

In an alternative embodiment, 3-methylcrotonyl-CoA is directly converted into 3-methylcrotonic acid, preferably by making use of an enzyme which belongs to the family of CoA-transferases (EC 2.8.3.-). This reaction is schematically shown in FIG. 18.

Examples for preferred CoA transferases (EC 2.8.3.-) are a propionate:acetate-CoA transferase (EC 2.8.3.1), an acetate CoA-transferase (EC 2.8.3.8) and a succinyl-CoA:acetate CoA-transferase (EC 2.8.3.18) (step Via as shown in FIG. 1).

Thioesterases (TEs; also referred to as thioester hydrolases) are enzymes which are classified as EC 3.1.2. Presently thioesterases are classified as EC 3.1.2.1 through EC 3.1.2.30 while TEs which are not yet classified/unclassified are grouped as enzymes belonging to EC 3.1.2.-. Cantu et al. (Protein Science 19 (2010), 1281-1295) describe that there are 23 families of thioesterases which are unrelated to each other as regards the primary structure. However, it is assumed that all members of the same family have essentially the same tertiary structure. Thioesterases hydrolyze the thioester bond between a carbonyl group and a sulfur atom.

In a preferred embodiment, a thioesterase employed in a method according to the present invention for converting 3-methylcrotonyl-CoA into 3-methylcrotonic acid is selected from the group consisting of:

acetyl-CoA hydrolase (EC 3.1.2.1);
palmitoyl-CoA hydrolase (EC 3.1.2.2);
3-hydroxyisobutyryl-CoA hydrolase (EC 3.1.2.4);
oleoyl-[acyl-carrier-protein] hydrolase (EC 3.1.2.14);
ADP-dependent short-chain-acyl-CoA hydrolase (EC 3.1.2.18);
ADP-dependent medium-chain-acyl-CoA hydrolase (EC 3.1.2.19); and
acyl-CoA hydrolase (EC 3.1.2.20).

As described above, the direct conversion of 3-methylcrotonyl-CoA into 3-methylcrotonic acid can also be achieved by making use of an enzyme which is classified as a CoA-transferase (EC 2.8.3.-) capable of transferring the CoA group of 3-methylcrotonyl-CoA to a carboxylic acid.

CoA-transferases are found in organisms from all lines of descent. Most of the CoA-transferases belong to two well-known enzyme families (referred to in the following as families I and II) and there exists a third family which had been identified in anaerobic metabolic pathways of bacteria. A review describing the different families can be found in Heider (FEBS Letters 509 (2001), 345-349).

Family I contains, e.g., the following CoA-transferases:

For 3-oxo acids: enzymes classified in EC 2.8.3.5 or EC 2.8.3.6;
For short chain fatty acids: enzymes classified in EC 2.8.3.8 or EC 2.8.3.9;
For succinate: succinyl-CoA:acetate CoA-transferases, i.e. enzymes classified in EC 2.8.3.18 (see also Mullins et al., Biochemistry 51(2012), 8422-34; Mullins et al., J. Bacteriol. 190 (2006), 4933-4940).

Most enzymes of family I naturally use succinyl-CoA or acetyl-CoA as CoA donors. These enzymes contain two dissimilar subunits in different aggregation states. Two conserved amino acid sequence motives have been identified:

Prosites entry PS01273 (http://prosite.expasy.org/cgi-bin/prosite/prosite-search-ac?PD0000980)
COA_TRANSF_1, PS01273; Coenzyme A transferases signature 1 (PATTERN)
Consensus pattern:
[DN]-[GN]-x(2)-[LIVMFA](3)-G-G-F-x(3)-G-x-P
and
Prosites entries PS01273 (http://prosite.expasy.org/cgi-bin/prosite/prosite-search-ac?PD0000980)
COA_TRANSF_2, PS01274; Coenzyme A transferases signature 2 (PATTERN) Consensus pattern:
[LF]-[HQ]-S-E-N-G-[LIVF](2)-[GA]
E (glutamic acid) is an active site residue.

The family II of CoA-transferases consists of the homodimeric α-subunits of citrate lyase (EC 2.8.3.10) and citramalate lyase (EC 2.8.3.11). These enzymes catalyse the transfer of acyl carrier protein (ACP) which contains a covalently bound CoA-derivative. It was shown that such enzymes also accept free CoA-thioester in vitro, such as acetyl-CoA, propionyl-CoA, butyryl-CoA in the case of citrate lyase (Dimroth et al., Eur. J. Biochem. 80 (1977), 479-488) and acetyl-CoA and succinyl-CoA in the case of citramalate lyase (Dimroth et al., Eur. J. Biochem. 80 (1977), 469-477).

According to Heider (loc. cit.) family III of CoA-transferases consists of formyl-CoA: oxalate CoA-transferase, succinyl-CoA:(R)-benzylsuccinate CoA-transferase, (E)-cinnamoyl-CoA:(R)-phenyllactate CoA-transferase and butyrobetainyl-CoA:(R)-carnitine CoA-transferase. A further member of family III is succinyl-CoA:L-malate CoA-transferase whose function in autrophic $CO_2$ fixation of Chloroflexus *aurantiacus* is to activate L-malate to its CoA thioester with succinyl-CoA as the CoA donor (Friedman S. et al. J. Bacteriol. 188 (2006), 2646-2655). The amino acid sequences of the CoA-tranferase of this family show only a low degree of sequence identity to those of families I and II. These CoA-transferases occur in prokaryotes and eukaryotes.

In a preferred embodiment the CoA-transferase employed in a method according to the present invention is a CoA-transferase which belongs to family I or II as described herein-above.

Preferably, the CoA-transferase employed in a method according to the present invention for the direct conversion of 3-methylcrotonyl-CoA into 3-methylcrotonic acid is selected from the group consisting of:

propionate:acetate-CoA transferase (EC 2.8.3.1);
acetate CoA-transferase (EC 2.8.3.8); and
butyrate-acetoacetate CoA-transferase (EC 2.8.3.9).

Figure 19:
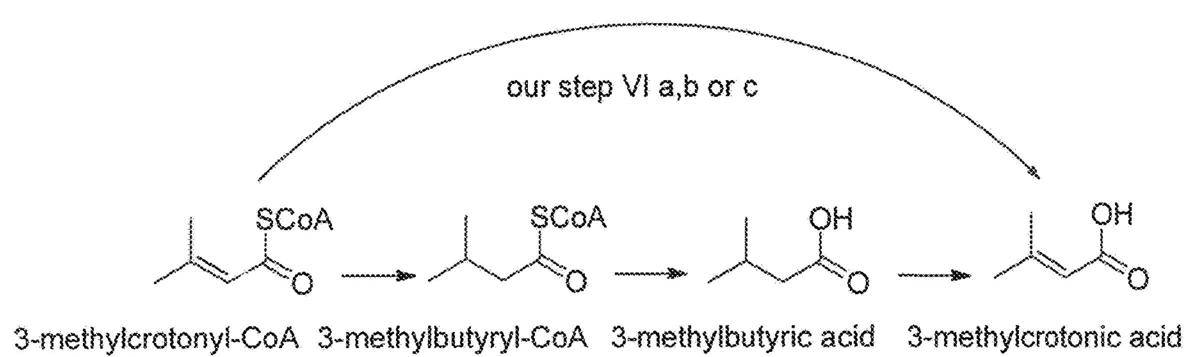

The Enzymatic Conversion of 3-Methylcrotonyl-CoA into 3-Methylcrotonic Acid: An Alternative Route to the Above-Described Step VI In another preferred embodiment, the conversion of 3-methylcrotonyl-CoA into 3-methylcrotonic acid is achieved by an alternative route wherein 3-methylcrotonyl-CoA is first enzymatically converted into 3-methylbutyryl-CoA which is then enzymatically converted into 3-methylbutyric acid which is then ultimately converted into 3-methylcrotonic acid. This alternative conversion of 3-methylcrotonyl-CoA into 3-methylcrotonic acid via 3-methylbutyryl-CoA and 3-methylbutyric acid is schematically illustrated in FIG. 19.

Accordingly, the present invention relates to a method for producing isobutene from 3-methylcrotonyl-CoA in which 3-methylcrotonyl-CoA is first enzymatically converted into 3-methylbutyryl-CoA which is then enzymatically converted into 3-methylbutyric acid which is then converted into 3-methylcrotonic acid which is then further converted into isobutene as described herein above.

The first enzymatic conversion, i.e., the conversion of 3-methylcrotonyl-CoA into 3-methylbutyryl-CoA, is a desaturation reaction, i.e., reduction of the double bond C═C of 3-methylcrotonyl-CoA into 3-methylbutyryl-CoA. The enzymatic conversion of 3-methylcrotonyl-CoA into 3-methylbutyryl-CoA, i.e. the reduction of the double bond in 3-methylcrotonyl-CoA, can, for example, be achieved by employing an enzyme classified as EC 1.3._._. Enzymes classified as EC 1.3._._ are oxidoreductases acting on the CH—CH group of a donor molecule. This subclass contains enzymes that reversibly catalyze the conversion of a carbon-carbon single bond to a carbon-carbon double bond between two carbon atoms. Sub-classes of EC 1.3 are classified depending on the acceptor. In one preferred embodiment the enzyme is an enzyme which is classified as EC 1.3._._ and which uses NADH or NADPH as co-factor.

In one particularly preferred embodiment the enzyme is an enzyme which uses NADPH as a co-factor. In a preferred embodiment the enzyme is selected from the group consisting of:

acyl-CoA dehydrogenase (NADP+) (EC 1.3.1.8);
enoyl-[acyl-carrier-protein] reductase (NADPH, Si-specific) (EC 1.3.1.10);
cis-2-enoyl-CoA reductase (NADPH) (EC 1.3.1.37);
trans-2-enoyl-CoA reductase (NADPH) (EC 1.3.1.38);
enoyl-[acyl-carrier-protein] reductase (NADPH, Re-specific) (EC 1.3.1.39); and
crotonyl-CoA reductase (EC 1.3.1.86).

The second enzymatic conversion, i.e., the conversion of 3-methylbutyryl-CoA into 3-methylbutyric acid, can be achieved by different enzymatic conversions. One possibility is the direct conversion via a hydrolysis reaction. Another possibility is the direct conversion via a reaction catalyzed by a CoA-transferase and a third possibility is a two-step conversion via 3-methylbutyryl phosphate.

Thus, according to the present invention, the enzymatic conversion of 3-methylbutyryl-CoA into 3-methylbutyric acid is achieved by (a) a single enzymatic reaction in which 3-methylbutyryl-CoA is directly converted into 3-methylbutyric acid, preferably by making use of a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18);
(b) a single enzymatic reaction in which 3-methylbutyryl-CoA is directly converted into 3-methylbutyric acid, preferably by making use of a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20); or
(c) two enzymatic steps comprising
    (i) first enzymatically converting 3-methylbutyryl-CoA into 3-methylbutyryl phosphate; and
    (ii) then enzymatically converting the thus obtained 3-methylbutyryl phosphate into said 3-methylbutyric acid.

As regards the enzyme capable of converting 3-methylbutyryl-CoA into 3-methylbutyryl phosphate and the enzyme capable of converting 3-methylbutyryl phosphate into said 3-methylbutyric acid, the same applies as has been set forth above in connection with the enzymatic conversion of step VIa, step VIb and step VIc according to the invention.

The third enzymatic conversion, i.e., the conversion of 3-methylbutyric acid into 3-methylcrotonic acid can, e.g., be achieved by a 2-enoate reductase (EC 1.3.1.31).

The Enzymatic Conversion of 3-Methylalutaconyl-CoA into 3-Methylcrotonyl-CoA: Step VII as Shown in FIG. 1

Figure 20:
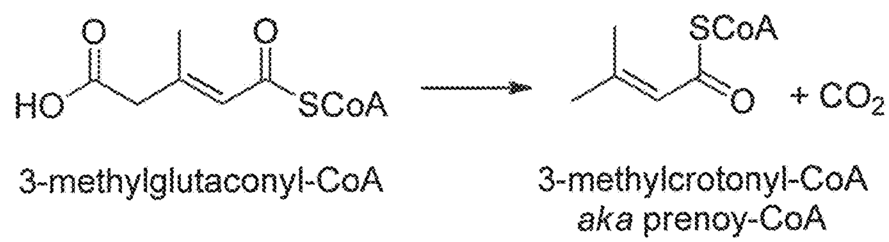

The 3-methylcrotonyl-CoA which is converted according to the method of the present invention into 3-methylcrotonic acid according to any of the above described methods (and further converted according to the method of the present invention into isobutene according to any of the above described methods) may itself be provided by an enzymatic reaction, namely the enzymatic conversion of 3-methylglutaconyl-CoA into 3-methylcrotonyl-CoA. The conversion of 3-methylglutaconyl-CoA into 3-methylcrotonyl-CoA is schematically illustrated in FIG. 20.

Accordingly, the present invention relates to a method for producing isobutene from 3-methylglutaconyl-CoA in which 3-methylglutaconyl-CoA is first converted into 3-methylcrotonyl-CoA which is then further converted into 3-methylcrotonic acid which is then further converted into isobutene as described herein above.

The conversion of 3-methylglutaconyl-CoA into 3-methylcrotonyl-CoA may be catalyzed by different enzymes. According to the present invention, the conversion of 3-methylglutaconyl-CoA into said 3-methylcrotonyl-CoA preferably makes use of (i) a methylcrotonyl-CoA carboxylase (EC 6.4.1.4); or (ii) a geranoyl-CoA carboxylase (EC 6.4.1.5) (as shown in step VII of FIG. 1).

In another preferred embodiment the conversion of 3-methylglutaconyl-CoA via decarboxylation into 3-methylcrotonyl-CoA is catalyzed by a 3-methylglutaconyl-CoA decarboxylase, e.g. a 3-methylglutaconyl-CoA decarboxylase of *Myxococcus xanthus* encoded by the liuB gene. This gene codes for an enzyme having the two subunits AibA and AibB (Li et al., Angew. Chem. Int. Ed. 52 (2013), 1304-1308).

The Enzymatic Conversion of 3-Hydroxy-3-Methylglutaryl-CoA into 3-Methylglutaconyl-CoA: Step VIII as Shown in FIG. 1

Figure 21:
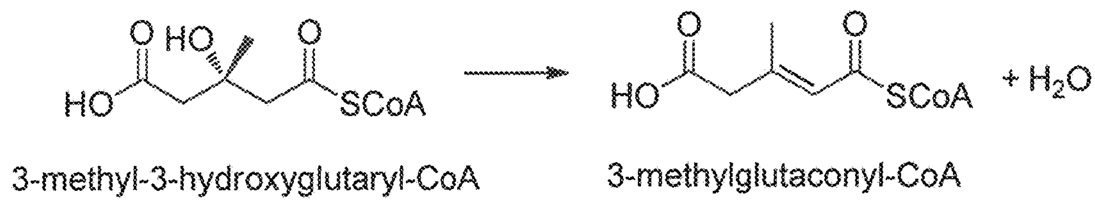

The 3-methylglutaconyl-CoA which is converted into 3-methylcrotonyl-CoA may itself be provided by an enzymatic reaction, namely the enzymatic conversion of 3-hydroxy-3-methylglutaryl-CoA into 3-methylglutaconyl-CoA; see FIG. 21.

Accordingly, the present invention also relates to a method for producing isobutene from 3-hydroxy-3-methylglutaryl-CoA in which 3-hydroxy-3-methylglutaryl-CoA is first converted into 3-methylglutaconyl-CoA which is then converted into 3-methylcrotonyl-CoA which is then further converted into 3-methylcrotonic acid which is then further converted into isobutene as described herein above.

According to the present invention, the enzymatic conversion of 3-hydroxy-3-methylglutaryl-CoA into 3-methylglutaconyl-CoA is an enzymatic dehydration reaction which occurs naturally, and which is catalyzed, e.g., by enzymes classified as 3-methylglutaconyl-coenzyme A hydratase (EC 4.2.1.18). Accordingly, the enzymatic conversion of 3-hydroxy-3-methylglutaryl-CoA into 3-methylglutaconyl-CoA preferably makes use of a 3-methylglutaconyl-coenzyme A hydratase (EC 4.2.1.18) (as shown in step VIII of FIG. 1).

The conversion of 3-hydroxy-3-methylglutaryl-CoA into 3-methylglutaconyl-CoA can also be achieved by making use of a 3-hydroxy-3-methylglutaryl-coenzyme A dehydratase activity which has been identified, e.g., in *Myxococcus xanthus* and which is encoded by the liuC gene (Li et al., Angew. Chem. Int. Ed. 52 (2013), 1304-1308). The 3-hydroxy-3-methylglutaryl-coenzyme A dehydratase derived from *Myxococcus xanthus* has the Uniprot Accession number Q1 D5Y4.

The enzymatic conversion of 3-hydroxy-3-methylglutaryl-CoA into 3-methylglutaconyl-CoA can also be achieved by making use of a 3-hydroxyacyl-CoA dehydratase or an enoyl-CoA hydratase. 3-hydroxyacyl-CoA dehydratases and enoyl-CoA hydratases catalyze the same reaction while the name of one of these enzymes denotes one direction of the corresponding reaction while the other name denotes the reverse reaction. As the reaction is reversible, both enzyme names can be used.

3-hydroxyacyl-CoA dehydratases and enoyl-CoA hydratases belong to enzymes classified as EC 4.2.1.-.

The Enzymatic Conversion of Acetoacetyl-CoA into 3-Hydroxy-3-Methylglutaryl-CoA: Step IX as Shown in FIG. 1

Figure 22:
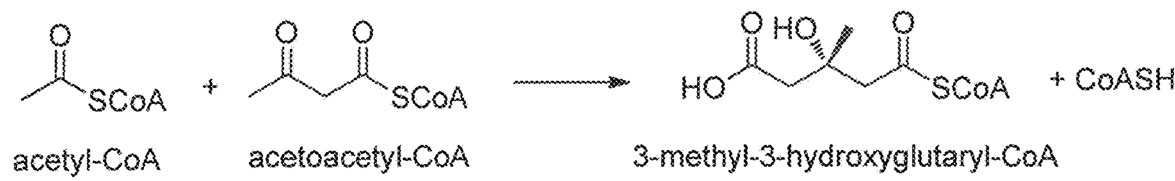

The 3-hydroxy-3-methylglutaryl-CoA which is converted into 3-methylglutaconyl-CoA may itself be provided by an enzymatic reaction, namely the enzymatic condensation of acetoacetyl-CoA and acetyl-CoA into 3-hydroxy-3-methylglutaryl-CoA; see FIG. 22.

Accordingly, the present invention also relates to a method for producing isobutene from acetoacetyl-CoA and acetyl-CoA in which acetoacetyl-CoA and acetyl-CoA are first condensed into 3-hydroxy-3-methylglutaryl-CoA which is then converted into 3-methylglutaconyl-CoA which is then converted into 3-methylcrotonyl-CoA which is then further converted into 3-methylcrotonic acid which is then further converted into isobutene as described herein above.

According to the present invention, the enzymatic condensation of acetoacetyl-CoA and acetyl-CoA into 3-hydroxy-3-methylglutaryl-CoA makes preferably use of a 3-hydroxy-3-methylglutaryl-CoA synthase (see step IX of FIG. 1).

The condensation of acetyl-CoA and acetoacetyl-CoA is a reaction which is naturally catalyzed by the enzyme 3-hydroxy-3-methylglutaryl-CoA synthase (also referred to as HMG-CoA synthase). Thus, preferably, the condensation of acetyl-CoA and acetoacetyl-CoA into 3-hydroxy-3-methylglutaryl-CoA makes use of a 3-hydroxy-3-methylglutaryl-CoA synthase (also referred to as HMG-CoA synthase). HMG-CoA synthases are classified in EC 2.3.3.10 (formerly, HMG-CoA synthase has been classified as EC 4.1.3.5 but has been transferred to EC 2.3.3.10). The term “HMG-CoA synthase” refers to any enzyme which is able to catalyze the reaction where acetyl-CoA condenses with acetoacetyl-CoA to form 3-hydroxy-3-methylglutaryl-CoA (HMG-CoA) (see FIG. 22). HMG-CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG-CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases.

The Enzymatic Conversion of Acetyl-CoA into Acetoacetyl-CoA: Steps XIII, XIV and XV as Shown in FIG. 1

Figure 23:
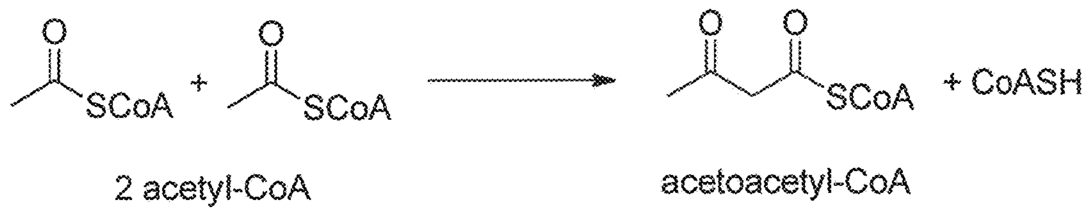

The acetoacetyl-CoA which is either converted into 3-hydroxy-3-methylglutaryl-CoA or which is converted into acetoacetate may itself be provided by an enzymatic reaction, namely the enzymatic conversion of acetyl-CoA into acetoacetyl-CoA. According to the present invention, the conversion of acetyl-CoA into said acetoacetyl-CoA can be achieved by different routes. One possibility is to first convert acetyl-CoA into malonyl-CoA (step XIV as shown in FIG. 1) and then to further condense said malonyl-CoA and acetyl-CoA into acetoacetyl-CoA (step XV as shown in FIG. 1). Another possibility is to directly condense in a single enzymatic reaction two molecules of acetyl-CoA into acetoacetyl-CoA (step XIII as shown in FIG. 1). These reactions are schematically shown in FIG. 23 (step XIII), FIG. 24 (step XIV) and FIG. 25 (step XV), respectively.

Thus, the present invention also relates to a method for producing isobutene from acetyl-CoA in which acetyl-CoA is first converted into acetoacetyl-CoA by any of the above-mentioned routes which is then condensed with acetyl-CoA into 3-hydroxy-3-methylglutaryl-CoA which is then converted into 3-methylglutaconyl-CoA which is then converted into 3-methylcrotonyl-CoA which is then further converted into 3-methylcrotonic acid which is then further converted into isobutene as described herein above.

Moreover, the present invention also relates to a method for producing isobutene from acetyl-CoA in which acetyl-CoA is first converted into acetoacetyl-CoA by any of the above-mentioned routes by any of the above-mentioned routes which is then converted into acetoacetate which is then converted into acetone which is then condensed with acetyl-CoA into 3-hydroxyisovalerate (HIV) which is then converted into 3-methylcrotonic acid as described herein above. Further, said 3-methylcrotonic acid is then further converted into isobutene as described herein above.

According to the present invention, the enzymatic conversion of acetyl-CoA into malonyl-CoA preferably makes use of an acetyl-CoA carboxylase (EC 6.4.1.2) (step XIV as shown in FIG. 1). This naturally occurring reaction fixes $CO_2$ on acetyl-CoA utilizing ATP resulting in malonyl-CoA.

Moreover, according to the present invention, the enzymatic condensation of malonyl-CoA and acetyl-CoA into said acetoacetyl-CoA preferably makes use of an acetoacetyl-CoA synthase (EC 2.3.1.194) (step XV as shown in FIG. 1). This is a natural occurring reaction and condenses malonyl-CoA and acetyl-CoA in a decarboxylation reaction.

Alternatively, the enzymatic conversion of acetyl-CoA into said acetoacetyl-CoA consists of a single enzymatic reaction in which acetyl-CoA is directly converted into acetoacetyl-CoA by the enzymatic condensation of two molecules of acetyl-CoA into acetoacetyl-CoA. Preferably, the enzymatic conversion of acetyl-CoA into acetoacetyl-CoA is achieved by making use of an acetyl-CoA acetyltransferase (EC 2.3.1.9). This reaction is a naturally occurring reaction.

The Enzymatic Recycling of Metabolites Occurring in the Pathway of the Present Invention: Steps Xa, Xb, XI and XII as Shown in FIG. 1

The above-described method of the present invention for producing isobutene from acetyl-CoA may be supplemented by one or more of the following reactions as shown in step Xa, step Xb, step XI and step XII of FIG. 1.

These steps relate to alternative bioconversions which may occur concomitantly to any of the above-described methods for producing isobutene.

Figure 27:
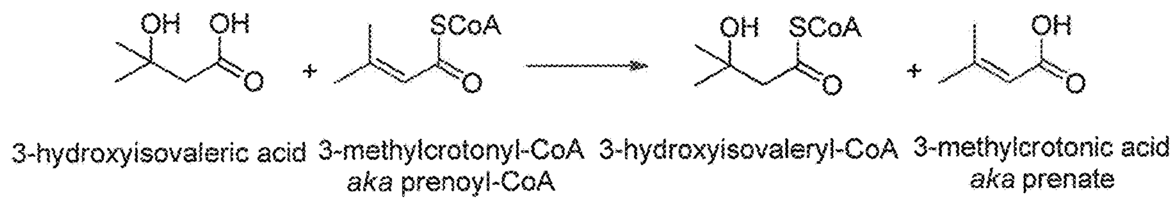
Figure 28:
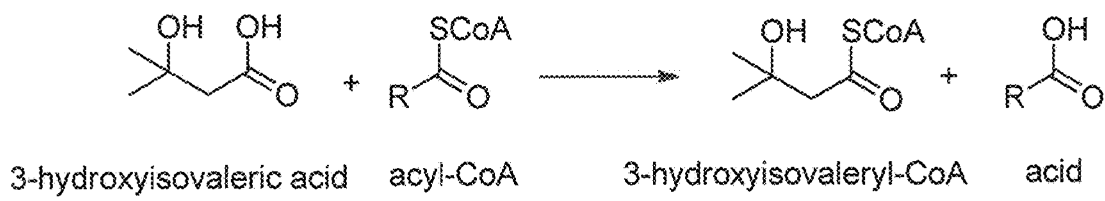
Figure 29:
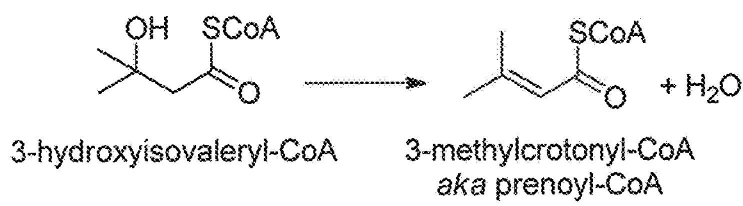
Figure 30:
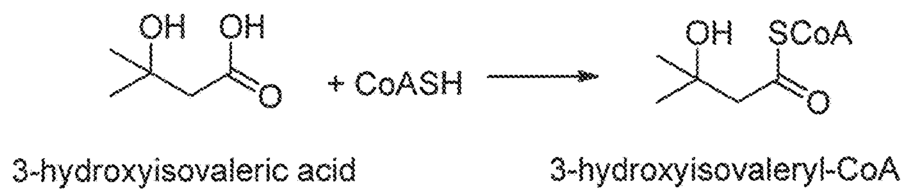

Thus, the present invention relates to any of the above-described methods for producing isobutene from 3-methylcrotonic acid (or from any of the above-described intermediates in the described pathways from acetyl-CoA into isobutene) wherein additionally a) 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 27); and/or
b) 3-hydroxyisovalerate (HIV) is enzymatically converted into 3-hydroxyisovaleryl-CoA (step Xb as schematically shown in FIG. 28); and/or
c) 3-hydroxyisovaleryl-CoA is enzymatically converted into 3-methylcrotonyl-CoA (step XI as schematically shown in FIG. 29); and/or
d) 3-hydroxyisovalerate (HIV) is enzymatically converted into 3-hydroxyisovaleryl-CoA (step XII as schematically shown in FIG. 30).

These reactions which will be described in more detail in the following, may occur concomitantly to any of the above-described methods for producing isobutene are beneficial for several reasons. First, it is known that the hydration of an enoyl-CoA (such as, e.g., 3-methylcrotonyl-CoA) is a favoured reaction in vivo in an aqueous medium. Accordingly, the above reactions represent possibilities which allow to drive the metabolic flux toward the precursor of isobutene, i.e., 3-methylcrotonic acid, even in case the pathway "leaks" into the direction of 3-hydroxyisovalerate (HIV) and/or 3-hydroxyisovaleryl-CoA. Second, the above conversions beneficially involve the conservation of energy into a thioester CoA bond via a transfer of a thioester group.

Figure 26:
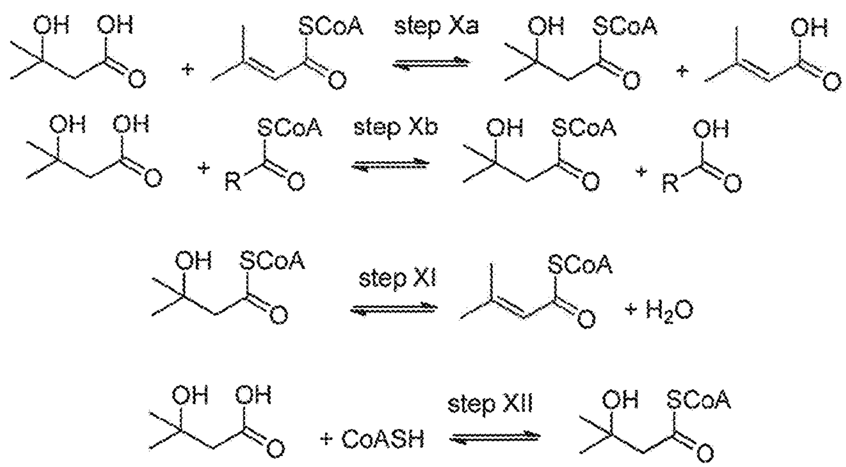

The Enzymatic Conversion of 3-Hydroxyisovalerate (HIV) into 3-Methylcrotonic Acid with a Concomitant Transfer of CoA from 3-Methylcrotonyl-CoA on 3-Hydroxyisovalerate (HIV) to Result in 3-Hydroxyisovaleryl-CoA as Shown in Step Xa of FIG. 26

Thus, in a first aspect, the 3-methylcrotonic acid which is converted into isobutene may be provided by an enzymatic reaction wherein 3-hydroxyisovalerate (HIV) is enzymatically converted into 3-methylcrotonic acid with a concomitant transfer of CoA from 3-methylcrotonyl-CoA to 3-hydroxyisovalerate (HIV) to result in 3-hydroxyisovaleryl-CoA (step Xa as shown in FIG. 18). This reaction is schematically illustrated in FIG. 27.

Thus, the present invention also relates to a method for producing isobutene from 3-hydroxyisovalerate (HIV) wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA. Further, the thus produced 3-methylcrotonic acid is then enzymatically converted into isobutene as described herein above.

Moreover, the present invention also relates to a method for producing 3-methylcrotonic acid and 3-hydroxyisovaleryl-CoA from 3-hydroxyisovalerate (HIV) and from 3-methylcrotonyl-CoA wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA.

According to the present invention, the conversion of 3-hydroxyisovalerate (HIV) and 3-methylcrotonyl-CoA into 3-methylcrotonic acid and 3-hydroxyisovaleryl-CoA wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA preferably makes use of an enzyme which is classified as a CoA-transferase (EC 2.8.3.-) capable of transferring the CoA group of 3-methylcrotonyl-CoA to a carboxylic acid, i.e., 3-hydroxyisovalerate (HIV).

CoA-transferases (EC 2.8.3.-) have already been described above. Accordingly, as regards these enzymes, the same applies to the conversion of 3-hydroxyisovalerate (HIV) and 3-methylcrotonyl-CoA into 3-methylcrotonic acid and 3-hydroxyisovaleryl-CoA as has been set forth above.

Preferably, the CoA-transferase employed in a method according to the present invention in the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA is a CoA-transferase selected from the group consisting of:

propionate:acetate-CoA transferase (EC 2.8.3.1);
acetate CoA-transferase (EC 2.8.3.8); and
butyrate-acetoacetate CoA-transferase (EC 2.8.3.9).

The Enzymatic Conversion of 3-Hydroxyisovalerate (HIV) into 3-Hydroxyisovaleryl-CoA as Shown in Step Xb of FIG. 26

In addition or in the alternative to the above-described methods (step Xa), the 3-hydroxyisovaleryl-CoA may also be provided by an enzymatic conversion of 3-hydroxyisovalerate into said 3-hydroxyisovaleryl-CoA (step Xb as shown in FIG. 26). In this reaction, 3-hydroxyisovalerate reacts with an acyl-CoA to result in 3-hydroxyisovaleryl-CoA and an acid. This reaction is schematically illustrated in FIG. 27.

Preferably, said acyl-CoA is acetyl-CoA.

Thus, the present invention also relates to a method for producing 3-hydroxyisovaleryl-CoA from 3-hydroxyisovalerate (HIV) wherein 3-hydroxyisovalerate reacts with an acyl-CoA, preferably with acetyl-CoA, to result in 3-hydroxyisovaleryl-CoA and a respective acid.

Preferably, this conversion is achieved by making use of an enzyme which is classified as a CoA-transferase (EC 2.8.3.-). As regards the preferred embodiments of said CoA-transferase (EC 2.8.3.-) in the context of step Xb, the same applies, mutatis mutandis, as has been set forth above with respect to the CoA-transferases (EC 2.8.3.-) in the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as shown in FIG. 26).

The Enzymatic Conversion of 3-Hydroxyisovaleryl-CoA into 3-Methylcrotonyl-CoA as Shown in Step XI of FIG. 26

In addition or in the alternative to the above-described methods (step VII), the 3-methylcrotonyl-CoA may be provided by an enzymatic reaction wherein 3-hydroxyisovaleryl-CoA is enzymatically converted into 3-methylcrotonyl-CoA (step XI as shown in FIG. 26). This reversible reaction is a dehydration reaction wherein 3-hydroxyisovaleryl-CoA is dehydrated into 3-methylcrotonyl-CoA and is schematically illustrated in FIG. 29.

Thus, the present invention also relates to a method for producing isobutene from 3-hydroxyisovaleryl-CoA wherein 3-hydroxyisovaleryl-CoA is first enzymatically converted into 3-methylcrotonyl-CoA wherein 3-methylcrotonyl-CoA is further enzymatically converted into 3-methylcrotonic acid according to any of the above-described methods. Further, the thus produced 3-methylcrotonic acid is then enzymatically converted into isobutene as described herein above.

According to the present invention, the enzymatic conversion of 3-hydroxyisovaleryl-CoA into 3-methylcrotonyl-CoA preferably makes use of (i) an enoyl-CoA hydratase (EC 4.2.1.17);
(ii) a long-chain-enoyl-CoA hydratase (EC 4.2.1.74);
(iii) a 3-hydroxypropionyl-CoA dehydratase (EC 4.2.1.116);
(iv) a 3-hydroxybutyryl-CoA dehydratase (EC 4.2.1.55);
(v) a 3-hydroxyoctanoyl-[acyl-carrier-protein] dehydratase (EC 4.2.1.59);
(vi) a crotonyl-[acyl-carrier-protein] hydratase (EC 4.2.1.58);
(vii) a 3-hydroxydecanoyl-[acyl-carrier-protein] dehydratase (EC 4.2.1.60);
(viii) a 3-hydroxypalmitoyl-[acyl-carrier-protein] dehydratase (EC 4.2.1.61); or
(ix) a 3-methylglutaconyl-CoA hydratase (EC 4.2.1.18).

The Enzymatic Conversion of 3-Hydroxyisovalerate (HIV) into 3-Hydroxyisovaleryl-CoA as Shown in Step XII of FIG. 26

In addition or in the alternative to the above-described methods (step Xa or step Xb), the 3-hydroxyisovaleryl-CoA may also be provided by an enzymatic conversion of 3-hydroxyisovalerate (HIV) into said 3-hydroxyisovaleryl-CoA (step XII as shown in FIG. 26). This general reaction wherein coenzyme A (CoASH) is fixed is schematically illustrated in FIG. 30.

Thus, the present invention also relates to a method for producing isobutene from 3-hydroxyisovalerate (HIV) in which 3-hydroxyisovalerate (HIV) is first converted into 3-hydroxyisovaleryl-CoA wherein 3-hydroxyisovaleryl-CoA is then enzymatically converted into 3-methylcrotonyl-CoA wherein 3-methylcrotonyl-CoA is further enzymatically converted into 3-methylcrotonic acid according to any of the above-described methods. Further, the thus produced 3-methylcrotonic acid is then enzymatically converted into isobutene as described herein above.

Figure 31:
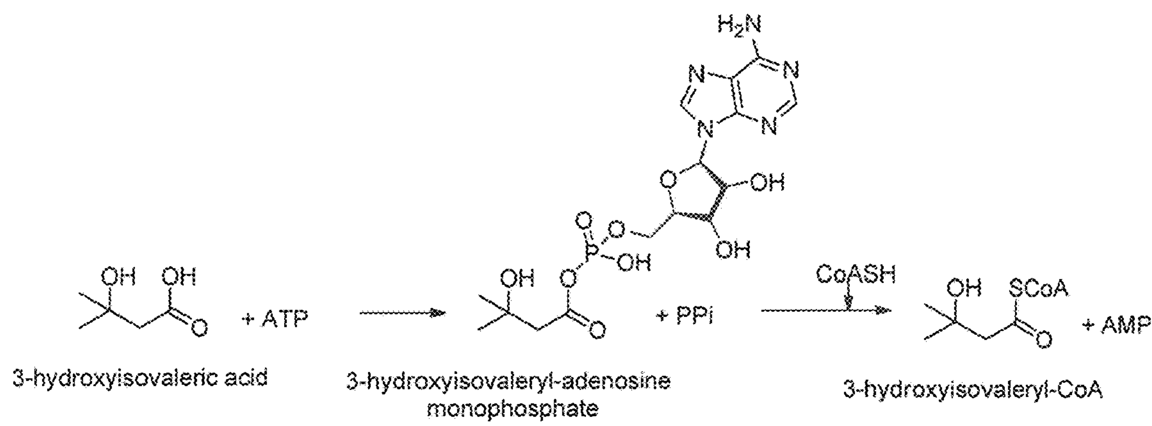
Figure 32:
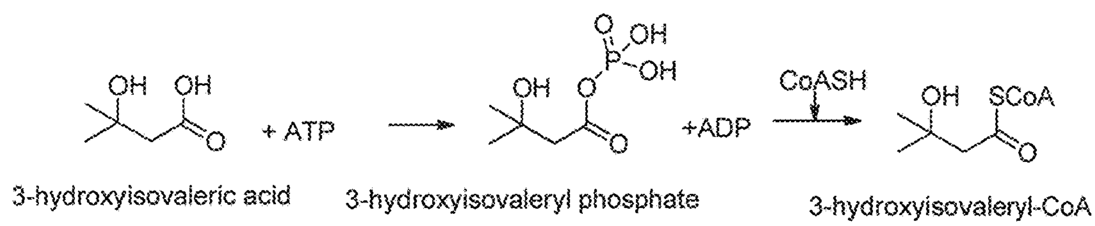

According to the present invention, the enzymatic conversion of 3-hydroxyisovalerate (HIV) into 3-hydroxyisovaleryl-CoA preferably makes use of an enzyme belonging to the family of ligases forming a carbon-sulfur bond (EC 6.2.1.-). The general reaction of the enzymatic conversion of 3-hydroxyisovalerate (HIV) into 3-hydroxyisovaleryl-CoA wherein coenzyme A (CoASH) is fixed can be catalyzed by an enzyme belonging to the family of ligases forming a carbon-sulfur bond (EC 6.2.1.-) via two alternative mechanisms. In a first alternative reaction, an acyl-AMP is generated as an intermediate before coenzyme A is fixed as schematically illustrated in FIG. 31. In a second alternative reaction, an acyl phosphate is generated as an intermediate before coenzyme A is fixed as schematically illustrated in FIG. 32.

Enzymes which belong to the family of ligases forming a carbon-sulfur bond (EC 6.2.1.-) which are capable of enzymatically converting 3-hydroxyisovalerate (HIV) into 3-hydroxyisovaleryl-CoA wherein an acyl-AMP intermediate (i.e., the acyl adenylate intermediate 3-hydroxyisovaleryl-adenosine monophosphate) is generated before coenzyme A is fixed coenzyme A (CoASH) share common structural motifs which are referenced in the InterPro (InterPro44.0; Release Sep. 25, 2013) as InterPro IPR020845, AMP-binding, conserved site (http://www.ebi.ac.uk/interpro/entry/IPR020845) and IPR000873 (http://www.ebi.ac.uk/interpro/entry/IPR000873). The accession number for these enzymes in the Pfam database is PF00501.

As regards the first alternative reaction (wherein an acyl-AMP is generated as an intermediate before coenzyme A is fixed as schematically illustrated in FIG. 23), examples of enzymes which belong to the above family of ligases forming a carbon-sulfur bond (EC 6.2.1.-) which are capable of enzymatically converting 3-hydroxyisovalerate (HIV) into 3-hydroxyisovaleryl-CoA wherein an acyl-AMP intermediate (i.e., the acyl adenylate intermediate 3-hydroxyisovaleryl-adenosine monophosphate) is generated before coenzyme A is fixed coenzyme A (CoASH) and which may be used in the method for producing 3-hydroxyisovaleryl-CoA from 3-hydroxyisovalerate (HIV) are summarized in the following Table A:

TABLE A

CoA ligases (EC 6.2.1.-) capable of enzymatically converting 3-hydroxyisovalerate (HIV) into 3-hydroxyisovaleryl-CoA involving an acyl-adenylate as an intermediate

| Enzyme name | EC number |
|---|---|
| Acetate-CoA ligase | 6.2.1.1 |
| Butyrate-CoA ligase | 6.2.1.2 |
| Long chain fatty-acid-CoA ligase | 6.2.1.3 |
| 4-coumarate-CoA ligase | 6.2.1.12 |
| Arachidonate-CoA ligase | 6.2.1.15 |
| Propionate-CoA ligase | 6.2.1.17 |
| Phytanate-CoA ligase | 6.2.1.24 |
| o-succinylbenzoate-CoA ligase | 6.2.1.26 |
| 3-alpha,7-alpha-dihydroxy-5-beta-cholestanate-CoA ligase | 6.2.1.28 |
| 2-furoate-CoA ligase | 6.2.1.31 |
| 4-chlorobenzoate-CoA ligase | 6.2.1.33 |
| 3-hydroxybenzoate-CoA ligase | 6.2.1.37 |
| 4-hydroxybutyrate-CoA ligase | 6.2.1.40 |
| 3-oxocholest-4-en-26-oate--CoA ligase | 6.2.1.42 |
| 3-(methylthio)propionyl-CoA ligase | 6.2.1.44 |
| Cholate-CoA ligase | 6.2.1.7 |
| Oxalate-CoA ligase | 6.2.1.8 |
| Biotin-CoA ligase | 6.2.1.11 |
| 6-carboxyhexanoate-CoA ligase | 6.2.1.14 |
| Acetoacetate--CoA ligase | 6.2.1.16 |
| Dicarboxylate-CoA ligase | 6.2.1.23 |
| Benzoate-CoA ligase | 6.2.1.25 |
| 4-hydroxybenzoate-CoA ligase | 6.2.1.27 |
| Phenylacetate-CoA ligase | 6.2.1.30 |
| Anthranilate-CoA ligase | 6.2.1.32 |
| 3-hydroxypropionyl-CoA synthase | 6.2.1.36 |
| (2,2,3-trimethyl-5-oxocyclopent-3-enyl)acetyl-CoA synthase | 6.2.1.38 |
| 3-((3aS,4S,7aS)-7a-methyl-1,5-dioxo-octahydro-1H-inden-4-yl)propanoate-CoA ligase | 6.2.1.41 |
| 2-hydroxy-7-methoxy-5-methyl-1-naphthoate--CoA ligase | 6.2.1.43 |
| Malonate-CoA ligase | 6.2.1.n3 |

In a preferred embodiment, the enzymatic conversion of 3-hydroxyisovalerate (HIV) into 3-hydroxyisovaleryl-CoA via an acyl adenylate intermediate can, e.g., be achieved by the use of a butanoate:CoA ligase (AMP forming) (EC 6.2.1.2).

As regards the second alternative reaction (wherein an acyl phosphate is generated as an intermediate before coenzyme A is fixed as schematically illustrated in FIG. 32), examples of enzymes which belong to the above family of ligases forming a carbon-sulfur bond (EC 6.2.1.-) which are capable of enzymatically converting 3-hydroxyisovalerate (HIV) into 3-hydroxyisovaleryl-CoA wherein an acyl phosphate intermediate (i.e., the acyl phosphate intermediate 3-hydroxyisovaleryl phosphate) is generated before coenzyme A is fixed coenzyme A (CoASH) and which may be used in the method for producing 3-hydroxyisovaleryl-CoA from 3-hydroxyisovalerate (HIV) are summarized in the following Table B.

TABLE B

CoA ligases (EC 6.2.1.-) capable of enzymatically converting 3-hydroxyisovalerate (HIV) into 3-hydroxyisovaleryl-CoA involving an acyl phosphate as an intermediate

| Enzyme name | EC number |
|---|---|
| Succinate-CoA ligase (GDP-forming) | 6.2.1.4 |
| Glutarate-CoA ligase | 6.2.1.6 |
| Acid-CoA ligase (GDP-forming) | 6.2.1.10 |
| Citrate-CoA ligase | 6.2.1.18 |
| enzyme name | EC number |
| Succinate-CoA ligase (ADP-forming) | 6.2.1.5 |
| Malate-CoA ligase | 6.2.1.9 |
| Acetate-CoA ligase (ADP-forming) | 6.2.1.13 |

The Alternative Route for the Enzymatic Conversion from Acetyl-CoA into Isobutene Via 3-Methyl-3-Butenoyl-CoA and 3-Methyl-3-Butenoic Acid In an alternative to the above, the present invention also relates to a method for the production of isobutene via an alternative route as also shown in FIG. 1 wherein isobutene is produced by the enzymatic conversion of 3-methyl-3-butenoic acid into isobutene. Thus, the present invention provides a method for the production of isobutene comprising the enzymatic conversion of 3-methyl-3-butenoic acid into isobutene. Preferably, the enzymatic conversion of 3-methyl-3-butenoic acid into isobutene is achieved by making use of an 3-methyl-3-butenoic acid decarboxylase.

In accordance with this alternative route, the present invention not only relates to a method for the production of isobutene from 3-methyl-3-butenoic acid. Rather, as will be outlined in more detail further below, this conversion is preferably embedded in a pathway for the production of isobutene starting from acetyl-CoA which is a central component and an important key molecule in metabolism used in many biochemical reactions.

Therefore, the present invention also relates to a pathway starting from acetyl-CoA wherein two acetyl-CoA molecules are enzymatically condensed into acetoacetyl-CoA. Alternatively, acetyl-CoA is enzymatically converted into malonyl-CoA which may then be converted into said acetoacetyl-CoA by the enzymatic condensation of malonyl-CoA and acetyl-CoA into said acetoacetyl-CoA.

Further, the thus produced acetoacetyl-CoA can enzymatically be converted into 3-methyl-3-butenoic acid (which is then ultimately converted into isobutene) via the following briefly summarized pathway.

In this pathway, the thus produced acetoacetyl-CoA can further enzymatically be converted into 3-hydroxy-3-methylglutaryl-CoA. Moreover, the thus produced 3-hydroxy-3-methylglutaryl-CoA can further enzymatically be converted into 3-methylglutaconyl-CoA. Further, the thus produced 3-methylglutaconyl-CoA can enzymatically be converted into 3-methyl-3-butenoyl-CoA. Further, the thus produced 3-methyl-3-butenoyl-CoA can further be converted in a subsequent enzymatic reaction into 3-methyl-3-butenoic acid (which can then ultimately be converted into isobutene as described above and further below).

The Enzymatic Conversion of 3-Methyl-3-Butenoic Acid into Isobutene: Step XVI as Shown in FIG. 1

According to the present invention, the enzymatic conversion of 3-methyl-3-butenoic acid into isobutene can be achieved by a decarboxylation. "Decarboxylation" is generally a chemical reaction that removes a carboxyl group and releases carbon dioxide ($CO_2$); see FIG. 33.

The enzymatic conversion of 3-methyl-3-butenoic acid into isobutene can preferably be achieved by making use of an 3-methyl-3-butenoic acid decarboxylase. In accordance with the present invention, an 3-methyl-3-butenoic acid decarboxylase is an enzyme which is capable of converting 3-methyl-3-butenoic acid into isobutene.

In preferred embodiments, the 3-methyl-3-butenoic acid decarboxylase is selected from the group consisting of:

(i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5); or
(v) a protocatechuate (PCA) decarboxylase (EC 4.1.1.63).

In other preferred embodiments, the 3-methyl-3-butenoic acid decarboxylase is selected from the group consisting of: 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68).

The Enzymatic Conversion of 3-Methyl-3-Butenoyl-CoA into 3-Methyl-3-Butenoic Acid: Steps XVIIa, XVIIb or XVIIc as Shown in FIG. 1

Figure 34:
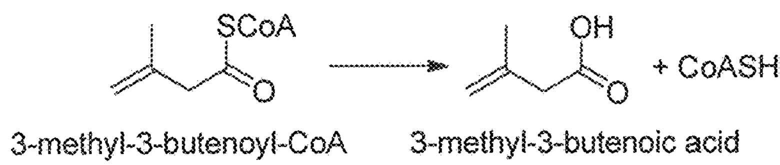

The 3-methyl-3-butenoic acid may itself be provided by an enzymatic reaction, namely the enzymatic conversion of 3-methyl-3-butenoyl-CoA into 3-methyl-3-butenoic acid; see FIG. 34.

Accordingly, the present invention relates to a method for producing isobutene from 3-methyl-3-butenoyl-CoA in which 3-methyl-3-butenoyl-CoA is first converted into 3-methyl-3-butenoic acid which is then further converted into isobutene as described herein above.

According to the present invention, the conversion of 3-methyl-3-butenoyl-CoA into 3-methyl-3-butenoic acid can, e.g., be achieved by three different alternative enzymatic routes, i.e., by:

(a) a single enzymatic reaction (see FIG. 35) in which 3-methyl-3-butenoyl-CoA is directly converted into 3-methyl-3-butenoic acid, preferably by making use of a CoA transferase (EC 2.8.3.-), preferably a propionate: acetate-CoA transferase (EC 2.8.3.1), an acetate CoA-transferase (EC 2.8.3.8) or a succinyl-CoA:acetate CoA-transferase (EC 2.8.3.18);
(b) a single enzymatic reaction (see FIG. 36) in which 3-methyl-3-butenoyl-CoA is directly converted into 3-methyl-3-butenoic acid, preferably by making use of a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20); or
(c) two enzymatic steps (see FIG. 37) comprising
  (i) first enzymatically converting 3-methyl-3-butenoyl-CoA into 3-methyl-3-butenoyl phosphate, preferably by making use of a phosphate butyryltransferase (EC 2.3.1.19) or a phosphate acetyltransferase (EC 2.3.1.8); and
  (ii) then enzymatically converting the thus obtained 3-methyl-3-butenoyl phosphate into said 3-methyl-3-butenoic acid, preferably by making use of a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14).

The Enzymatic Conversion of 3-Methylalutaconyl-CoA into 3-Methyl-3-Butenoyl-CoA: Step XVIII as Shown in FIG. 1

Figure 38:
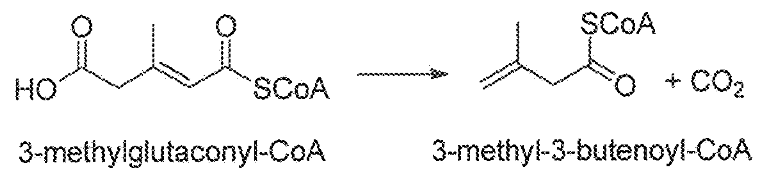

The 3-methyl-3-butenoyl-CoA may itself be provided by an enzymatic reaction, namely the enzymatic conversion of 3-methylglutaconyl-CoA into 3-methyl-3-butenoyl-CoA; see FIG. 38.

Accordingly, the present invention relates to a method for producing isobutene from 3-methyl-3-butenoyl-CoA in which 3-methylglutaconyl-CoA is first converted into 3-methyl-3-butenoyl-CoA which is then further converted into 3-methyl-3-butenoic acid which is then further converted into isobutene as described herein above.

Moreover, the present invention relates to a method for producing 3-methyl-3-butenoyl-CoA by converting 3-methylglutaconyl-CoA into 3-methyl-3-butenoyl-CoA. According to the present invention, the conversion of 3-methylglutaconyl-CoA into 3-methyl-3-butenoyl-CoA can preferably be achieved by making use of (a) (i) a methylcrotonyl-CoA carboxylase (EC 6.4.1.4); or
  (ii) a geranoyl-CoA carboxylase (EC 6.4.1.5), (b) an N-terminal domain of CurF from Lynbya majuscula multifunctional protein or a 3-methylglutaconyl-CoA decarboxylase, preferably a 3-methylglutaconyl-CoA decarboxylase of *Myxococcus xanthus* encoded by the liuB gene; or (c) an enzyme of the 4-oxalocrotonate decarboxylase family.

As regards the aforementioned embodiments, for the methylcrotonyl-CoA carboxylase (EC 6.4.1.4), the geranoyl-CoA carboxylase (EC 6.4.1.5) and the 3-methylglutaconyl-CoA decarboxylase, preferably the 3-methylglutaconyl-CoA decarboxylase of *Myxococcus xanthus* encoded by the liuB gene, the same applies as has been set forth above in connection with the other methods of the present invention.

Figure 39:
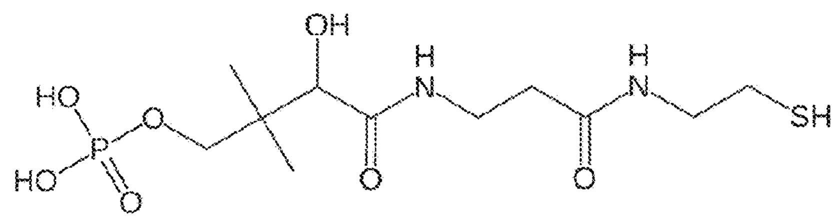

In a preferred embodiment the conversion of 3-methylglutaconyl-CoA via decarboxylation into 3-methyl-3-butenoyl-CoA is catalyzed by an N-terminal domain of CurF from Lynbya majuscula multifunctional protein. The N-terminal domain of CurF from Lynbya majuscula multifunctional protein is a domain of a polyketide synthase (PKS)/non ribosomale peptide synthase (NRPS) of the CurF multifunctional protein from Lyngbya majuscula. This N-terminal domain of CurF has been classified as a protein belonging to the crotonase superfamily by studying the crystal structure and it naturally catalyzes the decarboxylation of 3-methylglutaconyl-ACP (Acyl Carrier Protein) into 3-methyl-crotonyl-ACP. ACP is similar to CoA as both molecules have a phosphopantetheine moiety in common (as shown in FIG. 39). Moreover, both ACP and CoA can form a thioester with a biological acid (J. Biol. Chem. 289: 35957-35963 (2007) and Chemistry & Biology 11:817-833 (2004)).

In another preferred embodiment the conversion of 3-methylglutaconyl-CoA via decarboxylation into 3-methyl-3-butenoyl-CoA is catalyzed by an enzyme of the 4-oxalocrotonate decarboxylase family (EC 4.1.1.77).

The Enzymatic Conversion of 3-Hydroxy-3-Methylglutaryl-CoA into 3-Methylplutaconyl-CoA: Step VIII as Shown in FIG. 1

The 3-methylglutaconyl-CoA which can be converted into 3-methyl-3-butenoyl-CoA according to any of the above described methods may itself be provided by an enzymatic reaction, namely the enzymatic conversion of 3-hydroxy-3-methylglutaryl-CoA into 3-methylglutaconyl-CoA.

Accordingly, the present invention also relates to a method for producing isobutene from 3-hydroxy-3-methylglutaryl-CoA in which 3-hydroxy-3-methylglutaryl-CoA is first converted into 3-methylglutaconyl-CoA which is then converted into 3-methyl-3-butenoyl-CoA which is then further converted into 3-methyl-3-butenoic acid which is then further converted into isobutene as described herein above.

According to the present invention, the enzymatic conversion of 3-hydroxy-3-methylglutaryl-CoA into 3-methylglutaconyl-CoA is an enzymatic dehydration reaction which occurs naturally, and which is catalyzed, e.g., by enzymes classified as 3-methylglutaconyl-coenzyme A hydratase (EC 4.2.1.18). Accordingly, the enzymatic conversion of 3-hydroxy-3-methylglutaryl-CoA into 3-methylglutaconyl-CoA preferably makes use of a 3-methylglutaconyl-coenzyme A hydratase (EC 4.2.1.18).

As regards the afore-mentioned embodiment, for the enzymes classified as 3-methylglutaconyl-coenzyme A hydratase (EC 4.2.1.18), the same applies as has been set forth above in connection with the other methods of the present invention.

The Enzymatic Conversion of Acetoacetyl-CoA into 3-Hydroxy-3-Methylglutaryl-CoA: Step IX as Shown in FIG. 1

The 3-hydroxy-3-methylglutaryl-CoA may itself be provided by an enzymatic reaction, namely the enzymatic condensation of acetoacetyl-CoA and acetyl-CoA into 3-hydroxy-3-methylglutaryl-CoA which has already been described in detail above.

Accordingly, the present invention also relates to a method for producing isobutene from acetoacetyl-CoA and acetyl-CoA in which acetoacetyl-CoA and acetyl-CoA are first condensed into 3-hydroxy-3-methylglutaryl-CoA which is then converted into 3-methylglutaconyl-CoA which is then converted into 3-methyl-3-butenoyl-CoA which is then further converted into 3-methyl-3-butenoic acid which is then further converted into isobutene as described herein above.

The Enzymatic Conversion of Acetyl-CoA into Acetoacetyl-CoA: Step XIII, Step XIV and Step XV as Shown in FIG. 1

The acetoacetyl-CoA may itself be provided by an enzymatic reaction, namely the enzymatic conversion of acetyl-CoA into acetoacetyl-CoA via several different routes which have already been described in detail above.

Thus, the present invention also relates to a method for producing isobutene from acetyl-CoA in which acetyl-CoA is first converted into acetoacetyl-CoA by any of the above-mentioned routes which is then condensed with acetyl-CoA into 3-hydroxy-3-methylglutaryl-CoA which is then converted into 3-methylglutaconyl-CoA which is then converted into 3-methyl-3-butenoyl-CoA which is then further converted into 3-methyl-3-butenoic acid which is then further converted into isobutene as described herein above.

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing the enzymes described above for the conversions of the methods according to the present invention as described herein above. A method which employs a microorganism for carrying out a method according to the invention is referred to as an "in vivo" method. It is possible to use a microorganism which naturally produces the enzymes described above for the conversions of the methods according to the present invention or a microorganism which had been genetically modified so that it expresses (including overexpresses) one or more of such enzymes. Thus, the microorganism can be an engineered microorganism which expresses enzymes described above for the conversions of the methods according to the present invention, i.e. which has in its genome a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express enzymes described above for the conversions of the methods according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (micro)organisms, i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have the respective enzyme activity but which is genetically modified so as to comprise a nucleotide sequence allowing the expression of a corresponding enzyme. Similarly, the microorganism may also be a microorganism which naturally has the respective enzyme activity but which is genetically modified so as to enhance such an activity, e.g. by the introduction of an exogenous nucleotide sequence encoding a corresponding enzyme or by the introduction of a promoter for the endogenous gene encoding the enzyme to increase endogenous production to overexpressed (non-natural) levels.

If a microorganism is used which naturally expresses a corresponding enzyme, it is possible to modify such a microorganism so that the respective activity is overexpressed in the microorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above. The genetic modification of microorganisms to express an enzyme of interest will also be further described in detail below.

In a preferred embodiment, the method of the present invention makes use of an organism, preferably a microorganism, which is capable of consuming glucose.

In another preferred embodiment, the method of the present invention makes use of an organism, preferably a microorganism, which is capable of consuming fructose.

In another preferred embodiment, the method of the present invention makes use of an organism, preferably a microorganism, which is capable of consuming xylose.

In another preferred embodiment, the method of the present invention makes use of an organism, preferably a microorganism, which is capable of consuming mannose.

In another preferred embodiment, the method of the present invention makes use of an organism, preferably a microorganism, which is capable of consuming more than one sugar. Preferably, said more than one sugar comprises sucrose, glucose, mannose and/or xylose. In a more preferred embodiment, the method of the present invention makes use of an organism, preferably a microorganism, which is capable of consuming two or more sugars selected from the group consisting of sucrose, glucose, mannose and xylose. Organisms and/or microorganisms which are capable of consuming glucose, fructose, xylose and/or mannose do naturally occur and are known in the art.

In another embodiment, said organism and/or microorganism is genetically modified in order to be capable of consuming glucose, fructose, xylose and/or mannose and/or genetically modified in order to increase the organism's and/or microorganism's capability of consuming glucose, fructose, xylose and/or mannose. Corresponding genetic modifications are known in the art.

In another preferred embodiment, the method of the present invention makes use of an organism, preferably a microorganism which is capable of consuming sugar through a Phosphotransferase Transport System (PTS).

In another preferred embodiment, the method of the present invention makes use of an organism, preferably a microorganism which is capable of consuming sugar through a non-Phosphotransferase Transport System (non-PTS).

Organisms and/or microorganisms which are capable of consuming sugar through a Phosphotransferase Transport System (PTS) and/or through a non-Phosphotransferase Transport System (non-PTS) are known in the art.

In another embodiment, said organism and/or microorganism is genetically modified in order to be capable of consuming sugar through a Phosphotransferase Transport System (PTS) or through a non-Phosphotransferase Transport System (non-PTS). In another preferred embodiment, said organism and/or microorganism is genetically modified in order to increase the organism's and/or microorganism's capability of consuming sugar through a Phosphotransferase Transport System (PTS) or through a non-Phosphotransferase Transport System (non-PTS). Corresponding genetic modifications are known in the art.

In another preferred embodiment, the method of the present invention makes use of an organism, preferably a microorganism having a diminished or inactivated Phosphotransferase Transport System (PTS).

Without being bound to theory, such an organism, preferably a microorganism, may preferably be genetically modified by deleting or inactivating (a) gene(s) of said Phosphotransferase Transport System (PTS).

Corresponding genetic modifications are known in the art.

In another preferred embodiment, the method of the present invention makes use of an organism, preferably a microorganism having an enhanced non-Phosphotransferase Transport System (non-PTS) for sugar uptake.

Without being bound to theory, such an organism, preferably a microorganism, may preferably be genetically modified by overexpressing (a) gene(s) of said non-Phosphotransferase Transport System (non-PTS) for sugar uptake.

Corresponding genetic modifications are known in the art.

In another preferred embodiment, the method of the present invention makes use of an organism, preferably a microorganism having a diminished or inactivated Phosphotransferase Transport System (PTS) and an enhanced non Phosphotransferase Transport System (non-PTS) for sugar uptake.

In another preferred embodiment, the method of the present invention makes use of an organism, preferably a microorganism which is capable of consuming sucrose through a non-Phosphotransferase Transport System (non-PTS).

In another preferred embodiment, the method of the present invention makes use of an organism, preferably a microorganism consuming sucrose, wherein said organism, preferably said microorganism, has genetically been modified by the introduction of at least one gene of a non-Phosphotransferase Transport System (non-PTS). Without being bound to theory, such an organism and/or microorganism has genetically been modified by introducing a gene selected from the group consisting of cscA, cscB, and cscK from *Escherichia coli* W (M. Bruschi et al., Biotechnology Advances 30 (2012) 1001-1010).

In another preferred embodiment, the method of the present invention makes use of an organism, preferably a microorganism which has genetically been modified to have a diminished or inactivated Phosphotransferase Transport System (PTS) and an overexpression of at least one gene selected from the group consisting of galP, glk and glf.

In a preferred embodiment, the method of the present invention makes use of an organism, preferably a microorganism, which is genetically modified in order to avoid the leakage of acetyl-CoA, thereby increasing the intracellular concentration of acetyl-CoA. Genetic modifications leading to an increase in the intracellular concentration of acetyl-CoA are known in the art. Without being bound to theory, such an organism, preferably a microorganism, may preferably be genetically modified by deleting or inactivating the following genes:

ΔackA (acetate kinase), Δldh (lactate dehydrogenase), ΔadhE (alcohol dehydrogenase), ΔfrdB and/or ΔfrdC (fumarate reductase and fumarate dehydrogenase).

Alternatively, or in addition to any of the above deletions, the organism or microorganism may genetically be modified by overexpressing the gene panK/coaA encoding Pantothenate kinase, thereby increasing the CoA/acetyl-CoA intracellular pool.

These modifications which avoid the leakage of acetyl-CoA are known in the art and corresponding modified organisms have been used in methods for the bioconversion of exogenous isoamyl alcohol into isoamyl acetate by an *E. coli* strain expressing ATF2 (Metab. Eng. 6 (2004), 294-309).

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

When carried out by making use of a microorganism, the method according to the present invention may, e.g. be designed as a continuous fermentation culturing method or as a batch culture or any suitable culture method known to the person skilled in the art.

In a preferred embodiment the method according to the present invention also comprises the step of recovering the isobutene produced by the method. For example, if the method according to the present invention is carried out in vivo by fermenting a corresponding microorganism expressing the necessary enzymes, the isobutene can be recovered from the fermentation off-gas by methods known to the person skilled in the art.

In a preferred embodiment, the present invention relates to a method as described herein above in which a microorganism as described herein above is employed, wherein the microorganism is capable of enzymatically converting 3-methylcrotonic acid into isobutene, wherein said method comprises culturing the microorganism in a culture medium.

The enzymes used in the method according to the invention can be naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called “directed evolution”.

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, NY, USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, “primer repair”, restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" or "improved activity" means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased"/"improved" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, NY, USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62

(1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, NY, USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

As mentioned above, the method according to the present invention is in particular useful for large scale production of isobutene in vivo, in particular for a commercial production. The present invention describes novel ways to commercially and cost-effectively produce large quantities of isobutene which has not been obtainable to date. The generated large quantities of isobutene can then be further converted, in a commercial setting, to produce large quantities of, e.g., drop-in gasoline (e.g. isooctane, ETBE, MTBE), jet-fuel, cosmetics, chemicals, such as methacrylic acid, polyisobutene, or butyl rubber. As used herein, "large scale production", "commercial production" and "bioprocessing" of isobutene in a fermentation reactor or in vitro is carried out at a capacity greater than at least 100 liters, and preferably greater than at least 400 liters, or more preferably production of 1,000 liters of scale or more, even more preferably production of 5,000 liters of scale or more. As used herein, "large quantities" specifically excludes trace amounts that may be produced inherently in a microorganism.

For example, in preferred embodiments, the yields for continuous cultures according to methods described herein are at least about 0.2 grams of isobutene per liter per day, at least about 0.3 grams of isobutene per liter per day, at least about 0.4 grams of isobutene per liter per day, at least about 0.5 grams of isobutene per liter per day, at least about 0.6 grams of isobutene per liter per day, at least about 0.7 grams of isobutene per liter per day, at least about 0.8 grams of isobutene per liter per day, or at least about 1.0 grams of isobutene per liter per day. In further embodiments, the yields for continuous cultures according to methods described herein are between about 0.3 grams and about 1.0 grams of isobutene per liter per day, between about 0.4 grams to about 1.0 grams of isobutene per liter per day, and between about 0.5 grams and about 1.0 grams of isobutene per liter per day. In other specific embodiments, the yields for continuous cultures according to methods described herein are between about 0.5 grams to about 0.75 grams of isobutene per liter per day. In other specific embodiments, the yields for continuous cultures according to methods described herein are between about 0.5 grams and about 1.5 grams of isobutene per liter per day.

In further embodiments, the yields for batch cultures according to methods described herein are at least about 2 grams per liter in batch culture, at least about 5 grams per liter in batch culture, at least about 10 grams per liter in batch culture, and at least about 15 grams per liter in batch culture. In some embodiments, the yields for batch cultures according to methods described herein are between about 2 grams and about 5 grams per liter in batch culture, between about 5 grams and about 10 grams per liter in batch culture, and still more preferably between about 10 grams and about 20 grams per liter in batch culture. In other specific embodiments, the yields for batch cultures according to methods described herein are between about 2.4 grams and about 4.8 grams per liter, and preferably between about 4.8 grams and about 9.4 grams per liter in batch culture, and still more preferably between about 9.4 grams and about 18.6 grams per liter in batch culture.

In additional embodiments, the concentration of the 3-methylcrotonic acid in the in vitro composition used to commercially produce isobutene is at least 1%, 2%, 3%, 4%, 5%, 6%, 7%, 8% 9%, 10% or 20% as compared to all components, preferably soluble components, of the in vitro composition. Alternatively, the concentration of the FMN-dependent decarboxylase associated with an FMN prenyl transferase in the in vitro composition used to commercially produce isobutene is at least 0.1%, 0.2%, 0.3%, 0.4%, 0.5%, 0.6%, 0.7%, 0.8% 0.9%, 1.0% or 2.0% as compared to all components, preferably soluble components, of the in vitro composition.

In additional embodiments, the concentration of the 3-methylcrotonic acid in the microorganism or organism used to commercially produce isobutene is at least 0.1%, 0.2%, 0.3%, 0.4%, 0.5%, 0.6%, 0.7%, 0.8% 0.9%, 1.0% or 2.0% as compared to all other molecules found in the microorganism or organism. Alternatively, the concentration of the FMN-dependent decarboxylase associated with an FMN prenyl transferase in the microorganism or organism used to commercially produce isobutene is at least 0.1 mM, 0.2 mM, 0.3 mM, 0.4 mM, 0.5 mM, 0.6 mM, 0.7 mM, 0.8 mM 0.9 mM, 1.0 mM or 2.0 mM as compared to all proteins and/or enzymes found in the microorganism or organism.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

Recombinant Organisms or Microorganisms Expressing Enzymes of Step I and any One of Route (i), (ii), (iii) and/or (iv) for the Provision of DMAP The present invention also relates to a recombinant organism or microorganism which recombinantly expresses an FMN-dependent decarboxylase associated with an FMN prenyl transferase (step I of FIG. 1);

wherein said recombinant organism or microorganism further recombinantly expresses at least one of the following (i) to (iv):

(i) an enzyme catalyzing the enzymatic conversion of dimethylallyl pyrophosphate (DMAPP) into dimethylallyl phosphate (DMAP), wherein said enzyme is a phosphatase, preferably an enzyme acting on phosphorous containing anhydrides (EC 3.6.1.-), more preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or preferably a phosphoric-monoester hydrolase (EC 3.1.3.-), more preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11); or preferably an isopentenyl phosphate kinase (EC 2.7.4.26);

(ii) an enzyme catalyzing the direct enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iii) an enzyme catalyzing the enzymatic conversion of DMAPP into prenol, wherein said enzyme is a phosphatase or pyrophosphatase, preferably an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and an enzyme catalyzing the thus obtained prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iv) an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

In another preferred embodiment, this recombinant organism or microorganism is a recombinant organism or microorganism, wherein the enzyme capable of enzymatically converting DMAPP into said DMAP of (i) is a phosphatase. In a more preferred embodiment, said phosphatase is:

an enzyme acting on phosphorous containing anhydrides (EC 3.6.1.-), preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or a phosphoric-monoester hydrolase (EC 3.1.3.-), preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11).

In another preferred embodiment, this recombinant organism or microorganism is a recombinant organism or microorganism, wherein the enzyme capable of enzymatically converting DMAPP into said DMAP of (i) is an isopentenyl phosphate kinase (EC 2.7.4.26).

In another preferred embodiment, this recombinant organism or microorganism is a recombinant organism or microorganism, wherein the enzyme capable of enzymatically converting prenol into DMAP of (ii) is a kinase. In a more preferred embodiment, said kinase is a phosphotransferase with an alcohol group as acceptor (EC 2.7.1.-), preferably a hydroxyethylthiazole kinase (EC 2.7.1.50).

In another preferred embodiment, this recombinant organism or microorganism is a recombinant organism or microorganism, wherein the enzyme capable of enzymatically converting DMAPP into prenol of (iii) is a phosphatase or pyrophosphatase and/or the enzyme capable of enzymatically converting prenol into DMAP of (iii) is a kinase. In a more preferred embodiment, said phosphatase or pyrophosphatase is:

an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and/or said kinase is a phosphotransferase with an alcohol group as acceptor (EC 2.7.1.-), preferably a hydroxyethylthiazole kinase (EC 2.7.1.50).

In another preferred embodiment, this recombinant organism or microorganism is a recombinant organism or microorganism, wherein the enzyme capable of enzymatically converting isopentenyl monophosphate (IMP) into said DMAP of (iv) is an isomerase. In a more preferred embodiment, said isomerase is an isopentenyl-diphosphate DELTA isomerase (EC 5.3.3.2).

As regards the enzymes mentioned herein above in connection with the organisms/microorganisms of the present invention and as regards preferred embodiments of these enzymes, the same applies as has been set forth above for the methods according to the present invention.

In a further aspect, the above recombinant organism or microorganism is an organism or microorganism which further recombinantly expresses an enzyme capable of enzymatically providing said DMAPP by the enzymatic conversion of isopentenyl pyrophosphate (IPP) into DMAPP. In a more preferred embodiment, said enzyme capable of enzymatically providing said DMAPP by the enzymatic conversion of isopentenyl pyrophosphate (IPP) into DMAPP is an isomerase, preferably an isopentenyl-diphosphate DELTA isomerase (EC 5.3.3.2).

As regards the isomerase and the isopentenyl-diphosphate DELTA isomerase (EC 5.3.3.2), the same applies to the recombinant organism or microorganism as has been set forth above for the methods according to the present invention.

In a further aspect, the above recombinant organism or microorganism is an organism or microorganism which further recombinantly expresses an enzyme capable of catalyzing the enzymatic conversion of riboflavin into flavin mononucleotide (FMN). In preferred embodiment, the enzyme capable of catalyzing the enzymatic conversion of riboflavin into FMN is a kinase, preferably

- an archaeal riboflavin kinase (EC 2.7.1.161),
- a flavokinase derived from *S. cerevisiae* or from *Rattus norvegicus,*
- a flavokinase derived from Megasphaera elsdenii,
- a phosphotransferase with an alcohol group as acceptor (EC 2.7.1), preferably an erythritol kinase (2.7.1.27) or a glycerol kinase (2.7.1.30),
- a phosphotransferase with a phosphate group as acceptor (EC 2.7.4), preferably an isopentenyl phosphate kinase (EC 2.7.4.26); or
- a bifunctional riboflavin kinase/FMN adenylyltransferase (ribF); or
- a variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived.

In a more preferred embodiment, said variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived is a variant having an amino acid sequence as shown in SEQ ID NO:34 or an amino acid sequence having at least 60% sequence identity to SEQ ID NO:34, in which one or more amino acid residues at a position selected from the group consisting of positions 29 and 32 in the amino acid sequence shown in SEQ ID NO:34 or at a position corresponding to any of these positions, are substituted with another amino acid residue or deleted or wherein an insertion has been effected at one or more of these positions.

More preferably, said variant is a variant wherein (1) an amino acid residue at position 29 in the amino acid sequence shown in SEQ ID NO:34 or at a position corresponding to this position, is deleted or substituted with alanine; and/or (2) an amino acid residue at position 32 in the amino acid sequence shown in SEQ ID NO:34 or at a position corresponding to this position, is deleted or substituted with serine or alanine.

As regards the enzymes mentioned herein above in connection with this aspect and preferred embodiments thereof, the same applies as has been set forth above for the methods according to the present invention.

Recombinant Organisms or Microorganisms Expressing Enzymes of Step I and any One of Route (v), (vi), and/or (vii) for the Provision of DMAPP The present invention also relates to a recombinant organism or microorganism which recombinantly expresses an FMN-dependent decarboxylase associated with an FMN prenyl transferase (step I of FIG. 1);

wherein said recombinant organism or microorganism further recombinantly expresses at least one of the following (v) to (vii):

(v) an enzyme catalyzing the enzymatic conversion of isopentenyl pyrophosphate (IPP) into said DMAPP, wherein said enzyme is an isomerase, preferably an isopentenyl-diphosphate DELTA isomerase (EC 5.3.3.2);

(vi) an enzyme catalyzing the enzymatic conversion of dimethylallyl phosphate (DMAP) into said DMAPP, wherein said enzyme is a kinase, preferably an isopentenyl monophosphate kinase (EC 2.7.4.26); and (vii) an enzyme catalyzing the enzymatic conversion of prenol into said DMAPP, wherein said enzyme is a diphosphotransferase (EC 2.7.6.-), preferably a thiamine diphosphokinase (EC 2.7.6.2) or a 2-amino-4-hydroxy-6-hydroxymethyldihydropteridine diphosphokinase.

As regards the enzymes mentioned herein above in connection with the organisms/microorganisms of the present invention and as regards preferred embodiments of these enzymes, the same applies as has been set forth above for the methods according to the present invention.

In a further aspect, the above recombinant organism or microorganism is an organism or microorganism which further recombinantly expresses an enzyme capable of catalyzing the enzymatic conversion of prenol into DMAP.

In a preferred embodiment, this recombinant organism or microorganism is a recombinant organism or microorganism, wherein said enzyme capable of catalyzing the enzymatic conversion of prenol into DMAP is a kinase, more preferably a phosphotransferase with an alcohol group as acceptor (EC 2.7.1.-), and even more preferably a hydroxyethylthiazole kinase (EC 2.7.1.50).

In a further aspect, the above recombinant organism or microorganism is an organism or microorganism which further recombinantly expresses an enzyme capable of catalyzing the enzymatic conversion of isopentenyl monophosphate (IMP) into DMAP. In a preferred embodiment, this recombinant organism or microorganism is a recombinant organism or microorganism, wherein said enzyme capable of catalyzing the enzymatic conversion of IMP into DMAP is an isomerase, preferably an isopentenyl-diphosphate DELTA isomerase (EC 5.3.3.2).

As regards the enzymes mentioned herein above in connection with the organisms/microorganisms of the present invention and as regards preferred embodiments of these enzymes, the same applies as has been set forth above for the methods according to the present invention.

In a further aspect, the above recombinant organism or microorganism is an organism or microorganism which further recombinantly expresses an enzyme capable of catalyzing the enzymatic conversion of riboflavin into flavin mononucleotide (FMN). In preferred embodiment, the enzyme capable of catalyzing the enzymatic conversion of riboflavin into FMN is a kinase, preferably an archaeal riboflavin kinase (EC 2.7.1.161), a flavokinase derived from *S. cerevisiae* or from *Rattus norvegicus,* a flavokinase derived from Megasphaera elsdenii, a phosphotransferase with an alcohol group as acceptor (EC 2.7.1), preferably an erythritol kinase (2.7.1.27) or a glycerol kinase (2.7.1.30), a phosphotransferase with a phosphate group as acceptor (EC 2.7.4), preferably an isopentenyl phosphate kinase (EC 2.7.4.26); or a bifunctional riboflavin kinase/FMN adenylyltransferase (ribF); or a variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived.

As regards the enzymes mentioned herein above in connection with this aspect and preferred embodiments thereof, the same applies as has been set forth above for the methods according to the present invention.

Recombinant Organisms or Microorganisms Expressing Enzymes of Step I and any One of Route (i), (ii), (iii) and/or (iv) for the Provision of DMAP and/or any One of Route (v), (vi) and/or (vii) for the Provision of DMAPP and/or FMN and Optionally Further Expressing Enzymes of Step II, Step III, Step IV and Step V as Well as Optionally Further Expressing Enzymes of Steps XIII, XIV and XV The present invention also relates to a recombinant organism or microorganism which expresses an enzyme capable of enzymatically converting 3-methylcrotonic acid into isobutene (step I as shown in FIG. 1) and an enzyme capable of providing DMAP of any one of routes (i) to (iv) and/or an enzyme capable of providing DMAPP of any one of routes (v) to (vii) and/or an enzyme capable of catalyzing the enzymatic conversion of riboflavin into flavin mononucleotide (FMN) as well as an enzyme capable of enzymatically converting 3-hydroxyisovalerate (HIV) into 3-methylcrotonic acid (step II as shown in FIG. 1).

In a preferred embodiment, the enzyme capable of enzymatically converting 3-hydroxyisovalerate (HIV) into 3-methylcrotonic acid is a hydro-lyase (EC 4.2.-.-) as defined herein above, preferably an aconitase (EC 4.2.1.3), a fumarase (EC 4.2.1.2) or an enoyl-CoA hydratase/dehydratease (EC 4.2.1.17) as defined herein above.

As regards these enzymes and preferred embodiments thereof, the same applies as has been set forth above for the methods according to the present invention.

In a further aspect, the above recombinant organism or microorganism is an organism or microorganism which further expresses an enzyme capable of enzymatically condensing acetone and acetyl-CoA into 3-hydroxyisovalerate (HIV) (step III as shown in FIG. 1). In a preferred embodiment, the enzyme capable of enzymatically condensing acetone and acetyl-CoA into 3-hydroxyisovalerate (HIV) is a HMG CoA synthase (EC 2.3.3.10) or a PksG protein or an enzyme with the activity of a C—C bond cleavage/condensation lyase, such as a HMG CoA lyase (EC 4.1.3.4) as defined herein above.

As regards these enzymes and preferred embodiments thereof, the same applies as has been set forth above for the methods according to the present invention.

In a further aspect, the above recombinant organism or microorganism is an organism or microorganism which further expresses an enzyme capable of enzymatically converting acetoacetate into acetone (step IV as shown in FIG. 1), preferably an acetoacetate decarboxylase (EC 4.1.1.4) as described herein above. As regards these enzymes and preferred embodiments thereof, the same applies as has been set forth above for the methods according to the present invention.

In a further aspect, the above recombinant organism or microorganism is an organism or microorganism which further expresses an enzyme capable of converting acetoacetyl-CoA into acetoacetate (step Va or Vb as shown in FIG. 1), preferably (i) an acetoacetyl-CoA hydrolase (EC 3.1.2.11); or (ii) an enzyme which is capable of transferring the CoA group of acetoacetyl-CoA on acetate as described herein above.

In a preferred embodiment, the enzyme capable of transferring the CoA group of acetoacetyl-CoA on acetate is a CoA transferase (EC 2.8.3.-), preferably an acetate CoA transferase (EC 2.8.3.8) as described herein above.

As regards these enzymes and preferred embodiments thereof, the same applies as has been set forth above for the methods according to the present invention.

In a further aspect, the above recombinant organism or microorganism is an organism or microorganism which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

In a preferred embodiment, the enzyme capable of converting acetyl-CoA into malonyl-CoA is an acetyl-CoA carboxylase (EC 6.4.1.2) as described herein above.

In another preferred embodiment, the enzyme capable of condensing malonyl-CoA and acetyl-CoA into acetoacetyl-CoA is an acetoacetyl-CoA synthetase (EC 2.3.1.194) as described herein above.

In a preferred embodiment, the enzyme capable of directly condensing two molecules of acetyl-CoA into acetoacetyl-CoA is an acetyl-CoA C-acetyltransferase (EC 2.3.1.9) as described herein above.

As regards the enzyme which is capable of converting acetyl-CoA into malonyl-CoA, these enzymes mentioned in connection with this aspect and preferred embodiments thereof, the same applies as has been set forth above for the methods according to the present invention.

Recombinant Organisms or Microorganisms Expressing Enzymes of Step I and any One of Route (i), (ii), (iii) and/or (iv) for the Provision of DMAP and/or any One of Route (v), (vi) and/or (vii) for the Provision of DMAPP and/or FMN and Optionally Further Expressing Enzymes of Step VI, Step VII, Step VIII and Step IX as Well as Optionally Further Expressing Enzymes of Steps XIII, XIV and XV The present invention also relates to a recombinant organism or microorganism which expresses an enzyme capable of enzymatically converting 3-methylcrotonic acid into isobutene (step I as shown in FIG. 1) and an enzyme capable of providing DMAP of any one of routes (i) to (iv) and/or an enzyme capable of providing DMAPP of any one of routes (v) to (vii) and/or an enzyme capable of catalyzing the enzymatic conversion of riboflavin into flavin mononucleotide (FMN) as well as an enzyme capable of enzymatically converting 3-methylcrotonyl-CoA into 3-methylcrotonic acid (step VIa, VIb or VIc as shown in FIG. 1).

In a preferred embodiment, the enzyme capable of converting 3-methylcrotonic acid into isobutene is a 3-methylcrotonic acid decarboxylase, preferably (i) an FMN-dependent decarboxylase associated with an FMN prenyl transferase; or (ii) an aconitate decarboxylase (EC 4.1.1.6); or (iii) a methylcrotonyl-CoA carboxylase (EC 6.4.1.4); or (iv) a geranoyl-CoA carboxylase (EC 6.4.1.5); or (v) a protocatechuate (PCA) decarboxylase (EC 4.1.1.63) as defined herein above.

As regards these enzymes and preferred embodiments thereof, the same applies as has been set forth above for the methods according to the present invention.

In a preferred embodiment, the enzyme capable of enzymatically converting 3-methylcrotonyl-CoA into 3-methylcrotonic acid is (a) an enzyme capable of directly converting 3-methylcrotonyl-CoA into 3-methylcrotonic acid wherein said enzyme capable of directly converting 3-methylcrotonyl-CoA into 3-methylcrotonic acid is a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step Via as shown in FIG. 1) as described herein above; or (b) an enzyme capable of directly converting 3-methylcrotonyl-CoA into 3-methylcrotonic acid wherein said enzyme capable of directly converting 3-methylcrotonyl-CoA into 3-methylcrotonic acid is a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step VIb as shown in FIG. 1) as described herein above.

In another preferred embodiment, the recombinant organism or microorganism is a recombinant organism or microorganism which expresses the following two enzymes, namely (c) (i) an enzyme capable of enzymatically converting 3-methylcrotonyl-CoA into 3-methylcrotonyl phosphate as described herein above; and (ii) an enzyme capable of converting 3-methylcrotonyl phosphate into 3-methylcrotonic acid (step VIc as shown in FIG. 1) as described herein above.

In a preferred embodiment, the enzyme capable of converting 3-methylcrotonyl-CoA into 3-methylcrotonyl phosphate is a phosphate butyryltransferase (EC 2.3.1.19) or a phosphate acetyltransferase (EC 2.3.1.8) and the enzyme capable of converting 3-methylcrotonyl phosphate into 3-methylcrotonic acid is a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14) as described herein above.

As regards the above-mentioned enzymes and preferred embodiments thereof, the same applies as has been set forth above for the methods according to the present invention.

In a further aspect, the above recombinant organism or microorganism is an organism or microorganism which further expresses an enzyme capable of enzymatically converting 3-methylglutaconyl-CoA into 3-methylcrotonyl-CoA (step VII as shown in FIG. 1), preferably (i) a methylcrotonyl-CoA carboxylase (EC 6.4.1.4); or (ii) a geranoyl-CoA carboxylase (EC 6.4.1.5) as described herein above.

As regards said enzymes as well as preferred embodiments of said enzymes, the same applies as has been set forth above for the methods according to the present invention.

In a further aspect, the above recombinant organism or microorganism is an organism or microorganism which further expresses an enzyme capable of enzymatically converting 3-hydroxy-3-methylglutaryl-CoA into 3-methylglutaconyl-CoA (step VIII as shown in FIG. 1), preferably a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).

As regards said enzymes as well as preferred embodiments of said enzymes, the same applies as has been set forth above for the methods according to the present invention.

In a further aspect, the above recombinant organism or microorganism is an organism or microorganism which further expresses an enzyme capable of enzymatically condensing acetoacetyl-CoA and acetyl-CoA into 3-hydroxy-3-methylglutaryl-CoA (step IX as shown in FIG. 1), preferably a 3-hydroxy-3-methylglutaryl-CoA synthase.

As regards said enzyme as well as preferred embodiments of said enzyme, the same applies as has been set forth above for the methods according to the present invention.

In a further aspect, the above recombinant organism or microorganism which expresses an enzyme capable of enzymatically converting 3-methylcrotonic acid into isobutene (step I as shown in FIG. 1) and an enzyme capable of providing DMAP of any one of routes (i) to (iv) and an enzyme capable of enzymatically converting 3-methylcrotonyl-CoA into 3-methylcrotonic acid (step VIa, VIb or VIc as shown in FIG. 1) (and optionally further expressing an enzyme capable of enzymatically converting 3-methylglutaconyl-CoA into 3-methylcrotonyl-CoA and optionally further expressing an enzyme capable of enzymatically converting 3-hydroxy-3-methylglutaryl-CoA into 3-methylgutaconyl-CoA and optionally further expressing an enzyme capable of enzymatically condensing acetoacetyl-CoA and acetyl-CoA into 3-hydroxy-3-methylglutaryl-CoA) is preferably an organism or microorganism which further expresses an enzyme capable of enzymatically converting acetyl-CoA into acetoacetyl-CoA, more preferably an enzyme capable of directly condensing two molecules of acetyl-CoA into acetoacetyl-CoA (step XIII as shown in FIG. 1).

In another preferred embodiment, the recombinant organism or microorganism is a recombinant organism or microorganism which expresses the following two enzymes, namely (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1).

In a preferred embodiment, the enzyme capable of converting acetyl-CoA into malonyl-CoA is an acetyl-CoA carboxylase (EC 6.4.1.2) as described herein above.

In another preferred embodiment, the enzyme capable of condensing malonyl-CoA and acetyl-CoA into acetoacetyl-CoA is an acetoacetyl-CoA synthetase (EC 2.3.1.194) as described herein above.

In a preferred embodiment, the enzyme capable of directly condensing two molecules of acetyl-CoA into acetoacetyl-CoA is an acetyl-CoA C-acetyltransferase (EC 2.3.1.9) as described herein above.

As regards the above-mentioned enzymes as well as the preferred embodiments of said enzymes, the same applies as has been set forth above for the methods according to the present invention.

Recombinant Organisms or Microorganisms Expressing Enzymes of any One of Route (i), (ii), (iii) and/or (iv) for the Provision of DMAP and/or any One of Route (v), (vi) and/or (vii) for the Provision of DMAPP and/or FMN, One or More Enzymes of the Alternative Route for the Enzymatic Conversion from Acetyl-CoA into Isobutene Via 3-Methyl-3-Butenoyl-CoA and 3-Methyl-3-Butenoic Acid: Recombinant Organisms or Microorganisms Expressing Enzymes of Step XVI and Step XVII, and Optionally Further Expressing Enzymes of Step XVIII, Step VIII and Step IX as Well as Optionally Further Expressing Enzymes of Steps XIII, XIV and XV As mentioned above, in an alternative to the above first route for the production of isobutene via 3-methylcrotonic acid, the present invention also relates to a method for the production of isobutene via an alternative route wherein isobutene is produced by the enzymatic conversion of 3-methyl-3-butenoic acid into isobutene. In the following, the recombinant organisms or microorganisms expressing enzymes of any one of route (i), (ii), (iii) and/or (iv) for the provision of DMAP and/or an enzyme capable of providing DMAPP of any one of routes (v) to (vii) and/or enzymes for the provision of FMN as well as enzymes of this alternative route for the enzymatic conversion from acetyl-CoA into isobutene via 3-methyl-3-butenoyl-CoA and 3-methyl-3-butenoic acid are described.

The present invention also relates to a recombinant organism or microorganism which expresses an enzyme capable of enzymatically converting 3-methyl-3-butenoic acid into isobutene (step XVI as shown in FIG. 1) and an enzyme capable of enzymatically converting 3-methyl-3-butenoyl-CoA into 3-methyl-3-butenoic acid (step XVII as shown in FIG. 1).

In a preferred embodiment, the enzyme capable of enzymatically converting 3-methyl-3-butenoic acid into isobutene is a 3-methyl-3-butenoic acid decarboxylase as described herein above, more preferably (i) an FMN-dependent decarboxylase associated with an FMN prenyl transferase; or (ii) an aconitate decarboxylase (EC 4.1.1.6); or (iii) a methylcrotonyl-CoA carboxylase (EC 6.4.1.4); or (iv) a geranoyl-CoA carboxylase (EC 6.4.1.5); or (v) a protocatechuate (PCA) decarboxylase (EC 4.1.1.63) as described herein above.

In another preferred embodiment, the 3-methyl-3-butenoic acid decarboxylase is selected from the group consisting of 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68) as described herein above.

As regards the above-mentioned enzymes as well as preferred embodiments of said enzymes, the same applies as has been set forth above for the methods according to the present invention.

In a preferred embodiment, the enzyme capable of enzymatically converting 3-methyl-3-butenoyl-CoA into 3-methyl-3-butenoic acid is (a) an enzyme capable of directly converting 3-methyl-3-butenoyl-CoA into 3-methyl-3-butenoic acid, wherein said enzyme capable of directly converting 3-methyl-3-butenoyl-CoA into 3-methyl-3-butenoic acid is a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step XVIIa as shown in FIG. 1) as described herein above.

In another preferred embodiment, the recombinant organism or microorganism is a recombinant organism or microorganism which expresses the following two enzymes, namely (b) an enzyme capable of directly converting 3-methyl-3-butenoyl-CoA into 3-methyl-3-butenoic acid, wherein said enzyme capable of directly converting 3-methyl-3-butenoyl-CoA into 3-methyl-3-butenoic acid is a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step XVIIb as shown in FIG. 1) as described herein above; or (c) (i) an enzyme capable of enzymatically converting 3-methyl-3-butenoyl-CoA into 3-methyl-3-butenoyl phosphate; and (ii) an enzyme capable of enzymatically converting 3-methyl-3-butenoyl phosphate into said 3-methyl-3-butenoic acid (step XVIIc as shown in FIG. 1) as described herein above.

In a preferred embodiment, the enzyme capable of enzymatically converting said 3-methyl-3-butenoyl-CoA into 3-methyl-3-butenoyl phosphate is a phosphate butyryltransferase (EC 2.3.1.19) or a phosphate acetyltransferase (EC 2.3.1.8) and the enzyme capable of enzymatically converting 3-methyl-3-butenoyl phosphate into 3-methyl-3-butenoic acid is a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14) as described herein above.

As regards the above-mentioned enzymes as well as preferred embodiments of said enzymes, the same applies as has been set forth above for the methods according to the present invention.

In a further aspect, the above recombinant organism or microorganism is an organism or microorganism which further expresses an enzyme capable of enzymatically converting 3-methylglutaconyl-CoA into 3-methyl-3-butenoyl-CoA (step XVIII as shown in FIG. 1), preferably (a) (i) a methylcrotonyl-CoA carboxylase (EC 6.4.1.4); or (ii) a geranoyl-CoA carboxylase (EC 6.4.1.5), or (b) an N-terminal domain of CurF from Lynbya majuscula multifunctional protein or a 3-methylglutaconyl-CoA decarboxylase, preferably a 3-methylglutaconyl-CoA decarboxylase of *Myxococcus xanthus* encoded by the liuB gene; or (c) an enzyme of the 4-oxalocrotonate decarboxylase family, as described herein above.

As regards the above-mentioned enzymes as well as preferred embodiments of said enzymes, the same applies as has been set forth above for the methods according to the present invention.

In a further aspect, the above recombinant organism or microorganism is an organism or microorganism which further expresses an enzyme capable of enzymatically converting 3-hydroxy-3-methylglutaryl-CoA into 3-methylglutaconyl-CoA (step VIII as shown in FIG. 1), preferably a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).

As regards the above-mentioned enzyme as well as preferred embodiments of said enzyme, the same applies as has been set forth above for the methods according to the present invention.

In a further aspect, the above recombinant organism or microorganism is an organism or microorganism which further expresses an enzyme capable of enzymatically condensing acetoacetyl-CoA and acetyl-CoA into 3-hydroxy-3-methylglutaryl-CoA (step IX as shown in FIG. 1).

In a preferred embodiment, the enzyme capable of enzymatically condensing acetoacetyl-CoA and acetyl-CoA into 3-hydroxy-3-methylglutaryl-CoA is a 3-hydroxy-3-methylglutaryl-CoA synthase.

As regards the afore-mentioned enzyme as well as preferred embodiments of said enzyme, the same applies as has been set forth above for the methods according to the present invention.

In a further aspect, the above recombinant organism or microorganism is an organism or microorganism which further expresses an enzyme or several enzymes capable of enzymatically converting acetyl-CoA into acetoacetyl-CoA.

In one preferred embodiment, the recombinant organism or microorganism expresses a combination of enzymes, namely (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1).

In an alternative embodiment, the recombinant organism or microorganism expresses an enzyme capable of directly condensing two molecules of acetyl-CoA into acetoacetyl-CoA (step XIII as shown in FIG. 1).

As regards the first above-mentioned embodiment, the enzyme capable of converting acetyl-CoA into malonyl-CoA is preferably an acetyl-CoA carboxylase (EC 6.4.1.2) as described herein above.

Moreover, the enzyme capable of condensing malonyl-CoA and acetyl-CoA into acetoacetyl-CoA is an acetoacetyl-CoA synthetase (EC 2.3.1.194) as described herein above.

As regards the second above-mentioned embodiment, the enzyme capable of directly condensing two molecules of acetyl-CoA into acetoacetyl-CoA is preferably an acetyl-CoA C-acetyltransferase (EC 2.3.1.9) as described herein above.

As regards the above-mentioned enzymes as well as the preferred embodiments of said enzymes, the same applies as has been set forth above for the methods according to the present invention.

Recombinant Organisms or Microorganisms Expressing Enzymes of the Additional/Supplemental Pathways of Steps Xa, Xb, XI and XII As mentioned above, the above-described methods of the present invention for producing isobutene from acetyl-CoA may be supplemented by one or more of the reactions as shown in step Xa, step Xb, step XI and step XII of FIG. 1 (also summarized in FIG. 26) and as described in detail herein above.

Thus, in a further aspect, the present invention relates to any of the above-described recombinant organism or microorganism wherein the organism or microorganism additionally further expresses a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or b) an enzyme capable of enzymatically converting 3-hydroxyisovalerate (HIV) into 3-hydroxyisovaleryl-CoA (step Xb as schematically shown in FIG. 20); and/or c) an enzyme capable of enzymatically converting 3-hydroxyisovaleryl-CoA into 3-methylcrotonyl-CoA (step XI as schematically shown in FIG. 21); and/or d) an enzyme capable of enzymatically converting 3-hydroxyisovalerate (HIV) into 3-hydroxyisovaleryl-CoA (step XII as schematically shown in FIG. 22)

as described herein above.

As regards the above-mentioned enzymes as well as preferred embodiments of said enzymes, the same applies as has been set forth above for the methods according to the present invention.

The above microorganism is preferably a bacterium, a yeast or a fungus. In another preferred embodiment, the organism is a plant or a non-human animal. As regards other preferred embodiments of the bacterium, recombinant organism or microorganism, the same applies as has been set forth above in connection with the methods according to the present invention.

The present invention also relates to the use of any of the above-described recombinant organisms or microorganisms for the production of isobutene from 3-methylcrotonic acid. Thus, the present invention furthermore relates to the use of a recombinant organism or microorganism for the production of isobutene wherein said recombinant organism or microorganism recombinantly expresses an FMN-dependent decarboxylase associated with an FMN prenyl transferase;

wherein said recombinant organism or microorganism further recombinantly expresses at least one of the following (i) to (iv):

(i) an enzyme catalyzing the enzymatic conversion of dimethylallyl pyrophosphate (DMAPP) into dimethylallyl phosphate (DMAP), wherein said enzyme is a phosphatase, preferably an enzyme acting on phosphorous containing anhydrides (EC 3.6.1.-), more preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or preferably a phosphoric-monoester hydrolase (EC 3.1.3.-), more preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11); or preferably an isopentenyl phosphate kinase (EC 2.7.4.26);

(ii) an enzyme catalyzing the direct enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iii) an enzyme catalyzing the enzymatic conversion of DMAPP into prenol, wherein said enzyme is a phosphatase or pyrophosphatase, preferably an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and an enzyme catalyzing the thus obtained prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iv) an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

The present invention furthermore relates to the use of any of the above-described recombinant organisms or microorganisms for the production of isobutene which further recombinantly expresses an enzyme catalyzing the enzymatic conversion of isopentenyl pyrophosphate (IPP) into DMAPP, wherein said enzyme is an isomerase, preferably an isopentenyl-diphosphate DELTA isomerase (EC 5.3.3.2).

The present invention furthermore relates to the use of a recombinant organism or microorganism for the production of isobutene wherein said recombinant organism or microorganism recombinantly expresses an FMN-dependent decarboxylase associated with an FMN prenyl transferase;

wherein said recombinant organism or microorganism further recombinantly expresses at least one of the following (v) to (vii):

(v) an enzyme catalyzing the enzymatic conversion of isopentenyl pyrophosphate (IPP) into said DMAPP, wherein said enzyme is an isomerase, preferably an isopentenyl-diphosphate DELTA isomerase (EC 5.3.3.2);

(vi) an enzyme catalyzing the enzymatic conversion of dimethylallyl phosphate (DMAP) into said DMAPP, wherein said enzyme is a kinase, preferably an isopentenyl monophosphate kinase (EC 2.7.4.26); and (vii) an enzyme catalyzing the enzymatic conversion of prenol into said DMAPP, wherein said enzyme is a diphosphotransferase (EC 2.7.6.-), preferably a thiamine diphosphokinase (EC 2.7.6.2) or a 2-amino-4-hydroxy-6-hydroxymethyldihydropteridine diphosphokinase.

The present invention furthermore relates to the use of any of the above-described recombinant organisms or microorganisms which further recombinantly expresses at least one of the above (v) to (vii) for the production of isobutene, wherein said recombinant organism or microorganism further recombinantly expresses an enzyme catalyzing the enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50).

The present invention furthermore relates to the use of any of the above-described recombinant organisms or microorganisms which further recombinantly expresses at least one of the above (v) to (vii) for the production of isobutene, wherein said recombinant organism or microorganism further recombinantly expresses an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

The present invention furthermore relates to the use of any of the above-described recombinant organisms or microorganisms for the production of isobutene which further recombinantly expresses an enzyme catalyzing the enzymatic conversion of riboflavin into flavin mononucleotide (FMN).

The present invention furthermore relates to the use of any of the above-described recombinant organisms or microorganisms for the production of isobutene which additionally recombinantly expresses one or more of the enzymes described above for the method steps preceding the production of 3-methylcrotonic acid or 3-methyl-butenoic acid.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

The present invention furthermore relates to the use a combination comprising an FMN-dependent decarboxylase associated with an FMN prenyl transferase and an enzyme or enzymes of any one of the following (i) to (iv):

(i) an enzyme catalyzing the enzymatic conversion of dimethylallyl pyrophosphate (DMAPP) into dimethylallyl phosphate (DMAP), wherein said enzyme is a phosphatase, preferably an enzyme acting on phosphorous containing anhydrides (EC 3.6.1.-), more preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or preferably a phosphoric-monoester hydrolase (EC 3.1.3.-), more preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11); or preferably an isopentenyl phosphate kinase (EC 2.7.4.26);

(ii) an enzyme catalyzing the direct enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iii) an enzyme catalyzing the enzymatic conversion of DMAPP into prenol, wherein said enzyme is a phosphatase or pyrophosphatase, preferably an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and an enzyme catalyzing the thus obtained prenol into DMAP, wherein said enzyme is a kinase, preferably a phosphotransferase with an alcohol group as acceptor (EC 2.7.1.-), more preferably a hydroxyethylthiazole kinase (EC 2.7.1.50); and (iv) an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2)

for the production of isobutene from 3-methylcrotonic acid.

In a further aspect, the present invention relates to any of the above uses of enzymes for the production of isobutene from 3-methylcrotonic acid, wherein additionally an enzyme catalyzing the enzymatic conversion of isopentenyl pyrophosphate (IPP) into DMAPP, wherein said enzyme is an isomerase, preferably an isopentenyl-diphosphate DELTA isomerase (EC 5.3.3.2) as described herein above is used.

The present invention furthermore relates to the use of a combination comprising an FMN-dependent decarboxylase associated with an FMN prenyl transferase and an enzyme or enzymes of at least one of the following (v) to (vii):

(v) an enzyme catalyzing the enzymatic conversion of isopentenyl pyrophosphate (IPP) into said DMAPP, wherein said enzyme is an isomerase, preferably an isopentenyl-diphosphate DELTA isomerase (EC 5.3.3.2);

(vi) an enzyme catalyzing the enzymatic conversion of dimethylallyl phosphate (DMAP) into said DMAPP, wherein said enzyme is a kinase, preferably an isopentenyl monophosphate kinase (EC 2.7.4.26); and (vii) an enzyme catalyzing the enzymatic conversion of prenol into said DMAPP, wherein said enzyme is a diphosphotransferase (EC 2.7.6.-), preferably a thiamine diphosphokinase (EC 2.7.6.2) or a 2-amino-4-hydroxy-6-hydroxymethyldihydropteridine diphosphokinase, for the production of isobutene from 3-methylcrotonic acid.

The present invention furthermore relates to any of the above-described uses for the production of isobutene from 3-methylcrotonic acid wherein at least one of the above (v) to (vii) enzymes is additionally used, wherein additionally an enzyme catalyzing the enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50) as described herein above is used.

The present invention furthermore relates to any of the above-described uses for the production of isobutene from 3-methylcrotonic acid wherein at least one of the above (v) to (vii) enzymes is further used, wherein, additionally, an enzyme catalyzing catalyzing the enzymatic conversion of isopentenyl monophosphate (IMP) into DMAP, wherein said enzyme is an isomerase, preferably an isopentenyl-diphosphate DELTA isomerase (EC 5.3.3.2) as described herein above is used.

In a further aspect, the present invention relates to any of the above uses of enzymes for the production of isobutene from 3-methylcrotonic acid, wherein additionally an enzyme catalyzing the enzymatic conversion of riboflavin into flavin mononucleotide (FMN) as described herein above is used.

In a further aspect, the present invention relates to any of the above uses of enzymes for the production of isobutene from 3-methylcrotonic acid, wherein additionally one or more of the enzymes described above for the method steps preceding the production of 3-methylcrotonic acid are used.

As regards the above-mentioned enzymes as well as preferred embodiments of said enzymes, the same applies to the use for the production of isobutene as has been set forth above for the methods and recombinant organisms or microorganisms according to the present invention.

Furthermore, the present invention relates to a composition comprising DMAPP, IMP and/or prenol and a recombinant organism or microorganism, wherein said recombinant organism or microorganism recombinantly expresses an FMN-dependent decarboxylase associated with an FMN prenyl transferase;

wherein said recombinant organism or microorganism further recombinantly expresses at least one of the following (i) to (iv):

(i) an enzyme catalyzing the enzymatic conversion of dimethylallyl pyrophosphate (DMAPP) into dimethylallyl phosphate (DMAP), wherein said enzyme is a phosphatase, preferably an enzyme acting on phosphorous containing anhydrides (EC 3.6.1.-), more preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or preferably a phosphoric-monoester hydrolase (EC 3.1.3.-), more preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11); or preferably an isopentenyl phosphate kinase (EC 2.7.4.26);

(ii) an enzyme catalyzing the direct enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iii) an enzyme catalyzing the enzymatic conversion of DMAPP into prenol, wherein said enzyme is a phosphatase or pyrophosphatase, preferably an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and an enzyme catalyzing the thus obtained prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iv) an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

The present invention furthermore relates to any of the above-described compositions wherein said recombinant organisms or microorganisms further recombinantly expresses an enzyme catalyzing the enzymatic conversion of isopentenyl pyrophosphate (IPP) into DMAPP, wherein said enzyme is an isomerase, preferably an isopentenyl-diphosphate DELTA isomerase (EC 5.3.3.2).

Furthermore, the present invention relates to a composition comprising DMAP, IPP and/or prenol and a recombinant organism or microorganism, wherein said recombinant organism or microorganism recombinantly expresses an FMN-dependent decarboxylase associated with an FMN prenyl transferase;

wherein said recombinant organism or microorganism further recombinantly expresses at least one of the following (v) to (vii):

(v) an enzyme catalyzing the enzymatic conversion of isopentenyl pyrophosphate (IPP) into said DMAPP, wherein said enzyme is an isomerase, preferably an isopentenyl-diphosphate DELTA isomerase (EC 5.3.3.2);

(vi) an enzyme catalyzing the enzymatic conversion of dimethylallyl phosphate (DMAP) into said DMAPP, wherein said enzyme is a kinase, preferably an isopentenyl monophosphate kinase (EC 2.7.4.26); and (vii) an enzyme catalyzing the enzymatic conversion of prenol into said DMAPP, wherein said enzyme is a diphosphotransferase (EC 2.7.6.-), preferably a thiamine diphosphokinase (EC 2.7.6.2) or a 2-amino-4-hydroxy-6-hydroxymethyldihydropteridine diphosphokinase.

The present invention furthermore relates to any of the above-described compositions wherein said recombinant organism or microorganism further recombinantly expresses at least one of the above (v) to (vii), wherein additionally, said recombinant organism or microorganism further recombinantly expresses an enzyme catalyzing the enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50).

The present invention furthermore relates to any of the above-described compositions wherein said recombinant organism or microorganism further recombinantly expresses at least one of the above (v) to (vii), wherein additionally, said recombinant organism or microorganism further recombinantly expresses an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

The present invention furthermore relates to any of the above-described compositions wherein said recombinant organisms or microorganisms further recombinantly expresses an enzyme catalyzing the enzymatic conversion of riboflavin into flavin mononucleotide (FMN).

The present invention furthermore relates to any of the above-described compositions wherein said recombinant organisms or microorganisms additionally recombinantly express one or more of the enzymes described above for the method steps preceding the production of 3-methylcrotonic acid or 3-methyl-butenoic acid.

In a further aspect, the present invention relates to a composition comprising DMAPP, IMP and/or prenol and an FMN-dependent decarboxylase associated with an FMN prenyl transferase and an enzyme or enzymes of any one of the following (i) to (iv):

(i) an enzyme catalyzing the enzymatic conversion of dimethylallyl pyrophosphate (DMAPP) into dimethylallyl phosphate (DMAP), wherein said enzyme is a phosphatase, preferably an enzyme acting on phosphorous containing anhydrides (EC 3.6.1.-), more preferably an ADP-ribose pyrophosphatase (EC 3.6.1.13), an 8-oxo-dGTP diphosphatase (EC 3.6.1.55), a bis(5'-nucleosyl)-tetraphosphatase (EC 3.6.1.41), an UDP-sugar diphosphatase (EC 3.6.1.45), exopolyphosphatase (EC 3.6.1.11), a guanosine-5'-triphosphate/3'-diphosphate pyrophosphatase (EC 3.6.1.40), an NADH pyrophosphatase (EC 3.6.1.22), a nucleotide diphosphatase (EC 3.6.1.9) or an acylphosphatase (EC 3.6.1.7); or preferably a phosphoric-monoester hydrolase (EC 3.1.3.-), more preferably a 3'(2'), 5'-bisphosphate nucleotidase (EC 3.1.3.7), a 5-amino-6-(5-phospho-D-ribitylamino) uracil phosphatase or a fructose-1 6-bisphosphatase (EC 3.1.3.11); or preferably an isopentenyl phosphate kinase (EC 2.7.4.26);

(ii) an enzyme catalyzing the direct enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50);

(iii) an enzyme catalyzing the enzymatic conversion of DMAPP into prenol, wherein said enzyme is a phosphatase or pyrophosphatase, preferably an alkaline phosphatase (EC 3.1.3.1), a sugar phosphatase (EC 3.1.3.23), a phosphatidylglycerophosphatase (EC 3.1.3.27), a diacylglycerol pyrophosphate phosphatase (EC 3.1.3.81), a phosphatidate phosphatase (EC 3.1.3.4), a phosphoserine phosphatase (EC 3.1.3.3), a phosphoglycolate phosphatase (EC 3.1.3.18), a pyrimidine 5'-nucleotidase (EC 3.1.3.5), a pyridoxal phosphate phosphatase (EC 3.1.3.74) or a fructose-1 6-bisphosphatase (EC 3.1.3.11); or an UDP-sugar diphosphatase (EC 3.6.1.45) or an undecaprenyl pyrophosphate phosphatase (EC 3.6.1.27); or a prenyl-diphosphatase (EC 3.1.7.1); or an isopentenyl phosphate kinase (EC 2.7.4.26); and an enzyme catalyzing the thus obtained prenol into DMAP, wherein said enzyme is a kinase, preferably a phosphotransferase with an alcohol group as acceptor (EC 2.7.1.-), more preferably a hydroxyethylthiazole kinase (EC 2.7.1.50); and (iv) an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

In a further aspect, the present invention relates to any of the above compositions which further additionally comprises an enzyme catalyzing the enzymatic conversion of isopentenyl pyrophosphate (IPP) into DMAPP, wherein said enzyme is an isomerase, preferably an isopentenyl-diphosphate DELTA isomerase (EC 5.3.3.2) as described herein above.

In a further aspect, the present invention relates to a composition comprising DMAP, IPP and/or prenol and an FMN-dependent decarboxylase associated with an FMN prenyl transferase and an enzyme or enzymes of at least one of the following (v) to (vii):

(v) an enzyme catalyzing the enzymatic conversion of isopentenyl pyrophosphate (IPP) into said DMAPP, wherein said enzyme is an isomerase, preferably an isopentenyl-diphosphate DELTA isomerase (EC 5.3.3.2);

(vi) an enzyme catalyzing the enzymatic conversion of dimethylallyl phosphate (DMAP) into said DMAPP, wherein said enzyme is a kinase, preferably an isopentenyl monophosphate kinase (EC 2.7.4.26); and (vii) an enzyme catalyzing the enzymatic conversion of prenol into said DMAPP, wherein said enzyme is a diphosphotransferase (EC 2.7.6.-), preferably a thiamine diphosphokinase (EC 2.7.6.2) or a 2-amino-4-hydroxy-6-hydroxymethyldihydropteridine diphosphokinase.

The present invention furthermore relates to any of the above-described compositions further comprising at least one of the above (v) to (vii), wherein additionally, said composition further comprises an enzyme catalyzing the enzymatic conversion of prenol into DMAP, wherein said enzyme is a kinase, preferably a phosphotransferase with an alcohol group as acceptor (EC 2.7.1.-), more preferably a hydroxyethylthiazole kinase (EC 2.7.1.50).

The present invention furthermore relates to any of the above-described compositions further comprising at least one of the above (v) to (vii), wherein additionally, said composition further comprises an enzyme catalyzing the enzymatic conversion of isopentenyl monophosphate (IMP) into DMAP, wherein said enzyme is an isomerase, preferably an isopentenyl-diphosphate DELTA isomerase (EC 5.3.3.2).

In a further aspect, the present invention relates to any of the above compositions which additionally further comprises an enzyme catalyzing the enzymatic conversion of riboflavin into flavin mononucleotide (FMN) as described herein above.

In a further aspect, the present invention relates to any of the above compositions which additionally comprises one or more of the enzymes described above for the method steps preceding the production of 3-methylcrotonic acid.

As regards the above-mentioned enzymes as well as preferred embodiments of said enzymes, the same applies to the compositions as has been set forth above for the methods according to the present invention.

FIG. 1: shows an artificial pathway for isobutene production from acetyl-CoA via 3-methylcrotonic acid. Moreover, enzymatic recycling of metabolites which may occur during the pathway are shown in steps Xa, Xb, XI and XII.

FIG. 2A: Schematic reaction of the enzymatic prenylation of a flavin mononucleotide (FMN) into the corresponding modified (prenylated) flavin cofactor.

FIG. 2B: Schematic reaction of the enzymatic conversion of 3-methylcrotonic acid into isobutene.

FIG. 3: Chemical structure of DMAP and DMAPP.

FIG. 4: Schematic reactions for the different routes for the provision of DMAP and to increase the DMAP pool.

FIG. 5: Schematic reaction of the enzymatic conversion/dephosphorylation of DMAPP into DMAP.

FIG. 6: Schematic reaction of the enzymatic conversion/dephosphorylation of DMAPP into DMAP by the formation ATP from ADP.

FIG. 7: Schematic reaction of the enzymatic conversion/phosphorylation of prenol into DMAP.

FIG. 8: Schematic reaction for the enzymatic conversion of DMAPP into prenol, the enzymatic conversion of prenol into DMAP as well as a preceding step of the enzymatic conversion of isopentenyl pyrophosphate into DMAPP.

FIG. 9: illustrates the pathway for the biosynthesis of flavin mononucleotide (FMN) starting from GTP.

FIG. 10: Schematic reaction of the enzymatic conversion of 3-hydroxyisovalerate (HIV) into 3-methylcrotonic acid.

FIG. 11: Schematic reaction of the enzymatic condensation of acetyl-CoA and acetone into 3-hydroxyisovalerate.

FIG. 12: Schematic reaction of the enzymatic conversion of acetoacetate into acetone.

FIG. 13: Schematic reaction of the enzymatic conversion of acetoacetyl-CoA into acetoacetate by hydrolysing the CoA thioester of acetoacetyl-CoA resulting in acetoacetate.

FIG. 14: Schematic reaction of the enzymatic conversion of acetoacetyl-CoA into acetoacetate by transferring the CoA group of acetoacetyl-CoA on acetate, resulting in the formation of acetoacetate and acetyl-CoA.

FIG. 15: Schematic reaction of the enzymatic conversion of 3-methylcrotonyl-CoA into 3-methylcrotonic acid.

FIG. 16: Schematic reaction of the enzymatic conversion of 3-methylcrotonyl-CoA into 3-methylcrotonic acid via step VIc as shown in FIG. 1.

FIG. 17: Schematic reaction of the enzymatic conversion of 3-methylcrotonyl-CoA into 3-methylcrotonic acid via step VIb as shown in FIG. 1.

FIG. 18: Schematic reaction of the enzymatic conversion of 3-methylcrotonyl-CoA into 3-methylcrotonic acid via step VIa as shown in FIG. 1.

FIG. 19: Schematic illustration for the conversion of 3-methylcrotonyl-CoA into 3-methylcrotonic acid via 3-methylbutyryl-CoA and 3-methylbutyric acid.

FIG. 20: Schematic reaction of the enzymatic conversion of 3-methylglutaconyl-CoA into 3-methylcrotonyl-CoA.

FIG. 21: Schematic reaction of the enzymatic conversion of 3-hydroxy-3-methylglutaryl-CoA into 3-methylglutaconyl-CoA.

FIG. 22: Schematic reaction of the enzymatic condensation of acetylCoA and acetoacetyl-CoA into 3-hydroxy-3-methylglutaryl-CoA.

FIG. 23: Schematic reaction of the enzymatic condensation of two molecules of acetyl-CoA into acetoacetyl-CoA.

Figure 24:
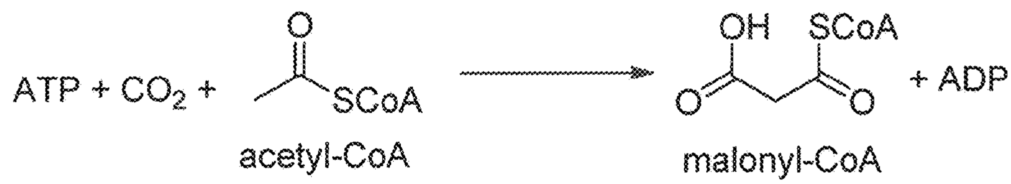

FIG. 24: Schematic reaction of the enzymatic conversion of acetyl-CoA into malonyl-CoA.

Figure 25:
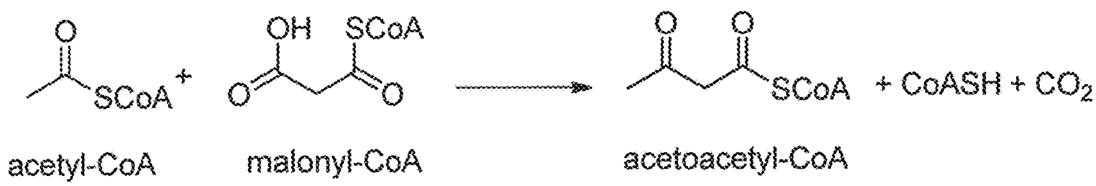

FIG. 25: Schematic reaction of the enzymatic condensation of malonyl-CoA and acetyl-CoA into acetoacetyl-CoA.

FIG. 26: shows enzymatic recycling steps of metabolites (steps Xa, Xb, XI and XII as also shown in FIG. 1) which may occur during the pathway of isobutene production from acetyl-CoA via 3-methylcrotonic acid.

FIG. 27: Schematic reaction of the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA.

FIG. 28: Schematic reaction of the enzymatic conversion of 3-hydroxyisovalerate (HIV) into 3-hydroxyisovaleryl-CoA.

FIG. 29: Schematic reaction of the enzymatic conversion of 3-hydroxyisovaleryl-CoA into 3-methylcrotonyl-CoA.

FIG. 30: Schematic reaction of the general enzymatic conversion of 3-hydroxyisovalerate (HIV) into 3-hydroxyisovaleryl-CoA.

FIG. 31: Schematic reaction of the enzymatic conversion of 3-hydroxyisovalerate (HIV) into 3-hydroxyisovaleryl-CoA via 3-hydroxyisovaleryl-adenosine monophosphate.

FIG. 32: Schematic reaction of the enzymatic conversion of 3-hydroxyisovalerate (HIV) into 3-hydroxyisovaleryl-CoA via 3-hydroxyisovaleryl phosphate.

Figure 33:
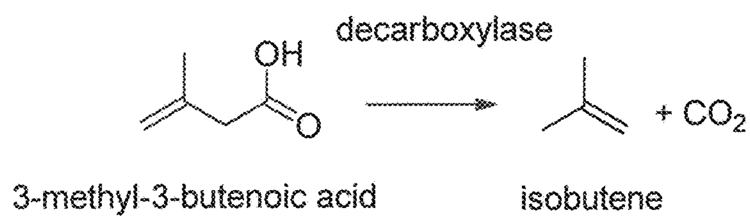

FIG. 33: Schematic reaction of the enzymatic conversion of 3-methyl-3-butenoic acid into isobutene.

FIG. 34: Schematic reaction of the enzymatic conversion of 3-methyl-3-butenoyl-CoA into 3-methyl-3-butenoic acid.

Figure 35:
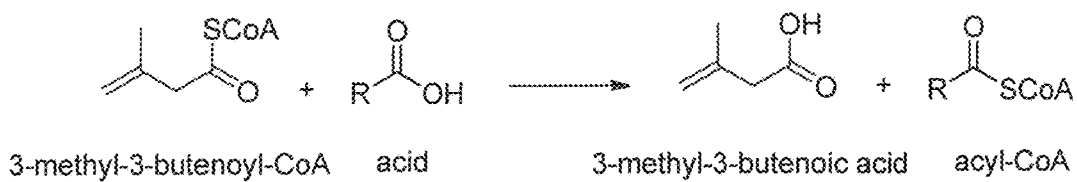

FIG. 35: Schematic reaction of the enzymatic conversion of 3-methyl-3-butenoyl-CoA into 3-methyl-3-butenoic acid by making use of a CoA-transferase.

Figure 36:
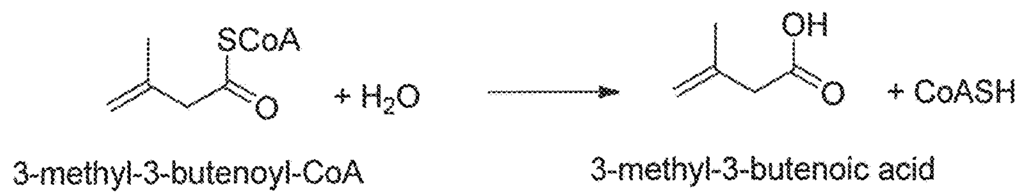

FIG. 36: Schematic reaction of the enzymatic conversion of 3-methyl-3-butenoyl-CoA into 3-methyl-3-butenoic acid by making use of a thioester hydrolase.

Figure 37:
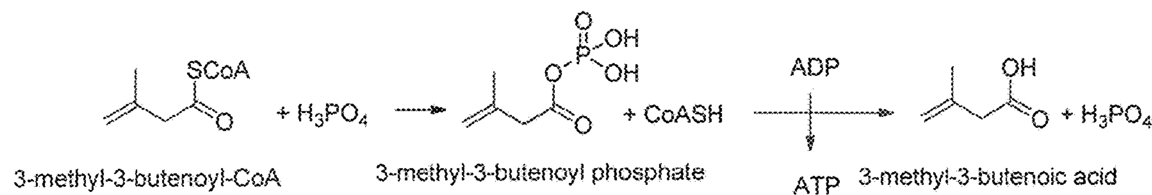

FIG. 37: Schematic reaction of the enzymatic conversion of 3-methyl-3-butenoyl-CoA into 3-methyl-3-butenoic acid in a two-step reaction via 3-methyl-3-butenoyl phosphate.

FIG. 38: Schematic reaction of the enzymatic conversion of 3-methylglutaconyl-CoA into 3-methyl-3-butenoyl-CoA.

FIG. 39: Structure of a phosphopantetheine moiety.

Figure 40:
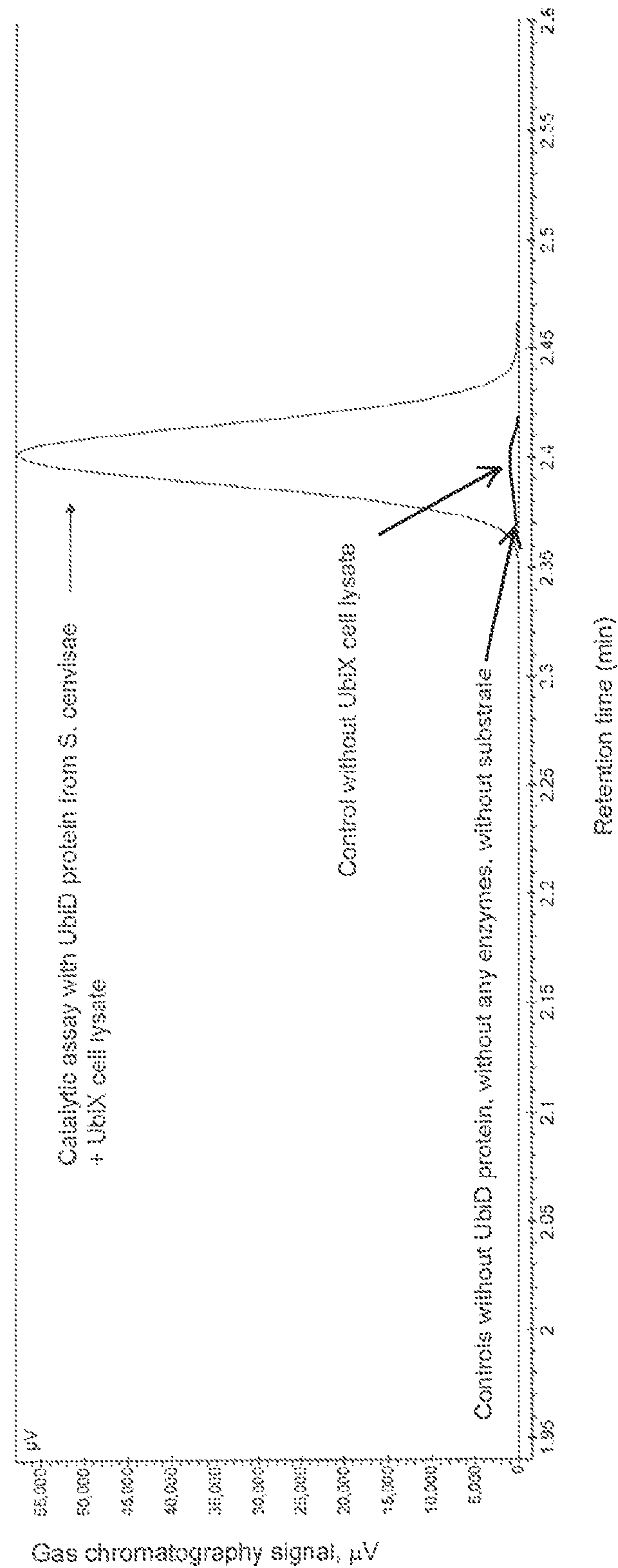

FIG. 40: shows an overlay of typical GC-chromatograms obtained for the catalytic assay of UbiD protein from *Saccharomyces cerevisiae* with the corresponding controls as outlined in Example 2.

Figure 41:
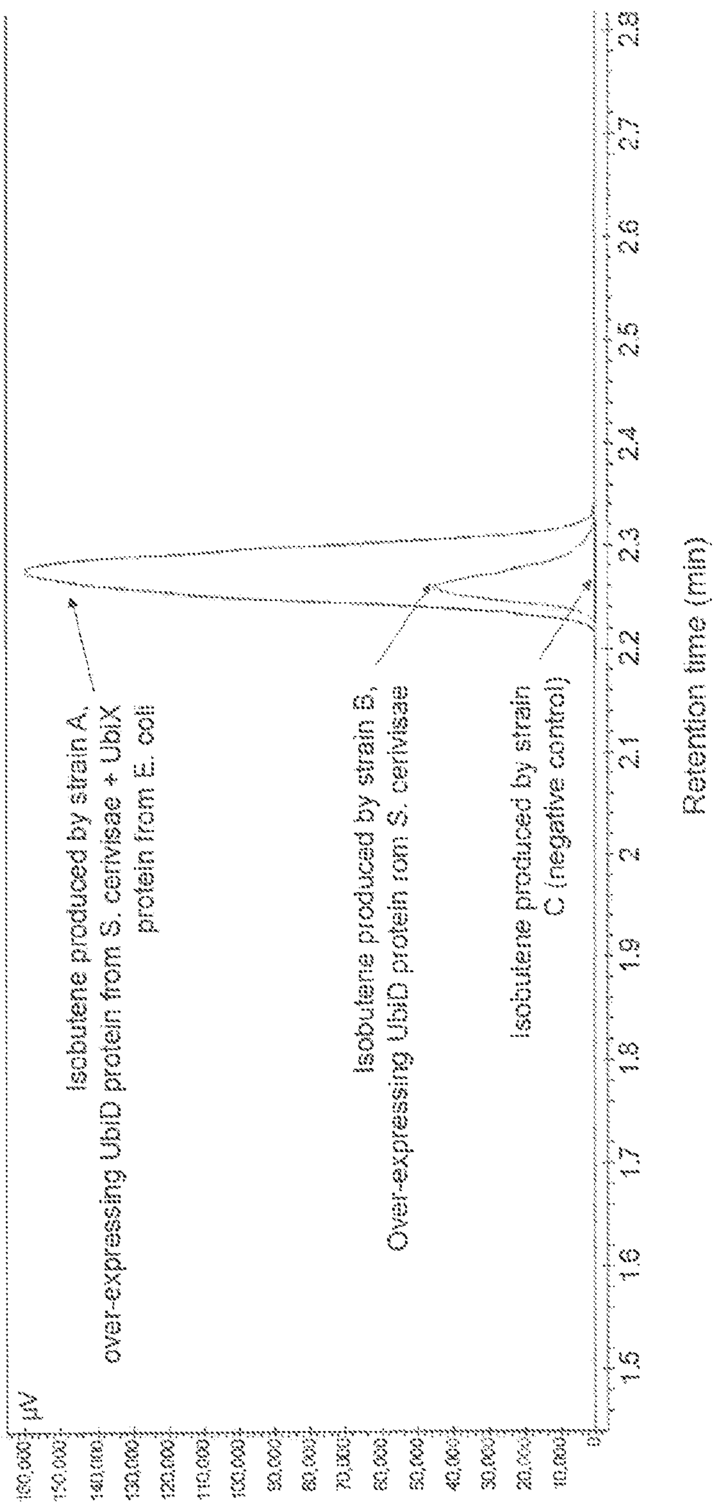

FIG. 41: shows an overlay of typical chromatograms obtained for the production of isobutene from 3-methylcrotonic in a recombinant *E. coli* strain overexpressing UbiD protein from *Saccharomyces cerevisiae* and UbiX protein from *Escherichia coli* (strain A) or overexpressing UbiD protein from *Saccharomyces cerevisiae* alone (strain B) or carrying an empty vector (negative control, strain C).

Figure 42A:
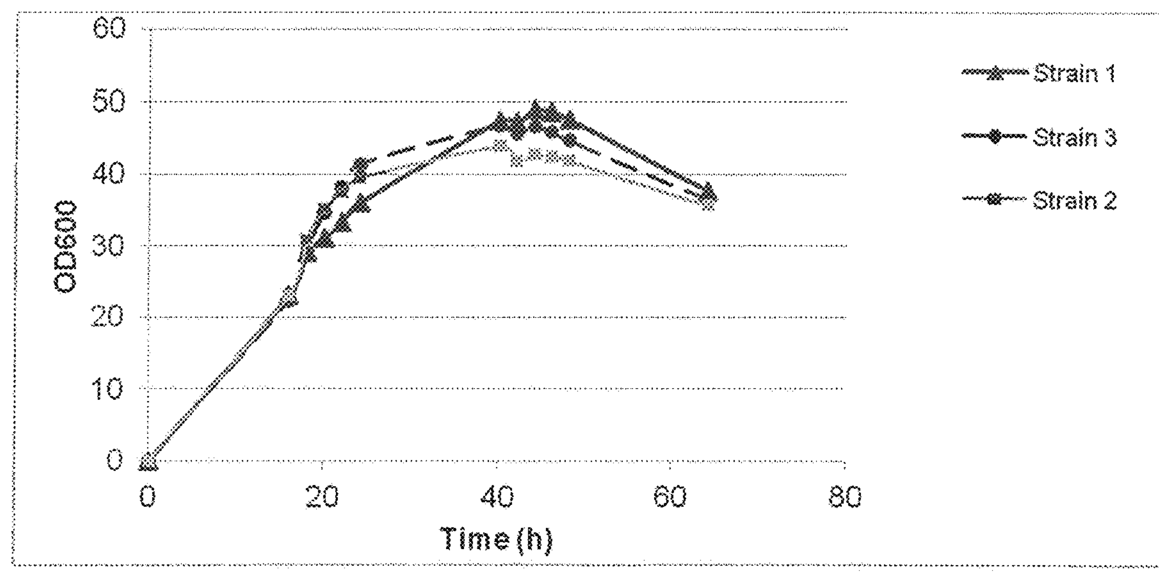
Figure 42B:
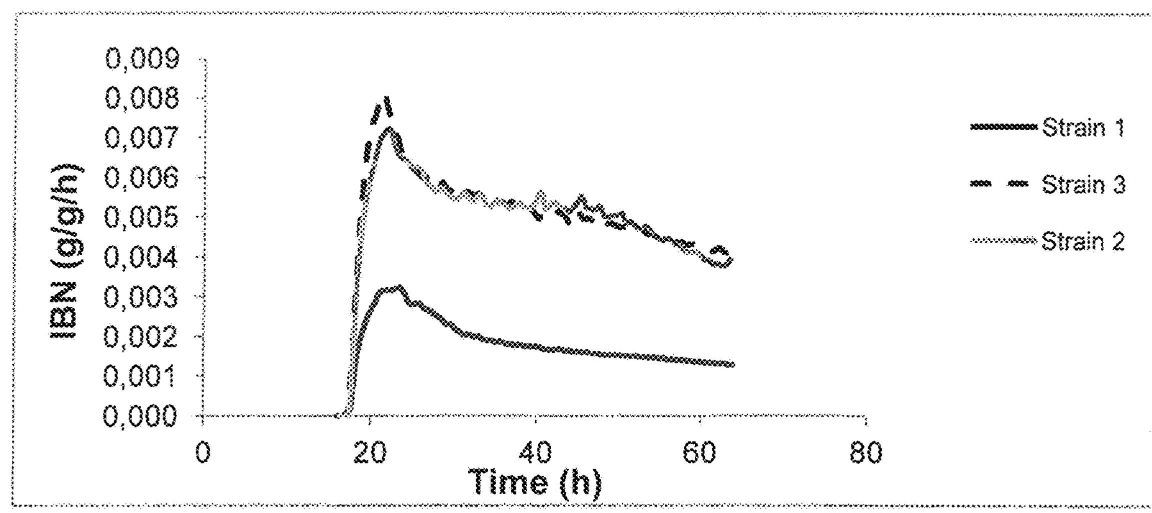

FIG. 42: shows bacterial growth and isobutene production without addition of external prenol.

a) Bacterial growth of the constructed *E. coli* strains.

b) Specific isobutene productivity obtained with the constructed *E. coli* strains.

Figure 43A:
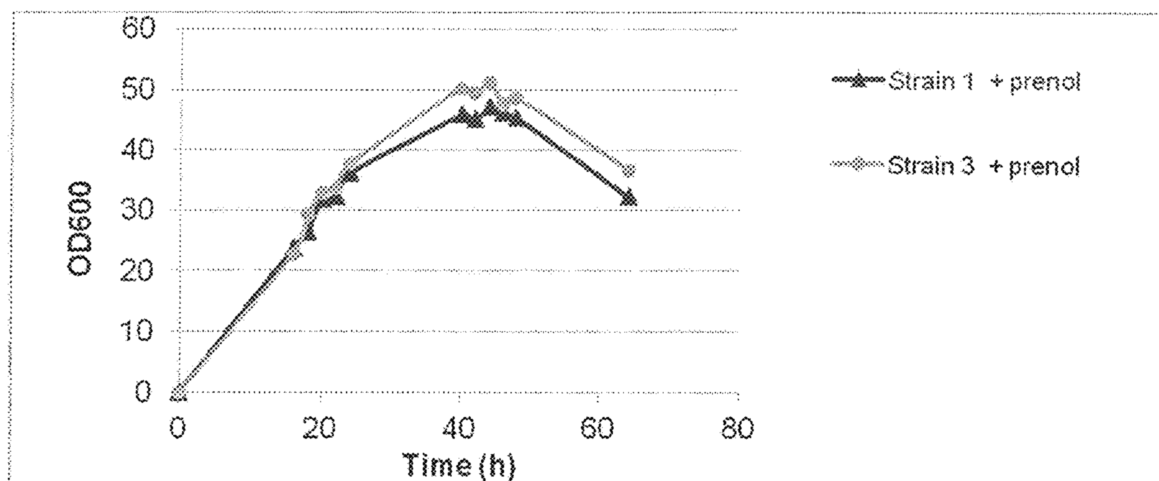
Figure 43B:
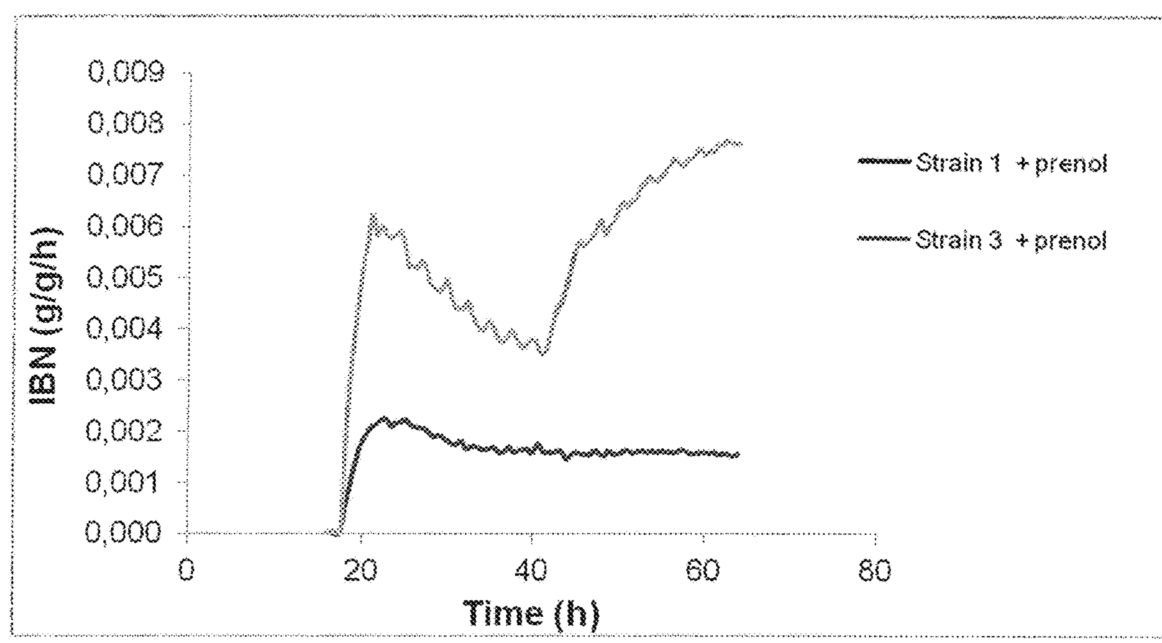

FIG. 43: shows bacterial growth and isobutene production with addition of external prenol.

a) Bacterial growth of the constructed *E. coli* strains.

b) Specific isobutene productivity obtained with the constructed *E. coli* strains.

FIG. 44: shows the schematic reactions of the mevalonate pathway.

FIG. 45: Schematic reactions for the different routes for the provision of DMAPP and to increase the DMAPP pool.

FIG. 46: Schematic reaction of the enzymatic conversion of DMAP into DMAPP.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

General Methods and Materials

All reagents and materials used in the experiences were obtained from Sigma-Aldrich Company (St. Louis, MO) unless otherwise specified. Materials and methods suitable for growth of bacterial cultures and protein expression are well known in the art.

Example 1: Gene Synthesis, Cloning and Expression of Recombinant Proteins as Used in the Below Examples 2 to 5

The sequences of the studied enzymes were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The gene thus synthesized was cloned in a pET-25b (+) expression vector (vectors were constructed by GeneArt®). Vector pCAN contained gene coding for UbiX protein (3-octaprenyl-4-hydroxybenzoate carboxy-lyase partner protein) from *Escherichia coli* (Uniprot Accession Number: P0AG03) was purchased from NAIST (Nara Institute of Science and Technology, Japan, ASKA collection). Provided vector contained a stretch of 6 histidine codons after the methionine initiation codon.

Competent *E. coli* BL21 (DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 30° C. and protein expression was continued at 18° C. overnight (approximately 16 h). For the recombinant strain over-expressing UbiX from *E. coli,* 500 μM of Flavin Mononucleotide (FMN) were added to the growth medium. The cells were collected by centrifugation at 4° C., 10,000 rpm for 20 min and the pellets were stored at −80° C.

Protein Purification and Concentration

The pellets from 200 ml of cultured cells were thawed on ice and resuspended in 6 ml of 50 mM Tris-HCl buffer pH 7.5 containing 100 mM NaCl in the case of the recombinant strain overexpressing UbiX protein and in 6 ml of 50 mM Tris-HCl buffer pH 7.5, 10 mM $MgCl_2$, 10 mM imidazole and 5 mM DTT in the case of the recombinant strain overexpressing UbiD protein. Twenty microliters of lysonase (Novagen) were added. Cells were then incubated 10 min at room temperature, returned to ice for 20 min and the lysis was completed by sonication 3×15 seconds. The cellular lysate contained UbiX protein was reserved on ice. The bacterial extracts contained UbiD proteins were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 100 mM Tris-HCl buffer pH 7.5 containing 100 mM NaCl and 250 mM imidazole. Eluates were then concentrated, desalted on Amicon Ultra-4 10 kDa filter unit (Millipore) and enzymes were resuspended in 50 mM Tris-HCl buffer pH 7.5, containing 50 mM NaCl and 5 mM DTT.

The purity of proteins thus purified varied from 80% to 90% as estimated by SDS-PAGE analysis. Protein concentration was determined by direct UV 280 nm measurement on the NanoDrop 1000 spectrophotometer (Thermo Scientific) and by Bradford assay (BioRad).

Example 2: In Vitro Decarboxylation of 3-Methylcrotonic Acid into Isobutene Catalyzed by an Association of Lysate, Containing UbiX Protein, with Purified UbiD Protein 0.5 M stock solution of 3-methylcrotonic acid was prepared in water and adjusted to pH 7.0 with 10 M solution of NaOH.

Two UbiD proteins (Table C) were purified according to the procedure described in Example 1.

Enzymatic assays were carried out in 2 ml glass vials (Interchim) under the following conditions:

50 mM Tris-HCl buffer pH 7.5
20 mM NaCl
10 mM $MgCl_2$
5 mM DTT
50 mM 3-methylcrotonic acid
1 mg/ml purified UbiD protein
50 μl lysate contained UbiX protein
Total volume of the assays were 300 μl.

A series of control assays were performed in parallel (Table C).

The vials were sealed and incubated for 120 min at 30° C. The assays were stopped by incubating for 2 min at 80° C. and the isobutene formed in the reaction headspace was analysed by Gas Chromatography (GC) equipped with Flame Ionization Detector (FID).

For the GC analysis, one ml of the headspace gas was separated in a Bruker GC-450 system equipped with a GS-alumina column (30 m×0.53 mm) (Agilent) using isothermal mode at 130° C. Nitrogen was used as carrier gas with a flow rate of 6 ml/min.

The enzymatic reaction product was identified by comparison with an isobutene standard. Under these GC conditions, the retention time of isobutene was 2.42 min. A significant production of isobutene from 3-methylcrotonic acid was observed in the combined assays (UbiD protein+UbiX protein). Incubation of lysate containing UbIX protein alone did not result in isobutene production. These data indicate that the two enzymes present in the assays cooperated to perform the decarboxylation of 3-methylcrotonic acid into isobutene. A typical chromatogram obtained in the assay with UbiD protein from *Saccharomyces cerevisiae* is shown on FIG. 40.

TABLE C

| Assay composition | Isobutene production, arbitrary units |
|---|---|
| UbiD protein from *C. dubliniensis* (Uniprot Acession Number : B9WJ66) + lysate contained UbiX protein from *E. coli* + substrate | 470 |
| UbiD protein from *C. dubliniensis* (Uniprot Acession Number : B9WJ66) + substrate | 9.2 |
| UbiD protein from *S. cervisiae* (Uniprot Acession Number : Q03034) + lysate contained UbiX protein from *E. coli* + substrate | 1923 |
| UbiD protein from *S. cerivisae* (Uniprot Acession Number : Q03034) + substrate | 31 |
| Lysate contained UbiX protein from *E. coli* + substrate | 0 |
| “No substrate control”: UbiD protein from *C. dubliniensis* (Uniprot Acession Number : B9WJ66) + lysate contained UbiX protein from *E. coli*, without substrate | 0 |
| “No substrate control” : UbiD protein from *S. cervisiae* (Uniprot Acession Number : Q03034) + lysate contained UbiX protein from *E. coli*, without substrate | 0 |

Example 3: In Vivo Decarboxylation of 3-Methylcrotonic Acid into Isobutene Catalyzed by an Association of UbiX Protein from *Escherichia coli* and UbiD Protein from *Saccharomyces cerevisiae*

The gene coding for UbiD protein from *S. cerevisiae* (Uniprot Accession Number: Q03034) was codon optimized for expression in *E. coli* and synthesized by GeneArt® (Life Technologies). This studied gene was then PCR amplified from the pMK-RQ vector (master plasmid provided by GeneArt) using forward primer with NcoI restriction site and a reverse primer, containing BamHI restriction site. The gene coding for UbiX protein from *E. coli* (Uniprot Accession Number: P0AG03) was amplified by PCR with a forward primer, containing NdeI restriction site and a reverse primer containing KpnI restriction site. The previously described pCAN vector (Example 1) served as template for this PCR step. These two obtained PCR products (UbiD protein and UbiX protein) were cloned into pET-Duet™-1 co-expression vector (Novagen). The constructed recombinant plasmid was verified by sequencing. Competent *E. coli* BL21(DE3) cells (Novagen) were transformed with this vector according to standard heat shock procedure and plated out onto LB agar plates supplemented with ampicillin (0.1 mg/ml) (termed “strain A”).

BL21(DE3) strain transformed with pET-25b(+) vector, carrying only the gene of UbiD protein from *S. cerevisiae* was also used in this study (termed “strain B”). BL21(DE3) strain transformed with an empty pET-25b(+) vector was used as a negative control in the subsequent assays (termed “strain C”).

Single transformants were used to inoculate LB medium, supplemented with ampicillin, followed by incubation at 30° C. overnight. 1 ml of this overnight culture was used to inoculate 300 ml of ZYM-5052 auto-inducing media (Studier F W (2005), local citation). The cultures were grown for 20 hours at 30° C. and 160 rpm shaking.

A volume of cultures corresponding to OD600 of 30 was removed and centrifuged. The pellet was resuspended in 30 ml of MS medium (Richaud C., Mengin-Leucreulx D., Pochet S., Johnson E J., Cohen G N. and MarHere P, The Journal of Biological Chemistry, 268, (1993), 26827-26835), containing glucose (45 g/L) and MgSO4 (1 mM) and supplemented with 10 mM 3-methylcrotonic acid. These cultures were then incubated in 160 ml bottles, sealed with a screw cap, at 30° C. with shaking for 22 h. The pH value of the cultures was adjusted to 8.5 after 8 hours of incubation by using 30% $NH_4OH$.

After an incubation period, the isobutene produced in the headspace was analysed by Gas Chromatography (GC) equipped Flame Ionization Detector (FID). One ml of the headspace gas phase was separated and analysed according to the method described in Example 2.

No isobutene was formed with the control strain C carrying an empty vector. The highest production of isobutene was observed for the strain A over-expressing the both genes, UbiD protein from *S. cerevisiae* and UbiX protein from *E. coli*. A significant production of isobutene was observed for the strain B over-expressing UbiD protein alone. Thus, endogenous UbiX of *E. coli* can probably contribute to activate UbiD protein from *S. cerevisiae* (FIG. 41).

Example 4: In Vitro Screening of the UbiD Proteins for the Decarboxylation of 3-Methylcrotonic Acid into Isobutene Several genes coding for UbiD protein were codon optimized for the expression in *E. coli* and synthesized by GeneArt® (Thermofisher). The corresponding enzymes were purified according to the procedure described in Example 1. The list of the studied enzymes is shown in Table D.

Enzymatic assays were carried out in 2 ml glass vials (Interchim) under the following conditions:

50 mM Tris-HCl buffer pH 7.5
20 mM NaCl
10 mM $MgCl_2$
1 mM DTT
50 mM 3-methylcrotonic acid
1 mg/ml purified UbiD protein
100 μl lysate contained UbiX protein from *E. coli*
Total volume of the assays were 300 μl.

A series of control assays were performed in parallel, in which either no UbiD protein was added, or no enzymes were added (Table D).

The vials were sealed and incubated for 60 min at 30° C. The assays were stopped by incubating for 2 min at 80° C. and the isobutene formed in the reaction headspace was analysed by Gas Chromatography (GC) equipped with Flame Ionization Detector (FID), according to the procedure described in Example 2.

The results of the GC analysis are shown in Table D. No isobutene production was observed in control reactions. These results show that all the UbiD proteins, studied under the conditions of this screening assay, were able to perform the decarboxylation of 3-methylcrotonic acid into isobutene in presence of *E. coli* cell lysate contained UbiX protein.

TABLE D

| Candidate UbiD protein | Assay composition | Isobutene produced, arbitrary units |
|---|---|---|
| *Saccharomyces cerevisiae* (Uniprot Accession Number: Q03034) | UbiD protein alone | 9 |
| | UbiD protein + Cell lysate contained UbiX protein | 945 |
| *Sphaerulina musiva* (Uniprot Accession Number: M3DF95) | UbiD protein alone | 70 |
| | UbiD protein + Cell lysate contained UbiX protein | 3430 |
| *Penicillium roqueforti* (Uniprot Accession Number: W6QKP7) | UbiD protein alone | 34 |
| | UbiD protein + Cell lysate contained UbiX protein | 1890 |
| *Hypocrea atroviridis* (Uniprot Accession Number: G9NLP8) | UbiD protein alone | 60 |
| | UbiD protein + Cell lysate contained UbiX protein | 5200 |
| *Fusarium oxysporum* sp. lycopersici (Uniprot Accession Number: W9LTH3) | UbiD protein alone | 13 |
| | UbiD protein + Cell lysate contained UbiX protein | 1390 |
| *Saccharomyces kudriavzevii* (Uniprot Accession Number: J8TRN5) | UbiD protein alone | 10 |
| | UbiD protein + Cell lysate contained UbiX protein | 920 |
| «No UbiD control»: Cell lysate contained UbiX protein alone | | 0 |
| Control without any enzymes | | 0 |

Example 5: Enzymatic Decarboxylation of 3-Methylcrotonic Acid into Isobutene Catalyzed in the Presence of a Lysate Containing UbiX Protein and with Purified Decarboxylase 0.5 M stock solution of 3-methylcrotonic acid was prepared in water and adjusted to pH 7.0 with 10 M solution of NaOH.

Proteins encoded by the aroY gene and one protein annotated as UbiD protein were produced according to the procedure described in Example 1.

Enzymatic assays were carried out in 2 ml glass vials (Interchim) under the following conditions:

50 mM potassium phosphate buffer pH 7.5
20 mM NaCl
10 mM $MgCl_2$
5 mM DTT
50 mM 3-methylcrotonic acid
1 mg/ml purified AroY or UbiD protein
50 μl lysate contained UbiX protein
Total volume of the assays were 300 μl.

A series of control assays were performed in parallel (Table E).

The vials were sealed and incubated for 120 min at 30° C. The assays were stopped by incubating for 2 min at 80° C. and the isobutene formed in the reaction headspace was analysed by Gas Chromatography (GC) equipped with Flame Ionization Detector (FID).

For the GC analysis, one ml of the headspace gas was separated in a Bruker GC-450 system equipped with a GS-alumina column (30 m×0.53 mm) (Agilent) using isothermal mode at 130° C. Nitrogen was used as carrier gas with a flow rate of 6 ml/min.

The enzymatic reaction product was identified by comparison with an isobutene standard. Under these GC conditions, the retention time of isobutene was 2.42 min.

A significant production of isobutene from 3-methylcrotonic acid was observed in the combined assays (AroY or UbiD protein+UbiX protein). Incubation of lysate containing UbiX protein alone did not result in isobutene production. These data indicate that the proteins encoded by aroY gene in association with UbiX protein can catalyze the decarboxylation of 3-methylcrotonic acid into isobutene.

TABLE E

| Assay composition | Isobutene production, arbitrary units |
|---|---|
| AroY protein from *K. pneumoniae* (Uniprot Acession Number : B9A9M6) + lysate contained UbiX protein from *E. coli* + substrate | 10.5 |
| AroY protein from *K. pneumoniae* (Uniprot Acession Number : B9A9M6) + substrate | 0 |
| UbiD protein from *E. cloacae* (Uniprot Acession Number : V3DX94) + lysate, contained UbiX protein from *E. coli* + substrate | 8 |
| UbiD protein from *E. cloacae* (Uniprot Acession Number : V3DX94) + substrate | 0 |
| AroY protein from *Leptolyngbya* sp. (Uniprot Acession Number : A0AOS3U6D8) + lysate, contained UbiX protein from *E. coli* + substrate | 5.5 |
| AroY protein from *Leptolyngbya* sp. (Uniprot Acession Number : A0AOS3U6D8) + substrate | 0 |
| AroY protein from *Phascolarctobacterium* sp. (Uniprot Acession Number :R6IIV6) + lysate, contained UbiX protein from *E. coli* + substrate | 5.5 |
| AroY protein from *Phascolarctobacterium* sp. (Uniprot Acession Number :R6IIV6) + substrate | 0 |
| Lysate contained UbiX protein from *E. coli* + substrate | 0 |

Example 6: Gene Synthesis, Cloning and Expression of Recombinant Proteins as Used in the Below Examples 7 to 8

Gene Synthesis, Cloning and Expression of Recombinant Proteins

The sequences of the studied enzymes inferred from the genomes of microorganisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a pET-25b(+) expression vector (vectors were constructed by GeneArt®), Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 20 h at 30° C. The cells were then collected by centrifugation at 4° C., 10,000 rpm for 20 min and the pellets were stored at −80° C.

Protein Purification and Concentration

The pellets from 500 ml of culture cells were thawed on ice and resuspended in 5 ml of 50 mM Tris-HCl buffer pH 7.5 containing 500 mM NaCl, 10 mM $MgCl_2$, 10 mM imidazole and 1 mM DTT. Fifty microliters of lysonase (Novagen) were added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min. The clarified bacterial lysates were loaded onto a PROTINO-2000 Ni-NTA column (Macherey-Nagel) allowing adsorption of 6-His tagged proteins. Columns were washed and the enzymes of interest were eluted with 6 ml of 50 mM Tris-HCl buffer pH 7.5 containing 300 mM NaCl, 200 mM imidazole. Eluates were then concentrated, desalted on Amicon Ultra-4 10 kDa filter unit (Millipore) and enzymes were resuspended in solution containing 50 mM Tris-HCl pH 7.5, containing 100 mM NaCl. Protein concentrations were quantified by direct UV 280 nm measurement on the NanoDrop 1000 spectrophotometer (Thermo Scientific). The purity of proteins was estimated by SDS-PAGE analysis.

Example 7: Conversion of DMAPP into DMAP Catalyzed by Isopentenyl Phosphate Kinases The genes coding for isopentenyl phosphate kinases were synthesized and the corresponding enzymes were further produced according to the procedure described in Example 6. The enzymatic assays were conducted in total reaction volume of 0.2 ml.

Standard reaction mixture contained:

50 mM Tris-HCl pH 7.5

20 mM dimethylallyl pyrophosphate (DMAPP) (Sigma-Aldrich)

20 mM ATP (Sigma-Aldrich)

5 mM $MgCl_2$ 100 mM NaCl 1 mg/ml of purified isopentenyl phosphate kinases

The enzyme free control was performed in parallel. The assays were incubated for 16 h hours at 34° C. with shaking and stopped by adding half volume of acetonitrile (ice cold). Assays were then centrifuged and an aliquot of the clarified supernatant were transferred into a clean vial for LC/MS analysis.

HPLC analyses were performed using a 1260 Infinity LC System (Agilent), equipped with column heating module and UV detector. 5 µl of samples were separated on Zorbax SB-Aq column (250×4.6 mm, 5 µm particle size, column temp. 30° C.) with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). Commercial dimethylallyl phosphate (DMAP) (Sigma-Aldrich) was used as reference. In these conditions, the retention time of DMAP was 4.32 min.

AI the tested isopentenyl phosphate kinases (EC 2.7.4.26) were able to catalyze this conversion (Table F).

TABLE F

| Isopentenyl phosphate kinases inferred from genome of | Uniprot Accession Number | DMAP formed in the assay, mM |
|---|---|---|
| *Methanocaldococcus jannaschii* | Q60352 | 8.7 |
| *Methanothermobacter thermautotrophicus* | O26153 | 8.7 |
| *Thermoplasma acidophilum* | Q9HLX1 | 8.0 |

Example 8: Microorganisms with Improved Production of Isobutene from 3-Methylcrotonic Acid This working example shows the production of isobutene by recombinant *E. coli*, expressing: (i) recombinant proteins, associated with isobutene production from 3-methylcrotonic acid (ii) different combinations of recombinant enzymes, associated with isobutene production from 3-methylcrotonic acid and enzymes to increase the pool of DMAP.

Recombinant Protein Expression

The sequences of the studied enzymes inferred from the genomes of the corresponding microorganisms were generated by oligonucleotide concatenation to fit the codon usage of *E. coli* (Table G). All the genes were commercially synthesized by GeneArt® (Thermofisher), except the gene encoding for UbiX protein, which was directly amplified from the genomic DNA of *E. coli* MG1655.

TABLE G

| Enzyme | Gene abbreviation | Uniprot Accession number |
|---|---|---|
| Flavin prenyl transferase from *Escherichia coli* (UbiX) SEQ N°5 | ubiX | P0AG03 |
| Variant of ferulic acid decarboxylase from *Hypocrea atroviridis* SEQ ID NO:35 | FDC1V4 | |
| Isopentenyl phosphate kinase from *Methanocaldococcus jannaschii* SEQ ID NO: 53 | MJ0044 | Q60352 |
| 4-methyl-5-(2-hydroxethyl) thiazole kinase from *E.coli* SEQ ID NO:31 | thiM | P76423 |

A pETDuet™-271 co-expression vector (Novagen) was used for the expression of the different combinations of ubiX, FDC1V4, thiM, MJ0044. The following constructions were created (Table H, Table I).

TABLE H

| Vector | Strain number |
|---|---|
| pGB6346 pETDuet PT7 FDC1V4 PT7 UbiX | Strain 1, expressing recombinant FDC1V4 and UbiX proteins |
| pGB6580 pETDuet PT7 UbiDv4 PT7 UbiX-MJ0044 | Strain 2, , expressing recombinant FDC1V4 and UbiX proteins and a recombinant Isopentenyl phosphate kinase MJ0044 |
| pGB6389 pETDuet PT7 UbiDv4 PT7 UbiX-thiM | Strain 3, expressing recombinant FDC1V4, and UbiX proteins and a recombinant 4-methyl-5-(2-hydroxethyl) thiazole kinase thiM |

TABLE I

Plasmids sequences used in this study

| Plasmid | Sequences |
|---|---|
| pGB6346 | ctctcccttatgcgactcctgcattaggaagcagcccagtagtaggttgaggccgttgagcaccgccgccgcaagga<br>atggtgcatgcaaggagatggcgcccaacagtcccccggccacggggcctgccaccatacccacgccgaaacaa<br>gcgctcatgagcccgaagtggcgagcccgatcttccccatcggtgatgtcggcgatataggcgccagcaaccgcac<br>ctgtggcgccggtgatgccggccacgatgcgtccggcgtagaggatcgagatcgatctcgatcccgcgaaattaata<br>cgactcactataggggaattgtgagcggataacaattcccctctagaaataattttgtttaactttaagaaggagatatac<br>catgagcagcaccacctataaaagtgaagcatttgatccggaaccgcctcatctgagctttcgtagctttgttaatgcac<br>tgcgtcaggatggggatctggtggatattaatgaaccggttgatccggatctggaagcagcagcaattacccgtctggt<br>ttgtgaaaccgatgataaagcaccgctgtttaataacgtgattggtgcaaaagatggtctgtggcgtattctgggtgcac<br>cggcaagcctgcgtgcgagcccgaaagaacgttttggtcgtctggcacgtcatctggcactgcctccgaccgcaagc<br>gcaaaagatattctggataaaatgctgagcgccaatagcattccgcctattgaaccggttattgttccgaccggtccggt<br>taaagaaaatagcattgaaggcgaaaacattgatctggaagccctgcctgcaccgatggttcatcagagtgatggtg<br>gcaagtatatcaatacctatggtatgcatgttatccagagtccggatggtgggtggaccaattggagcattgcccgtgc<br>aatggttagcggtaaacgtaccctggcaggtctggttattagtccgcagcatattcgtaaaattcaggatcagtggcgtg<br>caattggccaagaagaaattccttgggcactggcatttggtgttccgcctctggcaattatggcaagcagtatgccgatt<br>ccggatggtgttagcgaagcaggttatgttggtgcaattgccggtgaaccgattaaactggttaaatgcgataccaaca<br>atctgtatgttccggcaaatagcgaaattgttctggaaggcaccctgagcaccaccaaaatggcaccggaaggtccg<br>tttggtgaaatgcatggttatgtttatccgggtgaaagccatccgggtccggtttataccgttaacaaaattacctatcgca<br>acaatgcaattctgccgatgagcgcatgtggtcgtctgaccgatgaaacccagaccatgattccgaccctggcagca<br>gcagaaattcgtcagctgtgtcagagggcaggtctgccgattaccgatgcatttgcaccgtttgttggtcaggcaacctg<br>ggttgcactgaaagttgataccaaacgtctgcgtgcaatgaaaaccaatggtaaagcatttgcaaaagcggttggtga<br>tgttgtgtttacccagaaaccgggttttatgattcatcgtctgattctggttggtgatgatattgatgtgtatgacgataaagat<br>gtgatgtgggcatttgctacccgttgtcgtccgggtacagatgaagtttttttgatgatgttcctggcttttggctgatcccgt<br>atatgagtcatggtaatgccgaagcagtgaaaggtggtaaagttgttagtgatgcactgctgaccgcagaatatacca<br>ccggtaaagattgggaaagcgcagatttcaaaaacagctatccgaaacgtatccaggataaagttctgaatagctgg<br>gaacgcctgggtttcaaaaaactggattaataaggatccgaattcgagctcggcgcgcctgcaggtcgacaagcttg<br>cggccgcataatgcttaagtcgaacagaaagtaatcgtattgtacacggccgcataatcgaaattaatacgactcact<br>ataggggaattgtgagcggataacaattccccatcttagtatattagttaagtataagaaggagatatacatatgaaac<br>gactcattgtaggcatcagcggtgccagcggcgcgatttatggcgtgcgcttattacaggttctgcgcgatgtcacagat<br>atcgaaacgcatctggtgatgagccaggcagcgcgccagaccttatccctcgaaacggatttttctctgcgcgaagtg<br>caggcattagccgatgtcacgcacgatgcgcgcgatattgccgccagcatctcttccggttctttccagacgctgggga<br>tggtgattttaccctgttcaatcaaaaccctttccggcattgtccatagctatactgatggcttactgacccgtgcggcagat<br>gtggtgctgaaagagcgtcgcccgttggtgctctgcgtgcgtgaaacaccattgcacttaggccatctgcgtttaatgac<br>tcaggcggcagaaatcggtgcggtgattatgcctcccgttccggcgttttatcatcgcccgcaatcccttgatgatgtgat<br>aaatcagacggttaatcgtgttcttgaccagtttgcgataacccttcctgaagatctctttgcccgctggcagggcgcata<br>ataaggtaccctcgagtctggtaaagaaaccgctgctgcgaaatttgaacgccagcacatggactcgtctactagcg<br>cagcttaattaacctaggctgctgccaccgctgagcaataactagcataaccccttggggcctctaaacgggtcttgag<br>gggttttttgctgaaaggaggaactatatccggattggcgaatgggacgcgccctgtagcggcgcattaagcgcggc<br>gggtgtggtggttacgcgcagcgtgaccgctacacttgccagcgccctagcgcccgctcctttcgctttcttcccttccttt<br>ctcgccacgttcgccggctttccccgtcaagctctaaatcgggggctccctttagggttccgatttagtgctttacggcacc<br>tcgaccccaaaaaacttgattagggtgatggttcacgtagtgggccatcgccctgatagacggtttttcgccctttgacgt<br>tggagtccacgttctttaatagtggactcttgttccaaactggaacaacactcaaccctatctcggtctattcttttgatttata<br>agggattttgccgatttcggcctattggttaaaaaatgagctgatttaacaaaaatttaacgcgaattttaacaaaatatta<br>acgtttacaatttctggcggcacgatggcatgagattatcaaaaaggatcttcacctagatccttttaaattaaaaatgaa<br>gttttaaatcaatctaaagtatatatgagtaaacttggtctgacagttaccaatgcttaatcagtgaggcacctatctcagc<br>gatctgtctatttcgttcatccatagttgcctgactccccgtcgtgtagataactacgatacgggagggcttaccatctggc<br>cccagtgctgcaatgataccgcgagacccacgctcaccggctccagatttatcagcaataaaccagccagccggaa<br>gggccgagcgcagaagtggtcctgcaactttatccgcctccatccagtctattaattgttgccgggaagctagagtaag<br>tagttcgccagttaatagtttgcgcaacgttgttgccattgctacaggcatcgtggtgtcacgctcgtcgtttggtatggcttc<br>attcagctccggttcccaacgatcaaggcgagttacatgatcccccatgttgtgcaaaaaagcggttagctccttcggtc<br>ctccgatcgttgtcagaagtaagttggccgcagtgttatcactcatggttatggcagcactgcataattctcttactgtcatg<br>ccatccgtaagatgcttttctgtgactggtgagtactcaaccaagtcattctgagaatagtgtatgcggcgaccgagttgc<br>tcttgcccggcgtcaatacgggataataccgcgccacatagcagaactttaaaagtgctcatcattggaaaacgttctt<br>cggggcgaaaactctcaaggatcttaccgctgttgagatccagttcgatgtaacccactcgtgcacccaactgatcttc<br>agcatcttttactttcaccagcgtttctgggtgagcaaaaacaggaaggcaaaatgccgcaaaaaagggaataagg<br>gcgacacggaaatgttgaatactcatactcttcctttttcaatcatgattgaagcatttatcagggttattgtctcatgagcg<br>gatacatatttgaatgtatttagaaaaataaacaaataggtcatgaccaaaatcccttaacgtgagttttcgttccactga<br>gcgtcagaccccgtagaaaagatcaaaggatcttcttgagatcctttttttctgcgcgtaatctgctgcttgcaaacaaaa<br>aaaccaccgctaccagcggtggtttgtttgccggatcaagagctaccaactctttttccgaaggtaactggcttcagcag<br>agcgcagataccaaatactgtccttctagtgtagccgtagttaggccaccacttcaagaactctgtagcaccgcctaca<br>tacctcgctctgctaatcctgttaccagtggctgctgccagtggcgataagtcgtgtcttaccgggttggactcaagacga<br>tagttaccggataaggcgcagcggtcgggctgaacggggggttcgtgcacacagcccagcttggagcgaacgacc<br>tacaccgaactgagatacctacagcgtgagctatgagaaagcgccacgcttcccgaagggagaaaggcggacag<br>gtatccggtaagcggcagggtcggaacaggagagcgcacgagggagcttccagggggaaacgcctggtatcttta<br>tagtcctgtcgggtttcgccacctctgacttgagcgtcgatttttgtgatgctcgtcaggggggcggagcctatggaaaaa<br>cgccagcaacgcggcctttttacggttcctggccttttgctggccttttgctcacatgttctttcctgcgttatcccctgattctgt<br>ggataaccgtattaccgcctttgagtgagctgataccgctcgccgcagccgaacgaccgagcgcagcgagtcagtg<br>agcgaggaagcggaagagcgcctgatgcggtattttctccttacgcatctgtgcggtatttcacaccgcatatatggtgc<br>actctcagtacaatctgctctgatgccgcatagttaagccagtatacactccgctatcgctacgtgactgggtcatggctg<br>cgccccgacacccgccaacacccgctgacgcgccctgacgggcttgtctgctcccggcatccgcttacagacaagc<br>tgtgaccgtctccgggagctgcatgtgtcagaggttttcaccgtcatcaccgaaacgcgcgaggcagctgcggtaaa<br>gctcatcagcgtggtcgtgaagcgattcacagatgtctgcctgttcatccgcgtccagctcgttgagtttctccagaagcg<br>ttaatgtctggcttctgataaagcgggccatgttaagggcggtttttttcctgtttggtcactgatgcctccgtgtaaggggga<br>tttctgttcatgggggtaatgataccgatgaaacgagagaggatgctcacgatacgggttactgatgatgaacatgccc<br>ggttactggaacgttgtgagggtaaacaactggcggtatggatgcggcgggaccagagaaaaatcactcagggtca<br>atgccagcgcttcgttaatacagatgtaggtgttccacagggtagccagcagcatcctgcgatgcagatccggaacat<br>aatggtgcagggcgctgacttccgcgtttccagactttacgaaacacggaaaccgaagaccattcatgttgttgctcag |

TABLE I-continued

| Plasmids sequences used in this study | |
|---|---|
| Plasmid | Sequences |
| | gtcgcagacgttttgcagcagcagtcgcttcacgttcgctcgcgtatcggtgattcattctgctaaccagtaaggcaacc<br>ccgccagcctagccgggtcctcaacgacaggagcacgatcatgctagtcatgccccgcgcccaccggaaggagct<br>gactgggttgaaggctctcaagggcatcggtcgagatcccggtgcctaatgagtgagctaacttacattaattgcgttgc<br>gctcactgcccgctttccagtcgggaaacctgtcgtgccagctgcattaatgaatcggccaacgcgcggggagaggc<br>ggtttgcgtattgggcgccagggtggtttttcttttcaccagtgagacgggcaacagctgattgcccttcaccgcctggcc<br>ctgagagagttgcagcaagcggtccacgctggtttgccccagcaggcgaaaatcctgtttgatggtggttaacggcgg<br>gatataacatgagctgtcttcggtatcgtcgtatcccactaccgagatgtccgcaccaacgcgcagcccggactcggt<br>aatggcgcgcattgcgcccagcgccatctgatcgttggcaaccagcatcgcagtgggaacgatgccctcattcagca<br>tttgcatggtttgttgaaaaccggacatggcactccagtcgccttcccgttccgctatcggctgaatttgattgcgagtgag<br>atatttatgccagccagccagacgcagacgcgccgagacagaacttaatgggcccgctaacagcgcgatttgctggt<br>gacccaatgcgaccagatgctccacgcccagtcgcgtaccgtcttcatgggagaaaataatactgttgatgggtgtct<br>ggtcagagacatcaagaaataacgccggaacattagtgcaggcagcttccacagcaatggcatcctggtcatccag<br>cggatagttaatgatcagcccactgacgcgttgcgcgagaagattgtgcaccgccgctttacaggcttcgacgccgctt<br>cgttctaccatcgacaccaccacgctggcacccagttgatcggcgcgagatttaatcgccgcgacaatttgcgacggc<br>gcgtgcagggccagactggaggtggcaacgccaatcagcaacgactgtttgcccgccagttgttgtgccacgcggtt<br>gggaatgtaattcagctccgccatcgccgcttccactttttcccgcgttttcgcagaaacgtggctggcctggttcaccac<br>gcgggaaacggtctgataagagacaccggcatactctgcgacatcgtataacgttactggtttcacattcaccaccctg<br>aattgactctcttccgggcgctatcatgccataccgcgaaaggttttgcgccattcgatggtgtccgggatctcgacg<br>(SEQ ID NO: 36) |
| pGB6580 | caccgccgccgcaaggaatggtgcatgcaaggagatggcgcccaacagtcccccggccacggggcctgccacc<br>atacccacgccgaaacaagcgctcatgagcccgaagtggcgagcccgatcttccccatcggtgatgtcggcgatat<br>aggcgccagcaaccgcacctgtggcgccggtgatgccggccacgatgcgtccggcgtagaggatcgagatcgatc<br>tcgatcccgcgaaattaatacgactcactataggggaattgtgagcggataacaattcccctctagaaataattttgttta<br>actttaagaaggagatataccatgagcagcaccacctataaaagtgaagcatttgatccggaaccgcctcatctgag<br>ctttcgtagctttgttaatgcactgcgtcaggatggggatctggtggatattaatgaaccggttgatccggatctggaagc<br>agcagcaattacccgtctggtttgtgaaaccgatgataaagcaccgctgtttaataacgtgattggtgcaaaagatggt<br>ctgtggcgtattctgggtgcaccggcaagcctgcgtgcgagcccgaaagaacgttttggtcgtctggcacgtcatctgg<br>cactgcctccgaccgcaagcgcaaaagatattctggataaaatgctgagcgccaatagcattccgcctattgaaccg<br>gttattgttccgaccggtccggttaaagaaaatagcattgaaggcgaaaacattgatctggaagccctgcctgcaccg<br>atggttcatcagagtgatggtggcaagtatatcaatacctatggtatgcatgttatccagagtccggatggtgggtggac<br>caattggagcattgcccgtgcaatggttagcggtaaacgtaccctggcaggtctggttattagtccgcagcatattcgta<br>aaattcaggatcagtggcgtgcaattggccaagaagaaattccttgggcactggcatttggtgttccgcctctggcaatt<br>atggcaagcagtatgccgattccggatggtgttagcgaagcaggttatgttggtgcaattgccggtgaaccgattaaac<br>tggttaaatgcgataccaacaatctgtatgttccggcaaatagcgaaattgttctggaaggcaccctgagcaccacca<br>aaatggcaccggaaggtccgtttggtgaaatgcatggttatgtttatccgggtgaaagccatccgggtccggtttatacc<br>gttaacaaaattacctatcgcaacaatgcaattctgccgatgagcgcatgtggtcgtctgaccgatgaaacccagacc<br>atgattccgaccctggcagcagcagaaattcgtcagctgtgtcagagggcaggtctgccgattaccgatgcatttgca<br>ccgtttgttggtcaggcaacctgggttgcactgaaagttgataccaaacgtctgcgtgcaatgaaaaccaatggtaaa<br>gcatttgcaaaagcggttggtgatgttgtgtttacccagaaaccgggttttatgattcatcgtctgattctggttggtgatgat<br>attgatgtgtatgacgataaagatgtgatgtgggcatttgctacccgttgtcgtccgggtacagatgaagtttttttgatgat<br>gttcctggcttttggctgatcccgtatatgagtcatggtaatgccgaagcagtgaaaggtggtaaagttgttagtgatgca<br>ctgctgaccgcagaatataccaccggtaaagattgggaaagcgcagatttcaaaaacagctatccgaaacgtatcc<br>aggataaagttctgaatagctgggaacgcctgggtttcaaaaaactggattaataaggatccgaattcgagctcggcg<br>cgcctgcaggtcgacaagcttgcggccgcataatgcttaagtcgaacagaaagtaatcgtattgtacacggccgcat<br>aatcgaaattaatacgactcactataggggaattgtgagcggataacaattccccatcttagtatattagttaagtataag<br>aaggagatatacatatgaaacgactcattgtaggcatcagcggtgccagcggcgcgatttatggcgtgcgcttattac<br>aggttctgcgcgatgtcacagatatcgaaacgcatctggtgatgagccaggcagcgcgccagaccttatccctcgaa<br>acggatttttctctgcgcgaagtgcaggcattagccgatgtcacgcacgatgcgcgcgatattgccgccagcatctcttc<br>cggttctttccagacgctggggatggtgattttaccctgttcaatcaaaccctttccggcattgtccatagctatactgatg<br>gcttactgacccgtgcggcagatgtggtgctgaaagagcgtcgcccgttggtgctctgcgtgcgtgaaacaccattgc<br>acttaggccatctgcgtttaatgactcaggcggcagaaatcggtgcggtgattatgcctcccgttccggcgttttatcatc<br>gcccgcaatcccttgatgatgtgataaatcagacggttaatcgtgttcttgaccagtttgcgataacccttcctgaagatct<br>ctttgcccgctggcagggcgcataataaggtaccGAAGGAGATATACATATGCTGACCATTCTGA<br>AACTGGGTGGTAGCATTCTGAGCGATAAAAATGTTCCGTATAGCATTAAATGGG<br>ACAACCTGGAACGTATCGCAATGGAAATCAAAAATGCCCTGGACTACTACAAAA<br>ATCAGAATAAAGAAATTAAACTGATTCTGGTGCATGGTGGTGGTGCATTTGGTCA<br>TCCGGTTGCCAAAAAATACCTGAAAATTGAGGACGGCAAAAAAATCTTTATTAAC<br>ATGGAAAAAGGCTTTTGGGAAATCCAGCGTGCAATGCGTCGTTTTAACAACATT<br>ATCATTGATACCCTGCAGAGCTATGATATTCCGGCAGTTAGCATTCAGCCGAGC<br>AGCTTTGTTGTTTTTGGTGATAAACTGATCTTTGACACCAGCGCCATTAAAGAAA<br>TGCTGAAACGTAATCTGGTTCCGGTGATTCATGGTGATATTGTGATTGATGATAA<br>AAATGGCTACCGCATCATTAGCGGTGATGATATTGTTCCGTATCTGGCCAATGA<br>ACTGAAAGCAGATCTGATTCTGTATGCCACCGATGTTGATGGTGTTCTGATTGAT<br>AACAAACCGATTAAACGCATTGATAAAAACAATATCTATAAAATCCTGAATTATCT<br>GAGCGGCAGCAACAGCATTGATGTTACCGGTGGTATGAAATACAAAATCGACAT<br>GATTCGCAAAAACAAATGCCGTGGCTTTGTGTTCAATGGCAATAAAGCCAACAA<br>CATCTATAAAGCACTGCTGGGTGAAGTTGAAGGCACCGAAATTGATTTTAGCGA<br>ATAATAATTAATTAAcctaggctgctgccaccgctgagcaataactagcataaccccttggggcctctaaac<br>gggtcttgaggggttttttgctgaaaggaggaactatatccggattggcgaatgggacgcgccctgtagcggcgcatta<br>agcgcggcgggtgtggtggttacgcgcagcgtgaccgctacacttgccagcgccctagcgcccgctcctttcgctttctt<br>cccttcctttctcgccacgttcgccggctttccccgtcaagctctaaatcgggggctccctttagggttccgatttagtgcttt<br>acggcacctcgaccccaaaaaacttgattagggtgatggttcacgtagtgggccatcgccctgatagacggtttttcgc<br>cctttgacgttggagtccacgttctttaatagtggactcttgttccaaactggaacaacactcaaccctatctcggtctattct<br>tttgatttataagggattttgccgatttcggcctattggttaaaaaatgagctgatttaacaaaaatttaacgcgaattttaac<br>aaaatattaacgtttacaatttctggcggcacgatggcatgagattatcaaaaaggatcttcacctagatccttttaaatta |

TABLE I-continued

Plasmids sequences used in this study

| Plasmid | Sequences |
|---|---|
| | aaaatgaagttttaaatcaatctaaagtatatatgagtaaacttggtctgacagttaccaatgcttaatcagtgaggcacc<br>tatctcagcgatctgtctatttcgttcatccatagttgcctgactccccgtcgtgtagataactacgatacgggagggcttac<br>catctggccccagtgctgcaatgataccgcgagacccacgctcaccggctccagatttatcagcaataaaccagcca<br>gccggaagggccgagcgcagaagtggtcctgcaactttatccgcctccatccagtctattaattgttgccgggaagcta<br>gagtaagtagttcgccagttaatagtttgcgcaacgttgttgccattgctacaggcatcgtggtgtcacgctcgtcgtttggt<br>atggcttcattcagctccggttcccaacgatcaaggcgagttacatgatcccccatgttgtgcaaaaaagcggttagctc<br>cttcggtcctccgatcgttgtcagaagtaagttggccgcagtgttatcactcatggttatggcagcactgcataattctctta<br>ctgtcatgccatccgtaagatgcttttctgtgactggtgagtactcaaccaagtcattctgagaatagtgtatgcggcgac<br>cgagttgctcttgcccggcgtcaatacgggataataccgcgccacatagcagaactttaaaagtgctcatcattggaa<br>aacgttcttcggggcgaaaactctcaaggatcttaccgctgttgagatccagttcgatgtaacccactcgtgcacccaa<br>ctgatcttcagcatcttttactttcaccagcgtttctgggtgagcaaaaacaggaaggcaaaatgccgcaaaaaaggg<br>aataagggcgacacggaaatgttgaatactcatactcttcctttttcaatcatgattgaagcatttatcagggttattgtctc<br>atgagcggatacatatttgaatgtatttagaaaaataaacaaataggtcatgaccaaaatcccttaacgtgagttttcgtt<br>ccactgagcgtcagaccccgtagaaaagatcaaaggatcttcttgagatcctttttttctgcgcgtaatctgctgcttgca<br>aacaaaaaaaccaccgctaccagcggtggtttgtttgccggatcaagagctaccaactctttttccgaaggtaactgg<br>cttcagcagagcgcagataccaaatactgtccttctagtgtagccgtagttaggccaccacttcaagaactctgtagca<br>ccgcctacatacctcgctctgctaatcctgttaccagtggctgctgccagtggcgataagtcgtgtcttaccgggttggac<br>tcaagacgatagttaccggataaggcgcagcggtcgggctgaacggggggttcgtgcacacagcccagcttggag<br>cgaacgacctacaccgaactgagatacctacagcgtgagctatgagaaagcgccacgcttcccgaagggagaaa<br>ggcggacaggtatccggtaagcggcagggtcggaacaggagagcgcacgagggagcttccagggggaaacgc<br>ctggtatctttatagtcctgtcgggtttcgccacctctgacttgagcgtcgatttttgtgatgctcgtcaggggggcggagcc<br>tatggaaaaacgccagcaacgcggcctttttacggttcctggccttttgctggccttttgctcacatgttctttcctgcgttatc<br>ccctgattctgtggataaccgtattaccgcctttgagtgagctgataccgctcgccgcagccgaacgaccgagcgcag<br>cgagtcagtgagcgaggaagcggaagagcgcctgatgcggtattttctccttacgcatctgtgcggtatttcacaccgc<br>atatatggtgcactctcagtacaatctgctctgatgccgcatagttaagccagtatacactccgctatcgctacgtgactg<br>ggtcatggctgcgccccgacacccgccaacacccgctgacgcgccctgacgggcttgtctgctcccggcatccgctt<br>acagacaagctgtgaccgtctccgggagctgcatgtgtcagaggttttcaccgtcatcaccgaaacgcgcgaggcag<br>ctgcggtaaagctcatcagcgtggtcgtgaagcgattcacagatgtctgcctgttcatccgcgtccagctcgttgagtttct<br>ccagaagcgttaatgtctggcttctgataaagcgggccatgttaagggcggtttttcctgtttggtcactgatgcctccgtg<br>taagggggatttctgttcatgggggtaatgataccgatgaaacgagagaggatgctcacgatacgggttactgatgat<br>gaacatgcccggttactggaacgttgtgagggtaaacaactggcggtatggatgcggcgggaccagagaaaaatc<br>actcagggtcaatgccagcgcttcgttaatacagatgtaggtgttccacagggtagccagcagcatcctgcgatgcag<br>atccggaacataatggtgcagggcgctgacttccgcgtttccagactttacgaaacacggaaaccgaagaccattca<br>tgttgttgctcaggtcgcagacgttttgcagcagcagtcgcttcacgttcgctcgcgtatcggtgattcattctgctaaccag<br>taaggcaaccccgccagcctagccgggtcctcaacgacaggagcacgatcatgctagtcatgccccgcgcccacc<br>ggaaggagctgactgggttgaaggctctcaagggcatcggtcgagatcccggtgcctaatgagtgagctaacttaca<br>ttaattgcgttgcgctcactgcccgctttccagtcgggaaacctgtcgtgccagctgcattaatgaatcggccaacgcgc<br>ggggagaggcggtttgcgtattgggcgccagggtggtttttcttttcaccagtgagacgggcaacagctgattgcccttc<br>accgcctggccctgagagagttgcagcaagcggtccacgctggtttgccccagcaggcgaaaatcctgtttgatggtg<br>gttaacggcgggatataacatgagctgtcttcggtatcgtcgtatcccactaccgagatgtccgcaccaacgcgcagc<br>ccggactcggtaatggcgcgcattgcgcccagcgccatctgatcgttggcaaccagcatcgcagtgggaacgatgc<br>cctcattcagcatttgcatggtttgttgaaaaccggacatggcactccagtcgccttcccgttccgctatcggctgaatttg<br>attgcgagtgagatatttatgccagccagccagacgcagacgcgccgagacagaacttaatgggcccgctaacag<br>cgcgatttgctggtgacccaatgcgaccagatgctccacgcccagtcgcgtaccgtcttcatgggagaaaataatact<br>gttgatgggtgtctggtcagagacatcaagaaataacgccggaacattagtgcaggcagcttccacagcaatggcat<br>cctggtcatccagcggatagttaatgatcagcccactgacgcgttgcgcgagaagattgtgcaccgccgctttacagg<br>cttcgacgccgcttcgttctaccatcgacaccaccacgctggcacccagttgatcggcgcgagatttaatcgccgcga<br>caatttgcgacggcgcgtgcagggccagactggaggtggcaacgccaatcagcaacgactgtttgcccgccagttgt<br>tgtgccacgcggttgggaatgtaattcagctccgccatcgccgcttccactttttcccgcgttttcgcagaaacgtggctg<br>gcctggttcaccacgcgggaaacggtctgataagagacaccggcatactctgcgacatcgtataacgttactggtttc<br>acattcaccaccctgaattgactctcttccgggcgctatcatgccataccgcgaaaggttttgcgccattcgatggtgtcc<br>gggatctcgacgctctcccttatgcgactcctgcattaggaagcagcccagtagtaggttgaggccgttgag<br>(SEQ ID NO: 37) |
| pGB6389 | caccgccgccgcaaggaatggtgcatgcaaggagatggcgcccaacagtcccccggccacggggcctgccacc<br>atacccacgccgaaacaagcgctcatgagcccgaagtggcgagcccgatcttccccatcggtgatgtcggcgatat<br>aggcgccagcaaccgcacctgtggcgccggtgatgccggccacgatgcgtccggcgtagaggatcgagatcgatc<br>tcgatcccgcgaaattaatacgactcactataggggaattgtgagcggataacaattcccctctagaaataattttgttta<br>actttaagaaggagatataccatgagcagcaccacctataaaagtgaagcatttgatccggaaccgcctcatctgag<br>ctttcgtagctttgttaatgcactgcgtcaggatggggatctggtggatattaatgaaccggttgatccggatctggaagc<br>agcagcaattacccgtctggtttgtgaaaccgatgataaagcaccgctgtttaataacgtgattggtgcaaaagatggt<br>ctgtggcgtattctgggtgcaccggcaagcctgcgtgcgagcccgaaagaacgttttggtcgtctggcacgtcatctgg<br>cactgcctccgaccgcaagcgcaaaagatattctggataaaatgctgagcgccaatagcattccgcctattgaaccg<br>gttattgttccgaccggtccggttaaagaaaatagcattgaaggcgaaaacattgatctggaagccctgcctgcaccg<br>atggttcatcagagtgatggtggcaagtatatcaatacctatggtatgcatgttatccagagtccggatggtgggtggac<br>caattggagcattgcccgtgcaatggttagcggtaaacgtaccctggcaggtctggttattagtccgcagcatattcgta<br>aaattcaggatcagtggcgtgcaattggccaagaagaaattccttgggcactggcatttggtgttccgcctctggcaatt<br>atggcaagcagtatgccgattccggatggtgttagcgaagcaggttatgttggtgcaattgccggtgaaccgattaaac<br>tggttaaatgcgataccaacaatctgtatgttccggcaaatagcgaaattgttctggaaggcaccctgagcaccacca<br>aaatggcaccggaaggtccgtttggtgaaatgcatggttatgtttatccgggtgaaagccatccgggtccggtttatacc<br>gttaacaaaattacctatcgcaacaatgcaattctgccgatgagcgcatgtggtcgtctgaccgatgaaacccagacc<br>atgattccgaccctggcagcagcagaaattcgtcagctgtgtcagagggcaggtctgccgattaccgatgcatttgca<br>ccgtttgttggtcaggcaacctgggttgcactgaaagttgataccaaacgtctgcgtgcaatgaaaaccaatggtaaa<br>gcatttgcaaaagcggttggtgatgttgtgtttacccagaaaccgggttttatgattcatcgtctgattctggttggtgatgat<br>attgatgtgtatgacgataaagatgtgatgtgggcatttgctacccgttgtcgtccgggtacagatgaagtttttttgatgat<br>gttcctggcttttggctgatcccgtatatgagtcatggtaatgccgaagcagtgaaaggtggtaaagttgttagtgatgca |

TABLE I-continued

Plasmids sequences used in this study

| Plasmid | Sequences |
| --- | --- |
| | ctgctgaccgcagaatataccaccggtaaagattgggaaagcgcagatttcaaaaacagctatccgaaacgtatcc |
| | aggataaagttctgaatagctgggaacgcctgggtttcaaaaaactggattaataaggatccgaattcgagctcggcg |
| | cgcctgcaggtcgacaagcttgcggccgcataatgcttaagtcgaacagaaagtaatcgtattgtacacggccgcat |
| | aatcgaaattaatacgactcactataggggaattgtgagcggataacaattccccatcttagtatattagttaagtataag |
| | aaggagatatacatatgaaacgactcattgtaggcatcagcggtgccagcggcgcgatttatggcgtgcgcttattac |
| | aggttctgcgcgatgtcacagatatcgaaacgcatctggtgatgagccaggcagcgcgccagaccttatccctcgaa |
| | acggattttctctgcgcgaagtgcaggcattagccgatgtcacgcacgatgcgcgcgatattgccgccagcatctcttc |
| | cggttctttccagacgctggggatggtgattttaccctgttcaatcaaaaccctttccggcattgtccatagctatactgatg |
| | gcttactgacccgtgcggcagatgtggtgctgaaagagcgtcgcccgttggtgctctgcgtgcgtgaaacaccattgc |
| | acttaggccatctgcgtttaatgactcaggcggcagaaatcggtgcggtgattatgcctcccgttccggcgttttatcatc |
| | gcccgcaatcccttgatgatgtgataaatcagacggttaatcgtgttcttgaccagtttgcgataacccttcctgaagatct |
| | ctttgcccgctggcagggcgcataataaggtaccGAAGGAGATATACATATGCAGGTTGATCTG |
| | CTGGGTAGCGCACAGAGCGCACATGCACTGCACCTGTTTCATCAGCATAGTCC |
| | GCTGGTTCATTGTATGACCAATGATGTTGTTCAGACCTTTACCGCAAATACCCTG |
| | CTGGCACTGGGTGCAAGTCCGGCAATGGTTATTGAAACCGAAGAAGCAAGCCA |
| | GTTTGCAGCAATTGCAAGCGCACTGCTGATTAATGTTGGCACCCTGACCCAGCC |
| | TCGTGCACAGGCAATGCGTGCAGCAGTTGAACAGGCAAAAAGCAGCCAGACCC |
| | CGTGGACCCTGGACCCGGTTGCAGTTGGTGCACTGGATTATCGTCGTCATTTTT |
| | GTCATGAACTGCTGAGCTTTAAACCGGCAGCAATTCGTGGTAATGCAAGCGAAA |
| | TTATGGCACTGGCAGGTATTGCAAATGGTGGTCGTGGTGTTGATACCACCGATG |
| | CAGCAGCAAATGCAATTCCGGCAGCACAGACCCTGGCACGTGAAACCGGTGCA |
| | ATTGTTGTTGTTACCGGTGAAATGGATTATGTTACCGATGGTCATCGTATTATTG |
| | GTATTCATGGTGGTGATCCGCTGATGACCAAAGTTGTTGGCACCGGTTGTGCAC |
| | TGAGCGCAGTTGTTGCAGCATGTTGTGCACTGCCTGGTGATACCCTGGAAAATG |
| | TTGCAAGCGCATGTCATTGGATGAAACAGGCAGGCGAACGTGCAGTTGCACGT |
| | AGCGAAGGTCCGGGTAGCTTTGTTCCGCATTTTCTGGATGCACTGTGGCAGCT |
| | GACCCAGGAAGTTCAGGCATAATAATTAATTAAcctaggctgctgccaccgctgagcaataact |
| | agcataaccccttggggcctctaaacgggtcttgaggggttttttgctgaaaggaggaactatatccggattggcgaat |
| | gggacgcgccctgtagcggcgcattaagcgcggcgggtgtggtggttacgcgcagcgtgaccgctacacttgccag |
| | cgccctagcgcccgctcctttcgctttcttcccttcctttctcgccacgttcgccggctttccccgtcaagctctaaatcggg |
| | ggctccctttagggttccgatttagtgctttacggcacctcgaccccaaaaaacttgattagggtgatggttcacgtagtg |
| | ggccatcgccctgatagacggtttttcgccctttgacgttggagtccacgttctttaatagtggactcttgttccaaactgga |
| | acaacactcaaccctatctcggtctattcttttgatttataagggattttgccgatttcggcctattggttaaaaaatgagctg |
| | atttaacaaaaatttaacgcgaattttaacaaaatattaacgtttacaatttctggcggcacgatggcatgagattatcaa |
| | aaaggatcttcacctagatccttttaaattaaaaatgaagttttaaatcaatctaaagtatatatgagtaaacttggtctga |
| | cagttaccaatgcttaatcagtgaggcacctatctcagcgatctgtctatttcgttcatccatagttgcctgactccccgtcg |
| | tgtagataactacgatacgggagggcttaccatctggccccagtgctgcaatgataccgcgagacccacgctcaccg |
| | gctccagatttatcagcaataaaccagccagccggaagggccgagcgcagaagtggtcctgcaactttatccgcctc |
| | catccagtctattaattgttgccgggaagctagagtaagtagttcgccagttaatagtttgcgcaacgttgttgccattgct |
| | acaggcatcgtggtgtcacgctcgtcgtttggtatggcttcattcagctccggttcccaacgatcaaggcgagttacatg |
| | atcccccatgttgtgcaaaaaagcggttagctccttcggtcctccgatcgttgtcagaagtaagttggccgcagtgttatc |
| | actcatggttatggcagcactgcataattctcttactgtcatgccatccgtaagatgcttttctgtgactggtgagtactcaa |
| | ccaagtcattctgagaatagtgtatgcggcgaccgagttgctcttgcccggcgtcaatacgggataataccgcgccac |
| | atagcagaactttaaaagtgctcatcattggaaaacgttcttcggggcgaaaactctcaaggatcttaccgctgttgag |
| | atccagttcgatgtaacccactcgtgcacccaactgatcttcagcatcttttactttcaccagcgtttctgggtgagcaaaa |
| | acaggaaggcaaaatgccgcaaaaaagggaataagggcgacacggaaatgttgaatactcatactcttcctttttca |
| | atcatgattgaagcatttatcagggttattgtctcatgagcggatacatatttgaatgtatttagaaaaataaacaaatagg |
| | tcatgaccaaaatcccttaacgtgagttttcgttccactgagcgtcagaccccgtagaaaagatcaaaggatcttcttga |
| | gatcctttttttctgcgcgtaatctgctgcttgcaaacaaaaaaaccaccgctaccagcggtggtttgtttgccggatcaa |
| | gagctaccaactctttttccgaaggtaactggcttcagcagagcgcagataccaaatactgtccttctagtgtagccgta |
| | gttaggccaccacttcaagaactctgtagcaccgcctacatacctcgctctgctaatcctgttaccagtggctgctgcca |
| | gtggcgataagtcgtgtcttaccgggttggactcaagacgatagttaccggataaggcgcagcggtcgggctgaacg |
| | gggggttcgtgcacacagcccagcttggagcgaacgacctacaccgaactgagatacctacagcgtgagctatga |
| | gaaagcgccacgcttcccgaagggagaaaggcggacaggtatccggtaagcggcagggtcggaacaggagag |
| | cgcacgagggagcttccagggggaaacgcctggtatctttatagtcctgtcgggtttcgccacctctgacttgagcgtcg |
| | atttttgtgatgctcgtcaggggggcggagcctatggaaaaacgccagcaacgcggcctttttacggttcctggccttttg |
| | ctggccttttgctcacatgttctttcctgcgttatcccctgattctgtggataaccgtattaccgcctttgagtgagctgatacc |
| | gctcgccgcagccgaacgaccgagcgcagcgagtcagtgagcgaggaagcggaagagcgcctgatgcggtattt |
| | tctccttacgcatctgtgcggtatttcacaccgcatatatggtgcactctcagtacaatctgctctgatgccgcatagttaag |
| | ccagtatacactccgctatcgctacgtgactgggtcatggctgcgccccgacacccgccaacacccgctgacgcgcc |
| | ctgacgggcttgtctgctcccggcatccgcttacagacaagctgtgaccgtctccgggagctgcatgtgtcagaggtttt |
| | caccgtcatcaccgaaacgcgcgaggcagctgcggtaaagctcatcagcgtggtcgtgaagcgattcacagatgtct |
| | gcctgttcatccgcgtccagctcgttgagtttctccagaagcgttaatgtctggcttctgataaagcgggccatgttaagg |
| | gcggtttttttcctgtttggtcactgatgcctccgtgtaagggggatttctgttcatgggggtaatgataccgatgaaacgag |
| | agaggatgctcacgatacgggttactgatgatgaacatgcccggttactggaacgttgtgagggtaaacaactggcg |
| | gtatggatgcggcgggaccagagaaaaatcactcagggtcaatgccagcgcttcgttaatacagatgtaggtgttcc |
| | acagggtagccagcagcatcctgcgatgcagatccggaacataatggtgcagggcgctgacttccgcgtttccagac |
| | tttacgaaacacggaaaccgaagaccattcatgttgttgctcaggtcgcagacgttttgcagcagcagtcgcttcacgtt |
| | cgctcgcgtatcggtgattcattctgctaaccagtaaggcaaccccgccagcctagccgggtcctcaacgacaggag |
| | cacgatcatgctagtcatgccccgcgcccaccggaaggagctgactgggttgaaggctctcaagggcatcggtcga |
| | gatcccggtgcctaatgagtgagctaacttacattaattgcgttgcgctcactgcccgctttccagtcgggaaacctgtcg |
| | tgccagctgcattaatgaatcggccaacgcgcggggagaggcggtttgcgtattgggcgccagggtggtttttcttttca |
| | ccagtgagacgggcaacagctgattgcccttcaccgcctggccctgagagagttgcagcaagcggtccacgctggtt |
| | tgccccagcaggcgaaaatcctgtttgatggtggttaacggcgggatataacatgagctgtcttcggtatcgtcgtatcc |
| | cactaccgagatgtccgcaccaacgcgcagcccggactcggtaatggcgcgcattgcgcccagcgccatctgatcg |
| | ttggcaaccagcatcgcagtgggaacgatgccctcattcagcatttgcatggtttgttgaaaaccggacatggcactcc |

TABLE I-continued

| Plasmids sequences used in this study | |
|---|---|
| Plasmid | Sequences |
| | agtcgccttcccgttccgctatcggctgaatttgattgcgagtgagatatttatgccagccagccagacgcagacgcgc<br>cgagacagaacttaatgggcccgctaacagcgcgatttgctggtgacccaatgcgaccagatgctccacgcccagt<br>cgcgtaccgtcttcatgggagaaaataatactgttgatgggtgtctggtcagagacatcaagaaataacgccggaac<br>attagtgcaggcagcttccacagcaatggcatcctggtcatccagcggatagttaatgatcagcccactgacgcgttgc<br>gcgagaagattgtgcaccgccgctttacaggcttcgacgccgcttcgttctaccatcgacaccaccacgctggcaccc<br>agttgatcggcgcgagatttaatcgccgcgacaatttgcgacggcgcgtgcagggccagactggaggtggcaacgc<br>caatcagcaacgactgtttgcccgccagttgttgtgccacgcggttgggaatgtaattcagctccgccatcgccgcttcc<br>actttttcccgcgttttcgcagaaacgtggctggcctggttcaccacgcgggaaacggtctgataagagacaccggcat<br>actctgcgacatcgtataacgttactggtttcacattcaccaccctgaattgactctcttccgggcgctatcatgccatacc<br>gcgaaaggttttgcgccattcgatggtgtccgggatctcgacgctctcccttatgcgactcctgcattaggaagcagccc<br>agtagtaggttgaggccgttgag<br>(SEQ ID NO: 38) |

A BL21(DE3) strain was transformed with the constructed vectors. The single transformants were used to inoculate LB medium, supplemented with ampicillin, followed by incubation at 30° C. overnight. This overnight pre-cultures were then used to inoculate 0.5 L of batch medium in 1 L bioreactor so to obtain an initial OD600 around of 0.05.

Bioreactor Fermentation Conditions

The fermentation assays were performed in 1 liter bioreactors (Multifors). The culture medium was composed of ZYM auto-induction medium (Studier F W, Prot. Exp. Pur. 41, (2005), 207-234) complemented with 0.5 mM riboflavin, 10 g/L Glycerol, 2.5 g/L Glucose, 4 g/L lactose and ampicillin (0.1 g/L). During the phase of bacterial growth, the operational fermentation parameters were temperature 30° C., medium pH 6.8 (adjusting by $NH_4OH$ and $H_3PO_4$), $pO_2$ 20%. The phase of bacterial growth was conducted until OD600 around of 20-30. The isobutene production was then initiated by modifying the fermentation parameters as:

- Temperature was increased to reach 34° C.
- Glucose concentration was increased to 3 g/L and then maintained beyond 1 g/L during isobutene (IBN) production phase.
- 3-methylcrotonic acid was added to the culture medium at initial concentration of 25 mM and then maintained beyond 20 mM during IBN production phase.
- When the external prenol was added to the culture medium, initial concentration was 8 mM through a pulse addition. There was no further addition of prenol during IBN production phase.

The isobutene (IBN) production was analyzed continuously using a Prima Pro Process mass spectrometer (Thermo Scientific) calibrated with 0.5% mol isobutene in argon.

The results are shown in FIG. 42 and FIG. 43.

As can be derived from the results, the over-expression of enzymes capable of increasing the pool of DMAP led to an increase in the production of isobutene.

Example 9: Assay for the Formation of Prenylated FMN by Using Either DMAP or DMAPP as Co-Substrate by Different FMN Prenyl Transferases The following enzymes were used in this study (Table J).

TABLE J

| Enzyme | Organism | Gene abbreviation | Uniprot accession number |
|---|---|---|---|
| Flavin prenyltransferase UbiX SEQ ID NO:5 | *Escherichia coli* (strain K12) | ubiX | P0AG03 |

TABLE J-continued

| Enzyme | Organism | Gene abbreviation | Uniprot accession number |
|---|---|---|---|
| UbiX-like flavin prenyltransferase SEQ ID NO:66 | *Escherichia coli* O157:H7 | ecdB | P69772 |
| UbiX-like flavin prenyltransferase SEQ ID NO:70 | *Klebsiella pneumoniae* | kpdB | Q462H4 |
| Flavin prenyltransferase PAD1, mitochondrial SEQ ID NO:71 | *Hypocrea atroviridis* (strain ATCC 20476/ IMI 206040) (*Trichoderma atroviride*) | PAD1 | G9NTN1 |

Enzyme Expression and Production

The sequences of the studied enzymes were generated and cloned in a pET-25b (+) expression vector as described in Example 1. The enzymes were then expressed and purified according to the procedure from Example 1, with the following modifications. The transformed cells were grown without added Flavin Mononucleotide. 50 mM phosphate pH7.5, containing 100 mM NaCl and 10% glycerol was used during protein purification instead of a Tris-HCl buffer. The purity of proteins was estimated to be around 90-95% according to SDS-PAGE analysis.

Enzymatic biosynthesis of prenylated FMN

Standard assay mixture contained:

- 50 mM phosphate buffer pH 7.5 containing 100 mM NaCl.
- 10 mM dimethylallyl pyrophosphate (DMAPP) or 10 mM dimethylallyl phosphate
- (DMAP) (Sigma-Aldrich)
- 5 mM Flavin Mononucleotide (FMN)
- 10 mM sodium dithionite All the components of the assay (buffer, FMN, DMAP or DMAPP, sodium dithionite) were made up as stock solution, transferred into the anaerobic chamber (Whitley DG250 anaerobic workstation) and incubated for at least one hour. Enzymatic assays were typically performed in 1.5 mL Eppendorf opaque black microtubes (Dutscher) with a total assay volume of 0.25 mL. Reactions were initiated by the addition of prenyl transferase (200 μM final concentration). The enzyme free controls were performed in parallel. The assays were incubated for 1 hour at 30° C. Then, the enzymes were removed from the incubation mixture by ultrafiltration using 10 kDa Amicon filter while being in the anaerobic chamber.

The supernatant containing prenylated FMN thus synthesized was diluted by adding half a volume of acetonitrile (ice cold). Assays were then centrifuged and an aliquot of the clarified supernatant were transferred into a clean vial for HPLC analysis.

HPLC Analysis of Prenylated FMN

The amount of prenylated FMN was determined by alkyl reverse phase using a 1260 Infinity LC System (Agilent), equipped with a column heating module and a UV detector. 5 μl of samples were separated on Zorbax SB-Aq column (250×4.6 mm, 5 μm particle size, column temp. 30° C.) with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). FMN was used as reference to estimate the amount of produced prenylated FMN.

The consumption of DMAP or DMAPP as well as FMN was followed in parallel. In the described conditions, the retention time of FMN and prenylated FMN were 4.8 min and 5.7 min, respectively and the retention time of DMAPP and DMAP were 3.5 min and 4.4 min, respectively.

The amount of prenylated FMN formed in the enzymatic assays with DMAP and DMAPP are shown in the Table K.

TABLE K

| | Concentration of prenylated FMN formed in the assays, mM | |
|---|---|---|
| Enzyme | With DMAP as co-substrate | With DMAPP as co-substrate |
| Flavin prenyltransferase UbiX from *Escherichia coli* (strain K12) | 2.9 | 2.4 |
| UbiX-like flavin prenyltransferase *Escherichia coli* O157:H7 | 3.7 | 3.7 |
| UbiX-like flavin prenyltransferase from *Klebsiella pneumoniae* | 3.4 | 3.9 |
| Flavin prenyltransferase PAD1, mitochondrial from *Hypocrea atroviridis* (strain ATCC 20476/IMI 206040) | 0.3(traces) | 2.4 |

No prenylated FMN was observed in the control assays without enzymes either with DMAP or DMAPP as co-substrate.

The invention claimed is:

1. A method for the production of isobutene comprising the enzymatic conversion of 3-methylcrotonic acid into isobutene wherein the enzymatic conversion of 3-methylcrotonic acid into isobutene is achieved by making use of an FMN-dependent decarboxylase associated with a prokaryotic FMN prenyl transferase, wherein said FMN prenyl transferase catalyzes the prenylation of a flavin cofactor (FMN or FAD) utilizing dimethylallyl pyrophosphate (DMAPP), wherein said method further comprises providing said DMAPP enzymatically by:

(i) the enzymatic conversion of isopentenyl pyrophosphate (IPP) into said DMAPP; or (ii) the enzymatic conversion of dimethylallyl phosphate (DMAP) into said DMAPP; or (iii) the enzymatic conversion of prenol into said DMAPP;

(iv) or by a combination of any one of (i) to (iii).

2. The method of claim 1, further comprising providing said flavin cofactor enzymatically by the enzymatic conversion of riboflavin into flavin mononucleotide (FMN).

3. The method of claim 2, wherein the enzymatic conversion of riboflavin into FMN is achieved by making use of:

a kinase, a phosphotransferase with an alcohol group as acceptor (EC 2.7.1), a phosphotransferase with a phosphate group as acceptor (EC 2.7.4); or a bifunctional riboflavin kinase/FMN adenylyltransferase (ribF); or a variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived.

4. The method of claim 3, wherein:

(a) the kinase is an archaeal riboflavin kinase (EC 2.7.1.161), a flavokinase derived from *S. cerevisiae* or from *Rattus norvegicus*, or a flavokinase derived from Megasphaera elsdenii;

(b) the phosphotransferase with an alcohol group as acceptor (EC 2.7.1) is an erythritol kinase (2.7.1.27) or a glycerol kinase (2.7.1.30); or (c) the phosphotransferase with a phosphate group as acceptor (EC 2.7.4) is an isopentenyl phosphate kinase (EC 2.7.4.26).

5. The method of claim 3, wherein said variant of a bifunctional riboflavin kinase/FMN adenylyltransferase (ribF) which shows an improved activity in converting riboflavin into FMN over the corresponding bifunctional riboflavin kinase/FMN adenylyltransferase from which it is derived is a variant having an amino acid sequence as shown in SEQ ID NO:34 or an amino acid sequence having at least 30% sequence identity to SEQ ID NO:34, in which one or more amino acid residues at a position selected from the group consisting of positions 29 and 32 in the amino acid sequence shown in SEQ ID NO:34 or at a position corresponding to any of these positions, are substituted with another amino acid residue or deleted or wherein an insertion has been effected at one or more of these positions.

6. The method of claim 5, wherein (1) an amino acid residue at position 29 in the amino acid sequence shown in SEQ ID NO:34 or at a position corresponding to this position, is deleted or substituted with alanine; and/or (2) an amino acid residue at position 32 in the amino acid sequence shown in SEQ ID NO:34 or at a position corresponding to this position, is deleted or substituted with serine or alanine.

7. The method of claim 1 (i), wherein the enzymatic conversion of isopentenyl pyrophosphate (IPP) into said DMAPP is achieved by making use of an isomerase.

8. The method of claim 7, wherein the isomerase is an isopentenyl-diphosphate DELTA isomerase (EC 5.3.3.2).

9. The method of claim 1 (ii), wherein the enzymatic conversion of dimethylallyl phosphate (DMAP) into said DMAPP is achieved by making use of a kinase.

10. The method of claim 9, wherein the kinase is an isopentenyl monophosphate kinase (EC 2.7.4.26).

11. The method of claim 9, further comprising providing the DMAP by the enzymatic conversion of prenol into DMAP or by the enzymatic conversion of isopentenyl monophosphate (IMP) into DMAP.

12. The method of claim 11, wherein the enzymatic conversion of prenol into said DMAP is achieved by making use of a kinase.

13. The method of claim 12, wherein the kinase is a phosphotransferase with an alcohol group as acceptor (EC 2.7.1.-).

14. The method of claim 13, wherein the phosphotransferase with an alcohol group as acceptor (EC 2.7.1.-) is a hydroxyethylthiazole kinase (EC 2.7.1.50).

15. The method of claim 11, wherein the enzymatic conversion of isopentenyl monophosphate (IMP) into DMAP is achieved by making use of an isomerase.

16. The method of claim 15, wherein the isomerase is an isopentenyl-diphosphate DELTA isomerase (EC 5.3.3.2).

17. The method of claim 1 (iii), wherein the enzymatic conversion of prenol into DMAPP is achieved by making use of a diphosphotransferase (EC 2.7.6.-).

18. The method of claim 17, wherein the diphosphotransferase (EC 2.7.6.-) is a thiamine diphosphokinase (EC 2.7.6.2) or a 2-amino-4-hydroxy-6-hydroxymethyldihydropteridine diphosphokinase (EC 2.7.6.3).

19. The method of claim 1, wherein said method is carried out in vitro.

20. The method of claim 1, wherein said method is carried out by a recombinant organism or microorganism.

* * * * *

SEQUENCE LISTING

```
<160> NUMBER OF SEQ ID NOS: 71

<210> SEQ ID NO 1
<211> LENGTH: 229
<212> TYPE: PRT
<213> ORGANISM: Candida albicans
<220> FEATURE:
<223> OTHER INFORMATION: Candida albicans (strain SC5314 / ATCC
      MYA-2876)

<400> SEQUENCE: 1

Met Ile Ala Arg Val Cys Leu Arg Arg Ser Asn Val Leu Pro Ile Phe
1               5                   10                  15

Gln Ile Pro Ser Arg Lys Tyr Ser Ile Asn Tyr Glu Lys Val Asn Asn
            20                  25                  30

Ser Ile Tyr Asn Asn Val Ile Lys Pro Lys Arg Ile Val Leu Ala Ile
        35                  40                  45

Thr Gly Ala Thr Gly Thr Gln Ile Gly Val Arg Leu Leu Glu Ile Leu
    50                  55                  60

Lys Glu Leu Gly Val Glu Thr His Leu Val Met Ser Lys Trp Gly Ile
65                  70                  75                  80

Ala Thr Leu Lys Tyr Glu Thr Asp Tyr Gln Val Asp Tyr Val Thr Ser
                85                  90                  95

Leu Ala Thr Lys Thr Tyr Ser Ala Arg Asp Val Thr Ala Pro Ile Ser
            100                 105                 110

Ser Gly Ser Phe Val His Asp Gly Met Ile Val Ala Pro Cys Ser Met
        115                 120                 125

Lys Ser Leu Ser Ala Ile Arg Thr Gly Phe Thr Glu Asp Leu Ile Val
    130                 135                 140

Arg Ala Ala Asp Val Ser Leu Lys Glu Arg Arg Lys Leu Leu Leu Val
145                 150                 155                 160

Ala Arg Glu Thr Pro Leu Ser Asp Ile His Leu Asp Asn Met Leu Tyr
                165                 170                 175

Leu Ser Arg Met Gly Val Thr Ile Phe Pro Pro Val Pro Ala Phe Tyr
            180                 185                 190

Thr Lys Pro Lys Thr Ile Asp Asp Ile Val Glu Gln Thr Cys Gly Arg
        195                 200                 205
```

Ile Leu Asp Asn Phe Gly Ile Asn Ile Asp Thr Phe Glu Arg Trp Asp
    210                 215                 220

Gly Ile Asn His Arg
225

<210> SEQ ID NO 2
<211> LENGTH: 227
<212> TYPE: PRT
<213> ORGANISM: Aspergillus niger

<400> SEQUENCE: 2

Met Phe Asn Ser Leu Leu Ser Gly Thr Thr Thr Pro Asn Ser Gly Arg
1               5                   10                  15

Ala Ser Pro Pro Ala Ser Glu Met Pro Ile Asp Asn Asp His Val Ala
            20                  25                  30

Val Ala Arg Pro Ala Pro Arg Arg Arg Arg Ile Val Val Ala Met Thr
        35                  40                  45

Gly Ala Thr Gly Ala Met Leu Gly Ile Lys Val Leu Ile Ala Leu Arg
    50                  55                  60

Arg Leu Asn Val Glu Thr His Leu Val Met Ser Lys Trp Ala Glu Ala
65                  70                  75                  80

Thr Ile Lys Tyr Glu Thr Asp Tyr His Pro Ser Asn Val Arg Ala Leu
                85                  90                  95

Ala Asp Tyr Val His Asn Ile Asn Asp Met Ala Ala Pro Val Ser Ser
            100                 105                 110

Gly Ser Phe Arg Ala Asp Gly Met Ile Val Val Pro Cys Ser Met Lys
        115                 120                 125

Thr Leu Ala Ala Ile His Ser Gly Phe Cys Asp Asp Leu Ile Ser Arg
    130                 135                 140

Thr Ala Asp Val Met Leu Lys Glu Arg Arg Arg Leu Val Leu Val Ala
145                 150                 155                 160

Arg Glu Thr Pro Leu Ser Glu Ile His Leu Arg Asn Met Leu Glu Val
                165                 170                 175

Thr Arg Ala Gly Ala Val Ile Phe Pro Pro Val Pro Ala Phe Tyr Ile
            180                 185                 190

Lys Ala Gly Ser Ile Glu Asp Leu Ile Asp Gln Ser Val Gly Arg Met
        195                 200                 205

Leu Asp Leu Phe Asp Leu Asp Thr Gly Asp Phe Glu Arg Trp Asn Gly
    210                 215                 220

Trp Glu Lys
225

<210> SEQ ID NO 3
<211> LENGTH: 242
<212> TYPE: PRT
<213> ORGANISM: Saccharomyces cerevisiae S288c

<400> SEQUENCE: 3

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr His Lys Leu Ser Lys Glu Val Thr Arg Ala Ser
        35                  40                  45

Thr Ser Pro Pro Arg Pro Lys Arg Ile Val Val Ala Ile Thr Gly Ala
    50                  55                  60

```
Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
        115                 120                 125

Phe Gln His Asp Gly Met Ile Val Val Pro Cys Ser Met Lys Ser Leu
    130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
        195                 200                 205

Lys Ser Leu His Asp Leu Leu Glu Gln Ser Val Gly Arg Ile Leu Asp
    210                 215                 220

Cys Phe Gly Ile His Ala Asp Thr Phe Pro Arg Trp Glu Gly Ile Lys
225                 230                 235                 240

Ser Lys


<210> SEQ ID NO 4
<211> LENGTH: 180
<212> TYPE: PRT
<213> ORGANISM: Cryptococcus gattii WM276
<220> FEATURE:
<223> OTHER INFORMATION: serotype B

<400> SEQUENCE: 4

Met Arg Arg Lys Arg Tyr Val Val Ala Val Thr Gly Ala Thr Gly Ala
1               5                   10                  15

Thr Leu Ala Ile Arg Leu Leu Gln Ala Leu Arg Ala Leu Asp Ile Glu
            20                  25                  30

Thr His Leu Ile Ile Ser Lys Trp Ala Val Lys Thr Leu Lys Tyr Glu
        35                  40                  45

Thr Asp Met Ile Glu Arg Glu Leu Lys Asp Leu Ala Asp Tyr Ser Tyr
    50                  55                  60

Ser Asn Ser Asp Leu Ala Ala Pro Pro Ser Ser Gly Ser Phe Ile His
65                  70                  75                  80

Asp Gly Met Phe Ile Ile Pro Cys Ser Met Lys Thr Leu Ala Ala Val
                85                  90                  95

Arg Ile Gly Leu Gly Asp Glu Leu Ile Ser Arg Ser Ala Asp Val Cys
            100                 105                 110

Leu Lys Glu Gly Arg Lys Leu Met Leu Val Val Arg Glu Thr Pro Leu
        115                 120                 125

Asn Asp Ile His Leu Glu Asn Met Leu Phe Leu Arg Arg Ala Gly Ala
    130                 135                 140

Ile Ile Phe Pro Pro Val Pro Ala Tyr Tyr Ile Arg Pro Gln Thr Ile
145                 150                 155                 160

Asp Asp Leu Thr Asn Gln Thr Val Gly Arg Ile Leu Asp Ser Ser Lys
                165                 170                 175
```

Cys Ser Gln Lys
180

<210> SEQ ID NO 5
<211> LENGTH: 189
<212> TYPE: PRT
<213> ORGANISM: Escherichia coli K-12

<400> SEQUENCE: 5

Met Lys Arg Leu Ile Val Gly Ile Ser Gly Ala Ser Gly Ala Ile Tyr
1 5 10 15

Gly Val Arg Leu Leu Gln Val Leu Arg Asp Val Thr Asp Ile Glu Thr
20 25 30

His Leu Val Met Ser Gln Ala Ala Arg Gln Thr Leu Ser Leu Glu Thr
35 40 45

Asp Phe Ser Leu Arg Glu Val Gln Ala Leu Ala Asp Val Thr His Asp
50 55 60

Ala Arg Asp Ile Ala Ala Ser Ile Ser Ser Gly Ser Phe Gln Thr Leu
65 70 75 80

Gly Met Val Ile Leu Pro Cys Ser Ile Lys Thr Leu Ser Gly Ile Val
85 90 95

His Ser Tyr Thr Asp Gly Leu Leu Thr Arg Ala Ala Asp Val Val Leu
100 105 110

Lys Glu Arg Arg Pro Leu Val Leu Cys Val Arg Glu Thr Pro Leu His
115 120 125

Leu Gly His Leu Arg Leu Met Thr Gln Ala Ala Glu Ile Gly Ala Val
130 135 140

Ile Met Pro Pro Val Pro Ala Phe Tyr His Arg Pro Gln Ser Leu Asp
145 150 155 160

Asp Val Ile Asn Gln Thr Val Asn Arg Val Leu Asp Gln Phe Ala Ile
165 170 175

Thr Leu Pro Glu Asp Leu Phe Ala Arg Trp Gln Gly Ala
180 185

<210> SEQ ID NO 6
<211> LENGTH: 192
<212> TYPE: PRT
<213> ORGANISM: Bacillus subtilis

<400> SEQUENCE: 6

Met Lys Leu Val Ile Gly Met Thr Gly Ala Thr Gly Ala Ile Phe Gly
1 5 10 15

Ile Arg Leu Leu Glu Tyr Leu Lys Ala Ala Glu Ile Glu Thr His Leu
20 25 30

Val Val Ser Pro Trp Ala Asn Val Thr Ile Thr His Glu Thr Asp Tyr
35 40 45

Thr Leu Lys Asp Val Glu Lys Leu Ala Ser Tyr Thr Tyr Ser His Lys
50 55 60

Asp Gln Ala Ala Ala Ile Ser Ser Gly Ser Phe Glu Thr Asp Gly Met
65 70 75 80

Ile Ile Ala Pro Cys Ser Met Lys Ser Leu Ala Ser Ile Arg Thr Gly
85 90 95

Met Ala Asp Asn Leu Leu Thr Arg Ala Ala Asp Val Ile Leu Lys Glu
100 105 110

Arg Lys Lys Leu Val Leu Leu Thr Arg Glu Thr Pro Leu Ser Gln Ile
115 120 125

```
His Leu Glu Asn Met Leu Ala Leu Thr Lys Met Gly Ser Val Ile Leu
    130                 135                 140

Pro Pro Met Pro Ala Phe Tyr Asn Lys Pro Ala Asp Met Asp Glu Leu
145                 150                 155                 160

Ile Asp His Ile Val Phe Arg Thr Leu Asp Gln Phe Gly Ile Arg Leu
                165                 170                 175

Pro Glu Ala Lys Arg Trp Tyr Gly Ile Glu Lys Gln Lys Gly Gly Ile
            180                 185                 190


<210> SEQ ID NO 7
<211> LENGTH: 209
<212> TYPE: PRT
<213> ORGANISM: Pseudomonas aeruginosa

<400> SEQUENCE: 7

Met Ser Gly Pro Glu Arg Ile Thr Leu Ala Met Thr Gly Ala Ser Gly
1               5                   10                  15

Ala Gln Tyr Gly Leu Arg Leu Leu Asp Cys Leu Val Gln Glu Glu Arg
            20                  25                  30

Glu Val His Phe Leu Ile Ser Lys Ala Ala Gln Leu Val Met Ala Thr
        35                  40                  45

Glu Thr Asp Val Ala Leu Pro Ala Lys Pro Gln Ala Met Gln Ala Phe
    50                  55                  60

Leu Thr Glu Tyr Cys Gly Ala Ala Ala Gly Gln Ile Arg Val Phe Gly
65                  70                  75                  80

Gln Asn Asp Trp Met Ala Pro Pro Ala Ser Gly Ser Ser Ala Pro Asn
                85                  90                  95

Ala Met Val Ile Cys Pro Cys Ser Thr Gly Thr Leu Ser Ala Val Ala
            100                 105                 110

Thr Gly Ala Cys Asn Asn Leu Ile Glu Arg Ala Ala Asp Val Ala Leu
        115                 120                 125

Lys Glu Arg Arg Pro Leu Val Leu Val Pro Arg Glu Ala Pro Phe Ser
    130                 135                 140

Ser Ile His Leu Glu Asn Met Leu Lys Leu Ser Asn Leu Gly Ala Val
145                 150                 155                 160

Ile Leu Pro Ala Ala Pro Gly Phe Tyr His Gln Pro Gln Ser Val Glu
                165                 170                 175

Asp Leu Val Asp Phe Val Val Ala Arg Ile Leu Asn Thr Leu Gly Ile
            180                 185                 190

Pro Gln Asp Met Leu Pro Arg Trp Gly Glu Gln His Leu Val Ser Asp
        195                 200                 205

Glu


<210> SEQ ID NO 8
<211> LENGTH: 219
<212> TYPE: PRT
<213> ORGANISM: Enterobacter sp.
<220> FEATURE:
<223> OTHER INFORMATION: Enterobacter sp. DC4

<400> SEQUENCE: 8

Met Leu Arg Gln Val Arg Ala Asn Ala Leu Thr Cys Asn Ser Pro Gln
1               5                   10                  15

Asn Pro Ala Gln Ser Ala Leu Lys Ser Val Arg Ala Lys Ile Met Lys
            20                  25                  30

Arg Leu Ile Val Gly Leu Ser Gly Ala Ser Gly Ala Ile Tyr Gly Val
        35                  40                  45
```

```
Arg Leu Leu Gln Val Leu Arg Asn Val Ala Glu Val Glu Thr His Leu
    50                  55                  60

Val Met Ser Gln Ala Ala Arg Gln Thr Leu Ser Leu Glu Thr Asp Leu
65                  70                  75                  80

Ser Leu Arg Asp Val Gln Ala Leu Ala Asp Val Val His Asp Ala Arg
                85                  90                  95

Asp Ile Ala Ala Ser Ile Ser Ser Gly Ser Phe Lys Thr Ala Gly Met
            100                 105                 110

Val Ile Leu Pro Cys Ser Ile Lys Thr Leu Ser Gly Ile Val Asn Ser
        115                 120                 125

Tyr Thr Asp Thr Leu Val Thr Arg Ala Ala Asp Val Val Leu Lys Glu
    130                 135                 140

Arg Arg Pro Leu Val Leu Cys Val Arg Glu Thr Pro Leu His Leu Gly
145                 150                 155                 160

His Leu Arg Leu Met Thr Gln Ala Ala Glu Leu Gly Ala Ile Ile Met
                165                 170                 175

Pro Pro Val Pro Ala Phe Tyr His Arg Pro Thr Ser Leu Asp Asp Val
            180                 185                 190

Ile Asn Gln Thr Val Asn Arg Val Leu Asp Gln Phe Asp Ile Asp Leu
        195                 200                 205

Pro Glu Asp Leu Phe Thr Arg Trp Gln Gly Ala
    210                 215


<210> SEQ ID NO 9
<211> LENGTH: 503
<212> TYPE: PRT
<213> ORGANISM: Saccharomyces cerevisiae S288c

<400> SEQUENCE: 9

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190
```

```
His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 10
<211> LENGTH: 168
<212> TYPE: PRT
<213> ORGANISM: Enterobacter sp.
<220> FEATURE:
<223> OTHER INFORMATION: Enterobacter sp. MGH 24

<400> SEQUENCE: 10

```
Met Ser Thr Phe Asp Lys His Asp Leu Ser Gly Phe Val Gly Lys His
1               5                   10                  15

Leu Val Tyr Thr Tyr Asp Asn Gly Trp Asn Tyr Glu Ile Tyr Val Lys
            20                  25                  30

Asn Glu Thr Thr Leu Asp Tyr Arg Ile His Ser Gly Leu Val Ala Asn
        35                  40                  45
```

```
Arg Trp Val Lys Asp Gln Gln Ala Tyr Ile Val Arg Val Gly Glu Ser
    50                  55                  60

Ile Tyr Lys Ile Ser Trp Thr Glu Pro Thr Gly Thr Asp Val Ser Leu
65                  70                  75                  80

Ile Val Asn Leu Gly Asp Lys Leu Phe His Gly Thr Ile Phe Phe Pro
                85                  90                  95

Arg Trp Val Met Asn Asn Pro Glu Lys Thr Val Cys Phe Gln Asn Asp
            100                 105                 110

His Ile Pro Leu Met Asn Ser Tyr Arg Asp Ala Gly Pro Ala Tyr Pro
        115                 120                 125

Thr Glu Val Ile Asp Glu Phe Ala Thr Ile Thr Phe Val Arg Asp Cys
    130                 135                 140

Gly Ala Asn Asn Glu Ser Val Ile Ala Cys Ala Ala Ser Glu Leu Pro
145                 150                 155                 160

Asn Asp Phe Pro Ala Asn Leu Asn
                165


<210> SEQ ID NO 11
<211> LENGTH: 161
<212> TYPE: PRT
<213> ORGANISM: Bacillus pumilus

<400> SEQUENCE: 11

Met Asp Gln Phe Val Gly Leu His Met Ile Tyr Thr Tyr Glu Asn Gly
1               5                   10                  15

Trp Glu Tyr Glu Ile Tyr Ile Lys Asn Asp His Thr Ile Asp Tyr Arg
            20                  25                  30

Ile His Ser Gly Met Val Gly Gly Arg Trp Val Arg Asp Gln Glu Val
        35                  40                  45

Asn Ile Val Lys Leu Thr Lys Gly Val Tyr Lys Val Ser Trp Thr Glu
    50                  55                  60

Pro Thr Gly Thr Asp Val Ser Leu Asn Phe Met Pro Glu Glu Lys Arg
65                  70                  75                  80

Met His Gly Val Ile Phe Phe Pro Lys Trp Val His Glu Arg Pro Asp
                85                  90                  95

Ile Thr Val Cys Tyr Gln Asn Asp Tyr Ile Asp Leu Met Lys Glu Ser
            100                 105                 110

Arg Glu Lys Tyr Glu Thr Tyr Pro Lys Tyr Val Val Pro Glu Phe Ala
        115                 120                 125

Asp Ile Thr Tyr Ile His His Ala Gly Val Asn Asp Glu Thr Ile Ile
    130                 135                 140

Ala Glu Ala Pro Tyr Glu Gly Met Thr Asp Glu Ile Arg Ala Gly Arg
145                 150                 155                 160

Lys


<210> SEQ ID NO 12
<211> LENGTH: 534
<212> TYPE: PRT
<213> ORGANISM: Aspergillus niger CBS 513.88

<400> SEQUENCE: 12

Met Leu Arg Met Leu Arg Pro Gly Arg Arg Ile Pro Thr His Pro Ser
1               5                   10                  15

Arg Ser Phe Ser Thr Thr Pro His Arg Ser Asn Asp Ser Pro Ala Leu
            20                  25                  30
```

```
Asn Phe Arg Ser Leu Leu Ser Ala Leu Arg Ala Gln Asp Asp Leu Val
        35                  40                  45

Asp Ile Thr Gln Pro Ala Ser Pro Asp Leu Glu Ile Ala Ala Leu Thr
    50                  55                  60

Arg Arg Val Tyr Glu Ser His Ser Pro Ala Pro Leu Phe His Asn Val
65                  70                  75                  80

Thr Asp Thr Asp Pro Glu Thr Gly Leu Phe Lys Ile Leu Gly Ala Pro
                85                  90                  95

Val Gly Leu Arg Ala Asp Pro Ala Thr Arg Phe Gly Arg Leu Ala Ile
            100                 105                 110

Gln Leu Gly Leu Pro Gln Asn Ala Thr Pro Leu Asp Ile Leu Glu Lys
        115                 120                 125

Leu Ile Ala Ala Lys His Ser Thr Pro Leu Pro Pro Thr Pro Val Pro
    130                 135                 140

Ala Ser Ser Ala Pro Cys Lys Glu Asn Ile Leu His Gly Ser Gln Ile
145                 150                 155                 160

Asp Met Thr Lys Trp Pro Ile Pro Arg Leu His Pro Leu Asp Gly Gly
                165                 170                 175

Asn Tyr Leu Ala Thr Tyr Gly Phe His Ile Leu Gln Ser Pro Asp Lys
            180                 185                 190

Ala Trp Thr Ser Trp Ser Ile Ser Arg Thr Met His Val Ala Asn Thr
        195                 200                 205

Pro Arg Thr Ile Val Ala Pro Ile Met Pro Gly Gln His Ile Ala Gln
    210                 215                 220

Val His Gln Met Trp Ala Asp Gln Gly Ala Lys Asp Thr Pro Trp Ala
225                 230                 235                 240

Leu Val Leu Gly Gly Pro Pro Ala Ala Ala Phe Val Gly Gly Met Pro
                245                 250                 255

Leu Pro Ala Phe Val Ser Glu Asp Gly Tyr Ile Gly Ala Leu Cys Gly
            260                 265                 270

Glu Ala Met Asp Val Val Lys Cys Glu Thr Asn Asp Leu Tyr Val Pro
        275                 280                 285

Ala Asn Ala Glu Ile Val Leu Glu Gly Arg Ile Ser Thr Thr Glu Lys
    290                 295                 300

Val Gly Glu Gly Pro Met Gly Glu Tyr His Gly Tyr Met Phe Gln Asp
305                 310                 315                 320

Lys Ala Val Pro Glu Pro Arg Ile Glu Val Asp Cys Val Thr Tyr Arg
                325                 330                 335

Arg Asp Pro Val Val Pro Ile Cys Val Ala Gly Leu Ala Pro Asp Glu
            340                 345                 350

Thr His Thr Val Trp Gly Ala Ala Ile Ser Ala Glu Ile Leu Asp Ala
        355                 360                 365

Leu Arg Gly Ala Glu Leu Pro Val Lys Met Ala Trp Met Pro Tyr Glu
    370                 375                 380

Ala Gln Cys Cys Trp Val Val Val Ser Val Asp Val Glu Arg Leu Gly
385                 390                 395                 400

Arg Met Gly Ile Lys Lys Glu Glu Leu Ser Arg Arg Val Gly Glu Val
                405                 410                 415

Val Phe Gly Thr His Ala Gly Trp Glu Ala Pro Lys Val Phe Val Val
            420                 425                 430

Gly Asp Asp Val Asp Val Thr Asp Ile Gly Gln Phe Val Trp Ala Leu
        435                 440                 445
```

```
Ala Thr Arg Tyr Arg Pro Gly Ala Asp Glu Leu Val Phe Glu Glu Ala
    450                 455                 460

Asp Gly Leu Pro Met Ile Pro Tyr Met Thr Arg Ala Ser Arg Arg Glu
465                 470                 475                 480

Val Pro Asn Pro Gly Lys Gly Gly Lys Ser Val Val Asn Leu Leu Leu
                485                 490                 495

Pro Ser Glu Phe Glu Gly Lys Arg Pro Trp Val Pro Gly Ser Phe Glu
            500                 505                 510

Gly Leu Tyr Ser Glu Glu Leu Lys Gln Lys Val Leu Gly Arg Trp Gly
        515                 520                 525

Glu Leu Phe Glu Lys Lys
    530


<210> SEQ ID NO 13
<211> LENGTH: 513
<212> TYPE: PRT
<213> ORGANISM: Candida dubliniensis CD36

<400> SEQUENCE: 13

Met Ser Leu Asn Pro Ala Leu Lys Phe Arg Asp Phe Ile Gln Val Leu
1               5                   10                  15

Lys Asn Glu Gly Asp Leu Ile Glu Ile Asp Thr Glu Val Asp Pro Asn
            20                  25                  30

Leu Glu Val Gly Ala Ile Thr Arg Lys Ala Tyr Glu Asn Lys Leu Ala
        35                  40                  45

Ala Pro Leu Phe Asn Asn Leu Lys Gln Asp Pro Glu Asn Ile Asp Pro
    50                  55                  60

Lys Asn Leu Phe Arg Ile Leu Gly Cys Pro Gly Gly Leu Arg Gly Phe
65                  70                  75                  80

Gly Asn Asp His Ala Arg Ile Ala Leu His Leu Gly Leu Asp Ser Gln
                85                  90                  95

Thr Pro Met Lys Glu Ile Ile Asp Phe Leu Val Ala Asn Arg Asn Pro
            100                 105                 110

Lys Lys Tyr Ile Pro Pro Val Leu Val Pro Asn Asp Gln Ser Pro His
        115                 120                 125

Lys Lys His His Leu Thr Lys Glu Gln Ile Asp Leu Thr Lys Leu Pro
    130                 135                 140

Val Pro Leu Leu His His Gly Asp Gly Gly Lys Phe Ile Gln Thr Tyr
145                 150                 155                 160

Gly Met Trp Val Leu Gln Thr Pro Asp Lys Ser Trp Thr Asn Trp Ser
                165                 170                 175

Ile Ala Arg Gly Met Val His Asp Ser Lys Ser Ile Thr Gly Leu Val
            180                 185                 190

Ile Asn Pro Gln His Val Lys Gln Val Ser Asp Ala Trp Val Ala Ala
        195                 200                 205

Gly Lys Gly Asp Lys Ile Pro Phe Ala Leu Cys Phe Gly Val Pro Pro
    210                 215                 220

Ala Ala Ile Leu Val Ser Ser Met Pro Ile Pro Asp Gly Ala Thr Glu
225                 230                 235                 240

Ala Glu Tyr Ile Gly Gly Leu Cys Asn Gln Ala Val Pro Val Val Lys
                245                 250                 255

Cys Glu Thr Asn Asp Leu Glu Val Pro Ala Asp Cys Glu Met Val Phe
            260                 265                 270
```

```
Glu Gly Tyr Leu Asp Arg Asp Thr Leu Val Arg Glu Gly Pro Phe Gly
        275                 280                 285

Glu Met His Gly Tyr Cys Phe Pro Lys Asp His His Thr Gln Pro Leu
    290                 295                 300

Tyr Arg Val Asn His Ile Ser Tyr Arg Asp Gln Ala Ile Met Pro Ile
305                 310                 315                 320

Ser Asn Pro Gly Leu Cys Thr Asp Glu Thr His Thr Leu Ile Gly Gly
                325                 330                 335

Leu Val Ser Ala Glu Thr Lys Tyr Leu Ile Ser Gln His Pro Val Leu
            340                 345                 350

Ser Lys Ile Val Glu Asp Val Phe Thr Pro Tyr Glu Ala Gln Ala Leu
        355                 360                 365

Trp Leu Ala Val Lys Ile Asn Thr His Glu Leu Val Lys Leu Lys Thr
    370                 375                 380

Asn Ala Lys Glu Leu Ser Asn Leu Val Gly Asp Phe Leu Phe Arg Ser
385                 390                 395                 400

Lys Glu Cys Tyr Lys Val Cys Ser Ile Leu His Glu Ile Ile Leu Val
                405                 410                 415

Gly Asp Asp Ile Asp Ile Phe Asp Phe Lys Gln Leu Ile Trp Ala Tyr
            420                 425                 430

Thr Thr Arg His Thr Pro Val Gln Asp Gln Leu Tyr Phe Asp Asp Val
        435                 440                 445

Lys Pro Phe Ala Leu Ala Pro Phe Ala Ser Gln Gly Pro Leu Ile Lys
    450                 455                 460

Thr Arg Gln Gly Gly Lys Cys Val Thr Thr Cys Ile Phe Pro Lys Gln
465                 470                 475                 480

Phe Thr Asp Pro Asp Phe Glu Phe Val Thr Cys Asn Phe Asn Gly Tyr
                485                 490                 495

Pro Glu Glu Val Lys Asn Lys Ile Ser Gln Asn Trp Asp Lys Tyr Tyr
            500                 505                 510

Lys


<210> SEQ ID NO 14
<211> LENGTH: 502
<212> TYPE: PRT
<213> ORGANISM: Klebsiella pneumoniae

<400> SEQUENCE: 14

Met Thr Ala Pro Ile Gln Asp Leu Arg Asp Ala Ile Ala Leu Leu Gln
1               5                   10                  15

Gln His Asp Asn Gln Tyr Leu Glu Thr Asp His Pro Val Asp Pro Asn
            20                  25                  30

Ala Glu Leu Ala Gly Val Tyr Arg His Ile Gly Ala Gly Gly Thr Val
        35                  40                  45

Lys Arg Pro Thr Arg Ile Gly Pro Ala Met Met Phe Asn Asn Ile Lys
    50                  55                  60

Gly Tyr Pro His Ser Arg Ile Leu Val Gly Met His Ala Ser Arg Gln
65                  70                  75                  80

Arg Ala Ala Leu Leu Leu Gly Cys Glu Ala Ser Gln Leu Ala Leu Glu
                85                  90                  95

Val Gly Lys Ala Val Lys Lys Pro Val Ala Pro Val Val Val Pro Ala
            100                 105                 110

Ser Ser Ala Pro Cys Gln Glu Gln Ile Phe Leu Ala Asp Asp Pro Asp
        115                 120                 125
```

```
Phe Asp Leu Arg Thr Leu Leu Pro Ala Pro Thr Asn Thr Pro Ile Asp
    130                 135                 140

Ala Gly Pro Phe Phe Cys Leu Gly Leu Ala Leu Ala Ser Asp Pro Val
145                 150                 155                 160

Asp Ala Ser Leu Thr Asp Val Thr Ile His Arg Leu Cys Val Gln Gly
                165                 170                 175

Arg Asp Glu Leu Ser Met Phe Leu Ala Ala Gly Arg His Ile Glu Val
            180                 185                 190

Phe Arg Gln Lys Ala Glu Ala Ala Gly Lys Pro Leu Pro Ile Thr Ile
        195                 200                 205

Asn Met Gly Leu Asp Pro Ala Ile Tyr Ile Gly Ala Cys Phe Glu Ala
    210                 215                 220

Pro Thr Thr Pro Phe Gly Tyr Asn Glu Leu Gly Val Ala Gly Ala Leu
225                 230                 235                 240

Arg Gln Arg Pro Val Glu Leu Val Gln Gly Val Ser Val Pro Glu Lys
                245                 250                 255

Ala Ile Ala Arg Ala Glu Ile Val Ile Glu Gly Glu Leu Leu Pro Gly
            260                 265                 270

Val Arg Val Arg Glu Asp Gln His Thr Asn Ser Gly His Ala Met Pro
        275                 280                 285

Glu Phe Pro Gly Tyr Cys Gly Gly Ala Asn Pro Ser Leu Pro Val Ile
    290                 295                 300

Lys Val Lys Ala Val Thr Met Arg Asn Asn Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Trp Asn Ala Val Glu Ala Ala Ile Pro Gly Phe Leu Gln
            340                 345                 350

Asn Val Tyr Ala His Thr Ala Gly Gly Gly Lys Phe Leu Gly Ile Leu
        355                 360                 365

Gln Val Lys Lys Arg Gln Pro Ala Asp Glu Gly Arg Gln Gly Gln Ala
    370                 375                 380

Ala Leu Leu Ala Leu Ala Thr Tyr Ser Glu Leu Lys Asn Ile Ile Leu
385                 390                 395                 400

Val Asp Glu Asp Val Asp Ile Phe Asp Ser Asp Asp Ile Leu Trp Ala
                405                 410                 415

Met Thr Thr Arg Met Gln Gly Asp Val Ser Ile Thr Thr Ile Pro Gly
            420                 425                 430

Ile Arg Gly His Gln Leu Asp Pro Ser Gln Thr Pro Glu Tyr Ser Pro
        435                 440                 445

Ser Ile Arg Gly Asn Gly Ile Ser Cys Lys Thr Ile Phe Asp Cys Thr
    450                 455                 460

Val Pro Trp Ala Leu Lys Ser His Phe Glu Arg Ala Pro Phe Ala Asp
465                 470                 475                 480

Val Asp Pro Arg Pro Phe Ala Pro Glu Tyr Phe Ala Arg Leu Glu Lys
                485                 490                 495

Asn Gln Gly Ser Ala Lys
            500
```

<210> SEQ ID NO 15
<211> LENGTH: 510
<212> TYPE: PRT
<213> ORGANISM: Leptolyngbya sp.

<400> SEQUENCE: 15

```
Met Leu Ile Asp Gln Glu Gln Ala Lys Thr Asp His Pro Leu Gly Trp
1               5                   10                  15

Asn Val Pro Asp Ile Asn Asp Leu Arg Ala Ala Ile Ala His Leu Lys
            20                  25                  30

Lys Phe Lys Gly Gln Tyr Ile Glu Thr Asp His Pro Val Asp Pro Ile
        35                  40                  45

Ala Glu Leu Ala Gly Val Tyr Arg Tyr Ile Gly Ala Gly Gly Thr Val
    50                  55                  60

Met Arg Pro Thr Arg Ile Gly Pro Ala Met Thr Phe Asn Asn Val Lys
65                  70                  75                  80

Gly Tyr Pro Asn Ser Arg Val Leu Val Gly Met Met Ala Ser Arg Glu
                85                  90                  95

Arg Val Ser Ile Leu Leu Gly Ala Pro Thr Arg Glu Leu Gly Met Gln
            100                 105                 110

Met Gly Lys Ala Val Lys Thr Ile Val Pro Pro Ala Thr Ile Asp Ala
        115                 120                 125

Lys Asp Ala Pro Cys Gln Glu Glu Ile Tyr Arg Ala Asp Asp Pro Thr
    130                 135                 140

Phe Asp Leu Arg Lys Leu Leu Pro Ala Pro Thr Asn Thr Glu Glu Asp
145                 150                 155                 160

Ala Gly Pro Tyr Phe Cys Met Gly Leu Val Leu Gly Ser Asp Pro Asp
                165                 170                 175

Asp Glu Thr Asn Thr Asp Val Thr Ile His Arg Leu Cys Val Gln Ser
            180                 185                 190

Arg Asp Glu Met Ser Ile Phe Phe Ala Pro Gly Arg His Ile Asp Ala
        195                 200                 205

Tyr Arg Gln Lys Ala Glu Ala Ala Gly Lys Pro Leu Pro Ile Ser Val
    210                 215                 220

Asn Met Gly Leu Asp Pro Ala Ile His Ile Gly Ala Cys Phe Glu Ala
225                 230                 235                 240

Pro Thr Thr Pro Phe Gly Phe Asp Glu Leu Cys Val Ala Gly Gly Leu
                245                 250                 255

Arg Gly Lys Pro Val Glu Leu Val Asn Cys Val Thr Val Gln Gln Lys
            260                 265                 270

Ala Ile Ala Arg Ala Glu Ile Val Ile Glu Gly Glu Val Leu Pro Asn
        275                 280                 285

Val Arg Val Ala Glu Asp Gln Asn Thr His Thr Gly Tyr Ala Met Pro
    290                 295                 300

Glu Phe Pro Gly Tyr Thr Gly Pro Ala Asn Pro Ser Leu Pro Val Ile
305                 310                 315                 320

Lys Val Thr Ala Val Thr Met Arg His Asn Ala Ile Leu Gln Thr Leu
                325                 330                 335

Val Gly Pro Gly Glu Glu His Val Asn Leu Ala Gly Ile Pro Thr Glu
            340                 345                 350

Ala Ser Ile Tyr Asn Ala Val Glu Leu Ala Leu Pro Gly Leu Leu Gln
        355                 360                 365

Asn Val Tyr Ser His Ser Ser Gly Gly Gly Lys Phe Leu Ala Ile Leu
    370                 375                 380

Gln Ile Lys Lys Arg Val Ala Gly Asp Asp Gly Ser Ala Arg Gln Ala
385                 390                 395                 400

Ala Leu Ile Ala Leu Ala Val Tyr Arg Glu Val Lys Asn Ile Ile Leu
                405                 410                 415
```

```
Val Asp Glu Asp Val Asp Leu Phe Asp Ser Asp Asp Val Leu Trp Ala
            420                 425                 430

Met Gln Thr Arg Tyr Gln Gly Asp Thr Gly Thr Ile Val Val Pro Gly
        435                 440                 445

Ile Thr Gly His Val Leu Asp Pro Ser Gln Ile Pro Glu Tyr Ser Pro
    450                 455                 460

Ser Ile His Thr Lys Gly Ser Thr Cys Lys Thr Ile Phe Asp Cys Thr
465                 470                 475                 480

Val Pro Phe Ala Leu Lys Glu His Phe Lys Arg Ala Gln Phe Arg Glu
                485                 490                 495

Leu Asp Pro Arg Pro Phe Ala Pro Glu Leu Phe Asn Glu Pro
            500                 505                 510


<210> SEQ ID NO 16
<211> LENGTH: 492
<212> TYPE: PRT
<213> ORGANISM: Phascolarctobacterium sp.

<400> SEQUENCE: 16

Met Thr Thr Lys Ile Asn Asp Leu Arg Ser Ala Leu Asp Tyr Leu Arg
1               5                   10                  15

Thr Ile Pro Gly Gln Leu Val Glu Thr Asn Val Glu Ala Asp Pro Arg
            20                  25                  30

Ala Glu Ile Ser Gly Ile Tyr Arg Tyr Val Gly Ala Lys Gly Thr Val
        35                  40                  45

Lys Arg Pro Thr Arg Leu Gly Pro Ala Met Ile Phe Asn Asn Val Lys
    50                  55                  60

Gly His Pro Gly Ala Lys Val Ala Ile Gly Val Leu Ser Ser Arg Ala
65                  70                  75                  80

Arg Val Gly Tyr Leu Leu Gly Cys Glu Pro Glu Lys Leu Gly Phe Leu
                85                  90                  95

Leu Lys Asp Ser Val Ser Thr Pro Ile Ala Pro Val Val Val Ser Ala
            100                 105                 110

Asp Gln Ala Pro Cys Gln Glu Val Val His Leu Ala Thr Glu Glu Gly
        115                 120                 125

Phe Asp Ile Arg Lys Leu Ile Pro Ala Pro Thr Asn Thr Glu Glu Asp
    130                 135                 140

Ala Gly Pro Tyr Val Thr Met Gly Leu Cys Tyr Gly Thr Asp Pro Glu
145                 150                 155                 160

Thr Gly Asp Thr Asp Ile Thr Ile His Arg Leu Cys Leu Gln Gly Lys
                165                 170                 175

Asp Glu Ile Ser Met Tyr Phe Val Pro Gly Arg His Leu Asp Val Phe
            180                 185                 190

Arg Gln Lys Tyr Glu Lys Ala Gly Lys Pro Met Pro Ile Ser Ile Ser
        195                 200                 205

Ile Gly Val Asp Pro Ala Ile Glu Ile Ala Ala Cys Phe Glu Pro Pro
    210                 215                 220

Thr Thr Pro Leu Gly Phe Asn Glu Leu Ser Ile Ala Gly Ser Ile Arg
225                 230                 235                 240

Gly Glu Gly Val Gln Met Val Gln Cys Lys Thr Ile Asn Glu Lys Ala
                245                 250                 255

Ile Ala Arg Ala Glu Tyr Val Ile Glu Gly Glu Leu Leu Pro Asp Val
            260                 265                 270
```

```
Arg Val Arg Glu Asp Gln Asn Ser Asn Thr Gly Lys Ala Met Pro Glu
        275                 280                 285

Phe Pro Gly Tyr Thr Gly Ala Met Lys Pro Ala Ile Pro Leu Ile Lys
    290                 295                 300

Val Lys Ala Val Thr His Arg Arg Asp Pro Ile Met Gln Ser Cys Ile
305                 310                 315                 320

Gly Pro Ser Glu Glu His Val Asn Met Ala Gly Ile Pro Thr Glu Ala
                325                 330                 335

Ser Ile Leu Gly Met Thr Glu Lys Ala Leu Pro Gly Asn Val Lys Asn
            340                 345                 350

Val Tyr Ala His Cys Ser Gly Gly Gly Lys Tyr Met Ala Val Ile Gln
        355                 360                 365

Phe Val Lys Lys Ala Pro Pro Asp Glu Gly Arg Gln Arg Gln Ala Ala
    370                 375                 380

Leu Leu Ala Phe Ser Ala Phe Ser Glu Leu Lys His Val Ile Leu Val
385                 390                 395                 400

Asp Asp Asp Val Asp Leu Phe Asp Thr Asp Asp Val Leu Trp Ala Leu
                405                 410                 415

Asn Thr Arg Phe Gln Gly Asp Val Asp Val Ile Thr Ile Pro Gly Val
            420                 425                 430

Arg Cys His Pro Leu Asp Pro Ser Gln Ser Pro Glu Phe Ser Pro Ser
        435                 440                 445

Ile Arg Asp Val Gly Ile Ser Cys Lys Thr Ile Phe Asp Cys Thr Val
    450                 455                 460

Pro Phe Gly Leu Lys Glu His Phe Gln Arg Ser Lys Phe Lys Glu Val
465                 470                 475                 480

Asn Pro Ala Lys Trp Val Pro Glu Leu Phe Lys Lys
                485                 490


<210> SEQ ID NO 17
<211> LENGTH: 497
<212> TYPE: PRT
<213> ORGANISM: Escherichia coli K-12

<400> SEQUENCE: 17

Met Asp Ala Met Lys Tyr Asn Asp Leu Arg Asp Phe Leu Thr Leu Leu
1               5                   10                  15

Glu Gln Gln Gly Glu Leu Lys Arg Ile Thr Leu Pro Val Asp Pro His
            20                  25                  30

Leu Glu Ile Thr Glu Ile Ala Asp Arg Thr Leu Arg Ala Gly Gly Pro
        35                  40                  45

Ala Leu Leu Phe Glu Asn Pro Lys Gly Tyr Ser Met Pro Val Leu Cys
    50                  55                  60

Asn Leu Phe Gly Thr Pro Lys Arg Val Ala Met Gly Met Gly Gln Glu
65                  70                  75                  80

Asp Val Ser Ala Leu Arg Glu Val Gly Lys Leu Leu Ala Phe Leu Lys
                85                  90                  95

Glu Pro Glu Pro Pro Lys Gly Phe Arg Asp Leu Phe Asp Lys Leu Pro
            100                 105                 110

Gln Phe Lys Gln Val Leu Asn Met Pro Thr Lys Arg Leu Arg Gly Ala
        115                 120                 125

Pro Cys Gln Gln Lys Ile Val Ser Gly Asp Asp Val Asp Leu Asn Arg
    130                 135                 140
```

```
Ile Pro Ile Met Thr Cys Trp Pro Glu Asp Ala Ala Pro Leu Ile Thr
145                 150                 155                 160

Trp Gly Leu Thr Val Thr Arg Gly Pro His Lys Glu Arg Gln Asn Leu
                165                 170                 175

Gly Ile Tyr Arg Gln Gln Leu Ile Gly Lys Asn Lys Leu Ile Met Arg
            180                 185                 190

Trp Leu Ser His Arg Gly Gly Ala Leu Asp Tyr Gln Glu Trp Cys Ala
        195                 200                 205

Ala His Pro Gly Glu Arg Phe Pro Val Ser Val Ala Leu Gly Ala Asp
    210                 215                 220

Pro Ala Thr Ile Leu Gly Ala Val Thr Pro Val Pro Asp Thr Leu Ser
225                 230                 235                 240

Glu Tyr Ala Phe Ala Gly Leu Leu Arg Gly Thr Lys Thr Glu Val Val
                245                 250                 255

Lys Cys Ile Ser Asn Asp Leu Glu Val Pro Ala Ser Ala Glu Ile Val
            260                 265                 270

Leu Glu Gly Tyr Ile Glu Gln Gly Glu Thr Ala Pro Glu Gly Pro Tyr
        275                 280                 285

Gly Asp His Thr Gly Tyr Tyr Asn Glu Val Asp Ser Phe Pro Val Phe
    290                 295                 300

Thr Val Thr His Ile Thr Gln Arg Glu Asp Ala Ile Tyr His Ser Thr
305                 310                 315                 320

Tyr Thr Gly Arg Pro Pro Asp Glu Pro Ala Val Leu Gly Val Ala Leu
                325                 330                 335

Asn Glu Val Phe Val Pro Ile Leu Gln Lys Gln Phe Pro Glu Ile Val
            340                 345                 350

Asp Phe Tyr Leu Pro Pro Glu Gly Cys Ser Tyr Arg Leu Ala Val Val
        355                 360                 365

Thr Ile Lys Lys Gln Tyr Ala Gly His Ala Lys Arg Val Met Met Gly
    370                 375                 380

Val Trp Ser Phe Leu Arg Gln Phe Met Tyr Thr Lys Phe Val Ile Val
385                 390                 395                 400

Cys Asp Asp Asp Val Asn Ala Arg Asp Trp Asn Asp Val Ile Trp Ala
                405                 410                 415

Ile Thr Thr Arg Met Asp Pro Ala Arg Asp Thr Val Leu Val Glu Asn
            420                 425                 430

Thr Pro Ile Asp Tyr Leu Asp Phe Ala Ser Pro Val Ser Gly Leu Gly
        435                 440                 445

Ser Lys Met Gly Leu Asp Ala Thr Asn Lys Trp Pro Gly Glu Thr Gln
    450                 455                 460

Arg Glu Trp Gly Arg Pro Ile Lys Lys Asp Pro Asp Val Val Ala His
465                 470                 475                 480

Ile Asp Ala Ile Trp Asp Glu Leu Ala Ile Phe Asn Asn Gly Lys Ser
                485                 490                 495

Ala


<210> SEQ ID NO 18
<211> LENGTH: 473
<212> TYPE: PRT
<213> ORGANISM: Bacillus megaterium QM B1551

<400> SEQUENCE: 18

Met Ala Tyr Lys Asp Phe Arg Asp Phe Leu Asn Thr Leu His Lys Glu
1               5                   10                  15
```

```
Gly Gln Leu Leu Thr Val Thr Asp Glu Val Gln Pro Asp Pro Asp Leu
            20                  25                  30

Gly Ser Ala Gly Gln Ala Ile Ser Asn Leu Gly Asp Gln Thr Pro Gly
        35                  40                  45

Leu Leu Phe Thr Asn Ile Tyr Gly Tyr Asn Asn Ala Lys Val Ala Leu
    50                  55                  60

Asn Val Met Gly Ser Trp Ser Asn His Ala Leu Met Met Gly Leu Pro
65                  70                  75                  80

Lys Ser Thr Pro Val Lys Glu Gln Phe Phe Glu Phe Ala Arg Arg Tyr
                85                  90                  95

Glu Lys Phe Pro Val Lys Val Lys Arg Glu Glu Thr Ala Pro Phe His
            100                 105                 110

Glu Cys Glu Ile Lys Asp Asp Ile Asn Leu Phe Asp Leu Leu Pro Leu
        115                 120                 125

Phe Arg Leu Asn Gln Gly Asp Gly Gly Tyr Tyr Leu Asp Lys Ala Cys
    130                 135                 140

Val Ile Ser Arg Asp Gln His Asp Lys Glu Asn Phe Gly Lys Gln Asn
145                 150                 155                 160

Val Gly Ile Tyr Arg Met Gln Val Lys Gly Lys Asp Arg Leu Gly Ile
                165                 170                 175

Gln Pro Val Pro Gln His Asp Ile Ala Ile His Leu Lys Gln Ala Glu
            180                 185                 190

Glu Lys Gly Glu Asn Leu Pro Val Ser Ile Ala Leu Gly Cys Glu Pro
        195                 200                 205

Ala Ile Val Thr Ala Ala Ala Thr Pro Leu His Tyr Asp Gln Ser Glu
    210                 215                 220

Tyr Glu Met Ala Gly Ala Ile Gln Gly Glu Pro Tyr Arg Ile Val Lys
225                 230                 235                 240

Ser Gln Leu Ser Asp Leu Asp Val Pro Trp Gly Ala Glu Val Ile Leu
                245                 250                 255

Glu Gly Glu Ile Leu Ala Gly Glu Arg Glu Tyr Glu Gly Pro Phe Gly
            260                 265                 270

Glu Phe Thr Gly His Tyr Ser Gly Gly Arg Ser Met Pro Val Ile Lys
        275                 280                 285

Ile Asn Arg Val Tyr His Arg Lys Asp Pro Ile Phe Glu Ser Leu Tyr
    290                 295                 300

Ile Gly Met Pro Trp Thr Glu Thr Asp Tyr Leu Ile Gly Ile Asn Thr
305                 310                 315                 320

Ser Val Pro Leu Tyr Gln Gln Leu Lys Glu Ala Tyr Pro Glu Glu Ile
                325                 330                 335

Glu Ala Val Asn Ala Met Tyr Thr His Gly Leu Val Ala Ile Val Ser
            340                 345                 350

Thr Lys Ser Arg Tyr Gly Gly Phe Ala Lys Ala Val Gly Met Arg Ala
        355                 360                 365

Leu Thr Thr Pro His Gly Leu Gly Tyr Cys Lys Leu Val Ile Leu Val
    370                 375                 380

Asp Glu Asp Val Asp Pro Phe Asn Leu Pro Gln Val Met Trp Ala Leu
385                 390                 395                 400

Ser Thr Lys Met His Pro Lys His Asp Val Ile Thr Val Pro Asn Leu
                405                 410                 415

Ser Val Leu Pro Leu Asp Pro Gly Ser Glu Pro Ala Gly Ile Thr Asp
            420                 425                 430
```

```
Lys Met Ile Leu Asp Ala Thr Thr Pro Val Ala Pro Glu Thr Arg Gly
        435                 440                 445

His Tyr Ser Gln Pro Leu Asp Thr Pro Leu Glu Thr Glu Lys Trp Glu
    450                 455                 460

Lys Ile Leu Thr Asn Met Met Gln Lys
465                 470


<210> SEQ ID NO 19
<211> LENGTH: 423
<212> TYPE: PRT
<213> ORGANISM: Methanothermobacter sp. CaT2

<400> SEQUENCE: 19

Met Arg Asn Phe Leu Asp Lys Ile Gly Glu Glu Ala Leu Val Val Glu
1               5                   10                  15

Asp Glu Val Ser Thr Ser Phe Glu Ala Ala Ser Ile Leu Arg Glu His
            20                  25                  30

Pro Arg Asp Leu Val Ile Leu Lys Asn Leu Lys Glu Ser Asp Ile Pro
        35                  40                  45

Val Ile Ser Gly Leu Cys Asn Thr Arg Glu Lys Ile Ala Leu Ser Leu
    50                  55                  60

Asn Cys Arg Val His Glu Ile Thr His Arg Ile Val Glu Ala Met Glu
65                  70                  75                  80

Asn Pro Thr Pro Ile Ser Ser Val Gly Gly Leu Asp Gly Tyr Arg Ser
                85                  90                  95

Gly Arg Ala Asp Leu Ser Glu Leu Pro Ile Leu Arg His Tyr Arg Arg
            100                 105                 110

Asp Gly Gly Pro Tyr Ile Thr Ala Gly Val Ile Phe Ala Arg Asp Pro
        115                 120                 125

Asp Thr Gly Val Arg Asn Ala Ser Ile His Arg Met Met Val Ile Gly
    130                 135                 140

Asp Asp Arg Leu Ala Val Arg Ile Val Pro Arg His Leu Tyr Thr Tyr
145                 150                 155                 160

Leu Gln Lys Ala Glu Glu Arg Gly Glu Asp Leu Glu Ile Ala Ile Ala
                165                 170                 175

Ile Gly Met Asp Pro Ala Thr Leu Leu Ala Thr Thr Thr Ser Ile Pro
            180                 185                 190

Ile Asp Ala Asp Glu Met Glu Val Ala Asn Thr Phe His Glu Gly Glu
        195                 200                 205

Leu Glu Leu Val Arg Cys Glu Gly Val Asp Met Glu Val Pro Pro Ala
    210                 215                 220

Glu Ile Ile Leu Glu Gly Arg Ile Leu Cys Gly Val Arg Glu Arg Glu
225                 230                 235                 240

Gly Pro Phe Val Asp Leu Thr Asp Thr Tyr Asp Val Val Arg Asp Glu
                245                 250                 255

Pro Val Ile Ser Leu Glu Arg Met His Ile Arg Lys Asp Ala Met Tyr
            260                 265                 270

His Ala Ile Leu Pro Ala Gly Phe Glu His Arg Leu Leu Gln Gly Leu
        275                 280                 285

Pro Gln Glu Pro Arg Ile Tyr Arg Ala Val Lys Asn Thr Val Pro Thr
    290                 295                 300

Val Arg Asn Val Val Leu Thr Glu Gly Gly Cys Cys Trp Leu His Ala
305                 310                 315                 320

Ala Val Ser Ile Lys Lys Gln Thr Glu Gly Asp Gly Lys Asn Val Ile
                325                 330                 335
```

```
Met Ala Ala Leu Ala Ala His Pro Ser Leu Lys His Val Val Val Val
            340                 345                 350

Asp Glu Asp Ile Asp Val Leu Asp Pro Glu Glu Ile Glu Tyr Ala Ile
        355                 360                 365

Ala Thr Arg Val Lys Gly Asp Asp Asp Ile Leu Ile Val Pro Gly Ala
    370                 375                 380

Arg Gly Ser Ser Leu Asp Pro Ala Ala Leu Pro Asp Gly Thr Thr Thr
385                 390                 395                 400

Lys Val Gly Val Asp Ala Thr Ala Pro Leu Ala Ser Ala Glu Lys Phe
                405                 410                 415

Gln Arg Val Ser Arg Ser Glu
            420
```

```
<210> SEQ ID NO 20
<211> LENGTH: 494
<212> TYPE: PRT
<213> ORGANISM: Mycobacterium chelonae
<220> FEATURE:
<223> OTHER INFORMATION: Mycobacterium chelonae 1518

<400> SEQUENCE: 20

Met Ala Phe Asn Asp Leu Arg Arg Tyr Leu Ala Asp Leu Glu Ala His
1               5                   10                  15

Gly Glu Leu Arg Thr Ile Lys Thr Pro Val Ser Thr Glu Ile Gln Leu
            20                  25                  30

Gly Ala Ile Ala Arg Leu Ala Cys Glu Thr Tyr Gly Pro Ala Ala Leu
        35                  40                  45

Phe Glu Asn Leu Val Gly Tyr Pro Thr Phe Arg Gly Leu Ala Ala Phe
    50                  55                  60

Glu Thr Tyr Ser Gly Asn Pro Asp Asn Arg Ala Trp Arg Leu Ala Arg
65                  70                  75                  80

Ala Leu Gly Leu Ser Asp Asp Thr Thr Gly Asp Gln Ile Val Asp Phe
                85                  90                  95

Leu Ala Gly Phe Arg Asp Thr Ala Gly Val Ala Pro Val Leu Val Glu
            100                 105                 110

Thr Gly Pro Val His Glu Asn Ile Val Arg Asp Arg Gly Glu Leu Leu
        115                 120                 125

Asp Tyr Leu Pro Ile Pro His Leu His Pro Gly Asp Gly Gly Pro Tyr
    130                 135                 140

Val Asn Thr Ile Gly Phe Phe Val Leu Glu Ser Pro Asp Arg Ser Trp
145                 150                 155                 160

Val Asn Trp Ala Val Ala Arg Cys Met Lys Leu Asp Gly Asp Arg Met
                165                 170                 175

Val Gly Met Thr Ala Val Met Gln His Ile Gly Met Leu Arg Arg Glu
            180                 185                 190

Trp Asp Lys Ile Gly Thr Ser Val Pro Phe Ala Leu Val Leu Gly Ala
        195                 200                 205

Asp Pro Ile Thr Thr Leu Ile Ser Gly Gly Pro Leu Ala Lys Phe Gly
    210                 215                 220

Ala Ser Glu Gly Asp Ile Ile Gly Ala Ile Arg Gly Glu Pro Leu Glu
225                 230                 235                 240

Val Val Glu Cys Val Thr Ser Ser Leu Arg Val Pro Ala His Ala Glu
                245                 250                 255

Ile Val Ile Glu Gly Tyr Ile Asp Leu Thr Glu Ser Ala Asp Glu Gly
            260                 265                 270
```

```
Pro Met Ala Glu Tyr His Gly Tyr Ile Asp Lys Ala Lys Asn Thr Thr
        275                 280                 285

Gly Ala Pro Asp Phe Gly Val Tyr His Ile Thr Ala Val Thr His Arg
    290                 295                 300

Asn Asp Ala Ile Tyr Pro Ser Thr Cys Ala Gly Lys Pro Val Asp Glu
305                 310                 315                 320

Asp His Thr Ile Thr Gly Pro Gly Val Ala Ala Ala Ser Leu Asn Ala
                325                 330                 335

Leu Arg Ala Ala Ser Leu Pro Val Glu Lys Ala Trp Met Val Pro Glu
            340                 345                 350

Ser Ala Ser His Val Leu Ala Val Thr Val Ser Asp Gly Trp Ser Gly
        355                 360                 365

Glu Phe Pro Asp Ala Asn Glu Leu Cys Arg Lys Ile Gly Asn Ala Val
    370                 375                 380

Lys Thr Met Asp His Ser Ala Tyr Trp Val Gln Arg Ile Leu Val Thr
385                 390                 395                 400

Asp Asn Asp Ile Asp Pro Thr Ser Pro Ser Asp Leu Trp Trp Ala Tyr
                405                 410                 415

Ala Thr Arg Cys Arg Pro Gly Asp Asp Ser Ile Ile Leu Glu Asp Val
            420                 425                 430

Pro Ile Met Ala Leu Ser Pro Ile Val Asn Thr Arg Glu Glu Arg Thr
        435                 440                 445

Lys Thr Arg Gly Arg Val Glu Val Leu Asn Cys Leu Ile Pro Pro Tyr
    450                 455                 460

Ala Asp Asp Leu Ser Val Thr Ser Ala Ala Leu Arg Gln Ala Tyr Pro
465                 470                 475                 480

His Asp Ala Ile Ala Phe Ala Glu Arg Thr Tyr Leu Gly Glu
                485                 490


<210> SEQ ID NO 21
<211> LENGTH: 512
<212> TYPE: PRT
<213> ORGANISM: Hypocrea atroviridis
<220> FEATURE:
<223> OTHER INFORMATION: Hypocrea atroviridis (strain ATCC 20476)

<400> SEQUENCE: 21

Met Ser Ser Thr Thr Tyr Lys Ser Glu Ala Phe Asp Pro Glu Pro Pro
1               5                   10                  15

His Leu Ser Phe Arg Ser Phe Val Glu Ala Leu Arg Gln Asp Asn Asp
            20                  25                  30

Leu Val Asp Ile Asn Glu Pro Val Asp Pro Asp Leu Glu Ala Ala Ala
        35                  40                  45

Ile Thr Arg Leu Val Cys Glu Thr Asp Asp Lys Ala Pro Leu Phe Asn
    50                  55                  60

Asn Val Ile Gly Ala Lys Asp Gly Leu Trp Arg Ile Leu Gly Ala Pro
65                  70                  75                  80

Ala Ser Leu Arg Ser Ser Pro Lys Glu Arg Phe Gly Arg Leu Ala Arg
                85                  90                  95

His Leu Ala Leu Pro Pro Thr Ala Ser Ala Lys Asp Ile Leu Asp Lys
            100                 105                 110

Met Leu Ser Ala Asn Ser Ile Pro Pro Ile Glu Pro Val Ile Val Pro
        115                 120                 125

Thr Gly Pro Val Lys Glu Asn Ser Ile Glu Gly Glu Asn Ile Asp Leu
    130                 135                 140
```

```
Glu Ala Leu Pro Ala Pro Met Val His Gln Ser Asp Gly Gly Lys Tyr
145                 150                 155                 160

Ile Gln Thr Tyr Gly Met His Val Ile Gln Ser Pro Asp Gly Cys Trp
                165                 170                 175

Thr Asn Trp Ser Ile Ala Arg Ala Met Val Ser Gly Lys Arg Thr Leu
            180                 185                 190

Ala Gly Leu Val Ile Ser Pro Gln His Ile Arg Lys Ile Gln Asp Gln
        195                 200                 205

Trp Arg Ala Ile Gly Gln Glu Glu Ile Pro Trp Ala Leu Ala Phe Gly
    210                 215                 220

Val Pro Pro Thr Ala Ile Met Ala Ser Ser Met Pro Ile Pro Asp Gly
225                 230                 235                 240

Val Ser Glu Ala Gly Tyr Val Gly Ala Ile Ala Gly Glu Pro Ile Lys
                245                 250                 255

Leu Val Lys Cys Asp Thr Asn Asn Leu Tyr Val Pro Ala Asn Ser Glu
            260                 265                 270

Ile Val Leu Glu Gly Thr Leu Ser Thr Thr Lys Met Ala Pro Glu Gly
        275                 280                 285

Pro Phe Gly Glu Met His Gly Tyr Val Tyr Pro Gly Glu Ser His Pro
    290                 295                 300

Gly Pro Val Tyr Thr Val Asn Lys Ile Thr Tyr Arg Asn Asn Ala Ile
305                 310                 315                 320

Leu Pro Met Ser Ala Cys Gly Arg Leu Thr Asp Glu Thr Gln Thr Met
                325                 330                 335

Ile Gly Thr Leu Ala Ala Ala Glu Ile Arg Gln Leu Cys Gln Asp Ala
            340                 345                 350

Gly Leu Pro Ile Thr Asp Ala Phe Ala Pro Phe Val Gly Gln Ala Thr
        355                 360                 365

Trp Val Ala Leu Lys Val Asp Thr Lys Arg Leu Arg Ala Met Lys Thr
    370                 375                 380

Asn Gly Lys Ala Phe Ala Lys Arg Val Gly Asp Val Val Phe Thr Gln
385                 390                 395                 400

Lys Pro Gly Phe Thr Ile His Arg Leu Ile Leu Val Gly Asp Asp Ile
                405                 410                 415

Asp Val Tyr Asp Asp Lys Asp Val Met Trp Ala Phe Thr Thr Arg Cys
            420                 425                 430

Arg Pro Gly Thr Asp Glu Val Phe Phe Asp Asp Val Val Gly Phe Gln
        435                 440                 445

Leu Ile Pro Tyr Met Ser His Gly Asn Ala Glu Ala Ile Lys Gly Gly
    450                 455                 460

Lys Val Val Ser Asp Ala Leu Leu Thr Ala Glu Tyr Thr Thr Gly Lys
465                 470                 475                 480

Asp Trp Glu Ser Ala Asp Phe Lys Asn Ser Tyr Pro Lys Ser Ile Gln
                485                 490                 495

Asp Lys Val Leu Asn Ser Trp Glu Arg Leu Gly Phe Lys Lys Leu Asp
            500                 505                 510
```

<210> SEQ ID NO 22
<211> LENGTH: 508
<212> TYPE: PRT
<213> ORGANISM: Sphaerulina
<220> FEATURE:
<223> OTHER INFORMATION: Sphaerulina musiva (strain SO2202)

<400> SEQUENCE: 22

```
Met Ser Ser Ser Lys Gln Gln His Leu Ser His Ala Asn Gln Glu Leu
1               5                   10                  15

Pro His Leu Asn Phe Arg Ser Phe Val Gln Ala Leu Lys Asp Asp Gly
            20                  25                  30

Asp Leu Ile Glu Ile Asp Asp Glu Ile Asp Pro His Leu Glu Ala Gly
        35                  40                  45

Ala Ile Ile Arg Arg Ala Cys Glu Thr Asp Gly Lys Ala Pro Leu Leu
    50                  55                  60

Asn Asn Leu Lys Gly Ala Lys Asp Gly Leu Trp Arg Ile Leu Gly Ala
65                  70                  75                  80

Pro Ala Ser Leu Arg Ser Asp Pro Ser Gln Lys Tyr Gly Arg Val Ala
                85                  90                  95

Arg His Leu Ala Leu Pro Pro Thr Ala Thr Met Lys Asp Ile Leu Asp
            100                 105                 110

Lys Met Leu Ser Ala Ala His Ala Glu Pro Ile Pro Pro Asn Ile Val
        115                 120                 125

Glu Ser Gly Pro Val Lys Glu Asn Lys Leu Val Asp Gly Glu Phe Asp
    130                 135                 140

Leu Ser Thr Leu Pro Ala Pro Trp Leu His Gln Ala Asp Gly Gly Lys
145                 150                 155                 160

Tyr Ile Gln Thr Tyr Gly Met His Ile Val Gln Ser Pro Asp Gly Lys
                165                 170                 175

Trp Thr Asn Trp Ser Ile Ala Arg Ala Met Val His Asp Lys Asn His
            180                 185                 190

Leu Thr Gly Leu Val Ile Glu Pro Gln His Ile Trp Gln Ile His Gln
        195                 200                 205

Gln Trp Lys Lys Val Gly Lys Asp Val Pro Trp Ala Leu Ala Phe Gly
    210                 215                 220

Val Pro Pro Ala Ala Ile Met Ala Ala Ser Met Pro Ile Pro Asp Gly
225                 230                 235                 240

Val Thr Glu Ala Gly Tyr Ile Gly Ala Met Thr Gly Ser Ala Leu Asp
                245                 250                 255

Val Val Lys Cys Glu Thr Asn Gly Met Tyr Val Pro Ala Asn Ala Glu
            260                 265                 270

Ile Val Leu Glu Gly Thr Leu Ser Ile Thr Glu Thr Ala Pro Glu Gly
        275                 280                 285

Pro Phe Gly Glu Met His Gly Tyr Val Phe Pro Gly Asp Thr His Pro
    290                 295                 300

Trp Pro Lys Tyr Lys Val Asp Ala Ile Thr Tyr Arg Asn Gly Ala Ile
305                 310                 315                 320

Leu Pro Val Ser Asn Cys Gly Arg Ile Thr Asp Glu Thr His Thr Leu
                325                 330                 335

Ile Gly Pro Leu Ala Ala Ala Gln Ile Arg Gln Leu Cys Gln Asp Ala
            340                 345                 350

Gly Leu Pro Ile Thr Asp Ala Phe Ala Pro Phe His Thr Gln Val Thr
        355                 360                 365

Trp Val Ala Leu Lys Val Asp Ile Glu Lys Leu Gly Lys Met Asn Thr
    370                 375                 380

Thr Pro Glu Ala Phe Arg Lys Gln Val Gly Asp Leu Val Phe Asn His
385                 390                 395                 400
```

```
Lys Ala Gly Tyr Thr Ile His Arg Leu Val Leu Cys Gly Ser Asp Ile
                405                 410                 415

Asp Val Tyr Glu Trp Asp Asp Ile Ala Phe Ala Phe Ser Thr Arg Cys
            420                 425                 430

Arg Pro Asn Lys Asp Glu Thr Phe Tyr Glu Asp Cys Gln Gly Phe Pro
        435                 440                 445

Leu Ile Pro Tyr Met Ser His Gly Thr Gly Ser Pro Ile Lys Gly Gly
    450                 455                 460

Lys Val Ile Ser Asp Ala Leu Met Pro Ser Glu Tyr Arg Gly Gln Gln
465                 470                 475                 480

Asp Trp Gln Gln Ala Ser Phe Lys His Ser Tyr Pro Glu Ser Leu Gln
                485                 490                 495

Lys Ser Val Ile Glu Arg Trp Ala Ser Trp Gly Phe
            500                 505


<210> SEQ ID NO 23
<211> LENGTH: 498
<212> TYPE: PRT
<213> ORGANISM: Penicillium roqueforti

<400> SEQUENCE: 23

Met Ala Asn Ile Glu Pro His Leu Cys Phe Arg Ser Phe Val Glu Ala
1               5                   10                  15

Leu Lys Ala Asp Asn Asp Leu Val Glu Ile Asp Thr Pro Ile Asp Pro
            20                  25                  30

Asn Leu Glu Ala Ala Ala Ile Thr Arg Leu Val Cys Glu Thr Asn Asp
        35                  40                  45

Lys Ala Pro Leu Phe Asn Asn Ile Ile Gly Thr Glu Lys Gly Leu Phe
    50                  55                  60

Arg Ile Leu Gly Ala Pro Ala Ser Leu Arg Asn Ser Ser Lys Asp Arg
65                  70                  75                  80

Tyr Gly Arg Leu Ala Arg His Leu Ala Leu Pro Pro Thr Ala Ser Met
                85                  90                  95

Arg Asp Ile Leu Asp Lys Met Leu Ser Ala Gly Thr Pro Ile Pro Pro
            100                 105                 110

Asn Ile Val Ser Thr Gly Pro Cys Lys Glu Asn Phe Leu Glu Glu Ser
        115                 120                 125

Gln Ile Asp Leu Thr Lys Leu Pro Ala Pro Leu Ile His Gln Ala Asp
    130                 135                 140

Gly Gly Lys Tyr Ile Gln Thr Tyr Gly Met His Ile Val Gln Ser Pro
145                 150                 155                 160

Asp Gly Ser Trp Thr Asn Trp Ser Ile Ala Arg Ala Met Val Ser Asp
                165                 170                 175

Asp Lys His Leu Thr Gly Leu Val Ile Glu Pro Gln His Leu Trp Gln
            180                 185                 190

Ile His Gln Met Trp Lys Lys Glu Gly Arg Asp Ala Pro Trp Ala Leu
        195                 200                 205

Ala Phe Gly Val Pro Pro Ala Ala Ile Met Ala Ser Ser Met Pro Ile
    210                 215                 220

Pro Asp Gly Val Ser Glu Ala Gly Tyr Val Gly Ser Met Thr Gly Ser
225                 230                 235                 240

Ala Leu Asp Leu Val Lys Cys Asp Thr Asn Asp Leu Tyr Val Pro Ala
                245                 250                 255
```

```
Thr Ser Glu Ile Val Phe Glu Gly Thr Leu Ser Ile Thr Glu Lys Gly
            260                 265                 270

Pro Glu Gly Pro Phe Gly Glu Met His Gly Tyr Val Phe Pro Gly Asp
        275                 280                 285

Val His Leu Cys Pro Lys Tyr Lys Val Asn Arg Ile Thr Tyr Arg Asn
    290                 295                 300

Asp Pro Ile Met Pro Met Ser Ser Cys Gly Arg Leu Thr Asp Glu Thr
305                 310                 315                 320

His Thr Met Ile Gly Ser Leu Ala Ala Ala Val Ile Arg Lys Ile Cys
                325                 330                 335

Gln Gln Ala Gly Leu Pro Val Asn Asp Ala Phe Ala Pro Phe Glu Ser
            340                 345                 350

Gln Val Thr Trp Val Ala Leu Arg Ile Asp Thr Ala Lys Leu Arg Glu
        355                 360                 365

Met Lys Thr Thr Pro Lys Glu Phe Ser Lys Lys Val Gly Glu Leu Ile
    370                 375                 380

Phe Asn Ser Lys Ala Gly Tyr Thr Ile His Arg Leu Val Leu Cys Gly
385                 390                 395                 400

Asp Asp Ile Asp Val Tyr Asn Gly Lys Asp Val Met Trp Ala Phe Ser
                405                 410                 415

Thr Arg Cys Arg Pro Asn Leu Asp Glu Ile Phe Phe Glu Asp Val Pro
            420                 425                 430

Gly Phe Pro Leu Ile Pro Tyr Met Ser His Gly Asn Gly Ser Pro Val
        435                 440                 445

Lys Gly Gly Lys Val Val Ser Asp Ala Leu Leu Pro Cys Glu Tyr Thr
    450                 455                 460

Thr Gly Lys Asn Trp Glu Ala Ala Asp Phe Glu Ser Ser Tyr Pro Glu
465                 470                 475                 480

Ala Val Lys Gln Lys Val Leu Ala Asn Trp Thr Lys Met Gly Phe Arg
                485                 490                 495

Glu Glu


<210> SEQ ID NO 24
<211> LENGTH: 503
<212> TYPE: PRT
<213> ORGANISM: Fusarium oxysporum f. sp. lycopersici

<400> SEQUENCE: 24

Met Pro Ser Lys Thr Leu Pro His Met Asp Phe Arg Ser Tyr Val Glu
1               5                   10                  15

Ala Leu Glu Ala Asp Gly Asp Leu Val Ser Ile Thr Glu Glu Cys Asp
            20                  25                  30

Pro His Leu Glu Val Gly Ala Ile Ile Arg Lys Val Val Glu Asn Asn
        35                  40                  45

Asp Lys Ala Pro Leu Phe Asn Lys Leu Lys Gly Gln Asp Glu Asn Gly
    50                  55                  60

Phe Trp Arg Ile Leu Gly Ala Pro Asn Ser Leu Arg Ser Asp Pro Lys
65                  70                  75                  80

Gln Arg Tyr Gly Arg Leu Ala Arg His Leu Gly Leu Pro Thr Asp Ser
                85                  90                  95

Ser Met Lys Val Ile Leu Asp Lys Met Ile Ala Ala Lys Thr Thr Pro
            100                 105                 110

Pro Ile Pro Pro Thr Val Val Glu Thr Gly Pro Cys Lys Glu His Ile
        115                 120                 125
```

```
Leu Thr Pro Asp Gln Phe Asp Leu Thr Lys Leu Pro Ala Pro Leu Leu
    130                 135                 140

His Gln Ser Asp Gly Gly Lys Tyr Ile Gln Thr Tyr Gly Met His Ile
145                 150                 155                 160

Val Gln Ser Pro Asp Gly Lys Trp Thr Asn Trp Ser Ile Ala Arg Ala
                165                 170                 175

Met Val Tyr Asp Arg Asn His Leu Ala Gly Leu Val Ile Lys Pro Gln
            180                 185                 190

His Leu Tyr Gln Ile His Glu Met Trp Lys Lys Glu Gly Arg Asp Met
        195                 200                 205

Pro Trp Ala Leu Ala Phe Gly Val Pro Pro Ala Ala Ile Met Ala Ser
    210                 215                 220

Ser Met Pro Leu Pro Asp Gly Leu Ser Glu Ala Glu Tyr Ile Gly Ser
225                 230                 235                 240

Leu Val Gly Ser Ser Leu Asp Val Ile Lys Cys Glu Thr Asn Gly Leu
                245                 250                 255

Tyr Val Pro Ala Asn Ser Glu Ile Val Phe Glu Gly Thr Cys Ser Ile
            260                 265                 270

Thr Glu Thr Ala Pro Glu Gly Pro Phe Gly Glu Met His Gly Tyr Val
        275                 280                 285

Phe Pro Gly Asp Ala His Pro Trp Pro Lys Tyr Thr Val Asp Leu Ile
    290                 295                 300

Thr His Arg Lys Asp Ala Ile Leu Pro Val Ser Asn Cys Gly Arg Leu
305                 310                 315                 320

Thr Asp Glu Thr His Thr Met Ile Gly Pro Leu Ala Ala Ala Glu Ile
                325                 330                 335

Gly Phe Leu Leu Lys Ser Lys Gly Leu Pro Ile Lys Glu Ala Phe Ser
            340                 345                 350

Pro Phe Glu Ser Gln Val Thr Trp Val Ala Leu Gln Val Asp Thr Gln
        355                 360                 365

Lys Leu Arg Glu Met Lys Thr Thr Ser Glu Lys Phe Cys Arg Glu Ile
    370                 375                 380

Gly Asp Ile Ile Phe Asn His Lys Val Gly Tyr Thr Ile His Arg Leu
385                 390                 395                 400

Val Ile Val Gly Asp Asp Ile Asn Val Tyr Asp Phe Lys Asp Val Ile
                405                 410                 415

Trp Ala Phe Cys Thr Arg Cys Arg Pro Gly Thr Asp Glu Tyr Phe Phe
            420                 425                 430

Glu Asp Val Ala Gly Phe Pro Leu Ile Pro Tyr Met Ser His Gly Asn
        435                 440                 445

Gly Ala Pro Asn Arg Gly Gly Lys Val Val Ser Asp Ser Leu Leu Pro
    450                 455                 460

Val Glu Tyr Thr Thr Gly Lys Asn Trp Glu Ala Ala Asp Phe Glu Asn
465                 470                 475                 480

Ser Phe Pro Glu Glu Ile Lys Asp Arg Val Cys Ser Arg Trp Gln Thr
                485                 490                 495

Leu Gly Phe Ser Ser Ala Lys
            500
```

```
<210> SEQ ID NO 25
<211> LENGTH: 503
<212> TYPE: PRT
<213> ORGANISM: Saccharomyces kudriavzevii
<220> FEATURE:
```

```
<223> OTHER INFORMATION: Saccharomyces kudriavzevii (strain ATCC
      MYA-4449)

<400> SEQUENCE: 25

Met Ser Ala Leu Asn Pro Ala Leu Gln Phe Arg Asp Phe Ile Gln Val
1               5                   10                  15

Leu Lys Asp Glu Asp Asp Leu Ile Glu Ile Thr Lys Glu Val Asp Pro
            20                  25                  30

Asn Leu Glu Val Gly Ala Ile Met Arg Lys Ala Tyr Glu Ser Lys Leu
        35                  40                  45

Pro Ala Pro Phe Phe Lys Asn Ile Lys Gly Ala Ser Lys Asp Leu Phe
    50                  55                  60

Asn Ile Leu Gly Cys Pro Ala Gly Leu Arg Asn Lys Lys Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Asn Lys Lys Pro Leu
            100                 105                 110

Pro Pro Ser Ser Ile Ser Ala Ser Ser Ala Pro Cys Lys Ala His Val
        115                 120                 125

Leu Ser Glu Glu Glu Ile His Leu Glu Ser Leu Pro Thr Pro Tyr Leu
    130                 135                 140

His Thr Ser Asp Gly Gly Asn Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ala Trp Gly Ala Ile Gly Lys Gly Asn
        195                 200                 205

Lys Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Lys Pro Val Pro Val Val Lys Cys Glu Thr Asn
                245                 250                 255

Asp Leu Met Val Pro Ala Thr Ser Glu Ile Val Phe Glu Gly Thr Leu
            260                 265                 270

Ser Leu Thr Asp Thr His Ala Glu Gly Pro Phe Gly Glu Met His Gly
        275                 280                 285

Tyr Val Phe Gly Gly Gln Gly His Pro Cys Pro Leu Tyr Thr Val Lys
    290                 295                 300

Ala Met Thr His Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Lys Ser Gly Leu Pro Val Leu Asp Ala
            340                 345                 350

Phe Thr Pro Tyr Glu Ala Gln Ala Leu Trp Leu Val Leu Lys Val Asp
        355                 360                 365

Leu Lys Arg Leu Gln Ala Leu Lys Thr Thr Pro Glu Glu Phe Ser Lys
    370                 375                 380

Lys Val Gly Asp Ile Tyr Phe Arg Thr Lys Val Gly Phe Ile Ile His
385                 390                 395                 400
```

```
Glu Ile Val Leu Val Ala Asp Asp Ile Asp Ile Phe Asn Phe Lys Glu
                405                 410                 415

Val Phe Trp Ala Tyr Val Thr Arg His Thr Pro Val Ala Asp Gln Thr
            420                 425                 430

Ala Phe Asp Asp Val Thr Ser Phe Pro Leu Ala Pro Phe Val Ser Gln
        435                 440                 445

Ser Pro Arg Ser Lys Thr Met Lys Gly Gly Lys Cys Val Thr Asn Cys
    450                 455                 460

Ile Phe Arg Gln Gln Tyr Glu Arg Asp Phe Asp Tyr Val Thr Cys Ser
465                 470                 475                 480

Phe Glu Lys Gly Tyr Ser Lys Glu Leu Val Asp Arg Ile Asn Glu Asn
                485                 490                 495

Trp Arg Glu Tyr Gly Tyr Lys
            500


<210> SEQ ID NO 26
<211> LENGTH: 503
<212> TYPE: PRT
<213> ORGANISM: Saccharomyces cerevisiae S288c

<400> SEQUENCE: 26

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255
```

```
Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 27
<211> LENGTH: 503
<212> TYPE: PRT
<213> ORGANISM: Aspergillus parasiticus

<400> SEQUENCE: 27

```
Met Ala Ala Ile Ser Glu Val Asp His Ser Phe Arg Ala Phe Val Glu
1               5                   10                  15

Ala Leu Lys Ala Asp Asp Asp Leu Val Glu Ile Asn Thr Glu Ile Asp
            20                  25                  30

Ser Asn Leu Glu Ala Ala Ala Ile Thr Arg Leu Val Cys Glu Thr Asp
        35                  40                  45

Asp Lys Ala Pro Leu Phe Asn Asn Leu Lys Gly Met Gly Lys Asn Gly
    50                  55                  60

Leu Phe Arg Ile Leu Gly Ala Pro Gly Ser Leu Arg Lys Ser Lys Arg
65                  70                  75                  80

Asp Arg Tyr Gly Arg Leu Ala Arg His Leu Ala Leu Pro Pro Thr Ala
                85                  90                  95

Ser Met Lys Glu Ile Leu Asp Lys Met Leu Ser Ala Ser Gln Leu Pro
            100                 105                 110
```

```
Pro Ile Asp Pro Lys Ile Val Glu Thr Gly Pro Val Lys Glu Asn Ser
        115                 120                 125

Leu Glu Gly Asp Glu Ile Asp Leu Thr Ala Leu Pro Val Pro Met Val
    130                 135                 140

His Lys Ser Asp Gly Gly Lys Tyr Leu Gln Thr Tyr Gly Met His Ile
145                 150                 155                 160

Val Gln Ser Pro Asp Gly Lys Trp Thr Asn Trp Ser Ile Ala Arg Ala
                165                 170                 175

Met Val Lys Asp Lys Asn His Leu Thr Gly Leu Val Ile Glu Pro Gln
            180                 185                 190

His Ile Trp Gln Ile His Gln Met Trp Lys Lys Glu Gly Lys Asp Val
        195                 200                 205

Pro Trp Ala Leu Cys Phe Gly Val Pro Pro Ala Ala Ile Met Ala Ser
    210                 215                 220

Ser Met Pro Ile Pro Asp Gly Val Thr Glu Ala Gly Tyr Val Gly Ala
225                 230                 235                 240

Met Thr Gly Arg Ala Leu Glu Leu Val Lys Cys Asp Thr Asn His Leu
                245                 250                 255

Tyr Val Pro Ala Asn Ala Glu Ile Val Leu Glu Gly Thr Leu Ser Ile
            260                 265                 270

Thr Glu Thr Ala Asp Glu Gly Pro Phe Gly Glu Met His Gly Tyr Val
        275                 280                 285

Phe Pro Gly Asp Ser His Lys Cys Pro Val Tyr Lys Val Asn Lys Ile
    290                 295                 300

Thr Tyr Arg Thr Asp Ala Ile Leu Pro Met Ser Ala Cys Gly Arg Leu
305                 310                 315                 320

Thr Asp Glu Thr His Thr Met Ile Gly Ser Leu Ala Ala Ala Glu Ile
                325                 330                 335

Arg Lys Ile Cys Gln Leu Ala Gly Leu Pro Ile Thr Asp Thr Phe Ser
            340                 345                 350

Pro Phe Glu Ala Gln Val Thr Trp Val Ala Leu Lys Val Asp Thr Ala
        355                 360                 365

Lys Leu Arg Gln Met Asn Leu Thr Pro Lys Glu Leu Gln Lys Trp Val
    370                 375                 380

Gly Asp Val Val Phe Asn His Lys Ala Gly Tyr Thr Ile His Arg Leu
385                 390                 395                 400

Val Leu Val Gly Asp Asp Ile Asp Pro Tyr Glu Trp Lys Asp Val Met
                405                 410                 415

Trp Ala Phe Ala Thr Arg Cys Arg Pro Asn Ala Asp Glu Met Phe Phe
            420                 425                 430

Glu Asp Val Arg Gly Phe Pro Leu Ile Pro Tyr Met Gly His Gly Thr
        435                 440                 445

Gly Ser Pro Thr Lys Gly Gly Lys Val Val Ser Asp Ala Leu Met Pro
    450                 455                 460

Thr Glu Tyr Thr Thr Gly Ala Asp Trp Glu Ala Ala Asp Phe Glu His
465                 470                 475                 480

Ser Tyr Pro Glu Glu Ile Lys Ala Lys Val Arg Ala Gln Trp Gln Ala
                485                 490                 495

Leu Gly Phe Arg Lys Gln Glu
            500
```

<210> SEQ ID NO 28
<211> LENGTH: 513

```
<212> TYPE: PRT
<213> ORGANISM: Candida albicans

<400> SEQUENCE: 28

Met Ser Leu Asn Pro Ala Leu Lys Phe Arg Asp Phe Ile Gln Val Leu
1               5                   10                  15

Lys Asn Glu Gly Asp Leu Val Glu Ile Asp Thr Glu Val Asp Pro Asn
            20                  25                  30

Leu Glu Val Gly Ala Ile Thr Arg Lys Ala Tyr Glu Asn Lys Leu Ala
        35                  40                  45

Ala Pro Leu Phe Asn Asn Leu Lys Gln Asp Pro Gly Asn Val Asp Pro
    50                  55                  60

Lys Asn Leu Phe Arg Ile Leu Gly Cys Pro Gly Gly Leu Arg Gly Phe
65                  70                  75                  80

Gly Asn Asp His Ala Arg Ile Ala Leu His Leu Gly Leu Asp Ser Gln
                85                  90                  95

Thr Pro Met Lys Glu Ile Val Asp Phe Leu Val Ala Asn Arg Asn Pro
            100                 105                 110

Lys Lys Phe Ile Pro Pro Val Leu Val Pro Asn Glu Lys Ser Pro His
        115                 120                 125

Lys Lys His His Leu Thr His Glu Gln Ile Asp Leu Thr Lys Leu Pro
    130                 135                 140

Val Pro Leu Leu His His Gly Asp Gly Gly Lys Phe Ile Gln Thr Tyr
145                 150                 155                 160

Gly Met Trp Val Leu Gln Thr Pro Asp Lys Ser Trp Thr Asn Trp Ser
                165                 170                 175

Ile Ala Arg Gly Met Val His Asp Ser Lys Ser Ile Thr Gly Leu Val
            180                 185                 190

Ile Asn Pro Gln His Val Lys Gln Val Ser Asp Ala Trp Val Ala Ala
        195                 200                 205

Gly Lys Gly Asp Lys Ile Pro Phe Ala Leu Cys Phe Gly Val Pro Pro
    210                 215                 220

Ala Ala Ile Leu Val Ser Ser Met Pro Ile Pro Asp Gly Ala Thr Glu
225                 230                 235                 240

Ala Glu Tyr Ile Gly Gly Leu Cys Asn Gln Ala Val Pro Val Val Lys
                245                 250                 255

Cys Glu Thr Asn Asp Leu Glu Val Pro Ala Asp Cys Glu Met Val Phe
            260                 265                 270

Glu Gly Tyr Leu Asp Arg Asp Thr Leu Val Thr Glu Gly Pro Phe Gly
        275                 280                 285

Glu Met His Gly Tyr Cys Phe Pro Gln Asp His His Thr Gln Pro Leu
    290                 295                 300

Tyr Arg Val Asn His Ile Ser Tyr Arg Asp Glu Ala Ile Met Pro Ile
305                 310                 315                 320

Ser Asn Pro Gly Leu Cys Thr Asp Glu Thr His Thr Leu Ile Gly Gly
                325                 330                 335

Leu Val Ser Ala Glu Thr Lys Tyr Leu Ile Ser Gln His Leu Val Leu
            340                 345                 350

Ser Lys Ile Val Glu Asp Val Phe Thr Pro Tyr Glu Ala Gln Ala Leu
        355                 360                 365

Trp Leu Ala Val Lys Ile Asn Ile Gln Glu Leu Ile Lys Leu Lys Thr
    370                 375                 380

Asn Ala Lys Glu Leu Ser Asn Leu Val Gly Asp Phe Leu Phe Lys Ser
385                 390                 395                 400
```

```
Lys Glu Cys Tyr Lys Val Cys Ser Ile Leu His Glu Val Ile Leu Val
                405                 410                 415

Gly Asp Asp Ile Asp Ile Phe Asp Phe Lys Gln Leu Ile Trp Ala Tyr
            420                 425                 430

Thr Thr Arg His Thr Pro Val Gln Asp Gln Val Tyr Phe Asp Asp Val
        435                 440                 445

Lys Pro Phe Pro Leu Ala Pro Phe Ile Ser Gln Gly Ser Leu Ile Lys
    450                 455                 460

Thr Arg Gln Gly Gly Lys Cys Val Thr Ser Cys Ile Phe Pro Lys Gln
465                 470                 475                 480

Phe Thr Asp Pro Asp Phe Lys Phe Val Thr Cys Asn Phe Asp Gly Tyr
                485                 490                 495

Pro Glu Glu Val Lys Asn Lys Val Ser Gln Asn Trp Glu Lys Tyr Tyr
            500                 505                 510

Lys


<210> SEQ ID NO 29
<211> LENGTH: 500
<212> TYPE: PRT
<213> ORGANISM: Grosmannia clavigera kw1407

<400> SEQUENCE: 29

Met Ala Ser Ser Gln Asp Leu Pro His Met Ser Phe Arg Ala Phe Val
1               5                   10                  15

Asp Glu Leu Arg Ala Asp Gly Asp Ile Val Glu Ile Asn Asp Glu Cys
            20                  25                  30

Asp Ala Asp Leu Glu Val Gly Ala Ile Ile Arg Leu Ala Cys Glu Thr
        35                  40                  45

Asp Ala Lys Ala Pro Leu Phe Asn Lys Leu Lys Gly Met Asp Gly Asn
    50                  55                  60

Gly Leu Trp Arg Ile Leu Gly Ala Pro Asn Ser Leu Arg Ala Asp Pro
65                  70                  75                  80

Ala Gln Arg Phe Gly Arg Leu Ala Arg His Ile Asn Leu Pro Pro Thr
                85                  90                  95

Ala Ser Met Lys Glu Ile Leu Asp Lys Met Gly Ala Ala Lys Ser Thr
            100                 105                 110

Pro Pro Ile Pro Pro Lys Thr Val Pro Thr Gly Ser Cys Lys Glu Val
        115                 120                 125

Lys Leu Thr Pro Asp Gln Phe Asp Leu Thr Thr Leu Pro Ser Pro Gln
    130                 135                 140

Leu His Lys Ser Asp Gly Gly Lys Tyr Val Gln Thr Tyr Gly Met His
145                 150                 155                 160

Ile Val Gln Thr Pro Asp Gly Lys Trp Thr Asn Trp Ser Ile Ala Arg
                165                 170                 175

Ala Met Val His Asp Arg Asn His Leu Val Gly Leu Val Ile Pro Pro
            180                 185                 190

Gln His Ile Trp Lys Val Gln Gln Glu Trp Lys Lys Ile Gly Lys Asp
        195                 200                 205

Met Pro Trp Ala Leu Val Phe Gly Val Pro Pro Ala Ala Ile Met Ala
    210                 215                 220

Ala Ser Met Pro Leu Pro Asp Gly Leu Ser Glu Ala Glu Tyr Ile Gly
225                 230                 235                 240

Ser Leu Val Gly Thr Ala Leu Glu Val Thr Lys Cys Asp Thr Asn Asp
                245                 250                 255
```

```
Leu Leu Val Pro Ala Asn Ser Glu Ile Val Phe Glu Gly Phe Met Ser
            260                 265                 270

Ser Thr Glu Thr Ala Pro Glu Gly Pro Phe Gly Glu Met His Gly Tyr
        275                 280                 285

Val Phe Pro Gly Asp Ala His Pro Gln Pro Leu Tyr Thr Val Asn Met
    290                 295                 300

Ile Thr His Arg Lys Asp Ala Ile Leu Pro Val Ser Asn Cys Gly Arg
305                 310                 315                 320

Leu Thr Asp Glu Thr His Thr Met Ile Gly Pro Leu Val Ala Val Glu
                325                 330                 335

Ile Asn Val Met Leu Lys Ala Ala Gly Leu Pro Ile Thr Asp Ala Tyr
            340                 345                 350

Thr Pro Phe Glu Ser Gln Val Thr Trp Cys Ala Val Lys Val Asp Thr
        355                 360                 365

Ala Lys Leu Arg Glu Leu Lys Thr Thr Pro Lys Glu Phe Cys Arg Lys
    370                 375                 380

Ile Gly Asp Leu Ile Phe Asn Thr Lys Val Gly Ser Thr Ile His Arg
385                 390                 395                 400

Ile Ala Val Val Gly Asp Asp Ile Asp Ile Phe Asn Phe Lys Asp Val
                405                 410                 415

Ile Trp Ala Phe Cys Thr Arg Cys Arg Pro Gly Met Asp Glu Tyr Leu
            420                 425                 430

Phe Glu Asp Val Pro Gly Phe Pro Leu Ile Pro Tyr Met Ser His Gly
        435                 440                 445

Asn Gly Pro Ala Asn Arg Gly Gly Lys Val Val Ser Asp Cys Leu Leu
    450                 455                 460

Pro Lys Glu Tyr Thr Thr Gly Lys Asn Trp Glu Ala Ala Ser Phe Lys
465                 470                 475                 480

Glu Ser Ile Pro Glu Ser Val Gln Ala Lys Val Leu Gly Asn Trp Lys
                485                 490                 495

Ala Trp Gly Phe
            500
```

<210> SEQ ID NO 30
<211> LENGTH: 496
<212> TYPE: PRT
<213> ORGANISM: Enterobacter cloacae

<400> SEQUENCE: 30

```
Met Glu Asn Gln Ile Asn Asp Leu Arg Ser Ala Ile Ala Leu Leu Gln
1               5                   10                  15

Arg His Glu Gly Gln Tyr Ile Glu Thr Asp Arg Pro Val Asp Pro Asn
            20                  25                  30

Ala Glu Leu Ala Gly Val Tyr Arg His Ile Gly Ala Gly Gly Thr Val
        35                  40                  45

Lys Arg Pro Thr Arg Thr Gly Pro Ala Met Met Phe Asn Ser Ile Lys
    50                  55                  60

Gly Tyr Pro His Ser Arg Ile Leu Val Gly Met His Ala Ser Arg Glu
65                  70                  75                  80

Arg Ala Ala Leu Leu Leu Gly Cys Glu Pro Ser Glu Leu Ala Lys His
                85                  90                  95

Val Gly Gln Ala Val Lys Lys Pro Val Ala Pro Val Val Val Pro Ala
            100                 105                 110
```

```
Ser Gln Ala Pro Cys Gln Glu Gln Val Phe Tyr Ala Asp Asp Pro Asp
        115                 120                 125

Phe Asp Leu Arg Lys Leu Leu Pro Ala Pro Thr Asn Thr Pro Ile Asp
    130                 135                 140

Ala Gly Pro Phe Phe Cys Leu Gly Leu Val Leu Ala Ser Asp Pro Glu
145                 150                 155                 160

Asp Ser Ser Leu Thr Asp Val Thr Ile His Arg Leu Cys Val Gln Glu
                165                 170                 175

Arg Asp Glu Leu Ser Met Phe Leu Ala Ala Gly Arg His Ile Glu Val
            180                 185                 190

Phe Arg Lys Lys Ala Glu Asp Ala Gly Lys Pro Leu Pro Val Thr Ile
        195                 200                 205

Asn Met Gly Leu Asp Pro Ala Ile Tyr Ile Gly Ala Cys Phe Glu Ala
    210                 215                 220

Pro Thr Thr Pro Phe Gly Tyr Asn Glu Leu Gly Val Ala Gly Ala Leu
225                 230                 235                 240

Arg Gln Gln Pro Val Glu Leu Val Gln Gly Val Ala Val Lys Glu Lys
                245                 250                 255

Ala Ile Ala Arg Ala Glu Ile Ile Ile Glu Gly Glu Leu Leu Pro Gly
            260                 265                 270

Val Arg Val Arg Glu Asp Gln His Thr Asn Thr Gly His Ala Met Pro
        275                 280                 285

Glu Phe Pro Gly Tyr Cys Gly Glu Ala Asn Pro Ser Leu Pro Val Ile
    290                 295                 300

Lys Val Lys Ala Val Thr Met Arg Asn His Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Arg Asn Ala Val Glu Glu Ala Ile Pro Gly Phe Leu Gln
            340                 345                 350

Asn Val Tyr Ala His Thr Ala Gly Gly Gly Lys Phe Leu Gly Ile Leu
        355                 360                 365

Gln Val Lys Lys Arg Gln Pro Ser Asp Glu Gly Arg Gln Gly Gln Ala
    370                 375                 380

Ala Leu Ile Ala Leu Ala Thr Tyr Ser Glu Leu Lys Asn Ile Ile Leu
385                 390                 395                 400

Val Asp Glu Asp Val Asp Ile Phe Asp Ser Asp Asp Ile Leu Trp Ala
                405                 410                 415

Met Thr Thr Arg Met Gln Gly Asp Val Ser Ile Thr Asn Ile Pro Gly
            420                 425                 430

Ile Arg Gly His Gln Leu Asp Pro Ser Gln Ser Pro Asp Tyr Ser Thr
        435                 440                 445

Ser Ile Arg Gly Asn Gly Ile Ser Cys Lys Thr Ile Phe Asp Cys Thr
    450                 455                 460

Val Pro Trp Ala Leu Lys Asp Arg Phe Glu Arg Ala Pro Phe Met Glu
465                 470                 475                 480

Val Asp Pro Arg Pro Trp Ala Pro Glu Leu Phe Ala Asp Asn Thr Lys
                485                 490                 495
```

<210> SEQ ID NO 31
<211> LENGTH: 262
<212> TYPE: PRT
<213> ORGANISM: Escherichia coli (strain K12)

<400> SEQUENCE: 31

Met Gln Val Asp Leu Leu Gly Ser Ala Gln Ser Ala His Ala Leu His
1               5                   10                  15

Leu Phe His Gln His Ser Pro Leu Val His Cys Met Thr Asn Asp Val
            20                  25                  30

Val Gln Thr Phe Thr Ala Asn Thr Leu Leu Ala Leu Gly Ala Ser Pro
        35                  40                  45

Ala Met Val Ile Glu Thr Glu Glu Ala Ser Gln Phe Ala Ala Ile Ala
    50                  55                  60

Ser Ala Leu Leu Ile Asn Val Gly Thr Leu Thr Gln Pro Arg Ala Gln
65                  70                  75                  80

Ala Met Arg Ala Ala Val Glu Gln Ala Lys Ser Ser Gln Thr Pro Trp
                85                  90                  95

Thr Leu Asp Pro Val Ala Val Gly Ala Leu Asp Tyr Arg Arg His Phe
            100                 105                 110

Cys His Glu Leu Leu Ser Phe Lys Pro Ala Ala Ile Arg Gly Asn Ala
        115                 120                 125

Ser Glu Ile Met Ala Leu Ala Gly Ile Ala Asn Gly Gly Arg Gly Val
    130                 135                 140

Asp Thr Thr Asp Ala Ala Ala Asn Ala Ile Pro Ala Ala Gln Thr Leu
145                 150                 155                 160

Ala Arg Glu Thr Gly Ala Ile Val Val Val Thr Gly Glu Met Asp Tyr
                165                 170                 175

Val Thr Asp Gly His Arg Ile Ile Gly Ile His Gly Gly Asp Pro Leu
            180                 185                 190

Met Thr Lys Val Val Gly Thr Gly Cys Ala Leu Ser Ala Val Val Ala
        195                 200                 205

Ala Cys Cys Ala Leu Pro Gly Asp Thr Leu Glu Asn Val Ala Ser Ala
    210                 215                 220

Cys His Trp Met Lys Gln Ala Gly Glu Arg Ala Val Ala Arg Ser Glu
225                 230                 235                 240

Gly Pro Gly Ser Phe Val Pro His Phe Leu Asp Ala Leu Trp Gln Leu
                245                 250                 255

Thr Gln Glu Val Gln Ala
            260

<210> SEQ ID NO 32
<211> LENGTH: 272
<212> TYPE: PRT
<213> ORGANISM: Bacillus subtilis

<400> SEQUENCE: 32

Met Asp Ala Gln Ser Ala Ala Lys Cys Leu Thr Ala Val Arg Arg His
1               5                   10                  15

Ser Pro Leu Val His Ser Ile Thr Asn Asn Val Val Thr Asn Phe Thr
            20                  25                  30

Ala Asn Gly Leu Leu Ala Leu Gly Ala Ser Pro Val Met Ala Tyr Ala
        35                  40                  45

Lys Glu Glu Val Ala Asp Met Ala Lys Ile Ala Gly Ala Leu Val Leu
    50                  55                  60

Asn Ile Gly Thr Leu Ser Lys Glu Ser Val Glu Ala Met Ile Ile Ala
65                  70                  75                  80

Gly Lys Ser Ala Asn Glu His Gly Val Pro Val Ile Leu Asp Pro Val
                85                  90                  95

```
Gly Ala Gly Ala Thr Pro Phe Arg Thr Glu Ser Ala Arg Asp Ile Ile
            100                 105                 110

Arg Glu Val Arg Leu Ala Ala Ile Arg Gly Asn Ala Ala Glu Ile Ala
        115                 120                 125

His Thr Val Gly Val Thr Asp Trp Leu Ile Lys Gly Val Asp Ala Gly
    130                 135                 140

Glu Gly Gly Gly Asp Ile Ile Arg Leu Ala Gln Gln Ala Ala Gln Lys
145                 150                 155                 160

Leu Asn Thr Val Ile Ala Ile Thr Gly Glu Val Asp Val Ile Ala Asp
                165                 170                 175

Thr Ser His Val Tyr Thr Leu His Asn Gly His Lys Leu Leu Thr Lys
            180                 185                 190

Val Thr Gly Ala Gly Cys Leu Leu Thr Ser Val Val Gly Ala Phe Cys
        195                 200                 205

Ala Val Glu Glu Asn Pro Leu Phe Ala Ala Ile Ala Ala Ile Ser Ser
    210                 215                 220

Tyr Gly Val Ala Ala Gln Leu Ala Ala Gln Gln Thr Ala Asp Lys Gly
225                 230                 235                 240

Pro Gly Ser Phe Gln Ile Glu Leu Leu Asn Lys Leu Ser Thr Val Thr
                245                 250                 255

Glu Gln Asp Val Gln Glu Trp Ala Thr Ile Glu Arg Val Thr Val Ser
            260                 265                 270


<210> SEQ ID NO 33
<211> LENGTH: 267
<212> TYPE: PRT
<213> ORGANISM: Rhizobium leguminosarum bv. viciae (strain 3841)

<400> SEQUENCE: 33

Met Gln Thr Arg Thr Thr Pro Gly Ala Met Leu Lys Ala Met Arg Glu
1               5                   10                  15

Lys Pro Pro Leu Val Gln Cys Ile Thr Asn Tyr Val Ala Met Asn Ile
            20                  25                  30

Ala Ala Asn Val Leu Leu Ala Ala Gly Ala Ser Pro Ala Met Val His
        35                  40                  45

Ala Ala Glu Glu Ala Gly Glu Phe Ala Ala Ile Ala Ser Ala Leu Thr
    50                  55                  60

Ile Asn Ile Gly Thr Leu Ser Thr Gln Trp Ile Asp Gly Met Gln Ala
65                  70                  75                  80

Ala Ala Lys Ala Ala Thr Ser Ala Gly Lys Pro Trp Val Leu Asp Pro
                85                  90                  95

Val Ala His Tyr Ala Thr Ala Phe Arg Arg Asn Ala Val Ala Glu Leu
            100                 105                 110

Leu Ala Leu Lys Pro Thr Ile Ile Arg Gly Asn Ala Ser Glu Ile Ile
        115                 120                 125

Ala Leu Ala Gly Gly Glu Ser Arg Gly Gln Gly Val Asp Ser Arg Asp
    130                 135                 140

Pro Val Glu Gln Ala Glu Gly Ser Ala Arg Trp Leu Ala Glu Arg Gln
145                 150                 155                 160

Arg Ala Val Val Ala Val Thr Gly Ala Val Asp Phe Val Thr Asp Gly
                165                 170                 175

Glu Arg Ala Val Arg Ile Glu Gly Gly Ser Ala Leu Met Pro Gln Val
            180                 185                 190

Thr Ala Leu Gly Cys Ser Leu Thr Cys Leu Val Gly Ala Phe Ala Ala
        195                 200                 205
```

```
Thr Ala Pro Glu Asp Ile Phe Gly Ala Thr Val Ala Ala Leu Ser Thr
    210                 215                 220

Phe Ala Ile Ala Gly Glu Glu Ala Ala Leu Gly Ala Ala Gly Pro Gly
225                 230                 235                 240

Ser Phe Ser Trp Arg Phe Leu Asp Ala Leu Ala Ala Leu Asp Ala Glu
                245                 250                 255

Thr Leu Asp Ala Arg Ala Arg Ile Ser Ala Ala
            260                 265


<210> SEQ ID NO 34
<211> LENGTH: 313
<212> TYPE: PRT
<213> ORGANISM: Escherichia coli (strain K12)

<400> SEQUENCE: 34

Met Lys Leu Ile Arg Gly Ile His Asn Leu Ser Gln Ala Pro Gln Glu
1               5                   10                  15

Gly Cys Val Leu Thr Ile Gly Asn Phe Asp Gly Val His Arg Gly His
            20                  25                  30

Arg Ala Leu Leu Gln Gly Leu Gln Glu Glu Gly Arg Lys Arg Asn Leu
        35                  40                  45

Pro Val Met Val Met Leu Phe Glu Pro Gln Pro Leu Glu Leu Phe Ala
    50                  55                  60

Thr Asp Lys Ala Pro Ala Arg Leu Thr Arg Leu Arg Glu Lys Leu Arg
65                  70                  75                  80

Tyr Leu Ala Glu Cys Gly Val Asp Tyr Val Leu Cys Val Arg Phe Asp
                85                  90                  95

Arg Arg Phe Ala Ala Leu Thr Ala Gln Asn Phe Ile Ser Asp Leu Leu
            100                 105                 110

Val Lys His Leu Arg Val Lys Phe Leu Ala Val Gly Asp Asp Phe Arg
        115                 120                 125

Phe Gly Ala Gly Arg Glu Gly Asp Phe Leu Leu Leu Gln Lys Ala Gly
    130                 135                 140

Met Glu Tyr Gly Phe Asp Ile Thr Ser Thr Gln Thr Phe Cys Glu Gly
145                 150                 155                 160

Gly Val Arg Ile Ser Ser Thr Ala Val Arg Gln Ala Leu Ala Asp Asp
                165                 170                 175

Asn Leu Ala Leu Ala Glu Ser Leu Leu Gly His Pro Phe Ala Ile Ser
            180                 185                 190

Gly Arg Val Val His Gly Asp Glu Leu Gly Arg Thr Ile Gly Phe Pro
        195                 200                 205

Thr Ala Asn Val Pro Leu Arg Arg Gln Val Ser Pro Val Lys Gly Val
    210                 215                 220

Tyr Ala Val Glu Val Leu Gly Leu Gly Glu Lys Pro Leu Pro Gly Val
225                 230                 235                 240

Ala Asn Ile Gly Thr Arg Pro Thr Val Ala Gly Ile Arg Gln Gln Leu
                245                 250                 255

Glu Val His Leu Leu Asp Val Ala Met Asp Leu Tyr Gly Arg His Ile
            260                 265                 270

Gln Val Val Leu Arg Lys Lys Ile Arg Asn Glu Gln Arg Phe Ala Ser
        275                 280                 285
```

```
Leu Asp Glu Leu Lys Ala Gln Ile Ala Arg Asp Glu Leu Thr Ala Arg
    290                 295                 300

Glu Phe Phe Gly Leu Thr Lys Pro Ala
305                 310


<210> SEQ ID NO 35
<211> LENGTH: 512
<212> TYPE: PRT
<213> ORGANISM: Hypocrea atroviridis

<400> SEQUENCE: 35

Met Ser Ser Thr Thr Tyr Lys Ser Glu Ala Phe Asp Pro Glu Pro Pro
1               5                   10                  15

His Leu Ser Phe Arg Ser Phe Val Asn Ala Leu Arg Gln Asp Gly Asp
            20                  25                  30

Leu Val Asp Ile Asn Glu Pro Val Asp Pro Asp Leu Glu Ala Ala Ala
        35                  40                  45

Ile Thr Arg Leu Val Cys Glu Thr Asp Asp Lys Ala Pro Leu Phe Asn
    50                  55                  60

Asn Val Ile Gly Ala Lys Asp Gly Leu Trp Arg Ile Leu Gly Ala Pro
65                  70                  75                  80

Ala Ser Leu Arg Ala Ser Pro Lys Glu Arg Phe Gly Arg Leu Ala Arg
                85                  90                  95

His Leu Ala Leu Pro Pro Thr Ala Ser Ala Lys Asp Ile Leu Asp Lys
            100                 105                 110

Met Leu Ser Ala Asn Ser Ile Pro Pro Ile Glu Pro Val Ile Val Pro
        115                 120                 125

Thr Gly Pro Val Lys Glu Asn Ser Ile Glu Gly Glu Asn Ile Asp Leu
    130                 135                 140

Glu Ala Leu Pro Ala Pro Met Val His Gln Ser Asp Gly Gly Lys Tyr
145                 150                 155                 160

Ile Asn Thr Tyr Gly Met His Val Ile Gln Ser Pro Asp Gly Gly Trp
                165                 170                 175

Thr Asn Trp Ser Ile Ala Arg Ala Met Val Ser Gly Lys Arg Thr Leu
            180                 185                 190

Ala Gly Leu Val Ile Ser Pro Gln His Ile Arg Lys Ile Gln Asp Gln
        195                 200                 205

Trp Arg Ala Ile Gly Gln Glu Glu Ile Pro Trp Ala Leu Ala Phe Gly
    210                 215                 220

Val Pro Pro Leu Ala Ile Met Ala Ser Ser Met Pro Ile Pro Asp Gly
225                 230                 235                 240

Val Ser Glu Ala Gly Tyr Val Gly Ala Ile Ala Gly Glu Pro Ile Lys
                245                 250                 255

Leu Val Lys Cys Asp Thr Asn Asn Leu Tyr Val Pro Ala Asn Ser Glu
            260                 265                 270

Ile Val Leu Glu Gly Thr Leu Ser Thr Thr Lys Met Ala Pro Glu Gly
        275                 280                 285

Pro Phe Gly Glu Met His Gly Tyr Val Tyr Pro Gly Glu Ser His Pro
    290                 295                 300

Gly Pro Val Tyr Thr Val Asn Lys Ile Thr Tyr Arg Asn Asn Ala Ile
305                 310                 315                 320

Leu Pro Met Ser Ala Cys Gly Arg Leu Thr Asp Glu Thr Gln Thr Met
                325                 330                 335
```

```
Ile Pro Thr Leu Ala Ala Ala Glu Ile Arg Gln Leu Cys Gln Arg Ala
            340                 345                 350

Gly Leu Pro Ile Thr Asp Ala Phe Ala Pro Phe Val Gly Gln Ala Thr
        355                 360                 365

Trp Val Ala Leu Lys Val Asp Thr Lys Arg Leu Arg Ala Met Lys Thr
    370                 375                 380

Asn Gly Lys Ala Phe Ala Lys Ala Val Gly Asp Val Val Phe Thr Gln
385                 390                 395                 400

Lys Pro Gly Phe Met Ile His Arg Leu Ile Leu Val Gly Asp Asp Ile
                405                 410                 415

Asp Val Tyr Asp Asp Lys Asp Val Met Trp Ala Phe Ala Thr Arg Cys
            420                 425                 430

Arg Pro Gly Thr Asp Glu Val Phe Phe Asp Asp Val Pro Gly Phe Trp
        435                 440                 445

Leu Ile Pro Tyr Met Ser His Gly Asn Ala Glu Ala Val Lys Gly Gly
    450                 455                 460

Lys Val Val Ser Asp Ala Leu Leu Thr Ala Glu Tyr Thr Thr Gly Lys
465                 470                 475                 480

Asp Trp Glu Ser Ala Asp Phe Lys Asn Ser Tyr Pro Lys Arg Ile Gln
                485                 490                 495

Asp Lys Val Leu Asn Ser Trp Glu Arg Leu Gly Phe Lys Lys Leu Asp
            500                 505                 510


<210> SEQ ID NO 36
<211> LENGTH: 7452
<212> TYPE: DNA
<213> ORGANISM: Artificial Sequence
<220> FEATURE:
<223> OTHER INFORMATION: pGB6346

<400> SEQUENCE: 36

ctctccctta tgcgactcct gcattaggaa gcagcccagt agtaggttga ggccgttgag      60

caccgccgcc gcaaggaatg gtgcatgcaa ggagatggcg cccaacagtc ccccggccac     120

ggggcctgcc accataccca cgccgaaaca agcgctcatg agcccgaagt ggcgagcccg     180

atcttcccca tcggtgatgt cggcgatata ggcgccagca accgcacctg tggcgccggt     240

gatgccggcc acgatgcgtc cggcgtagag gatcgagatc gatctcgatc ccgcgaaatt     300

aatacgactc actatagggg aattgtgagc ggataacaat tcccctctag aaataatttt     360

gtttaacttt aagaaggaga tataccatga gcagcaccac ctataaaagt gaagcatttg     420

atccggaacc gcctcatctg agctttcgta gctttgttaa tgcactgcgt caggatgggg     480

atctggtgga tattaatgaa ccggttgatc cggatctgga agcagcagca attacccgtc     540

tggtttgtga aaccgatgat aaagcaccgc tgtttaataa cgtgattggt gcaaaagatg     600

gtctgtggcg tattctgggt gcaccggcaa gcctgcgtgc gagcccgaaa gaacgttttg     660

gtcgtctggc acgtcatctg gcactgcctc cgaccgcaag cgcaaaagat attctggata     720

aaatgctgag cgccaatagc attccgccta ttgaaccggt tattgttccg accggtccgg     780

ttaaagaaaa tagcattgaa ggcgaaaaca ttgatctgga agccctgcct gcaccgatgg     840

ttcatcagag tgatggtggc aagtatatca atacctatgg tatgcatgtt atccagagtc     900

cggatggtgg gtggaccaat tggagcattg cccgtgcaat ggttagcggt aaacgtaccc     960

tggcaggtct ggttattagt ccgcagcata ttcgtaaaat tcaggatcag tggcgtgcaa    1020

ttggccaaga agaaattcct tgggcactgg catttggtgt tccgcctctg gcaattatgg    1080
```

```
caagcagtat gccgattccg gatggtgtta gcgaagcagg ttatgttggt gcaattgccg   1140
gtgaaccgat taaactggtt aaatgcgata ccaacaatct gtatgttccg gcaaatagcg   1200
aaattgttct ggaaggcacc ctgagcacca ccaaaatggc accggaaggt ccgtttggtg   1260
aaatgcatgg ttatgtttat ccgggtgaaa gccatccggg tccggtttat accgttaaca   1320
aaattaccta tcgcaacaat gcaattctgc cgatgagcgc atgtggtcgt ctgaccgatg   1380
aaacccagac catgattccg accctggcag cagcagaaat tcgtcagctg tgtcagaggg   1440
caggtctgcc gattaccgat gcatttgcac cgtttgttgg tcaggcaacc tgggttgcac   1500
tgaaagttga taccaaacgt ctgcgtgcaa tgaaaaccaa tggtaaagca tttgcaaaag   1560
cggttggtga tgttgtgttt acccagaaac cgggttttat gattcatcgt ctgattctgg   1620
ttggtgatga tattgatgtg tatgacgata aagatgtgat gtgggcattt gctacccgtt   1680
gtcgtccggg tacagatgaa gtttttttttg atgatgttcc tggcttttgg ctgatcccgt   1740
atatgagtca tggtaatgcc gaagcagtga aaggtggtaa agttgttagt gatgcactgc   1800
tgaccgcaga atataccacc ggtaaagatt gggaaagcgc agatttcaaa aacagctatc   1860
cgaaacgtat ccaggataaa gttctgaata gctgggaacg cctgggtttc aaaaaactgg   1920
attaataagg atccgaattc gagctcggcg cgcctgcagg tcgacaagct tgcggccgca   1980
taatgcttaa gtcgaacaga aagtaatcgt attgtacacg gccgcataat cgaaattaat   2040
acgactcact ataggggaat tgtgagcgga taacaattcc ccatcttagt atattagtta   2100
agtataagaa ggagatatac atatgaaacg actcattgta ggcatcagcg gtgccagcgg   2160
cgcgatttat ggcgtgcgct tattacaggt tctgcgcgat gtcacagata tcgaaacgca   2220
tctggtgatg agccaggcag cgcgccagac cttatccctc gaaacggatt tttctctgcg   2280
cgaagtgcag gcattagccg atgtcacgca cgatgcgcgc gatattgccg ccagcatctc   2340
ttccggttct ttccagacgc tggggatggt gattttaccc tgttcaatca aaaccctttc   2400
cggcattgtc catagctata ctgatggctt actgacccgt gcggcagatg tggtgctgaa   2460
agagcgtcgc ccgttggtgc tctgcgtgcg tgaaacacca ttgcacttag gccatctgcg   2520
tttaatgact caggcggcag aaatcggtgc ggtgattatg cctcccgttc cggcgtttta   2580
tcatcgcccg caatcccttg atgatgtgat aaatcagacg gttaatcgtg ttcttgacca   2640
gtttgcgata acccttcctg aagatctctt tgcccgctgg cagggcgcat aataaggtac   2700
cctcgagtct ggtaaagaaa ccgctgctgc gaaatttgaa cgccagcaca tggactcgtc   2760
tactagcgca gcttaattaa cctaggctgc tgccaccgct gagcaataac tagcataacc   2820
ccttggggcc tctaaacggg tcttgagggg ttttttgctg aaaggaggaa ctatatccgg   2880
attggcgaat gggacgcgcc ctgtagcggc gcattaagcg cggcgggtgt ggtggttacg   2940
cgcagcgtga ccgctacact tgccagcgcc ctagcgcccg ctcctttcgc tttcttccct   3000
tcctttctcg ccacgttcgc cggctttccc cgtcaagctc taaatcgggg gctcccttta   3060
gggttccgat ttagtgcttt acggcacctc gaccccaaaa aacttgatta gggtgatggt   3120
tcacgtagtg ggccatcgcc ctgatagacg gtttttcgcc ctttgacgtt ggagtccacg   3180
ttctttaata gtggactctt gttccaaact ggaacaacac tcaaccctat ctcggtctat   3240
tcttttgatt tataagggat tttgccgatt tcggcctatt ggttaaaaaa tgagctgatt   3300
taacaaaaat ttaacgcgaa ttttaacaaa atattaacgt ttacaatttc tggcggcacg   3360
atggcatgag attatcaaaa aggatcttca cctagatcct tttaaattaa aaatgaagtt   3420
```

```
ttaaatcaat ctaaagtata tatgagtaaa cttggtctga cagttaccaa tgcttaatca   3480
gtgaggcacc tatctcagcg atctgtctat ttcgttcatc catagttgcc tgactccccg   3540
tcgtgtagat aactacgata cgggagggct taccatctgg ccccagtgct gcaatgatac   3600
cgcgagaccc acgctcaccg gctccagatt tatcagcaat aaaccagcca gccggaaggg   3660
ccgagcgcag aagtggtcct gcaactttat ccgcctccat ccagtctatt aattgttgcc   3720
gggaagctag agtaagtagt tcgccagtta atagtttgcg caacgttgtt gccattgcta   3780
caggcatcgt ggtgtcacgc tcgtcgtttg gtatggcttc attcagctcc ggttcccaac   3840
gatcaaggcg agttacatga tcccccatgt tgtgcaaaaa agcggttagc tccttcggtc   3900
ctccgatcgt tgtcagaagt aagttggccg cagtgttatc actcatggtt atggcagcac   3960
tgcataattc tcttactgtc atgccatccg taagatgctt ttctgtgact ggtgagtact   4020
caaccaagtc attctgagaa tagtgtatgc ggcgaccgag ttgctcttgc ccggcgtcaa   4080
tacgggataa taccgcgcca catagcagaa ctttaaaagt gctcatcatt ggaaaacgtt   4140
cttcggggcg aaaactctca aggatcttac cgctgttgag atccagttcg atgtaaccca   4200
ctcgtgcacc caactgatct tcagcatctt ttactttcac cagcgtttct gggtgagcaa   4260
aaacaggaag gcaaaatgcc gcaaaaaagg gaataagggc gacacggaaa tgttgaatac   4320
tcatactctt cctttttcaa tcatgattga agcatttatc agggttattg tctcatgagc   4380
ggatacatat ttgaatgtat ttagaaaaat aaacaaatag gtcatgacca aaatccctta   4440
acgtgagttt tcgttccact gagcgtcaga ccccgtagaa aagatcaaag gatcttcttg   4500
agatcctttt tttctgcgcg taatctgctg cttgcaaaca aaaaaaccac cgctaccagc   4560
ggtggtttgt ttgccggatc aagagctacc aactcttttt ccgaaggtaa ctggcttcag   4620
cagagcgcag ataccaaata ctgtccttct agtgtagccg tagttaggcc accacttcaa   4680
gaactctgta gcaccgccta catacctcgc tctgctaatc ctgttaccag tggctgctgc   4740
cagtggcgat aagtcgtgtc ttaccgggtt ggactcaaga cgatagttac cggataaggc   4800
gcagcggtcg ggctgaacgg ggggttcgtg cacacagccc agcttggagc gaacgaccta   4860
caccgaactg agatacctac agcgtgagct atgagaaagc gccacgcttc ccgaagggag   4920
aaaggcggac aggtatccgg taagcggcag ggtcggaaca ggagagcgca cgagggagct   4980
tccaggggga aacgcctggt atctttatag tcctgtcggg tttcgccacc tctgacttga   5040
gcgtcgattt ttgtgatgct cgtcaggggg gcggagccta tggaaaaacg ccagcaacgc   5100
ggccttttta cggttcctgg ccttttgctg gccttttgct cacatgttct ttcctgcgtt   5160
atcccctgat tctgtggata accgtattac cgcctttgag tgagctgata ccgctcgccg   5220
cagccgaacg accgagcgca gcgagtcagt gagcgaggaa gcggaagagc gcctgatgcg   5280
gtattttctc cttacgcatc tgtgcggtat ttcacaccgc atatatggtg cactctcagt   5340
acaatctgct ctgatgccgc atagttaagc cagtatacac tccgctatcg ctacgtgact   5400
gggtcatggc tgcgccccga cacccgccaa cacccgctga cgcgccctga cgggcttgtc   5460
tgctcccggc atccgcttac agacaagctg tgaccgtctc cgggagctgc atgtgtcaga   5520
ggttttcacc gtcatcaccg aaacgcgcga ggcagctgcg gtaaagctca tcagcgtggt   5580
cgtgaagcga ttcacagatg tctgcctgtt catccgcgtc cagctcgttg agtttctcca   5640
gaagcgttaa tgtctggctt ctgataaagc gggccatgtt aagggcggtt ttttcctgtt   5700
tggtcactga tgcctccgtg taagggggat ttctgttcat gggggtaatg ataccgatga   5760
aacgagagag gatgctcacg atacgggtta ctgatgatga acatgcccgg ttactggaac   5820
```

```
gttgtgaggg taaacaactg gcggtatgga tgcggcggga ccagagaaaa atcactcagg   5880

gtcaatgcca gcgcttcgtt aatacagatg taggtgttcc acagggtagc cagcagcatc   5940

ctgcgatgca gatccggaac ataatggtgc agggcgctga cttccgcgtt tccagacttt   6000

acgaaacacg gaaaccgaag accattcatg ttgttgctca ggtcgcagac gttttgcagc   6060

agcagtcgct tcacgttcgc tcgcgtatcg gtgattcatt ctgctaacca gtaaggcaac   6120

cccgccagcc tagccgggtc ctcaacgaca ggagcacgat catgctagtc atgccccgcg   6180

cccaccggaa ggagctgact gggttgaagg ctctcaaggg catcggtcga gatcccggtg   6240

cctaatgagt gagctaactt acattaattg cgttgcgctc actgcccgct ttccagtcgg   6300

gaaacctgtc gtgccagctg cattaatgaa tcggccaacg cgcggggaga ggcggtttgc   6360

gtattgggcg ccagggtggt ttttcttttc accagtgaga cgggcaacag ctgattgccc   6420

ttcaccgcct ggccctgaga gagttgcagc aagcggtcca cgctggtttg ccccagcagg   6480

cgaaaatcct gtttgatggt ggttaacggc gggatataac atgagctgtc ttcggtatcg   6540

tcgtatccca ctaccgagat gtccgcacca acgcgcagcc cggactcggt aatggcgcgc   6600

attgcgccca gcgccatctg atcgttggca accagcatcg cagtgggaac gatgccctca   6660

ttcagcattt gcatggtttg ttgaaaaccg gacatggcac tccagtcgcc ttcccgttcc   6720

gctatcggct gaatttgatt gcgagtgaga tatttatgcc agccagccag acgcagacgc   6780

gccgagacag aacttaatgg gcccgctaac agcgcgattt gctggtgacc caatgcgacc   6840

agatgctcca cgcccagtcg cgtaccgtct tcatgggaga aaataatact gttgatgggt   6900

gtctggtcag agacatcaag aaataacgcc ggaacattag tgcaggcagc ttccacagca   6960

atggcatcct ggtcatccag cggatagtta atgatcagcc cactgacgcg ttgcgcgaga   7020

agattgtgca ccgccgcttt acaggcttcg acgccgcttc gttctaccat cgacaccacc   7080

acgctggcac ccagttgatc ggcgcgagat ttaatcgccg cgacaatttg cgacggcgcg   7140

tgcagggcca gactggaggt ggcaacgcca atcagcaacg actgtttgcc cgccagttgt   7200

tgtgccacgc ggttgggaat gtaattcagc tccgccatcg ccgcttccac tttttcccgc   7260

gttttcgcag aaacgtggct ggcctggttc accacgcggg aaacggtctg ataagagaca   7320

ccggcatact ctgcgacatc gtataacgtt actggtttca cattcaccac cctgaattga   7380

ctctcttccg ggcgctatca tgccataccg cgaaaggttt tgcgccattc gatggtgtcc   7440

gggatctcga cg                                                       7452
```

<210> SEQ ID NO 37
<211> LENGTH: 8182
<212> TYPE: DNA
<213> ORGANISM: Artificial Sequence
<220> FEATURE:
<223> OTHER INFORMATION: pGB6580

<400> SEQUENCE: 37

```
caccgccgcc gcaaggaatg gtgcatgcaa ggagatggcg cccaacagtc ccccggccac     60

ggggcctgcc accataccca cgccgaaaca agcgctcatg agcccgaagt ggcgagcccg    120

atcttcccca tcggtgatgt cggcgatata ggcgccagca accgcacctg tggcgccggt    180

gatgccggcc acgatgcgtc cggcgtagag gatcgagatc gatctcgatc ccgcgaaatt    240

aatacgactc actatagggg aattgtgagc ggataacaat tcccctctag aaataatttt    300

gtttaacttt aagaaggaga tataccatga gcagcaccac ctataaaagt gaagcatttg    360
```

```
atccggaacc gcctcatctg agctttcgta gctttgttaa tgcactgcgt caggatgggg    420
atctggtgga tattaatgaa ccggttgatc cggatctgga agcagcagca attacccgtc    480
tggtttgtga aaccgatgat aaagcaccgc tgtttaataa cgtgattggt gcaaaagatg    540
gtctgtggcg tattctgggt gcaccggcaa gcctgcgtgc gagcccgaaa gaacgttttg    600
gtcgtctggc acgtcatctg gcactgcctc cgaccgcaag cgcaaaagat attctggata    660
aaatgctgag cgccaatagc attccgccta ttgaaccggt tattgttccg accggtccgg    720
ttaaagaaaa tagcattgaa ggcgaaaaca ttgatctgga agccctgcct gcaccgatgg    780
ttcatcagag tgatggtggc aagtatatca atacctatgg tatgcatgtt atccagagtc    840
cggatggtgg gtggaccaat tggagcattg cccgtgcaat ggttagcggt aaacgtaccc    900
tggcaggtct ggttattagt ccgcagcata ttcgtaaaat tcaggatcag tggcgtgcaa    960
ttggccaaga agaaattcct tgggcactgg catttggtgt tccgcctctg gcaattatgg   1020
caagcagtat gccgattccg gatggtgtta gcgaagcagg ttatgttggt gcaattgccg   1080
gtgaaccgat taaactggtt aaatgcgata ccaacaatct gtatgttccg gcaaatagcg   1140
aaattgttct ggaaggcacc ctgagcacca ccaaaatggc accggaaggt ccgtttggtg   1200
aaatgcatgg ttatgtttat ccgggtgaaa gccatccggg tccggtttat accgttaaca   1260
aaattaccta tcgcaacaat gcaattctgc cgatgagcgc atgtggtcgt ctgaccgatg   1320
aaacccagac catgattccg accctggcag cagcagaaat tcgtcagctg tgtcagaggg   1380
caggtctgcc gattaccgat gcatttgcac cgtttgttgg tcaggcaacc tgggttgcac   1440
tgaaagttga taccaaacgt ctgcgtgcaa tgaaaaccaa tggtaaagca tttgcaaaag   1500
cggttggtga tgttgtgttt acccagaaac cgggttttat gattcatcgt ctgattctgg   1560
ttggtgatga tattgatgtg tatgacgata aagatgtgat gtgggcattt gctacccgtt   1620
gtcgtccggg tacagatgaa gtttttttttg atgatgttcc tggcttttgg ctgatcccgt   1680
atatgagtca tggtaatgcc gaagcagtga aaggtggtaa agttgttagt gatgcactgc   1740
tgaccgcaga atataccacc ggtaaagatt gggaaagcgc agatttcaaa aacagctatc   1800
cgaaacgtat ccaggataaa gttctgaata gctgggaacg cctgggtttc aaaaaactgg   1860
attaataagg atccgaattc gagctcggcg cgcctgcagg tcgacaagct tgcggccgca   1920
taatgcttaa gtcgaacaga aagtaatcgt attgtacacg gccgcataat cgaaattaat   1980
acgactcact ataggggaat tgtgagcgga taacaattcc ccatcttagt atattagtta   2040
agtataagaa ggagatatac atatgaaacg actcattgta ggcatcagcg gtgccagcgg   2100
cgcgatttat ggcgtgcgct tattacaggt tctgcgcgat gtcacagata tcgaaacgca   2160
tctggtgatg agccaggcag cgcgccagac cttatccctc gaaacggatt tttctctgcg   2220
cgaagtgcag gcattagccg atgtcacgca cgatgcgcgc gatattgccg ccagcatctc   2280
ttccggttct ttccagacgc tggggatggt gattttaccc tgttcaatca aaacccttc    2340
cggcattgtc catagctata ctgatggctt actgacccgt gcggcagatg tggtgctgaa   2400
agagcgtcgc ccgttggtgc tctgcgtgcg tgaaacacca ttgcacttag gccatctgcg   2460
tttaatgact caggcggcag aaatcggtgc ggtgattatg cctcccgttc cggcgtttta   2520
tcatcgcccg caatcccttg atgatgtgat aaatcagacg gttaatcgtg ttcttgacca   2580
gtttgcgata acccttcctg aagatctctt tgcccgctgg cagggcgcat aataaggtac   2640
cgaaggagat atacatatgc tgaccattct gaaactgggt ggtagcattc tgagcgataa   2700
aaatgttccg tatagcatta aatgggacaa cctggaacgt atcgcaatgg aaatcaaaaa   2760
```

```
tgccctggac tactacaaaa atcagaataa agaaattaaa ctgattctgg tgcatggtgg   2820
tggtgcattt ggtcatccgg ttgccaaaaa atacctgaaa attgaggacg gcaaaaaaat   2880
ctttattaac atggaaaaag gcttttggga aatccagcgt gcaatgcgtc gttttaacaa   2940
cattatcatt gataccctgc agagctatga tattccggca gttagcattc agccgagcag   3000
ctttgttgtt tttggtgata aactgatctt tgacaccagc gccattaaag aaatgctgaa   3060
acgtaatctg gttccggtga ttcatggtga tattgtgatt gatgataaaa atggctaccg   3120
catcattagc ggtgatgata ttgttccgta tctggccaat gaactgaaag cagatctgat   3180
tctgtatgcc accgatgttg atggtgttct gattgataac aaaccgatta aacgcattga   3240
taaaaacaat atctataaaa tcctgaatta tctgagcggc agcaacagca ttgatgttac   3300
cggtggtatg aaatacaaaa tcgacatgat tcgcaaaaac aaatgccgtg gctttgtgtt   3360
caatggcaat aaagccaaca acatctataa agcactgctg ggtgaagttg aaggcaccga   3420
aattgatttt agcgaataat aattaattaa cctaggctgc tgccaccgct gagcaataac   3480
tagcataacc ccttggggcc tctaaacggg tcttgagggg ttttttgctg aaaggaggaa   3540
ctatatccgg attggcgaat gggacgcgcc ctgtagcggc gcattaagcg cggcgggtgt   3600
ggtggttacg cgcagcgtga ccgctacact tgccagcgcc ctagcgcccg ctcctttcgc   3660
tttcttccct tcctttctcg ccacgttcgc cggctttccc cgtcaagctc taaatcgggg   3720
gctcccttta gggttccgat ttagtgcttt acggcacctc gaccccaaaa aacttgatta   3780
gggtgatggt tcacgtagtg ggccatcgcc ctgatagacg gtttttcgcc ctttgacgtt   3840
ggagtccacg ttctttaata gtggactctt gttccaaact ggaacaacac tcaaccctat   3900
ctcggtctat tcttttgatt tataagggat tttgccgatt tcggcctatt ggttaaaaaa   3960
tgagctgatt taacaaaaat ttaacgcgaa ttttaacaaa atattaacgt ttacaatttc   4020
tggcggcacg atggcatgag attatcaaaa aggatcttca cctagatcct tttaaattaa   4080
aaatgaagtt ttaaatcaat ctaaagtata tatgagtaaa cttggtctga cagttaccaa   4140
tgcttaatca gtgaggcacc tatctcagcg atctgtctat ttcgttcatc catagttgcc   4200
tgactccccg tcgtgtagat aactacgata cgggagggct taccatctgg ccccagtgct   4260
gcaatgatac cgcgagaccc acgctcaccg gctccagatt tatcagcaat aaaccagcca   4320
gccggaaggg ccgagcgcag aagtggtcct gcaactttat ccgcctccat ccagtctatt   4380
aattgttgcc gggaagctag agtaagtagt tcgccagtta atagtttgcg caacgttgtt   4440
gccattgcta caggcatcgt ggtgtcacgc tcgtcgtttg gtatggcttc attcagctcc   4500
ggttcccaac gatcaaggcg agttacatga tcccccatgt tgtgcaaaaa agcggttagc   4560
tccttcggtc ctccgatcgt tgtcagaagt aagttggccg cagtgttatc actcatggtt   4620
atggcagcac tgcataattc tcttactgtc atgccatccg taagatgctt ttctgtgact   4680
ggtgagtact caaccaagtc attctgagaa tagtgtatgc ggcgaccgag ttgctcttgc   4740
ccggcgtcaa tacgggataa taccgcgcca catagcagaa ctttaaaagt gctcatcatt   4800
ggaaaacgtt cttcggggcg aaaactctca aggatcttac cgctgttgag atccagttcg   4860
atgtaaccca ctcgtgcacc caactgatct tcagcatctt ttactttcac cagcgtttct   4920
gggtgagcaa aaacaggaag gcaaaatgcc gcaaaaaagg gaataagggc gacacggaaa   4980
tgttgaatac tcatactctt cctttttcaa tcatgattga agcatttatc agggttattg   5040
tctcatgagc ggatacatat ttgaatgtat ttagaaaaat aaacaaatag gtcatgacca   5100
```

-continued

```
aaatccctta acgtgagttt tcgttccact gagcgtcaga ccccgtagaa aagatcaaag   5160
gatcttcttg agatcctttt tttctgcgcg taatctgctg cttgcaaaca aaaaaaccac   5220
cgctaccagc ggtggtttgt ttgccggatc aagagctacc aactcttttt ccgaaggtaa   5280
ctggcttcag cagagcgcag ataccaaata ctgtccttct agtgtagccg tagttaggcc   5340
accacttcaa gaactctgta gcaccgccta catacctcgc tctgctaatc ctgttaccag   5400
tggctgctgc cagtggcgat aagtcgtgtc ttaccgggtt ggactcaaga cgatagttac   5460
cggataaggc gcagcggtcg ggctgaacgg ggggttcgtg cacacagccc agcttggagc   5520
gaacgaccta caccgaactg agatacctac agcgtgagct atgagaaagc gccacgcttc   5580
ccgaagggag aaaggcggac aggtatccgg taagcggcag ggtcggaaca ggagagcgca   5640
cgagggagct tccaggggga aacgcctggt atctttatag tcctgtcggg tttcgccacc   5700
tctgacttga gcgtcgattt ttgtgatgct cgtcaggggg gcggagccta tggaaaaacg   5760
ccagcaacgc ggccttttta cggttcctgg ccttttgctg gccttttgct cacatgttct   5820
ttcctgcgtt atcccctgat tctgtggata accgtattac cgcctttgag tgagctgata   5880
ccgctcgccg cagccgaacg accgagcgca gcgagtcagt gagcgaggaa gcggaagagc   5940
gcctgatgcg gtattttctc cttacgcatc tgtgcggtat ttcacaccgc atatatggtg   6000
cactctcagt acaatctgct ctgatgccgc atagttaagc cagtatacac tccgctatcg   6060
ctacgtgact gggtcatggc tgcgccccga cacccgccaa cacccgctga cgcgccctga   6120
cgggcttgtc tgctcccggc atccgcttac agacaagctg tgaccgtctc cgggagctgc   6180
atgtgtcaga ggttttcacc gtcatcaccg aaacgcgcga ggcagctgcg gtaaagctca   6240
tcagcgtggt cgtgaagcga ttcacagatg tctgcctgtt catccgcgtc cagctcgttg   6300
agtttctcca gaagcgttaa tgtctggctt ctgataaagc gggccatgtt aagggcggtt   6360
ttttcctgtt tggtcactga tgcctccgtg taagggggat ttctgttcat gggggtaatg   6420
ataccgatga aacgagagag gatgctcacg atacgggtta ctgatgatga acatgcccgg   6480
ttactggaac gttgtgaggg taaacaactg gcggtatgga tgcggcggga ccagagaaaa   6540
atcactcagg gtcaatgcca gcgcttcgtt aatacagatg taggtgttcc acagggtagc   6600
cagcagcatc ctgcgatgca gatccggaac ataatggtgc agggcgctga cttccgcgtt   6660
tccagacttt acgaaacacg gaaaccgaag accattcatg ttgttgctca ggtcgcagac   6720
gttttgcagc agcagtcgct tcacgttcgc tcgcgtatcg gtgattcatt ctgctaacca   6780
gtaaggcaac cccgccagcc tagccgggtc ctcaacgaca ggagcacgat catgctagtc   6840
atgccccgcg cccaccggaa ggagctgact gggttgaagg ctctcaaggg catcggtcga   6900
gatcccggtg cctaatgagt gagctaactt acattaattg cgttgcgctc actgcccgct   6960
ttccagtcgg gaaacctgtc gtgccagctg cattaatgaa tcggccaacg cgcggggaga   7020
ggcggtttgc gtattgggcg ccagggtggt ttttcttttc accagtgaga cgggcaacag   7080
ctgattgccc ttcaccgcct ggccctgaga gagttgcagc aagcggtcca cgctggtttg   7140
ccccagcagg cgaaaatcct gtttgatggt ggttaacggc gggatataac atgagctgtc   7200
ttcggtatcg tcgtatccca ctaccgagat gtccgcacca acgcgcagcc cggactcggt   7260
aatggcgcgc attgcgccca gcgccatctg atcgttggca accagcatcg cagtgggaac   7320
gatgccctca ttcagcattt gcatggtttg ttgaaaaccg gacatggcac tccagtcgcc   7380
ttcccgttcc gctatcggct gaatttgatt gcgagtgaga tatttatgcc agccagccag   7440
acgcagacgc gccgagacag aacttaatgg gcccgctaac agcgcgattt gctggtgacc   7500
```

```
caatgcgacc agatgctcca cgcccagtcg cgtaccgtct tcatgggaga aaataatact   7560

gttgatgggt gtctggtcag agacatcaag aaataacgcc ggaacattag tgcaggcagc   7620

ttccacagca atggcatcct ggtcatccag cggatagtta atgatcagcc cactgacgcg   7680

ttgcgcgaga agattgtgca ccgccgcttt acaggcttcg acgccgcttc gttctaccat   7740

cgacaccacc acgctggcac ccagttgatc ggcgcgagat ttaatcgccg cgacaatttg   7800

cgacggcgcg tgcagggcca gactggaggt ggcaacgcca atcagcaacg actgtttgcc   7860

cgccagttgt tgtgccacgc ggttgggaat gtaattcagc tccgccatcg ccgcttccac   7920

tttttcccgc gttttcgcag aaacgtggct ggcctggttc accacgcggg aaacggtctg   7980

ataagagaca ccggcatact ctgcgacatc gtataacgtt actggtttca cattcaccac   8040

cctgaattga ctctcttccg ggcgctatca tgccataccg cgaaaggttt tgcgccattc   8100

gatggtgtcc gggatctcga cgctctccct tatgcgactc ctgcattagg aagcagccca   8160

gtagtaggtt gaggccgttg ag                                           8182
```

<210> SEQ ID NO 38
<211> LENGTH: 8188
<212> TYPE: DNA
<213> ORGANISM: Artificial Sequence
<220> FEATURE:
<223> OTHER INFORMATION: pGB6389

<400> SEQUENCE: 38

```
caccgccgcc gcaaggaatg gtgcatgcaa ggagatggcg cccaacagtc cccggccac     60

ggggcctgcc accataccca cgccgaaaca agcgctcatg agcccgaagt ggcgagcccg    120

atcttcccca tcggtgatgt cggcgatata ggcgccagca accgcacctg tggcgccggt    180

gatgccggcc acgatgcgtc cggcgtagag gatcgagatc gatctcgatc ccgcgaaatt    240

aatacgactc actatagggg aattgtgagc ggataacaat tcccctctag aaataatttt    300

gtttaacttt aagaaggaga tataccatga gcagcaccac ctataaaagt gaagcatttg    360

atccggaacc gcctcatctg agctttcgta gctttgttaa tgcactgcgt caggatgggg    420

atctggtgga tattaatgaa ccggttgatc cggatctgga agcagcagca attacccgtc    480

tggtttgtga aaccgatgat aaagcaccgc tgtttaataa cgtgattggt gcaaaagatg    540

gtctgtggcg tattctgggt gcaccggcaa gcctgcgtgc gagcccgaaa gaacgttttg    600

gtcgtctggc acgtcatctg gcactgcctc cgaccgcaag cgcaaaagat attctggata    660

aaatgctgag cgccaatagc attccgccta ttgaaccggt tattgttccg accggtccgg    720

ttaaagaaaa tagcattgaa ggcgaaaaca ttgatctgga agccctgcct gcaccgatgg    780

ttcatcagag tgatggtggc aagtatatca atacctatgg tatgcatgtt atccagagtc    840

cggatggtgg gtggaccaat tggagcattg cccgtgcaat ggttagcggt aaacgtaccc    900

tggcaggtct ggttattagt ccgcagcata ttcgtaaaat tcaggatcag tggcgtgcaa    960

ttggccaaga agaaattcct tgggcactgg catttggtgt tccgcctctg gcaattatgg   1020

caagcagtat gccgattccg gatggtgtta gcgaagcagg ttatgttggt gcaattgccg   1080

gtgaaccgat taaactggtt aaatgcgata ccaacaatct gtatgttccg gcaaatagcg   1140

aaattgttct ggaaggcacc ctgagcacca ccaaaatggc accggaaggt ccgtttggtg   1200

aaatgcatgg ttatgtttat ccgggtgaaa gccatccggg tccggtttat accgttaaca   1260

aaattaccta tcgcaacaat gcaattctgc cgatgagcgc atgtggtcgt ctgaccgatg   1320
```

-continued

```
aaacccagac catgattccg accctggcag cagcagaaat tcgtcagctg tgtcagaggg   1380
caggtctgcc gattaccgat gcatttgcac cgtttgttgg tcaggcaacc tgggttgcac   1440
tgaaagttga taccaaacgt ctgcgtgcaa tgaaaaccaa tggtaaagca tttgcaaaag   1500
cggttggtga tgttgtgttt acccagaaac cgggttttat gattcatcgt ctgattctgg   1560
ttggtgatga tattgatgtg tatgacgata aagatgtgat gtgggcattt gctacccgtt   1620
gtcgtccggg tacagatgaa gtttttttg atgatgttcc tggcttttgg ctgatcccgt   1680
atatgagtca tggtaatgcc gaagcagtga aaggtggtaa agttgttagt gatgcactgc   1740
tgaccgcaga atataccacc ggtaaagatt gggaaagcgc agatttcaaa aacagctatc   1800
cgaaacgtat ccaggataaa gttctgaata gctgggaacg cctgggtttc aaaaaactgg   1860
attaataagg atccgaattc gagctcggcg cgcctgcagg tcgacaagct tgcggccgca   1920
taatgcttaa gtcgaacaga aagtaatcgt attgtacacg gccgcataat cgaaattaat   1980
acgactcact ataggggaat tgtgagcgga taacaattcc ccatcttagt atattagtta   2040
agtataagaa ggagatatac atatgaaacg actcattgta ggcatcagcg gtgccagcgg   2100
cgcgatttat ggcgtgcgct tattacaggt tctgcgcgat gtcacagata tcgaaacgca   2160
tctggtgatg agccaggcag cgcgccagac cttatccctc gaaacggatt tttctctgcg   2220
cgaagtgcag gcattagccg atgtcacgca cgatgcgcgc gatattgccg ccagcatctc   2280
ttccggttct ttccagacgc tggggatggt gattttaccc tgttcaatca aaacccttc    2340
cggcattgtc catagctata ctgatggctt actgacccgt gcggcagatg tggtgctgaa   2400
agagcgtcgc ccgttggtgc tctgcgtgcg tgaaacacca ttgcacttag gccatctgcg   2460
tttaatgact caggcggcag aaatcggtgc ggtgattatg cctcccgttc cggcgtttta   2520
tcatcgcccg caatcccttg atgatgtgat aaatcagacg gttaatcgtg ttcttgacca   2580
gtttgcgata acccttcctg aagatctctt tgcccgctgg cagggcgcat aataaggtac   2640
cgaaggagat atacatatgc aggttgatct gctgggtagc gcacagagcg cacatgcact   2700
gcacctgttt catcagcata gtccgctggt tcattgtatg accaatgatg ttgttcagac   2760
ctttaccgca aataccctgc tggcactggg tgcaagtccg gcaatggtta ttgaaaccga   2820
agaagcaagc cagtttgcag caattgcaag cgcactgctg attaatgttg gcaccctgac   2880
ccagcctcgt gcacaggcaa tgcgtgcagc agttgaacag gcaaaaagca gccagacccc   2940
gtggaccctg gacccggttg cagttggtgc actggattat cgtcgtcatt tttgtcatga   3000
actgctgagc tttaaaccgg cagcaattcg tggtaatgca agcgaaatta tggcactggc   3060
aggtattgca aatggtggtc gtggtgttga taccaccgat gcagcagcaa atgcaattcc   3120
ggcagcacag accctggcac gtgaaaccgg tgcaattgtt gttgttaccg gtgaaatgga   3180
ttatgttacc gatggtcatc gtattattgg tattcatggt ggtgatccgc tgatgaccaa   3240
agttgttggc accggttgtg cactgagcgc agttgttgca gcatgttgtg cactgcctgg   3300
tgatacctg  gaaaatgttg caagcgcatg tcattggatg aaacaggcag gcgaacgtgc    3360
agttgcacgt agcgaaggtc cgggtagctt tgttccgcat tttctggatg cactgtggca   3420
gctgacccag gaagttcagg cataataatt aattaaccta ggctgctgcc accgctgagc   3480
aataactagc ataacccctt ggggcctcta aacgggtctt gaggggtttt ttgctgaaag   3540
gaggaactat atccggattg gcgaatggga cgcgccctgt agcggcgcat taagcgcggc   3600
gggtgtggtg gttacgcgca gcgtgaccgc tacacttgcc agcgccctag cgcccgctcc   3660
tttcgctttc ttcccttcct ttctcgccac gttcgccggc tttccccgtc aagctctaaa   3720
```

```
tcgggggctc cctttagggt tccgatttag tgctttacgg cacctcgacc ccaaaaaact   3780
tgattagggt gatggttcac gtagtgggcc atcgccctga tagacggttt ttcgcccttt   3840
gacgttggag tccacgttct ttaatagtgg actcttgttc caaactggaa caacactcaa   3900
ccctatctcg gtctattctt ttgatttata agggattttg ccgatttcgg cctattggtt   3960
aaaaaatgag ctgatttaac aaaaatttaa cgcgaatttt aacaaaatat taacgtttac   4020
aatttctggc ggcacgatgg catgagatta tcaaaaagga tcttcaccta gatcctttta   4080
aattaaaaat gaagttttaa atcaatctaa agtatatatg agtaaacttg gtctgacagt   4140
taccaatgct taatcagtga ggcacctatc tcagcgatct gtctatttcg ttcatccata   4200
gttgcctgac tccccgtcgt gtagataact acgatacggg agggcttacc atctggcccc   4260
agtgctgcaa tgataccgcg agacccacgc tcaccggctc cagatttatc agcaataaac   4320
cagccagccg gaagggccga gcgcagaagt ggtcctgcaa ctttatccgc ctccatccag   4380
tctattaatt gttgccggga agctagagta agtagttcgc cagttaatag tttgcgcaac   4440
gttgttgcca ttgctacagg catcgtggtg tcacgctcgt cgtttggtat ggcttcattc   4500
agctccggtt cccaacgatc aaggcgagtt acatgatccc ccatgttgtg caaaaaagcg   4560
gttagctcct tcggtcctcc gatcgttgtc agaagtaagt tggccgcagt gttatcactc   4620
atggttatgg cagcactgca taattctctt actgtcatgc catccgtaag atgcttttct   4680
gtgactggtg agtactcaac caagtcattc tgagaatagt gtatgcggcg accgagttgc   4740
tcttgcccgg cgtcaatacg ggataatacc gcgccacata gcagaacttt aaaagtgctc   4800
atcattggaa aacgttcttc ggggcgaaaa ctctcaagga tcttaccgct gttgagatcc   4860
agttcgatgt aacccactcg tgcacccaac tgatcttcag catcttttac tttcaccagc   4920
gtttctgggt gagcaaaaac aggaaggcaa aatgccgcaa aaaagggaat aagggcgaca   4980
cggaaatgtt gaatactcat actcttcctt tttcaatcat gattgaagca tttatcaggg   5040
ttattgtctc atgagcggat acatatttga atgtatttag aaaaataaac aaataggtca   5100
tgaccaaaat cccttaacgt gagttttcgt tccactgagc gtcagacccc gtagaaaaga   5160
tcaaaggatc ttcttgagat cctttttttc tgcgcgtaat ctgctgcttg caaacaaaaa   5220
aaccaccgct accagcggtg gtttgtttgc cggatcaaga gctaccaact ctttttccga   5280
aggtaactgg cttcagcaga gcgcagatac caaatactgt ccttctagtg tagccgtagt   5340
taggccacca cttcaagaac tctgtagcac cgcctacata cctcgctctg ctaatcctgt   5400
taccagtggc tgctgccagt ggcgataagt cgtgtcttac cgggttggac tcaagacgat   5460
agttaccgga taaggcgcag cggtcgggct gaacgggggg ttcgtgcaca cagcccagct   5520
tggagcgaac gacctacacc gaactgagat acctacagcg tgagctatga gaaagcgcca   5580
cgcttcccga agggagaaag gcggacaggt atccggtaag cggcagggtc ggaacaggag   5640
agcgcacgag ggagcttcca gggggaaacg cctggtatct ttatagtcct gtcgggtttc   5700
gccacctctg acttgagcgt cgatttttgt gatgctcgtc aggggggcgg agcctatgga   5760
aaaacgccag caacgcggcc tttttacggt tcctggcctt ttgctggcct tttgctcaca   5820
tgttctttcc tgcgttatcc cctgattctg tggataaccg tattaccgcc tttgagtgag   5880
ctgataccgc tcgccgcagc cgaacgaccg agcgcagcga gtcagtgagc gaggaagcgg   5940
aagagcgcct gatgcggtat tttctcctta cgcatctgtg cggtatttca caccgcatat   6000
atggtgcact ctcagtacaa tctgctctga tgccgcatag ttaagccagt atacactccg   6060
```

```
ctatcgctac gtgactgggt catggctgcg ccccgacacc cgccaacacc cgctgacgcg   6120
ccctgacggg cttgtctgct cccggcatcc gcttacagac aagctgtgac cgtctccggg   6180
agctgcatgt gtcagaggtt ttcaccgtca tcaccgaaac gcgcgaggca gctgcggtaa   6240
agctcatcag cgtggtcgtg aagcgattca cagatgtctg cctgttcatc cgcgtccagc   6300
tcgttgagtt tctccagaag cgttaatgtc tggcttctga taaagcgggc catgttaagg   6360
gcggtttttt cctgtttggt cactgatgcc tccgtgtaag ggggatttct gttcatgggg   6420
gtaatgatac cgatgaaacg agagaggatg ctcacgatac gggttactga tgatgaacat   6480
gcccggttac tggaacgttg tgagggtaaa caactggcgg tatggatgcg gcgggaccag   6540
agaaaaatca ctcagggtca atgccagcgc ttcgttaata cagatgtagg tgttccacag   6600
ggtagccagc agcatcctgc gatgcagatc cggaacataa tggtgcaggg cgctgacttc   6660
cgcgtttcca gactttacga aacacggaaa ccgaagacca ttcatgttgt tgctcaggtc   6720
gcagacgttt tgcagcagca gtcgcttcac gttcgctcgc gtatcggtga ttcattctgc   6780
taaccagtaa ggcaaccccg ccagcctagc cgggtcctca acgacaggag cacgatcatg   6840
ctagtcatgc cccgcgccca ccggaaggag ctgactgggt tgaaggctct caagggcatc   6900
ggtcgagatc ccggtgccta atgagtgagc taacttacat taattgcgtt gcgctcactg   6960
cccgctttcc agtcgggaaa cctgtcgtgc cagctgcatt aatgaatcgg ccaacgcgcg   7020
gggagaggcg gtttgcgtat tgggcgccag ggtggttttt cttttcacca gtgagacggg   7080
caacagctga ttgcccttca ccgcctggcc ctgagagagt tgcagcaagc ggtccacgct   7140
ggtttgcccc agcaggcgaa aatcctgttt gatggtggtt aacggcggga tataacatga   7200
gctgtcttcg gtatcgtcgt atcccactac cgagatgtcc gcaccaacgc gcagcccgga   7260
ctcggtaatg gcgcgcattg cgcccagcgc catctgatcg ttggcaacca gcatcgcagt   7320
gggaacgatg ccctcattca gcatttgcat ggtttgttga aaaccggaca tggcactcca   7380
gtcgccttcc cgttccgcta tcggctgaat ttgattgcga gtgagatatt tatgccagcc   7440
agccagacgc agacgcgccg agacagaact taatgggccc gctaacagcg cgatttgctg   7500
gtgacccaat gcgaccagat gctccacgcc cagtcgcgta ccgtcttcat gggagaaaat   7560
aatactgttg atgggtgtct ggtcagagac atcaagaaat aacgccggaa cattagtgca   7620
ggcagcttcc acagcaatgg catcctggtc atccagcgga tagttaatga tcagcccact   7680
gacgcgttgc gcgagaagat tgtgcaccgc cgctttacag gcttcgacgc cgcttcgttc   7740
taccatcgac accaccacgc tggcacccag ttgatcggcg cgagatttaa tcgccgcgac   7800
aatttgcgac ggcgcgtgca gggccagact ggaggtggca acgccaatca gcaacgactg   7860
tttgcccgcc agttgttgtg ccacgcggtt gggaatgtaa ttcagctccg ccatcgccgc   7920
ttccactttt tcccgcgttt tcgcagaaac gtggctggcc tggttcacca cgcgggaaac   7980
ggtctgataa gagacaccgg catactctgc gacatcgtat aacgttactg gtttcacatt   8040
caccaccctg aattgactct cttccgggcg ctatcatgcc ataccgcgaa aggttttgcg   8100
ccattcgatg gtgtccggga tctcgacgct ctcccttatg cgactcctgc attaggaagc   8160
agcccagtag taggttgagg ccgttgag                                      8188
```

<210> SEQ ID NO 39
<211> LENGTH: 209
<212> TYPE: PRT
<213> ORGANISM: Escherichia coli
<220> FEATURE:
<223> OTHER INFORMATION: nudF Escherichia coli (strain K12)

<400> SEQUENCE: 39

```
Met Leu Lys Pro Asp Asn Leu Pro Val Thr Phe Gly Lys Asn Asp Val
1               5                   10                  15

Glu Ile Ile Ala Arg Glu Thr Leu Tyr Arg Gly Phe Phe Ser Leu Asp
            20                  25                  30

Leu Tyr Arg Phe Arg His Arg Leu Phe Asn Gly Gln Met Ser His Glu
        35                  40                  45

Val Arg Arg Glu Ile Phe Glu Arg Gly His Ala Ala Val Leu Leu Pro
    50                  55                  60

Phe Asp Pro Val Arg Asp Glu Val Val Leu Ile Glu Gln Ile Arg Ile
65                  70                  75                  80

Ala Ala Tyr Asp Thr Ser Glu Thr Pro Trp Leu Leu Glu Met Val Ala
                85                  90                  95

Gly Met Ile Glu Glu Gly Glu Ser Val Glu Asp Val Ala Arg Arg Glu
            100                 105                 110

Ala Ile Glu Glu Ala Gly Leu Ile Val Lys Arg Thr Lys Pro Val Leu
        115                 120                 125

Ser Phe Leu Ala Ser Pro Gly Gly Thr Ser Glu Arg Ser Ser Ile Met
    130                 135                 140

Val Gly Glu Val Asp Ala Thr Thr Ala Ser Gly Ile His Gly Leu Ala
145                 150                 155                 160

Asp Glu Asn Glu Asp Ile Arg Val His Val Val Ser Arg Glu Gln Ala
                165                 170                 175

Tyr Gln Trp Val Glu Glu Gly Lys Ile Asp Asn Ala Ala Ser Val Ile
            180                 185                 190

Ala Leu Gln Trp Leu Gln Leu His His Gln Ala Leu Lys Asn Glu Trp
        195                 200                 205

Ala
```

<210> SEQ ID NO 40
<211> LENGTH: 129
<212> TYPE: PRT
<213> ORGANISM: Escherichia coli
<220> FEATURE:
<223> OTHER INFORMATION: mutT Escherichia coli (strain K12)

<400> SEQUENCE: 40

```
Met Lys Lys Leu Gln Ile Ala Val Gly Ile Ile Arg Asn Glu Asn Asn
1               5                   10                  15

Glu Ile Phe Ile Thr Arg Arg Ala Ala Asp Ala His Met Ala Asn Lys
            20                  25                  30

Leu Glu Phe Pro Gly Gly Lys Ile Glu Met Gly Glu Thr Pro Glu Gln
        35                  40                  45

Ala Val Val Arg Glu Leu Gln Glu Glu Val Gly Ile Thr Pro Gln His
    50                  55                  60

Phe Ser Leu Phe Glu Lys Leu Glu Tyr Glu Phe Pro Asp Arg His Ile
65                  70                  75                  80

Thr Leu Trp Phe Trp Leu Val Glu Arg Trp Glu Gly Glu Pro Trp Gly
                85                  90                  95

Lys Glu Gly Gln Pro Gly Glu Trp Met Ser Leu Val Gly Leu Asn Ala
            100                 105                 110

Asp Asp Phe Pro Pro Ala Asn Glu Pro Val Ile Ala Lys Leu Lys Arg
        115                 120                 125

Leu
```

<210> SEQ ID NO 41
<211> LENGTH: 280
<212> TYPE: PRT
<213> ORGANISM: Escherichia coli
<220> FEATURE:
<223> OTHER INFORMATION: apaH Escherichia coli (strain K12)

<400> SEQUENCE: 41

Met Ala Thr Tyr Leu Ile Gly Asp Val His Gly Cys Tyr Asp Glu Leu
1 5 10 15

Ile Ala Leu Leu His Lys Val Glu Phe Thr Pro Gly Lys Asp Thr Leu
20 25 30

Trp Leu Thr Gly Asp Leu Val Ala Arg Gly Pro Gly Ser Leu Asp Val
35 40 45

Leu Arg Tyr Val Lys Ser Leu Gly Asp Ser Val Arg Leu Val Leu Gly
50 55 60

Asn His Asp Leu His Leu Leu Ala Val Phe Ala Gly Ile Ser Arg Asn
65 70 75 80

Lys Pro Lys Asp Arg Leu Thr Pro Leu Leu Glu Ala Pro Asp Ala Asp
85 90 95

Glu Leu Leu Asn Trp Leu Arg Arg Gln Pro Leu Leu Gln Ile Asp Glu
100 105 110

Glu Lys Lys Leu Val Met Ala His Ala Gly Ile Thr Pro Gln Trp Asp
115 120 125

Leu Gln Thr Ala Lys Glu Cys Ala Arg Asp Val Glu Ala Val Leu Ser
130 135 140

Ser Asp Ser Tyr Pro Phe Phe Leu Asp Ala Met Tyr Gly Asp Met Pro
145 150 155 160

Asn Asn Trp Ser Pro Glu Leu Arg Gly Leu Gly Arg Leu Arg Phe Ile
165 170 175

Thr Asn Ala Phe Thr Arg Met Arg Phe Cys Phe Pro Asn Gly Gln Leu
180 185 190

Asp Met Tyr Ser Lys Glu Ser Pro Glu Glu Ala Pro Ala Pro Leu Lys
195 200 205

Pro Trp Phe Ala Ile Pro Gly Pro Val Ala Glu Glu Tyr Ser Ile Ala
210 215 220

Phe Gly His Trp Ala Ser Leu Glu Gly Lys Gly Thr Pro Glu Gly Ile
225 230 235 240

Tyr Ala Leu Asp Thr Gly Cys Cys Trp Gly Gly Thr Leu Thr Cys Leu
245 250 255

Arg Trp Glu Asp Lys Gln Tyr Phe Val Gln Pro Ser Asn Arg His Lys
260 265 270

Asp Leu Gly Glu Ala Ala Ala Ser
275 280

<210> SEQ ID NO 42
<211> LENGTH: 550
<212> TYPE: PRT
<213> ORGANISM: Escherichia coli
<220> FEATURE:
<223> OTHER INFORMATION: ushA Escherichia coli (strain K12)

<400> SEQUENCE: 42

Met Lys Leu Leu Gln Arg Gly Val Ala Leu Ala Leu Leu Thr Thr Phe
1 5 10 15

```
Thr Leu Ala Ser Glu Thr Ala Leu Ala Tyr Glu Gln Asp Lys Thr Tyr
            20                  25                  30

Lys Ile Thr Val Leu His Thr Asn Asp His His Gly His Phe Trp Arg
        35                  40                  45

Asn Glu Tyr Gly Glu Tyr Gly Leu Ala Ala Gln Lys Thr Leu Val Asp
    50                  55                  60

Gly Ile Arg Lys Glu Val Ala Ala Glu Gly Gly Ser Val Leu Leu Leu
65                  70                  75                  80

Ser Gly Gly Asp Ile Asn Thr Gly Val Pro Glu Ser Asp Leu Gln Asp
                85                  90                  95

Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160

Gln Asp Leu Lys Ile Ala Val Ile Gly Leu Thr Thr Asp Asp Thr Ala
                165                 170                 175

Lys Ile Gly Asn Pro Glu Tyr Phe Thr Asp Ile Glu Phe Arg Lys Pro
            180                 185                 190

Ala Asp Glu Ala Lys Leu Val Ile Gln Glu Leu Gln Gln Thr Glu Lys
        195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
                245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285

His Glu Trp Gly Lys Tyr Val Gly Arg Ala Asp Phe Glu Phe Arg Asn
    290                 295                 300

Gly Glu Met Lys Met Val Asn Tyr Gln Leu Ile Pro Val Asn Leu Lys
305                 310                 315                 320

Lys Lys Val Thr Trp Glu Asp Gly Lys Ser Glu Arg Val Leu Tyr Thr
                325                 330                 335

Pro Glu Ile Ala Glu Asn Gln Gln Met Ile Ser Leu Leu Ser Pro Phe
            340                 345                 350

Gln Asn Lys Gly Lys Ala Gln Leu Glu Val Lys Ile Gly Glu Thr Asn
        355                 360                 365

Gly Arg Leu Glu Gly Asp Arg Asp Lys Val Arg Phe Val Gln Thr Asn
    370                 375                 380

Met Gly Arg Leu Ile Leu Ala Ala Gln Met Asp Arg Thr Gly Ala Asp
385                 390                 395                 400

Phe Ala Val Met Ser Gly Gly Gly Ile Arg Asp Ser Ile Glu Ala Gly
                405                 410                 415

Asp Ile Ser Tyr Lys Asn Val Leu Lys Val Gln Pro Phe Gly Asn Val
            420                 425                 430
```

```
Val Val Tyr Ala Asp Met Thr Gly Lys Glu Val Ile Asp Tyr Leu Thr
        435                 440                 445

Ala Val Ala Gln Met Lys Pro Asp Ser Gly Ala Tyr Pro Gln Phe Ala
    450                 455                 460

Asn Val Ser Phe Val Ala Lys Asp Gly Lys Leu Asn Asp Leu Lys Ile
465                 470                 475                 480

Lys Gly Glu Pro Val Asp Pro Ala Lys Thr Tyr Arg Met Ala Thr Leu
                485                 490                 495

Asn Phe Asn Ala Thr Gly Gly Asp Gly Tyr Pro Arg Leu Asp Asn Lys
            500                 505                 510

Pro Gly Tyr Val Asn Thr Gly Phe Ile Asp Ala Glu Val Leu Lys Ala
        515                 520                 525

Tyr Ile Gln Lys Ser Ser Pro Leu Asp Val Ser Val Tyr Glu Pro Lys
    530                 535                 540

Gly Glu Val Ser Trp Gln
545                 550


<210> SEQ ID NO 43
<211> LENGTH: 513
<212> TYPE: PRT
<213> ORGANISM: Escherichia coli
<220> FEATURE:
<223> OTHER INFORMATION: ppX Escherichia coli (strain K12)

<400> SEQUENCE: 43

Met Pro Ile His Asp Lys Ser Pro Arg Pro Gln Glu Phe Ala Ala Val
1               5                   10                  15

Asp Leu Gly Ser Asn Ser Phe His Met Val Ile Ala Arg Val Val Asp
            20                  25                  30

Gly Ala Met Gln Ile Ile Gly Arg Leu Lys Gln Arg Val His Leu Ala
        35                  40                  45

Asp Gly Leu Gly Pro Asp Asn Met Leu Ser Glu Glu Ala Met Thr Arg
    50                  55                  60

Gly Leu Asn Cys Leu Ser Leu Phe Ala Glu Arg Leu Gln Gly Phe Ser
65                  70                  75                  80

Pro Ala Ser Val Cys Ile Val Gly Thr His Thr Leu Arg Gln Ala Leu
                85                  90                  95

Asn Ala Thr Asp Phe Leu Lys Arg Ala Glu Lys Val Ile Pro Tyr Pro
            100                 105                 110

Ile Glu Ile Ile Ser Gly Asn Glu Glu Ala Arg Leu Ile Phe Met Gly
        115                 120                 125

Val Glu His Thr Gln Pro Glu Lys Gly Arg Lys Leu Val Ile Asp Ile
    130                 135                 140

Gly Gly Gly Ser Thr Glu Leu Val Ile Gly Glu Asn Phe Glu Pro Ile
145                 150                 155                 160

Leu Val Glu Ser Arg Arg Met Gly Cys Val Ser Phe Ala Gln Leu Tyr
                165                 170                 175

Phe Pro Gly Gly Val Ile Asn Lys Glu Asn Phe Gln Arg Ala Arg Met
            180                 185                 190

Ala Ala Ala Gln Lys Leu Glu Thr Leu Thr Trp Gln Phe Arg Ile Gln
        195                 200                 205

Gly Trp Asn Val Ala Met Gly Ala Ser Gly Thr Ile Lys Ala Ala His
    210                 215                 220

Glu Val Leu Met Glu Met Gly Glu Lys Asp Gly Ile Ile Thr Pro Glu
225                 230                 235                 240
```

```
Arg Leu Glu Lys Leu Val Lys Glu Val Leu Arg His Arg Asn Phe Ala
                245                 250                 255

Ser Leu Ser Leu Pro Gly Leu Ser Glu Glu Arg Lys Thr Val Phe Val
            260                 265                 270

Pro Gly Leu Ala Ile Leu Cys Gly Val Phe Asp Ala Leu Ala Ile Arg
        275                 280                 285

Glu Leu Arg Leu Ser Asp Gly Ala Leu Arg Glu Gly Val Leu Tyr Glu
    290                 295                 300

Met Glu Gly Arg Phe Arg His Gln Asp Val Arg Ser Arg Thr Ala Ser
305                 310                 315                 320

Ser Leu Ala Asn Gln Tyr His Ile Asp Ser Glu Gln Ala Arg Arg Val
                325                 330                 335

Leu Asp Thr Thr Met Gln Met Tyr Glu Gln Trp Arg Glu Gln Gln Pro
            340                 345                 350

Lys Leu Ala His Pro Gln Leu Glu Ala Leu Leu Arg Trp Ala Ala Met
        355                 360                 365

Leu His Glu Val Gly Leu Asn Ile Asn His Ser Gly Leu His Arg His
    370                 375                 380

Ser Ala Tyr Ile Leu Gln Asn Ser Asp Leu Pro Gly Phe Asn Gln Glu
385                 390                 395                 400

Gln Gln Leu Met Met Ala Thr Leu Val Arg Tyr His Arg Lys Ala Ile
                405                 410                 415

Lys Leu Asp Asp Leu Pro Arg Phe Thr Leu Phe Lys Lys Lys Gln Phe
            420                 425                 430

Leu Pro Leu Ile Gln Leu Leu Arg Leu Gly Val Leu Leu Asn Asn Gln
        435                 440                 445

Arg Gln Ala Thr Thr Thr Pro Pro Thr Leu Thr Leu Ile Thr Asp Asp
    450                 455                 460

Ser His Trp Thr Leu Arg Phe Pro His Asp Trp Phe Ser Gln Asn Ala
465                 470                 475                 480

Leu Val Leu Leu Asp Leu Glu Lys Glu Gln Glu Tyr Trp Glu Gly Val
                485                 490                 495

Ala Gly Trp Arg Leu Lys Ile Glu Glu Ser Thr Pro Glu Ile Ala
            500                 505                 510

Ala


<210> SEQ ID NO 44
<211> LENGTH: 494
<212> TYPE: PRT
<213> ORGANISM: Escherichia coli
<220> FEATURE:
<223> OTHER INFORMATION: gppA Escherichia coli (strain K12)

<400> SEQUENCE: 44

Met Gly Ser Thr Ser Ser Leu Tyr Ala Ala Ile Asp Leu Gly Ser Asn
1               5                   10                  15

Ser Phe His Met Leu Val Val Arg Glu Val Ala Gly Ser Ile Gln Thr
            20                  25                  30

Leu Thr Arg Ile Lys Arg Lys Val Arg Leu Ala Ala Gly Leu Asn Ser
        35                  40                  45

Glu Asn Ala Leu Ser Asn Glu Ala Met Glu Arg Gly Trp Gln Cys Leu
    50                  55                  60

Arg Leu Phe Ala Glu Arg Leu Gln Asp Ile Pro Pro Ser Gln Ile Arg
65                  70                  75                  80
```

```
Val Val Ala Thr Ala Thr Leu Arg Leu Ala Val Asn Ala Gly Asp Phe
                85                  90                  95

Ile Ala Lys Ala Gln Glu Ile Leu Gly Cys Pro Val Gln Val Ile Ser
            100                 105                 110

Gly Glu Glu Glu Ala Arg Leu Ile Tyr Gln Gly Val Ala His Thr Thr
        115                 120                 125

Gly Gly Ala Asp Gln Arg Leu Val Val Asp Ile Gly Gly Ala Ser Thr
    130                 135                 140

Glu Leu Val Thr Gly Thr Gly Ala Gln Thr Thr Ser Leu Phe Ser Leu
145                 150                 155                 160

Ser Met Gly Cys Val Thr Trp Leu Glu Arg Tyr Phe Ala Asp Arg Asn
                165                 170                 175

Leu Gly Gln Glu Asn Phe Asp Ala Ala Glu Lys Ala Ala Arg Glu Val
            180                 185                 190

Leu Arg Pro Val Ala Asp Glu Leu Arg Tyr His Gly Trp Lys Val Cys
        195                 200                 205

Val Gly Ala Ser Gly Thr Val Gln Ala Leu Gln Glu Ile Met Met Ala
    210                 215                 220

Gln Gly Met Asp Glu Arg Ile Thr Leu Glu Lys Leu Gln Gln Leu Lys
225                 230                 235                 240

Gln Arg Ala Ile His Cys Gly Arg Leu Glu Glu Leu Glu Ile Asp Gly
                245                 250                 255

Leu Thr Leu Glu Arg Ala Leu Val Phe Pro Ser Gly Leu Ala Ile Leu
            260                 265                 270

Ile Ala Ile Phe Thr Glu Leu Asn Ile Gln Cys Met Thr Leu Ala Gly
        275                 280                 285

Gly Ala Leu Arg Glu Gly Leu Val Tyr Gly Met Leu His Leu Ala Val
    290                 295                 300

Glu Gln Asp Ile Arg Ser Arg Thr Leu Arg Asn Ile Gln Arg Arg Phe
305                 310                 315                 320

Met Ile Asp Ile Asp Gln Ala Gln Arg Val Ala Lys Val Ala Ala Asn
                325                 330                 335

Phe Phe Asp Gln Val Glu Asn Glu Trp His Leu Glu Ala Ile Ser Arg
            340                 345                 350

Asp Leu Leu Ile Ser Ala Cys Gln Leu His Glu Ile Gly Leu Ser Val
        355                 360                 365

Asp Phe Lys Gln Ala Pro Gln His Ala Ala Tyr Leu Val Arg Asn Leu
    370                 375                 380

Asp Leu Pro Gly Phe Thr Pro Ala Gln Lys Lys Leu Leu Ala Thr Leu
385                 390                 395                 400

Leu Leu Asn Gln Thr Asn Pro Val Asp Leu Ser Ser Leu His Gln Gln
                405                 410                 415

Asn Ala Val Pro Pro Arg Val Ala Glu Gln Leu Cys Arg Leu Leu Arg
            420                 425                 430

Leu Ala Ile Ile Phe Ala Ser Arg Arg Arg Asp Asp Leu Val Pro Glu
        435                 440                 445

Met Thr Leu Gln Ala Asn His Glu Leu Leu Thr Leu Thr Leu Pro Gln
    450                 455                 460

Gly Trp Leu Thr Gln His Pro Leu Gly Lys Glu Ile Ile Ala Gln Glu
465                 470                 475                 480

Ser Gln Trp Gln Ser Tyr Val His Trp Pro Leu Glu Val His
                485                 490
```

<210> SEQ ID NO 45
<211> LENGTH: 257
<212> TYPE: PRT
<213> ORGANISM: Escherichia coli
<220> FEATURE:
<223> OTHER INFORMATION: nudC Escherichia coli (strain K12)

<400> SEQUENCE: 45

```
Met Asp Arg Ile Ile Glu Lys Leu Asp His Gly Trp Trp Val Val Ser
1               5                   10                  15

His Glu Gln Lys Leu Trp Leu Pro Lys Gly Glu Leu Pro Tyr Gly Glu
            20                  25                  30

Ala Ala Asn Phe Asp Leu Val Gly Gln Arg Ala Leu Gln Ile Gly Glu
        35                  40                  45

Trp Gln Gly Glu Pro Val Trp Leu Val Gln Gln Gln Arg Arg His Asp
    50                  55                  60

Met Gly Ser Val Arg Gln Val Ile Asp Leu Asp Val Gly Leu Phe Gln
65                  70                  75                  80

Leu Ala Gly Arg Gly Val Gln Leu Ala Glu Phe Tyr Arg Ser His Lys
                85                  90                  95

Tyr Cys Gly Tyr Cys Gly His Glu Met Tyr Pro Ser Lys Thr Glu Trp
            100                 105                 110

Ala Met Leu Cys Ser His Cys Arg Glu Arg Tyr Tyr Pro Gln Ile Ala
        115                 120                 125

Pro Cys Ile Ile Val Ala Ile Arg Arg Asp Asp Ser Ile Leu Leu Ala
    130                 135                 140

Gln His Thr Arg His Arg Asn Gly Val His Thr Val Leu Ala Gly Phe
145                 150                 155                 160

Val Glu Val Gly Glu Thr Leu Glu Gln Ala Val Ala Arg Glu Val Met
                165                 170                 175

Glu Glu Ser Gly Ile Lys Val Lys Asn Leu Arg Tyr Val Thr Ser Gln
            180                 185                 190

Pro Trp Pro Phe Pro Gln Ser Leu Met Thr Ala Phe Met Ala Glu Tyr
        195                 200                 205

Asp Ser Gly Asp Ile Val Ile Asp Pro Lys Glu Leu Leu Glu Ala Asn
    210                 215                 220

Trp Tyr Arg Tyr Asp Asp Leu Pro Leu Leu Pro Pro Pro Gly Thr Val
225                 230                 235                 240

Ala Arg Arg Leu Ile Glu Asp Thr Val Ala Met Cys Arg Ala Glu Tyr
                245                 250                 255

Glu
```

<210> SEQ ID NO 46
<211> LENGTH: 197
<212> TYPE: PRT
<213> ORGANISM: Escherichia coli
<220> FEATURE:
<223> OTHER INFORMATION: yhdE Escherichia coli (strain K12)

<400> SEQUENCE: 46

```
Met Thr Ser Leu Tyr Leu Ala Ser Gly Ser Pro Arg Arg Gln Glu Leu
1               5                   10                  15

Leu Ala Gln Leu Gly Val Thr Phe Glu Arg Ile Val Thr Gly Ile Glu
            20                  25                  30

Glu Gln Arg Gln Pro Gln Glu Ser Ala Gln Gln Tyr Val Val Arg Leu
        35                  40                  45
```

```
Ala Arg Glu Lys Ala Arg Ala Gly Val Ala Gln Thr Ala Lys Asp Leu
    50                  55                  60

Pro Val Leu Gly Ala Asp Thr Ile Val Ile Leu Asn Gly Glu Val Leu
65                  70                  75                  80

Glu Lys Pro Arg Asp Ala Glu His Ala Ala Gln Met Leu Arg Lys Leu
                85                  90                  95

Ser Gly Gln Thr His Gln Val Met Thr Ala Val Ala Leu Ala Asp Ser
            100                 105                 110

Gln His Ile Leu Asp Cys Leu Val Val Thr Asp Val Thr Phe Arg Thr
        115                 120                 125

Leu Thr Asp Glu Asp Ile Ala Gly Tyr Val Ala Ser Asp Glu Pro Leu
    130                 135                 140

Asp Lys Ala Gly Ala Tyr Gly Ile Gln Gly Leu Gly Gly Cys Phe Val
145                 150                 155                 160

Arg Lys Ile Asn Gly Ser Tyr His Ala Val Val Gly Leu Pro Leu Val
                165                 170                 175

Glu Thr Tyr Glu Leu Leu Ser Asn Phe Asn Ala Leu Arg Glu Lys Arg
            180                 185                 190

Asp Lys His Asp Gly
        195


<210> SEQ ID NO 47
<211> LENGTH: 246
<212> TYPE: PRT
<213> ORGANISM: Escherichia coli
<220> FEATURE:
<223> OTHER INFORMATION: cysQ Escherichia coli (strain K12)

<400> SEQUENCE: 47

Met Leu Asp Gln Val Cys Gln Leu Ala Arg Asn Ala Gly Asp Ala Ile
1               5                   10                  15

Met Gln Val Tyr Asp Gly Thr Lys Pro Met Asp Val Val Ser Lys Ala
            20                  25                  30

Asp Asn Ser Pro Val Thr Ala Ala Asp Ile Ala Ala His Thr Val Ile
        35                  40                  45

Met Asp Gly Leu Arg Thr Leu Thr Pro Asp Val Pro Val Leu Ser Glu
    50                  55                  60

Glu Asp Pro Pro Gly Trp Glu Val Arg Gln His Trp Gln Arg Tyr Trp
65                  70                  75                  80

Leu Val Asp Pro Leu Asp Gly Thr Lys Glu Phe Ile Lys Arg Asn Gly
                85                  90                  95

Glu Phe Thr Val Asn Ile Ala Leu Ile Asp His Gly Lys Pro Ile Leu
            100                 105                 110

Gly Val Val Tyr Ala Pro Val Met Asn Val Met Tyr Ser Ala Ala Glu
        115                 120                 125

Gly Lys Ala Trp Lys Glu Glu Cys Gly Val Arg Lys Gln Ile Gln Val
    130                 135                 140

Arg Asp Ala Arg Pro Pro Leu Val Val Ile Ser Arg Ser His Ala Asp
145                 150                 155                 160

Ala Glu Leu Lys Glu Tyr Leu Gln Gln Leu Gly Glu His Gln Thr Thr
                165                 170                 175

Ser Ile Gly Ser Ser Leu Lys Phe Cys Leu Val Ala Glu Gly Gln Ala
            180                 185                 190

Gln Leu Tyr Pro Arg Phe Gly Pro Thr Asn Ile Trp Asp Thr Ala Ala
        195                 200                 205
```

```
Gly His Ala Val Ala Ala Ala Ala Gly Ala His Val His Asp Trp Gln
    210                 215                 220

Gly Lys Pro Leu Asp Tyr Thr Pro Arg Glu Ser Phe Leu Asn Pro Gly
225                 230                 235                 240

Phe Arg Val Ser Ile Tyr
                245


<210> SEQ ID NO 48
<211> LENGTH: 238
<212> TYPE: PRT
<213> ORGANISM: Escherichia coli
<220> FEATURE:
<223> OTHER INFORMATION: yigB Escherichia coli (strain K12)

<400> SEQUENCE: 48

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Glu Ala Ser Ala
                85                  90                  95

Gly Ala His Ala Ala Met Ile Asn Phe Ala Lys Trp Arg Ser Arg Ile
            100                 105                 110

Asp Val Pro Gln Gln Thr His Asp Thr Leu Lys Gln Leu Ala Lys Lys
        115                 120                 125

Trp Pro Leu Val Ala Ile Thr Asn Gly Asn Ala Gln Pro Glu Leu Phe
    130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175

Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Arg
        195                 200                 205

Pro Glu Asn Gly Asp Leu Met Gln Thr Trp Asp Ser Arg Leu Leu Pro
    210                 215                 220

His Leu Glu Ile Ser Arg Leu Ala Ser Leu Thr Ser Leu Ile
225                 230                 235


<210> SEQ ID NO 49
<211> LENGTH: 271
<212> TYPE: PRT
<213> ORGANISM: Escherichia coli
<220> FEATURE:
<223> OTHER INFORMATION: ybjl Escherichia coli (strain K12)

<400> SEQUENCE: 49

Met Ser Ile Lys Leu Ile Ala Val Asp Met Asp Gly Thr Phe Leu Ser
1               5                   10                  15

Asp Gln Lys Thr Tyr Asn Arg Glu Arg Phe Met Ala Gln Tyr Gln Gln
            20                  25                  30
```

```
Met Lys Ala Gln Gly Ile Arg Phe Val Val Ala Ser Gly Asn Gln Tyr
        35                  40                  45

Tyr Gln Leu Ile Ser Phe Phe Pro Glu Ile Ala Asn Glu Ile Ala Phe
    50                  55                  60

Val Ala Glu Asn Gly Gly Trp Val Val Ser Glu Gly Lys Asp Val Phe
65                  70                  75                  80

Asn Gly Glu Leu Ser Lys Asp Ala Phe Ala Thr Val Val Glu His Leu
                85                  90                  95

Leu Thr Arg Pro Glu Val Glu Ile Ile Ala Cys Gly Lys Asn Ser Ala
            100                 105                 110

Tyr Thr Leu Lys Lys Tyr Asp Asp Ala Met Lys Thr Val Ala Glu Met
        115                 120                 125

Tyr Tyr His Arg Leu Glu Tyr Val Asp Asn Phe Asp Asn Leu Glu Asp
    130                 135                 140

Ile Phe Phe Lys Phe Gly Leu Asn Leu Ser Asp Glu Leu Ile Pro Gln
145                 150                 155                 160

Val Gln Lys Ala Leu His Glu Ala Ile Gly Asp Ile Met Val Ser Val
                165                 170                 175

His Thr Gly Asn Gly Ser Ile Asp Leu Ile Ile Pro Gly Val His Lys
            180                 185                 190

Ala Asn Gly Leu Arg Gln Leu Gln Lys Leu Trp Gly Ile Asp Asp Ser
        195                 200                 205

Glu Val Val Val Phe Gly Asp Gly Gly Asn Asp Ile Glu Met Leu Arg
    210                 215                 220

Gln Ala Gly Phe Ser Phe Ala Met Glu Asn Ala Gly Ser Ala Val Val
225                 230                 235                 240

Ala Ala Ala Lys Tyr Arg Ala Gly Ser Asn Asn Arg Glu Gly Val Leu
                245                 250                 255

Asp Val Ile Asp Lys Val Leu Lys His Glu Ala Pro Phe Asp Gln
            260                 265                 270


<210> SEQ ID NO 50
<211> LENGTH: 332
<212> TYPE: PRT
<213> ORGANISM: Escherichia coli
<220> FEATURE:
<223> OTHER INFORMATION: fbp Escherichia coli (strain K12)

<400> SEQUENCE: 50

Met Lys Thr Leu Gly Glu Phe Ile Val Glu Lys Gln His Glu Phe Ser
1               5                   10                  15

His Ala Thr Gly Glu Leu Thr Ala Leu Leu Ser Ala Ile Lys Leu Gly
            20                  25                  30

Ala Lys Ile Ile His Arg Asp Ile Asn Lys Ala Gly Leu Val Asp Ile
        35                  40                  45

Leu Gly Ala Ser Gly Ala Glu Asn Val Gln Gly Glu Val Gln Gln Lys
    50                  55                  60

Leu Asp Leu Phe Ala Asn Glu Lys Leu Lys Ala Ala Leu Lys Ala Arg
65                  70                  75                  80

Asp Ile Val Ala Gly Ile Ala Ser Glu Glu Glu Asp Glu Ile Val Val
                85                  90                  95

Phe Glu Gly Cys Glu His Ala Lys Tyr Val Val Leu Met Asp Pro Leu
            100                 105                 110

Asp Gly Ser Ser Asn Ile Asp Val Asn Val Ser Val Gly Thr Ile Phe
        115                 120                 125
```

```
Ser Ile Tyr Arg Arg Val Thr Pro Val Gly Thr Pro Val Thr Glu Glu
    130                 135                 140

Asp Phe Leu Gln Pro Gly Asn Lys Gln Val Ala Ala Gly Tyr Val Val
145                 150                 155                 160

Tyr Gly Ser Ser Thr Met Leu Val Tyr Thr Thr Gly Cys Gly Val His
                165                 170                 175

Ala Phe Thr Tyr Asp Pro Ser Leu Gly Val Phe Cys Leu Cys Gln Glu
            180                 185                 190

Arg Met Arg Phe Pro Glu Lys Gly Lys Thr Tyr Ser Ile Asn Glu Gly
        195                 200                 205

Asn Tyr Ile Lys Phe Pro Asn Gly Val Lys Lys Tyr Ile Lys Phe Cys
    210                 215                 220

Gln Glu Glu Asp Lys Ser Thr Asn Arg Pro Tyr Thr Ser Arg Tyr Ile
225                 230                 235                 240

Gly Ser Leu Val Ala Asp Phe His Arg Asn Leu Leu Lys Gly Gly Ile
                245                 250                 255

Tyr Leu Tyr Pro Ser Thr Ala Ser His Pro Asp Gly Lys Leu Arg Leu
            260                 265                 270

Leu Tyr Glu Cys Asn Pro Met Ala Phe Leu Ala Glu Gln Ala Gly Gly
        275                 280                 285

Lys Ala Ser Asp Gly Lys Glu Arg Ile Leu Asp Ile Ile Pro Glu Thr
    290                 295                 300

Leu His Gln Arg Arg Ser Phe Phe Val Gly Asn Asp His Met Val Glu
305                 310                 315                 320

Asp Val Glu Arg Phe Ile Arg Glu Phe Pro Asp Ala
                325                 330


<210> SEQ ID NO 51
<211> LENGTH: 248
<212> TYPE: PRT
<213> ORGANISM: Haloferax volcanii
<220> FEATURE:
<223> OTHER INFORMATION: Haloferax volcanii (strain ATCC 29605 / DSM
      3757 / JCM 8879 / NBRC 14742 / NCIMB 2012 / VKM B-1768 / DS2)

<400> SEQUENCE: 51

Met Ser Leu Val Val Leu Lys Leu Gly Gly Ser Val Val Thr Asp Lys
1               5                   10                  15

Asp Glu Pro Glu Thr Val Asp Glu Ala Gly Leu Ala Ala Ala Ala Asp
            20                  25                  30

Ala Val Ala Pro Leu Ala Glu Ser Arg Arg Val Val Val Val His Gly
        35                  40                  45

Gly Gly Ser Phe Gly His His His Ala Ala Glu His Gly Val Ser Ser
    50                  55                  60

Glu Ser Gly Ser His Asp Ala Arg Gly Val Arg Ala Ile His Asp Ala
65                  70                  75                  80

Met Lys Arg Leu Asn Asp Ala Val Leu Asp Ala Leu Glu Glu Arg Gly
                85                  90                  95

Val Ala Ala Leu Pro Val His Pro Leu Ser Ala Gly Ala Arg Glu Ala
            100                 105                 110

Asp Gly Ser Leu Ser Leu Pro Leu Ala Ala Thr Glu Thr Met Leu Asp
        115                 120                 125

Glu Gly Phe Val Pro Val Leu His Gly Asp Val Ile Ser His Ala Gly
    130                 135                 140
```

```
Lys Gly Ala Thr Ile Val Ser Gly Asp Asp Leu Val Val Ser Leu Ala
145                 150                 155                 160

Ser Gly Leu Gly Ala Asp Arg Val Gly Leu Cys Ser Thr Val Pro Gly
                165                 170                 175

Val Leu Asp Ala Asp Gly Asp Val Ile Pro Glu Ile Thr Ala Phe Ala
            180                 185                 190

Asp Ala Ala Asp Ala Leu Gly Gly Ser Asp Ser Thr Asp Val Thr Gly
        195                 200                 205

Gly Met Ala Ala Lys Val Arg Lys Leu Leu Ala Leu Gly Ala Pro Ala
    210                 215                 220

His Val Phe Gly Pro Glu Gly Leu Ser Ala Phe Val Ala Gly Glu Ser
225                 230                 235                 240

Pro Gly Thr Val Ile Arg Gly Glu
                245


<210> SEQ ID NO 52
<211> LENGTH: 266
<212> TYPE: PRT
<213> ORGANISM: Methanothermobacter thermautotrophicus
<220> FEATURE:
<223> OTHER INFORMATION: Methanothermobacter thermautotrophicus (strain
      ATCC 29096 / DSM 1053 / JCM 10044 / NBRC 100330 / Delta H)

<400> SEQUENCE: 52

Met Ile Ile Leu Lys Leu Gly Gly Ser Val Ile Thr Arg Lys Asp Ser
1               5                   10                  15

Glu Glu Pro Ala Ile Asp Arg Asp Asn Leu Glu Arg Ile Ala Ser Glu
            20                  25                  30

Ile Gly Asn Ala Ser Pro Ser Ser Leu Met Ile Val His Gly Ala Gly
        35                  40                  45

Ser Phe Gly His Pro Phe Ala Gly Glu Tyr Arg Ile Gly Ser Glu Ile
    50                  55                  60

Glu Asn Glu Glu Asp Leu Arg Arg Arg Arg Phe Gly Phe Ala Leu Thr
65                  70                  75                  80

Gln Asn Trp Val Lys Lys Leu Asn Ser His Val Cys Asp Ala Leu Leu
                85                  90                  95

Ala Glu Gly Ile Pro Ala Val Ser Met Gln Pro Ser Ala Phe Ile Arg
            100                 105                 110

Ala His Ala Gly Arg Ile Ser His Ala Asp Ile Ser Leu Ile Arg Ser
        115                 120                 125

Tyr Leu Glu Glu Gly Met Val Pro Val Val Tyr Gly Asp Val Val Leu
    130                 135                 140

Asp Ser Asp Arg Arg Leu Lys Phe Ser Val Ile Ser Gly Asp Gln Leu
145                 150                 155                 160

Ile Asn His Phe Ser Leu Arg Leu Met Pro Glu Arg Val Ile Leu Gly
                165                 170                 175

Thr Asp Val Asp Gly Val Tyr Thr Arg Asn Pro Lys Lys His Pro Asp
            180                 185                 190

Ala Arg Leu Leu Asp Val Ile Gly Ser Leu Asp Asp Leu Glu Ser Leu
        195                 200                 205

Asp Gly Thr Leu Asn Thr Asp Val Thr Gly Gly Met Val Gly Lys Ile
    210                 215                 220

Arg Glu Leu Leu Leu Leu Ala Glu Lys Gly Val Glu Ser Glu Ile Ile
225                 230                 235                 240
```

```
Asn Ala Ala Val Pro Gly Asn Ile Glu Arg Ala Leu Leu Gly Glu Glu
                245                 250                 255

Val Arg Gly Thr Arg Ile Thr Gly Lys His
            260                 265


<210> SEQ ID NO 53
<211> LENGTH: 260
<212> TYPE: PRT
<213> ORGANISM: Methanocaldococcus jannaschii
<220> FEATURE:
<223> OTHER INFORMATION: Methanocaldococcus jannaschii (strain ATCC
      43067 / DSM 2661 / JAL-1 / JCM 10045 / NBRC 100440)

<400> SEQUENCE: 53

Met Leu Thr Ile Leu Lys Leu Gly Gly Ser Ile Leu Ser Asp Lys Asn
1               5                   10                  15

Val Pro Tyr Ser Ile Lys Trp Asp Asn Leu Glu Arg Ile Ala Met Glu
            20                  25                  30

Ile Lys Asn Ala Leu Asp Tyr Tyr Lys Asn Gln Asn Lys Glu Ile Lys
        35                  40                  45

Leu Ile Leu Val His Gly Gly Gly Ala Phe Gly His Pro Val Ala Lys
    50                  55                  60

Lys Tyr Leu Lys Ile Glu Asp Gly Lys Lys Ile Phe Ile Asn Met Glu
65                  70                  75                  80

Lys Gly Phe Trp Glu Ile Gln Arg Ala Met Arg Arg Phe Asn Asn Ile
                85                  90                  95

Ile Ile Asp Thr Leu Gln Ser Tyr Asp Ile Pro Ala Val Ser Ile Gln
            100                 105                 110

Pro Ser Ser Phe Val Val Phe Gly Asp Lys Leu Ile Phe Asp Thr Ser
        115                 120                 125

Ala Ile Lys Glu Met Leu Lys Arg Asn Leu Val Pro Val Ile His Gly
    130                 135                 140

Asp Ile Val Ile Asp Asp Lys Asn Gly Tyr Arg Ile Ile Ser Gly Asp
145                 150                 155                 160

Asp Ile Val Pro Tyr Leu Ala Asn Glu Leu Lys Ala Asp Leu Ile Leu
                165                 170                 175

Tyr Ala Thr Asp Val Asp Gly Val Leu Ile Asp Asn Lys Pro Ile Lys
            180                 185                 190

Arg Ile Asp Lys Asn Asn Ile Tyr Lys Ile Leu Asn Tyr Leu Ser Gly
        195                 200                 205

Ser Asn Ser Ile Asp Val Thr Gly Gly Met Lys Tyr Lys Ile Asp Met
    210                 215                 220

Ile Arg Lys Asn Lys Cys Arg Gly Phe Val Phe Asn Gly Asn Lys Ala
225                 230                 235                 240

Asn Asn Ile Tyr Lys Ala Leu Leu Gly Glu Val Glu Gly Thr Glu Ile
                245                 250                 255

Asp Phe Ser Glu
            260


<210> SEQ ID NO 54
<211> LENGTH: 245
<212> TYPE: PRT
<213> ORGANISM: Thermoplasma acidophilum
<220> FEATURE:
<223> OTHER INFORMATION: Thermoplasma acidophilum (strain ATCC
      25905 / DSM 1728 / JCM 9062 / NBRC 15155 / AMRC-C165)
```

<400> SEQUENCE: 54

```
Met Met Ile Leu Lys Ile Gly Gly Ser Val Ile Thr Asp Lys Ser Ala
1               5                   10                  15

Tyr Arg Thr Ala Arg Thr Tyr Ala Ile Arg Ser Ile Val Lys Val Leu
            20                  25                  30

Ser Gly Ile Glu Asp Leu Val Cys Val Val His Gly Gly Gly Ser Phe
        35                  40                  45

Gly His Ile Lys Ala Met Glu Phe Gly Leu Pro Gly Pro Lys Asn Pro
    50                  55                  60

Arg Ser Ser Ile Gly Tyr Ser Ile Val His Arg Asp Met Glu Asn Leu
65                  70                  75                  80

Asp Leu Met Val Ile Asp Ala Met Ile Glu Met Gly Met Arg Pro Ile
                85                  90                  95

Ser Val Pro Ile Ser Ala Leu Arg Tyr Asp Gly Arg Phe Asp Tyr Thr
            100                 105                 110

Pro Leu Ile Arg Tyr Ile Asp Ala Gly Phe Val Pro Val Ser Tyr Gly
        115                 120                 125

Asp Val Tyr Ile Lys Asp Glu His Ser Tyr Gly Ile Tyr Ser Gly Asp
    130                 135                 140

Asp Ile Met Ala Asp Met Ala Glu Leu Leu Lys Pro Asp Val Ala Val
145                 150                 155                 160

Phe Leu Thr Asp Val Asp Gly Ile Tyr Ser Lys Asp Pro Lys Arg Asn
                165                 170                 175

Pro Asp Ala Val Leu Leu Arg Asp Ile Asp Thr Asn Ile Thr Phe Asp
            180                 185                 190

Arg Val Gln Asn Asp Val Thr Gly Gly Ile Gly Lys Lys Phe Glu Ser
        195                 200                 205

Met Val Lys Met Lys Ser Ser Val Lys Asn Gly Val Tyr Leu Ile Asn
    210                 215                 220

Gly Asn His Pro Glu Arg Ile Gly Asp Ile Gly Lys Glu Ser Phe Ile
225                 230                 235                 240

Gly Thr Val Ile Arg
                245
```

<210> SEQ ID NO 55
<211> LENGTH: 471
<212> TYPE: PRT
<213> ORGANISM: Escherichia coli
<220> FEATURE:
<223> OTHER INFORMATION: phoA Escherichia coli (strain K12)

<400> SEQUENCE: 55

```
Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Leu Glu Asn Arg
            20                  25                  30

Ala Ala Gln Gly Asp Ile Thr Ala Pro Gly Gly Ala Arg Arg Leu Thr
        35                  40                  45

Gly Asp Gln Thr Ala Ala Leu Arg Asp Ser Leu Ser Asp Lys Pro Ala
    50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95
```

```
Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
        115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
            180                 185                 190

Pro Ser Ala Thr Ser Glu Lys Cys Pro Gly Asn Ala Leu Glu Lys Gly
        195                 200                 205

Gly Lys Gly Ser Ile Thr Glu Gln Leu Leu Asn Ala Arg Ala Asp Val
    210                 215                 220

Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
            260                 265                 270

Gln Gln Lys Pro Leu Leu Gly Leu Phe Ala Asp Gly Asn Met Pro Val
        275                 280                 285

Arg Trp Leu Gly Pro Lys Ala Thr Tyr His Gly Asn Ile Asp Lys Pro
    290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
            340                 345                 350

His Ala Ala Asn Pro Cys Gly Gln Ile Gly Glu Thr Val Asp Leu Asp
        355                 360                 365

Glu Ala Val Gln Arg Ala Leu Glu Phe Ala Lys Lys Glu Gly Asn Thr
    370                 375                 380

Leu Val Ile Val Thr Ala Asp His Ala His Ala Ser Gln Ile Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
            420                 425                 430

Glu His Thr Gly Ser Gln Leu Arg Ile Ala Ala Tyr Gly Pro His Ala
        435                 440                 445

Ala Asn Val Val Gly Leu Thr Asp Gln Thr Asp Leu Phe Tyr Thr Met
    450                 455                 460

Lys Ala Ala Leu Gly Leu Lys
465                 470
```

```
<210> SEQ ID NO 56
<211> LENGTH: 271
<212> TYPE: PRT
<213> ORGANISM: Escherichia coli
<220> FEATURE:
<223> OTHER INFORMATION: ybiV Escherichia coli (strain K12)
```

<400> SEQUENCE: 56

```
Met Ser Val Lys Val Ile Val Thr Asp Met Asp Gly Thr Phe Leu Asn
1               5                   10                  15

Asp Ala Lys Thr Tyr Asn Gln Pro Arg Phe Met Ala Gln Tyr Gln Glu
            20                  25                  30

Leu Lys Lys Arg Gly Ile Lys Phe Val Val Ala Ser Gly Asn Gln Tyr
        35                  40                  45

Tyr Gln Leu Ile Ser Phe Phe Pro Glu Leu Lys Asp Glu Ile Ser Phe
    50                  55                  60

Val Ala Glu Asn Gly Ala Leu Val Tyr Glu His Gly Lys Gln Leu Phe
65                  70                  75                  80

His Gly Glu Leu Thr Arg His Glu Ser Arg Ile Val Ile Gly Glu Leu
                85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
        115                 120                 125

His Tyr His Arg Leu Lys Pro Val Lys Asp Tyr Gln Glu Ile Asp Asp
    130                 135                 140

Val Leu Phe Lys Phe Ser Leu Asn Leu Pro Asp Glu Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Ile Pro Gly Leu His Lys
            180                 185                 190

Ala Asn Gly Ile Ser Arg Leu Leu Lys Arg Trp Asp Leu Ser Pro Gln
        195                 200                 205

Asn Val Val Ala Ile Gly Asp Ser Gly Asn Asp Ala Glu Met Leu Lys
    210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270
```

<210> SEQ ID NO 57
<211> LENGTH: 270
<212> TYPE: PRT
<213> ORGANISM: Escherichia coli
<220> FEATURE:
<223> OTHER INFORMATION: yidA Escherichia coli (strain K12)

<400> SEQUENCE: 57

```
Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80
```

```
Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270


<210> SEQ ID NO 58
<211> LENGTH: 172
<212> TYPE: PRT
<213> ORGANISM: Escherichia coli
<220> FEATURE:
<223> OTHER INFORMATION: pgpA Escherichia coli (strain K12)

<400> SEQUENCE: 58

Met Thr Ile Leu Pro Arg His Lys Asp Val Ala Lys Ser Arg Leu Lys
1               5                   10                  15

Met Ser Asn Pro Trp His Leu Leu Ala Val Gly Phe Gly Ser Gly Leu
            20                  25                  30

Ser Pro Ile Val Pro Gly Thr Met Gly Ser Leu Ala Ala Ile Pro Phe
        35                  40                  45

Trp Tyr Leu Met Thr Phe Leu Pro Trp Gln Leu Tyr Ser Leu Val Val
    50                  55                  60

Met Leu Gly Ile Cys Ile Gly Val Tyr Leu Cys His Gln Thr Ala Lys
65                  70                  75                  80

Asp Met Gly Val His Asp His Gly Ser Ile Val Trp Asp Glu Phe Ile
                85                  90                  95

Gly Met Trp Ile Thr Leu Met Ala Leu Pro Thr Asn Asp Trp Gln Trp
            100                 105                 110

Val Ala Ala Gly Phe Val Ile Phe Arg Ile Leu Asp Met Trp Lys Pro
        115                 120                 125

Trp Pro Ile Arg Trp Phe Asp Arg Asn Val His Gly Gly Met Gly Ile
    130                 135                 140

Met Ile Asp Asp Ile Val Ala Gly Val Ile Ser Ala Gly Ile Leu Tyr
145                 150                 155                 160

Phe Ile Gly His His Trp Pro Leu Gly Ile Leu Ser
                165                 170
```

<210> SEQ ID NO 59
<211> LENGTH: 211
<212> TYPE: PRT
<213> ORGANISM: Escherichia coli
<220> FEATURE:
<223> OTHER INFORMATION: pgpC Escherichia coli (strain K12)

<400> SEQUENCE: 59

```
Met Ala Thr His Glu Arg Arg Val Val Phe Phe Asp Leu Asp Gly Thr
1               5                   10                  15

Leu His Gln Gln Asp Met Phe Gly Ser Phe Leu Arg Tyr Leu Leu Arg
            20                  25                  30

Arg Gln Pro Leu Asn Ala Leu Leu Val Leu Pro Leu Leu Pro Ile Ile
        35                  40                  45

Ala Ile Ala Leu Leu Ile Lys Gly Arg Ala Ala Arg Trp Pro Met Ser
    50                  55                  60

Leu Leu Leu Trp Gly Cys Thr Phe Gly His Ser Glu Ala Arg Leu Gln
65                  70                  75                  80

Thr Leu Gln Ala Asp Phe Val Arg Trp Phe Arg Asp Asn Val Thr Ala
                85                  90                  95

Phe Pro Leu Val Gln Glu Arg Leu Thr Thr Tyr Leu Leu Ser Ser Asp
            100                 105                 110

Ala Asp Ile Trp Leu Ile Thr Gly Ser Pro Gln Pro Leu Val Glu Ala
        115                 120                 125

Val Tyr Phe Asp Thr Pro Trp Leu Pro Arg Val Asn Leu Ile Ala Ser
    130                 135                 140

Gln Ile Gln Arg Gly Tyr Gly Gly Trp Val Leu Thr Met Arg Cys Leu
145                 150                 155                 160

Gly His Glu Lys Val Ala Gln Leu Glu Arg Lys Ile Gly Thr Pro Leu
                165                 170                 175

Arg Leu Tyr Ser Gly Tyr Ser Asp Ser Asn Gln Asp Asn Pro Leu Leu
            180                 185                 190

Tyr Phe Cys Gln His Arg Trp Arg Val Thr Pro Arg Gly Glu Leu Gln
        195                 200                 205

Gln Leu Glu
    210
```

<210> SEQ ID NO 60
<211> LENGTH: 254
<212> TYPE: PRT
<213> ORGANISM: Escherichia coli
<220> FEATURE:
<223> OTHER INFORMATION: pgpB Escherichia coli (strain K12)

<400> SEQUENCE: 60

```
Met Arg Ser Ile Ala Arg Arg Thr Ala Val Gly Ala Ala Leu Leu Leu
1               5                   10                  15

Val Met Pro Val Ala Val Trp Ile Ser Gly Trp Arg Trp Gln Pro Gly
            20                  25                  30

Glu Gln Ser Trp Leu Leu Lys Ala Ala Phe Trp Val Thr Glu Thr Val
        35                  40                  45

Thr Gln Pro Trp Gly Val Ile Thr His Leu Ile Leu Phe Gly Trp Phe
    50                  55                  60

Leu Trp Cys Leu Arg Phe Arg Ile Lys Ala Ala Phe Val Leu Phe Ala
65                  70                  75                  80

Ile Leu Ala Ala Ala Ile Leu Val Gly Gln Gly Val Lys Ser Trp Ile
                85                  90                  95
```

```
Lys Asp Lys Val Gln Glu Pro Arg Pro Phe Val Ile Trp Leu Glu Lys
            100                 105                 110

Thr His His Ile Pro Val Asp Glu Phe Tyr Thr Leu Lys Arg Ala Glu
        115                 120                 125

Arg Gly Asn Leu Val Lys Glu Gln Leu Ala Glu Glu Lys Asn Ile Pro
    130                 135                 140

Gln Tyr Leu Arg Ser His Trp Gln Lys Glu Thr Gly Phe Ala Phe Pro
145                 150                 155                 160

Ser Gly His Thr Met Phe Ala Ala Ser Trp Ala Leu Leu Ala Val Gly
                165                 170                 175

Leu Leu Trp Pro Arg Arg Arg Thr Leu Thr Ile Ala Ile Leu Leu Val
            180                 185                 190

Trp Ala Thr Gly Val Met Gly Ser Arg Leu Leu Leu Gly Met His Trp
        195                 200                 205

Pro Arg Asp Leu Val Val Ala Thr Leu Ile Ser Trp Ala Leu Val Ala
    210                 215                 220

Val Ala Thr Trp Leu Ala Gln Arg Ile Cys Gly Pro Leu Thr Pro Pro
225                 230                 235                 240

Ala Glu Glu Asn Arg Glu Ile Ala Gln Arg Glu Gln Glu Ser
                245                 250
```

<210> SEQ ID NO 61
<211> LENGTH: 322
<212> TYPE: PRT
<213> ORGANISM: Escherichia coli
<220> FEATURE:
<223> OTHER INFORMATION: serB Escherichia coli (strain K12)

<400> SEQUENCE: 61

```
Met Pro Asn Ile Thr Trp Cys Asp Leu Pro Glu Asp Val Ser Leu Trp
1               5                   10                  15

Pro Gly Leu Pro Leu Ser Leu Ser Gly Asp Glu Val Met Pro Leu Asp
            20                  25                  30

Tyr His Ala Gly Arg Ser Gly Trp Leu Leu Tyr Gly Arg Gly Leu Asp
        35                  40                  45

Lys Gln Arg Leu Thr Gln Tyr Gln Ser Lys Leu Gly Ala Ala Met Val
    50                  55                  60

Ile Val Ala Ala Trp Cys Val Glu Asp Tyr Gln Val Ile Arg Leu Ala
65                  70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
            100                 105                 110

Leu Val Met Asp Met Asp Ser Thr Ala Ile Gln Ile Glu Cys Ile Asp
        115                 120                 125

Glu Ile Ala Lys Leu Ala Gly Thr Gly Glu Met Val Ala Glu Val Thr
    130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
        195                 200                 205
```

```
Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
        275                 280                 285

Tyr His Ala Lys Pro Lys Val Asn Glu Lys Ala Glu Val Thr Ile Arg
    290                 295                 300

His Ala Asp Leu Met Gly Val Phe Cys Ile Leu Ser Gly Ser Leu Asn
305                 310                 315                 320

Gln Lys


<210> SEQ ID NO 62
<211> LENGTH: 252
<212> TYPE: PRT
<213> ORGANISM: Escherichia coli
<220> FEATURE:
<223> OTHER INFORMATION: gph Escherichia coli (strain K12)

<400> SEQUENCE: 62

Met Asn Lys Phe Glu Asp Ile Arg Gly Val Ala Phe Asp Leu Asp Gly
1               5                   10                  15

Thr Leu Val Asp Ser Ala Pro Gly Leu Ala Ala Ala Val Asp Met Ala
            20                  25                  30

Leu Tyr Ala Leu Glu Leu Pro Val Ala Gly Glu Glu Arg Val Ile Thr
        35                  40                  45

Trp Ile Gly Asn Gly Ala Asp Val Leu Met Glu Arg Ala Leu Thr Trp
    50                  55                  60

Ala Arg Gln Glu Arg Ala Thr Gln Arg Lys Thr Met Gly Lys Pro Pro
65                  70                  75                  80

Val Asp Asp Asp Ile Pro Ala Glu Glu Gln Val Arg Ile Leu Arg Lys
                85                  90                  95

Leu Phe Asp Arg Tyr Tyr Gly Glu Val Ala Glu Glu Gly Thr Phe Leu
            100                 105                 110

Phe Pro His Val Ala Asp Thr Leu Gly Ala Leu Gln Ala Lys Gly Leu
        115                 120                 125

Pro Leu Gly Leu Val Thr Asn Lys Pro Thr Pro Phe Val Ala Pro Leu
    130                 135                 140

Leu Glu Ala Leu Asp Ile Ala Lys Tyr Phe Ser Val Val Ile Gly Gly
145                 150                 155                 160

Asp Asp Val Gln Asn Lys Lys Pro His Pro Asp Pro Leu Leu Leu Val
                165                 170                 175

Ala Glu Arg Met Gly Ile Ala Pro Gln Gln Met Leu Phe Val Gly Asp
            180                 185                 190

Ser Arg Asn Asp Ile Gln Ala Ala Lys Ala Ala Gly Cys Pro Ser Val
        195                 200                 205

Gly Leu Thr Tyr Gly Tyr Asn Tyr Gly Glu Ala Ile Asp Leu Ser Gln
    210                 215                 220

Pro Asp Val Ile Tyr Gln Ser Ile Asn Asp Leu Leu Pro Ala Leu Gly
225                 230                 235                 240
```

```
Leu Pro His Ser Glu Asn Gln Glu Ser Lys Asn Asp
                245                 250


<210> SEQ ID NO 63
<211> LENGTH: 225
<212> TYPE: PRT
<213> ORGANISM: Escherichia coli
<220> FEATURE:
<223> OTHER INFORMATION: yjjG Escherichia coli (strain K12)

<400> SEQUENCE: 63

Met Lys Trp Asp Trp Ile Phe Phe Asp Ala Asp Glu Thr Leu Phe Thr
1               5                   10                  15

Phe Asp Ser Phe Thr Gly Leu Gln Arg Met Phe Leu Asp Tyr Ser Val
            20                  25                  30

Thr Phe Thr Ala Glu Asp Phe Gln Asp Tyr Gln Ala Val Asn Lys Pro
        35                  40                  45

Leu Trp Val Asp Tyr Gln Asn Gly Ala Ile Thr Ser Leu Gln Leu Gln
    50                  55                  60

His Gly Arg Phe Glu Ser Trp Ala Glu Arg Leu Asn Val Glu Pro Gly
65                  70                  75                  80

Lys Leu Asn Glu Ala Phe Ile Asn Ala Met Ala Glu Ile Cys Thr Pro
                85                  90                  95

Leu Pro Gly Ala Val Ser Leu Leu Asn Ala Ile Arg Gly Asn Ala Lys
            100                 105                 110

Ile Gly Ile Ile Thr Asn Gly Phe Ser Ala Leu Gln Gln Val Arg Leu
        115                 120                 125

Glu Arg Thr Gly Leu Arg Asp Tyr Phe Asp Leu Leu Val Ile Ser Glu
    130                 135                 140

Glu Val Gly Val Ala Lys Pro Asn Lys Lys Ile Phe Asp Tyr Ala Leu
145                 150                 155                 160

Glu Gln Ala Gly Asn Pro Asp Arg Ser Arg Val Leu Met Val Gly Asp
                165                 170                 175

Thr Ala Glu Ser Asp Ile Leu Gly Gly Ile Asn Ala Gly Leu Ala Thr
            180                 185                 190

Cys Trp Leu Asn Ala His His Arg Glu Gln Pro Glu Gly Ile Ala Pro
        195                 200                 205

Thr Trp Thr Val Ser Ser Leu His Glu Leu Glu Gln Leu Leu Cys Lys
    210                 215                 220

His
225


<210> SEQ ID NO 64
<211> LENGTH: 266
<212> TYPE: PRT
<213> ORGANISM: Escherichia coli
<220> FEATURE:
<223> OTHER INFORMATION: yjgL Escherichia coli (strain K12)

<400> SEQUENCE: 64

Met Tyr Gln Val Val Ala Ser Asp Leu Asp Gly Thr Leu Leu Ser Pro
1               5                   10                  15

Asp His Thr Leu Ser Pro Tyr Ala Lys Glu Thr Leu Lys Leu Leu Thr
            20                  25                  30

Ala Arg Gly Ile Asn Phe Val Phe Ala Thr Gly Arg His His Val Asp
        35                  40                  45

Val Gly Gln Ile Arg Asp Asn Leu Glu Ile Lys Ser Tyr Met Ile Thr
    50                  55                  60
```

```
Ser Asn Gly Ala Arg Val His Asp Leu Asp Gly Asn Leu Ile Phe Ala
65                  70                  75                  80

His Asn Leu Asp Arg Asp Ile Ala Ser Asp Leu Phe Gly Val Val Asn
                85                  90                  95

Asp Asn Pro Asp Ile Ile Thr Asn Val Tyr Arg Asp Asp Glu Trp Phe
            100                 105                 110

Met Asn Arg His Arg Pro Glu Glu Met Arg Phe Phe Lys Glu Ala Val
        115                 120                 125

Phe Gln Tyr Ala Leu Tyr Glu Pro Gly Leu Leu Glu Pro Glu Gly Val
    130                 135                 140

Ser Lys Val Phe Phe Thr Cys Asp Ser His Glu Gln Leu Leu Pro Leu
145                 150                 155                 160

Glu Gln Ala Ile Asn Ala Arg Trp Gly Asp Arg Val Asn Val Ser Phe
                165                 170                 175

Ser Thr Leu Thr Cys Leu Glu Val Met Ala Gly Gly Val Ser Lys Gly
            180                 185                 190

His Ala Leu Glu Ala Val Ala Lys Lys Leu Gly Tyr Ser Leu Lys Asp
        195                 200                 205

Cys Ile Ala Phe Gly Asp Gly Met Asn Asp Ala Glu Met Leu Ser Met
    210                 215                 220

Ala Gly Lys Gly Cys Ile Met Gly Ser Ala His Gln Arg Leu Lys Asp
225                 230                 235                 240

Leu His Pro Glu Leu Glu Val Ile Gly Thr Asn Ala Asp Asp Ala Val
                245                 250                 255

Pro His Tyr Leu Arg Lys Leu Tyr Leu Ser
            260                 265


<210> SEQ ID NO 65
<211> LENGTH: 550
<212> TYPE: PRT
<213> ORGANISM: Escherichia coli
<220> FEATURE:
<223> OTHER INFORMATION: ushA Escherichia coli (strain K12)

<400> SEQUENCE: 65

Met Lys Leu Leu Gln Arg Gly Val Ala Leu Ala Leu Leu Thr Thr Phe
1               5                   10                  15

Thr Leu Ala Ser Glu Thr Ala Leu Ala Tyr Glu Gln Asp Lys Thr Tyr
            20                  25                  30

Lys Ile Thr Val Leu His Thr Asn Asp His His Gly His Phe Trp Arg
        35                  40                  45

Asn Glu Tyr Gly Glu Tyr Gly Leu Ala Ala Gln Lys Thr Leu Val Asp
    50                  55                  60

Gly Ile Arg Lys Glu Val Ala Ala Glu Gly Gly Ser Val Leu Leu Leu
65                  70                  75                  80

Ser Gly Gly Asp Ile Asn Thr Gly Val Pro Glu Ser Asp Leu Gln Asp
                85                  90                  95

Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160
```

```
Gln Asp Leu Lys Ile Ala Val Ile Gly Leu Thr Thr Asp Asp Thr Ala
                165                 170                 175

Lys Ile Gly Asn Pro Glu Tyr Phe Thr Asp Ile Glu Phe Arg Lys Pro
            180                 185                 190

Ala Asp Glu Ala Lys Leu Val Ile Gln Glu Leu Gln Gln Thr Glu Lys
        195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
                245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285

His Glu Trp Gly Lys Tyr Val Gly Arg Ala Asp Phe Glu Phe Arg Asn
    290                 295                 300

Gly Glu Met Lys Met Val Asn Tyr Gln Leu Ile Pro Val Asn Leu Lys
305                 310                 315                 320

Lys Lys Val Thr Trp Glu Asp Gly Lys Ser Glu Arg Val Leu Tyr Thr
                325                 330                 335

Pro Glu Ile Ala Glu Asn Gln Gln Met Ile Ser Leu Leu Ser Pro Phe
            340                 345                 350

Gln Asn Lys Gly Lys Ala Gln Leu Glu Val Lys Ile Gly Glu Thr Asn
        355                 360                 365

Gly Arg Leu Glu Gly Asp Arg Asp Lys Val Arg Phe Val Gln Thr Asn
    370                 375                 380

Met Gly Arg Leu Ile Leu Ala Ala Gln Met Asp Arg Thr Gly Ala Asp
385                 390                 395                 400

Phe Ala Val Met Ser Gly Gly Gly Ile Arg Asp Ser Ile Glu Ala Gly
                405                 410                 415

Asp Ile Ser Tyr Lys Asn Val Leu Lys Val Gln Pro Phe Gly Asn Val
            420                 425                 430

Val Val Tyr Ala Asp Met Thr Gly Lys Glu Val Ile Asp Tyr Leu Thr
        435                 440                 445

Ala Val Ala Gln Met Lys Pro Asp Ser Gly Ala Tyr Pro Gln Phe Ala
    450                 455                 460

Asn Val Ser Phe Val Ala Lys Asp Gly Lys Leu Asn Asp Leu Lys Ile
465                 470                 475                 480

Lys Gly Glu Pro Val Asp Pro Ala Lys Thr Tyr Arg Met Ala Thr Leu
                485                 490                 495

Asn Phe Asn Ala Thr Gly Gly Asp Gly Tyr Pro Arg Leu Asp Asn Lys
            500                 505                 510

Pro Gly Tyr Val Asn Thr Gly Phe Ile Asp Ala Glu Val Leu Lys Ala
        515                 520                 525

Tyr Ile Gln Lys Ser Ser Pro Leu Asp Val Ser Val Tyr Glu Pro Lys
    530                 535                 540

Gly Glu Val Ser Trp Gln
545                 550
```

<210> SEQ ID NO 66
<211> LENGTH: 197

```
<212> TYPE: PRT
<213> ORGANISM: Escherichia coli
<220> FEATURE:
<223> OTHER INFORMATION: UbiX-like flavin prenyltransferase from
      Escherichia coli O157:H7

<400> SEQUENCE: 66

Met Lys Leu Ile Val Gly Met Thr Gly Ala Thr Gly Ala Pro Leu Gly
1               5                   10                  15

Val Ala Leu Leu Gln Ala Leu Arg Glu Met Pro Asn Val Glu Thr His
            20                  25                  30

Leu Val Met Ser Lys Trp Ala Lys Thr Thr Ile Glu Leu Glu Thr Pro
        35                  40                  45

Tyr Ser Ala Arg Asp Val Ala Ala Leu Ala Asp Phe Ser His Asn Pro
    50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Asp Gly Leu Val Gly Arg Ala Ala Asp Val Val Leu Lys
            100                 105                 110

Glu Gly Arg Lys Leu Val Leu Val Pro Arg Glu Met Pro Leu Ser Thr
        115                 120                 125

Ile His Leu Glu Asn Met Leu Ala Leu Ser Arg Met Gly Val Ala Met
    130                 135                 140

Val Pro Pro Met Pro Ala Phe Tyr Asn His Pro Glu Thr Val Asp Asp
145                 150                 155                 160

Ile Val His His Val Val Ala Arg Val Leu Asp Gln Phe Gly Leu Glu
                165                 170                 175

His Pro His Ala Arg Arg Trp Gln Gly Leu Pro Gln Ala Arg Asn Phe
            180                 185                 190

Ser Gln Glu Asn Glu
        195


<210> SEQ ID NO 67
<211> LENGTH: 92
<212> TYPE: PRT
<213> ORGANISM: Escherichia coli (strain K12)

<400> SEQUENCE: 67

Met Ser Lys Val Cys Ile Ile Ala Trp Val Tyr Gly Arg Val Gln Gly
1               5                   10                  15

Val Gly Phe Arg Tyr Thr Thr Gln Tyr Glu Ala Lys Arg Leu Gly Leu
            20                  25                  30

Thr Gly Tyr Ala Lys Asn Leu Asp Asp Gly Ser Val Glu Val Val Ala
        35                  40                  45

Cys Gly Glu Glu Gly Gln Val Glu Lys Leu Met Gln Trp Leu Lys Ser
    50                  55                  60

Gly Gly Pro Arg Ser Ala Arg Val Glu Arg Val Leu Ser Glu Pro His
65                  70                  75                  80

His Pro Ser Gly Glu Leu Thr Asp Phe Arg Ile Arg
                85                  90


<210> SEQ ID NO 68
<211> LENGTH: 862
<212> TYPE: PRT
<213> ORGANISM: Saccharomyces cerevisiae (strain ATCC 204508 / S288 c)
```

<400> SEQUENCE: 68

Met Gln Tyr Val Gly Arg Ala Leu Gly Ser Val Ser Lys Thr Trp Ser
1               5                   10                  15

Ser Ile Asn Pro Ala Thr Leu Ser Gly Ala Ile Asp Val Ile Val Val
            20                  25                  30

Glu His Pro Asp Gly Arg Leu Ser Cys Ser Pro Phe His Val Arg Phe
        35                  40                  45

Gly Lys Phe Gln Ile Leu Lys Pro Ser Gln Lys Lys Val Gln Val Phe
    50                  55                  60

Ile Asn Glu Lys Leu Ser Asn Met Pro Met Lys Leu Ser Asp Ser Gly
65                  70                  75                  80

Glu Ala Tyr Phe Val Phe Glu Met Gly Asp Gln Val Thr Asp Val Pro
                85                  90                  95

Asp Glu Leu Leu Val Ser Pro Val Met Ser Ala Thr Ser Ser Pro Pro
            100                 105                 110

Gln Ser Pro Glu Thr Ser Ile Leu Glu Gly Gly Thr Glu Gly Glu Gly
        115                 120                 125

Glu Gly Glu Asn Glu Asn Lys Lys Lys Glu Lys Lys Val Leu Glu Glu
    130                 135                 140

Pro Asp Phe Leu Asp Ile Asn Asp Thr Gly Asp Ser Gly Ser Lys Asn
145                 150                 155                 160

Ser Glu Thr Thr Gly Ser Leu Ser Pro Thr Glu Ser Ser Thr Thr Thr
                165                 170                 175

Pro Pro Asp Ser Val Glu Glu Arg Lys Leu Val Glu Gln Arg Thr Lys
            180                 185                 190

Asn Phe Gln Gln Lys Leu Asn Lys Lys Leu Thr Glu Ile His Ile Pro
        195                 200                 205

Ser Lys Leu Asp Asn Asn Gly Asp Leu Leu Leu Asp Thr Glu Gly Tyr
    210                 215                 220

Lys Pro Asn Lys Asn Met Met His Asp Thr Asp Ile Gln Leu Lys Gln
225                 230                 235                 240

Leu Leu Lys Asp Glu Phe Gly Asn Asp Ser Asp Ile Ser Ser Phe Ile
                245                 250                 255

Lys Glu Asp Lys Asn Gly Asn Ile Lys Ile Val Asn Pro Tyr Glu His
            260                 265                 270

Leu Thr Asp Leu Ser Pro Pro Gly Thr Pro Pro Thr Met Ala Thr Ser
        275                 280                 285

Gly Ser Val Leu Gly Leu Asp Ala Met Glu Ser Gly Ser Thr Leu Asn
    290                 295                 300

Ser Leu Ser Ser Ser Pro Ser Gly Ser Asp Thr Glu Asp Glu Thr Ser
305                 310                 315                 320

Phe Ser Lys Glu Gln Ser Ser Lys Ser Glu Lys Thr Ser Lys Lys Gly
                325                 330                 335

Thr Ala Gly Ser Gly Glu Thr Glu Lys Arg Tyr Ile Arg Thr Ile Arg
            340                 345                 350

Leu Thr Asn Asp Gln Leu Lys Cys Leu Asn Leu Thr Tyr Gly Glu Asn
        355                 360                 365

Asp Leu Lys Phe Ser Val Asp His Gly Lys Ala Ile Val Thr Ser Lys
    370                 375                 380

Leu Phe Val Trp Arg Trp Asp Val Pro Ile Val Ile Ser Asp Ile Asp
385                 390                 395                 400

Gly Thr Ile Thr Lys Ser Asp Ala Leu Gly His Val Leu Ala Met Ile
                405                 410                 415

```
Gly Lys Asp Trp Thr His Leu Gly Val Ala Lys Leu Phe Ser Glu Ile
            420                 425                 430

Ser Arg Asn Gly Tyr Asn Ile Leu Tyr Leu Thr Ala Arg Ser Ala Gly
        435                 440                 445

Gln Ala Asp Ser Thr Arg Ser Tyr Leu Arg Ser Ile Glu Gln Asn Gly
    450                 455                 460

Ser Lys Leu Pro Asn Gly Pro Val Ile Leu Ser Pro Asp Arg Thr Met
465                 470                 475                 480

Ala Ala Leu Arg Arg Glu Val Ile Leu Lys Lys Pro Glu Val Phe Lys
                485                 490                 495

Ile Ala Cys Leu Asn Asp Ile Arg Ser Leu Tyr Phe Glu Asp Ser Asp
            500                 505                 510

Asn Glu Val Asp Thr Glu Glu Lys Ser Thr Pro Phe Phe Ala Gly Phe
        515                 520                 525

Gly Asn Arg Ile Thr Asp Ala Leu Ser Tyr Arg Thr Val Gly Ile Pro
    530                 535                 540

Ser Ser Arg Ile Phe Thr Ile Asn Thr Glu Gly Glu Val His Met Glu
545                 550                 555                 560

Leu Leu Glu Leu Ala Gly Tyr Arg Ser Ser Tyr Ile His Ile Asn Glu
                565                 570                 575

Leu Val Asp His Phe Phe Pro Pro Val Ser Leu Asp Ser Val Asp Leu
            580                 585                 590

Arg Thr Asn Thr Ser Met Val Pro Gly Ser Pro Pro Asn Arg Thr Leu
        595                 600                 605

Asp Asn Phe Asp Ser Glu Ile Thr Ser Gly Arg Lys Thr Leu Phe Arg
    610                 615                 620

Gly Asn Gln Glu Glu Lys Phe Thr Asp Val Asn Phe Trp Arg Asp Pro
625                 630                 635                 640

Leu Val Asp Ile Asp Asn Leu Ser Asp Ile Ser Asn Asp Asp Ser Asp
                645                 650                 655

Asn Ile Asp Glu Asp Thr Asp Val Ser Gln Gln Ser Asn Ile Ser Arg
            660                 665                 670

Asn Arg Ala Asn Ser Val Lys Thr Ala Lys Val Thr Lys Ala Pro Gln
        675                 680                 685

Arg Asn Val Ser Gly Ser Thr Asn Asn Asn Glu Val Leu Ala Ala Ser
    690                 695                 700

Ser Asp Val Glu Asn Ala Ser Asp Leu Val Ser Ser His Ser Ser Ser
705                 710                 715                 720

Gly Ser Thr Pro Asn Lys Ser Thr Met Ser Lys Gly Asp Ile Gly Lys
                725                 730                 735

Gln Ile Tyr Leu Glu Leu Gly Ser Pro Leu Ala Ser Pro Lys Leu Arg
            740                 745                 750

Tyr Leu Asp Asp Met Asp Asp Glu Asp Ser Asn Tyr Asn Arg Thr Lys
        755                 760                 765

Ser Arg Arg Ala Ser Ser Ala Ala Ala Thr Ser Ile Asp Lys Glu Phe
    770                 775                 780

Lys Lys Leu Ser Val Ser Lys Ala Gly Ala Pro Thr Arg Ile Val Ser
785                 790                 795                 800

Lys Ile Asn Val Ser Asn Asp Val His Ser Leu Gly Asn Ser Asp Thr
                805                 810                 815

Glu Ser Arg Arg Glu Gln Ser Val Asn Glu Thr Gly Arg Asn Gln Leu
            820                 825                 830
```

```
Pro His Asn Ser Met Asp Asp Lys Asp Leu Asp Ser Arg Val Ser Asp
        835                 840                 845

Glu Phe Asp Asp Asp Glu Phe Asp Glu Asp Glu Phe Glu Asp
    850                 855                 860


<210> SEQ ID NO 69
<211> LENGTH: 132
<212> TYPE: PRT
<213> ORGANISM: Methanocaldococcus jannaschii (strain ATCC 43067 / DSM
      2661 / JAL-1 /JCM 10045 / NBRC 100400)

<400> SEQUENCE: 69

Met Ile Ile Glu Gly Glu Val Val Ser Gly Leu Gly Glu Gly Arg Tyr
1               5                   10                  15

Phe Leu Ser Leu Pro Pro Tyr Lys Glu Ile Phe Lys Lys Ile Leu Gly
            20                  25                  30

Phe Glu Pro Tyr Glu Gly Thr Leu Asn Leu Lys Leu Asp Arg Glu Phe
        35                  40                  45

Asp Ile Asn Lys Phe Lys Tyr Ile Glu Thr Glu Asp Phe Glu Phe Asn
    50                  55                  60

Gly Lys Arg Phe Phe Gly Val Lys Val Leu Pro Ile Lys Ile Leu Ile
65                  70                  75                  80

Gly Asn Lys Lys Ile Asp Gly Ala Ile Val Val Pro Lys Lys Thr Tyr
                85                  90                  95

His Ser Ser Glu Ile Ile Glu Ile Ile Ala Pro Met Lys Leu Arg Glu
            100                 105                 110

Gln Phe Asn Leu Lys Asp Gly Asp Val Ile Lys Ile Leu Ile Lys Gly
        115                 120                 125

Asp Lys Asp Glu
    130


<210> SEQ ID NO 70
<211> LENGTH: 197
<212> TYPE: PRT
<213> ORGANISM: Klebsiella pneumoniae
<220> FEATURE:
<223> OTHER INFORMATION: UbiX-like flavin prenyltransferase from
      Klebsiella pneumoniae

<400> SEQUENCE: 70

Met Lys Leu Ile Ile Gly Met Thr Gly Ala Thr Gly Ala Pro Leu Gly
1               5                   10                  15

Val Ala Leu Leu Gln Ala Leu Arg Asp Met Pro Glu Val Glu Thr His
            20                  25                  30

Leu Val Met Ser Lys Trp Ala Lys Thr Thr Ile Glu Leu Glu Thr Pro
        35                  40                  45

Trp Thr Ala Arg Glu Val Ala Ala Leu Ala Asp Phe Ser His Ser Pro
    50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Glu Gly Leu Val Gly Arg Ala Ala Asp Val Val Leu Lys
            100                 105                 110

Glu Gly Arg Lys Leu Val Leu Val Pro Arg Glu Met Pro Leu Ser Thr
        115                 120                 125

Ile His Leu Glu Asn Met Leu Ala Leu Ser Arg Met Gly Val Ala Met
    130                 135                 140
```

```
Val Pro Pro Met Pro Ala Tyr Tyr Asn His Pro Glu Thr Val Asp Asp
145                 150                 155                 160

Ile Thr Asn His Ile Val Thr Arg Val Leu Asp Gln Phe Gly Leu Asp
                165                 170                 175

Tyr His Lys Ala Arg Arg Trp Asn Gly Leu Arg Thr Ala Glu Gln Phe
            180                 185                 190

Ala Gln Glu Ile Glu
        195


<210> SEQ ID NO 71
<211> LENGTH: 221
<212> TYPE: PRT
<213> ORGANISM: Hypocrea atroviridis (strain ATCC 20476 / IMI 206040)
<220> FEATURE:
<223> OTHER INFORMATION: Flavin prenyltransferase PAD1, mitochondrial
      from Hypocrea atroviridis (strain ATCC 20476 / IMI 206040)

<400> SEQUENCE: 71

Met Ser Pro Ser Leu Thr Asp Glu Glu Ser Leu Ala Ile Ser His Ala
1               5                   10                  15

Asn Gly Ser Asn Gly Thr Ala Pro Tyr Gln Pro Pro Gln Pro Arg Arg
            20                  25                  30

Lys Arg Ile Ile Val Ala Met Thr Gly Ala Thr Gly Thr Ile Leu Gly
        35                  40                  45

Ile Lys Leu Leu Ile Ala Leu Arg Arg Leu Asn Val Glu Thr His Leu
    50                  55                  60

Val Ile Ser Lys Trp Ala Glu Gln Thr Leu Lys Tyr Glu Thr Asp Tyr
65                  70                  75                  80

His Pro Ser Asn Val Arg Ala Leu Ala Asp His Val Tyr Gly Ile Asn
                85                  90                  95

Asp Met Ala Ala Ala Ile Ser Ser Gly Ser Phe Arg Val Asp Gly Met
            100                 105                 110

Ile Val Val Pro Cys Ser Met Lys Thr Leu Ala Gly Ile Thr Thr Gly
        115                 120                 125

Leu Cys Asp Asp Leu Ile Ser Arg Ala Ala Asp Val Met Leu Lys Glu
    130                 135                 140

Arg Arg Lys Leu Val Leu Val Ala Arg Glu Thr Pro Leu Ser Glu Ile
145                 150                 155                 160

His Leu Arg Asn Met Leu Asp Val Thr Arg Ala Gly Ala Ile Ile Phe
                165                 170                 175

Pro Pro Val Pro Ala Tyr Tyr Ile Arg Pro Ala Ser Val Asp Asp Leu
            180                 185                 190

Val Asn Gln Ser Val Gly Arg Met Leu Asp Leu Phe Asp Leu Asp Thr
        195                 200                 205

Glu Glu Phe Glu Arg Trp Asn Gly Trp Lys Lys Asp Asn
    210                 215                 220
```